US008835149B2

(12) United States Patent
Coppersmith et al.

(10) Patent No.: US 8,835,149 B2
(45) Date of Patent: Sep. 16, 2014

(54) DGAT GENES COMPRISING PLECKSTRIN HOMOLOGY DOMAINS AND METHODS OF USE FOR TRIGLYCERIDE PRODUCTION IN RECOMBINANT MICROORGANISMS

(71) Applicant: ExxonMobil Research and Engineering Company, Annandale, NJ (US)

(72) Inventors: Jennifer Coppersmith, San Diego, CA (US); Rekha Seshadri, San Diego, CA (US); Toby Howard Richardson, San Diego, CA (US)

(73) Assignee: ExxonMobil Research and Engineering Company, Annandale, NJ (US)

( * ) Notice: Subject to any disclaimer, the term of this patent is extended or adjusted under 35 U.S.C. 154(b) by 0 days.

(21) Appl. No.: 13/707,287

(22) Filed: Dec. 6, 2012

(65) Prior Publication Data
US 2014/0162329 A1    Jun. 12, 2014

(51) Int. Cl.
C12N 9/12     (2006.01)
C12N 1/20     (2006.01)
C12N 15/00    (2006.01)
C12Q 1/68     (2006.01)
C12P 7/64     (2006.01)
C12N 9/10     (2006.01)

(52) U.S. Cl.
CPC ............. *C12N 9/1029* (2013.01); *C12P 7/6463* (2013.01)
USPC ...................... 435/194; 435/252.3; 435/320.1; 435/6.1

(58) Field of Classification Search
USPC ............... 536/23.2; 435/320.1, 252.3, 6, 183, 435/194, 6.1
See application file for complete search history.

(56) References Cited

U.S. PATENT DOCUMENTS

| 5,447,858 | A  | 9/1995  | Key et al. ..................... 435/172.3 |
| 5,464,758 | A  | 11/1995 | Gossen et al. ................. 435/69.1 |
| 5,639,952 | A  | 6/1997  | Quail et al. .................... 800/205 |
| 5,661,017 | A  | 8/1997  | Dunahay et al. ........... 435/172.3 |
| 5,689,044 | A  | 11/1997 | Ryals et al. .................... 800/205 |
| 5,750,385 | A  | 5/1998  | Shewmaker et al. ....... 435/172.3 |
| 5,814,618 | A  | 9/1998  | Bujard et al. ..................... 514/44 |
| 6,027,900 | A  | 2/2000  | Allnutt et al. ....................... 435/6 |
| 6,252,140 | B1 | 6/2001  | Mitra et al. .................... 800/298 |
| 6,316,224 | B1 | 11/2001 | Xia .............................. 435/69.1 |
| 6,379,945 | B1 | 4/2002  | Jepson et al. .................. 435/243 |
| 6,410,828 | B1 | 6/2002  | Armstrong et al. ........... 800/287 |
| 7,135,290 | B2 | 11/2006 | Dillon ................................ 435/6 |
| 7,198,937 | B2 | 4/2007  | Xue et al. .................... 435/254.2 |
| 7,294,506 | B2 | 11/2007 | Daniell et al. .............. 435/320.1 |
| 7,642,405 | B2 | 1/2010  | Lee ............................... 800/296 |
| 7,901,928 | B2 | 3/2011  | Yadav et al. .............. 435/254.21 |
| 2008/0020415 | A1 | 1/2008 | Yadav et al. ..................... 435/15 |
| 2009/0104674 | A1 | 4/2009 | Yadav et al. ................... 435/134 |
| 2009/0317878 | A1 | 12/2009 | Champagne et al. ......... 435/134 |
| 2009/0317904 | A1 | 12/2009 | Vick et al. ................... 435/320.1 |
| 2010/0184169 | A1 | 7/2010 | Roberts et al. ................ 435/134 |
| 2010/0192258 | A1 | 7/2010 | Benning et al. ............... 800/281 |
| 2010/0255550 | A1 | 10/2010 | Benning et al. ............... 435/134 |
| 2010/0255551 | A1 | 10/2010 | Roberts et al. ................ 435/134 |
| 2010/0279390 | A1 | 11/2010 | Saphire ...................... 435/257.2 |
| 2010/0317073 | A1 | 12/2010 | Sayre et al. ................... 435/136 |
| 2011/0061130 | A1 | 3/2011 | Zou et al. ...................... 800/281 |
| 2011/0250659 | A1 | 10/2011 | Roberts et al. ................ 435/134 |
| 2014/0106417 | A1 | 4/2014 | Schneider et al. |

FOREIGN PATENT DOCUMENTS

| CN | 102492672       | 6/2012  | ............ C12N 15/54 |
| WO | WO 1997/45538   | 12/1997 | ............ C12N 15/10 |
| WO | WO 2000/62601   | 10/2000 | ............ A01H 13/00 |
| WO | WO 03/091413    | 11/2003 | |
| WO | WO 2005/005643  | 1/2005  | ............ C12N 15/82 |
| WO | WO 2007/133558  | 11/2007 | ............ E21B 37/00 |
| WO | WO 2009/149465  | 12/2009 | ............ C12N 15/82 |
| WO | WO 2011/026008  | 3/2011  | ............... C12P 1/00 |
| WO | WO 2011/034863  | 3/2011  | ............ A01H 13/00 |
| WO | WO 2011/156520  | 12/2011 | |
| WO | WO 2011/161093  | 12/2011 | |
| WO | WO 2012/059925  | 5/2012  | |
| WO | WO 2012/087982  | 6/2012  | |

OTHER PUBLICATIONS

Wang et al., UniProt. Database, Accession No. E9NME7, Apr. 2011.*
Abe, J., et al. (2008), "Expression of exogenous genes under the control of endogenous HSP70 and CAB promoters in the closterium peracerosum-strigosum-littorale complex", *Plant Cell Physiol*, 49(4): 625-632.
Altschul, S., et al. (1997), "Gapped BLAST and PSI-BLAST: a new generation of protein database search programs", *Nucleic Acids Research*, 25(17): 3389-3402.
Alvarez, HM, et al. (2002), "Triacylglycerols in prokaryotic microorganisms", *Appl Microbiol Biotechnol*, 60(4): 367-376.
Alvarez, A., et al., (2008), Cloning and characterization of a gene involved in triacylglycerol biosynthesis and identification of additional homologous genes in the oleaginous bacterium *Rhodococcus opacus* PD630, *Microbiology*, 154: 2327-2335.
Andrianov, V., et al., (2010), "Tobacco as a production platform for biofuel: overexpression of Arabidopsis DGAT and LEC2 genes increases accumulation and shifts the composition of lipids in green biomas", *Plant Biotechnol J.*, 8(3): 277-287.
Apt. K., et al., (2002), "In vivo characterization of diatom multipartite plastid targeting signals", *Journal of Cell Science*, 115: 4061-4069.

(Continued)

*Primary Examiner* — Maryam Monshipouri
(74) *Attorney, Agent, or Firm* — Harness, Dickey & Pierce, P.L.C.

(57) ABSTRACT

The present invention provides novel diacylglycerol acyltransferase (DGAT) genes comprising Pleckstrin Homology (PH) domains. The present invention also provides for recombinant cells, such as algae, transformed with acyltransferase genes, such as DGAT, comprising PH domains, and methods of using such recombinant cells to produce increased triglyceride levels.

20 Claims, 14 Drawing Sheets

(56) References Cited

OTHER PUBLICATIONS

Arabolaza, A., et al., (2008), "Multiple pathways for triacyclglycerol biosynthesis in *Streptomyces coelicolor*", *Applied and Environmental Microbiology*, 74(9): 2573-2582.

Barney, et aL, (2012), "Differences in substrate specificities of five bacterial wax ester synthases", *Appl. and Environmental Microbiology*, 78(16): 5734-5745.

Beopoulos, A., et al., (2012), "Identification and characterization of DGA2, an acyltransferase of the DGAT1 acyl-coa:diacylglycerol acyltransferase family in the oleaginous yeast *Yarrowia lipolytica*. New insights into the storage lipid metabolism of oleaginous yeasts" *Appl Microbiol Biotechnol*, 93:1523-1537.

Biester, E., et al., (2012), "Multifunctional Acyltransferases from *Tetrahymena thermophila*", *Lipids*, 47: 371-381.

Bouvier-Navé, P., et al., (2000), "Expression in yeast and tobacco of plant cDNAs encoding acyl CoA:diacylglycerol acyltransferase", *Eur. J. Biochem.*, 267, 85-96.

Buhman, K., et al., (2001), "The enzymes of neutral lipid synthesis", *Minireview*, 276(44): 40369-40372.

Cagliari, A., et al., (2011), "Biosynthesis of triacylglycerols (TAGs) in plants and algae", *International Journal of Plant Biology*, 2:e10.

Cases, S., et al. (1998), "Identification of a gene encoding an acyl coa:diacylglycerol acyltransferase,a key enzyme in triacylglycerol synthesis", *Proc. Natl. Acad. Sci. USA*, 95: 13018-13023.

Cases, S., et al. (2001), "Cloning of DGAT2, a second mammalian diacylglycerol acyltransferase, and related family members*", *The Journal of Biological Chemistry*, 276(42), 38870-38876.

Castruita, M., et al. (2011), "Systems biology approach in *Chlamydomonas* reveals connections between copper nutrition and multiple metabolic steps", *The Plant Cell*, 23: 1273-1292.

Chen, H., et al., (2008), "Conditional production of a functional fish growth hormone in the transgenic line of nannochloropsis octulata (Eustigmatophyceae)[1]", *J. Phycol.*, 44: 768-776.

Chen, W., et al., (2009), "A high throughput nile red method for quantitative measurement of neutral lipids in microalgae", *J Microbiol Methods*, 77(1): 41-47.

Chen, J., et al., (2011), "Correlation of Kennedy pathway efficiency with seed oil content of canola (*Brassica napus L.*) lines", *Can J. Plant Sci.*, 91: 251-259.

Chen, J., et al. (2012), "A look at diacylglycerol acyltransferases (DGATs) in algae", *Journal of Biotechnology*, 162: 28-39.

Courchesne, M., et al., (2009), "Enhancement of lipid production using biochemical, genetic and transcription factor engineering approaches", *Journal of Biotechnology*, 141: 31-41.

Daniel, J., et al. (2004), "Induction of a novel class of diacylglycerol acyltransferases and triacyglycerol accumulation in *Mycobacterium tuberculosis* as it goes into a dormancy-like state in culture", *Journal of Bacteriology*, 186(15): 5017-5030.

Duan, Y., et al., (2011), De novo Biosynthesis of biodiesel by *Escherichia coli* in optimized fed-batch cultivation, *PloS ONE*, 6(5): e20265.

Durrett, T., et al. (2010), "A distinct DGAT with sn-3 acetyltransferase activity that synthesizes unusual, reduced-viscosity oils in *Euonymus* and transgenic seeds", *Proc. National Acad Sci USA*, 107(20): 9464-9469.

Fan, J., et al., (2011), "Corrigendum to a cholorplast pathway for the de novo biosynthesis of triacylglycerol in *chlamydomonas reinhardtii*" [FEBS lett. 585 (2011) 1985-1991], *FEBS Letters*, 585: 4029.

Fan, J., et al., (2011), "A cholorplast pathway for the de novo biosynthesis of triacylglycerol in *chlamydomonas reinhardtii*", *FEBS letters*, 585: 1985-1991.

Ferrante, P. et al. (2008), "An optimized, chemically regulated gene expression system for *Chlamydomonas*", *PloS ONE*, 3(9): e3200.

Fischer, N., et al. (2001), "The flanking regions of PSaD drive efficient gene expression in the nucleus of the green alga *chlamydomonas reinhardtii*", *Mol Genet Genomics*, 265(5): 888-894.

Gouveia, L., et al. (2009), "Microalgae as a raw material for biofuels production", *J ind Microbiol Biotechnol*, 36: 269-274.

Greenspan, P., et al. (1985), "Nile red: a selective fluorescent stain for intracellular lipid droplets" *The Journal of Cell Biology*, 100: 965-973.

Greenwell., H., et al. (2010), "Placing microalgae on the biofuels priority list: a review of the technological challenges", *Journal of the Royal Society Interface*, 7: 703-726.

Hallmann, A., et al. (1997), "Gene replacement by homologous recombination in the multicellular green alga volvox carteri" *Proc. Natl. Acad. Sci USA*, 94:7469-7474.

Henikoff, S., et al. (1992), "Amino acid substitution matrices from protein blocks", *Proc. Natl. Acad. Sci USA*, 89:10915-10919.

Hernández, L., et aL, (2012), "A cytosolic acyltransferase contributes to triacylglycerol synthesis in surcrose-rescued arabidopsis seed oil catabolism mutants", *Plant Physiology*, 160: 215-225.

Hernàndez, M., et al, (2012), "The atf2 gene is involved in triacylglycerol biosynthesis and accumulation in the oleaginous *Rhodococcus opacus* PD630", *Applied Microbial and Cell Physiology*, DOI 10.1007/S00253-012-4360-1.

Hu, Q., et al., (2008), "Microalgal triacylglycerols as feedstocks for biofuel production: perspectives and advances", *The Plant Journal*, 54: 621-639.

Iwai, M., et al. (2004), "Improved genetic transformation of the thermophilic cyanobacterium, thermosynechoccus elongates BP-1", *Plant Cell Physiol.* 45(2):171-175.

Jako, C., et al. (2001), "Seed-specific over-expression of an arabidopsis cDNA encoding a diacylglycerol Acyltransferase enhances seed oil content and seed weight", *Plant Physiology*, 126: 861-874.

Kaddor, C., et al (2009), "Analysis of neutral lipid biosynthesis in *Streptomyces avermitilis* MA-4680 and characterization of an acyltransferase involved herein", *Appl Microbiol Biotechnol*, 84: 143-155.

Kalscheuer, R., et al. (2003), "A novel bifunctional wax ester synthase/acyl-coa:diacylglycerol acyltransferase mediates wax ester and triacylglycerol biosynthesis in *Acinetobacter calcoaceticus* ADP1*", *The Journal of Biological Chemistry*, 278(10): 8075-8082.

Karlin, S., et al. (1990), "Methods for assessing the statistical significance of molecular sequence features by using general scoring schemes", *Proc. Natl. Acad. Sci. USA*, 87: 2264-2268.

Kindle, K., et al. (1989), "Stable nuclear transformation of chlamydomonas using the chlamydomonas gene for nitrate reductase", *The Journal of Cell Biology*, 109 (6, Part 1), 2589-2601.

La Fontaine, S., et al. (2002), "Copper-dependent iron assimilation pathway in the model photosynthetic Eukaryote *Chlamydomonas reinhardtii*", *Eukaryotic Cell*, 1(5): 736-757.

La Russa, M., et al., (2012), "Functional analysis of three type-2 DGAT homologue genes for triacylglycerol production in the green microalga *Chlamydomonas reinhardtii*", *Journal of Biotechnology*, 162(1): 13-20.

Lardizabal, K., et al., (2008), "Expression of *Umbelopsis ramanniana* DGAT2A in seed increases oil in soybean", *Plant Physiology*, 148: 89-96.

Lemmon, M., et al., (2008), "Membrane recognition by phospholipid-binding domains", *Nature Reviews*, 9: 99-111.

Lung, SC., et al., (2006), "Diacylglycerol acyltransferase: a key mediator of plant triacylglycerol synthesis", *Lipids*, 41(12): 1073-1088.

Mendes, A., et al., (2009), "*Crypthecondinium cohnii* with emphasis on DHA production: a review", *J. Appl Phycol.*, 21: 199-214.

Méndez-Alvarez, S., et al. (1994), "Transformation of chlorobium limicola by a plasmid that confers the ability to utilize thiosulfate" *Journal of Bacteriology*, 176(23):7395-7397.

Merchant, S., et al. (2011), "TAG, you're It! Chlamydomonas as a reference organism for understanding algal triacylglycerol accumulation", *Current Opinion in Biotechnology*, 23: 1-12.

Miller, R., et al. (2010), "Changes in transcript abundance in *Chlamydomonas reinhardtii* following nitrogen deprivation predict diversion of metabolism", *Plant Physiology*, 154: 1737-1752.

Napier, JA., et al. (2010), "Tailoring plant lipid composition: designer oilseeds come of age", *Current Opinion Plant Biol.*, 13(3): 330-337.

(56) References Cited

OTHER PUBLICATIONS

No, D., et al. (1996), "Ecdysone-inducible gene expression in mammalian cells and transgenic mice", *Proc. Natl. Acad. Sci. USA*, 93: 3346-3351.

Oakes, J., et al. (2011), "Expression of fungal *diacylglycerol acyltransferase2* genes to increase kernel oil in maize", *Plant Physiology*, 155: 1146-1157.

Ohnuma M., et al. (2008), "Polyethylene glycol (PEG)-mediated transient gene expression in a red alga, cyanidioschyzon merolae 10D", *Plant Cell Physiol.* 49(1):117-120.

Pearson, W., et al. (1988), "Improved tools for biological sequence comparison", *Proc. Natl. Acad. Sci USA*, 85: 2444-2448.

Perrone, C., et al. (1998), "The chlamydomonas IDA7 locus encodes a 140 kDa dynein intermediate chain required to assemble the I1 inner arm complex", *Molecular biology of the Cell*, 9:3351-3365.

Philip, F., et al. (2002), "Multiple roles of Pleckstrin homology domains in phospholipase Cβfunction", *FEBS Letters*, 531: 28-32.

Poulsen, N., et al. (2005), "A new molecular tool for transgenic diatoms control of mRNA and protein biosynthesis by an inducible promoter-terminator cassette", *FEBS Journal*, 272: 3413-3423.

Quinn, J., et al. (2000), "Coordinate cooper-and Oxygen-responsive Cyc6 and Cpx1 expression in *Chlamydomonas* is mediated by the same element" *The Journal of Biological Chemistry*, 275(9): 6080-6089.

Quinn, J., et al. (2003), "Copper response element and Crr1-dependent $Ni^2$—responsive promoter for induced, reversible gene expression in *Chlamydomonas reinhardtii*" *Eukaryotic Cell*, 2(5): 995-1002.

Radakovits, R., et al., (2011), "Genetic engineering of fatty acid chain length in *phaeodactylum tricornutum*" *Metabolic Engineering*, 13: 89-95.

Ramesh, V., et al. (2004), "A simple method for chloroplast transformation in chlamydomonas reinhardtii" *Methods in Molecular Biology*, 274:301-307.

Ravindran, C., et al. (2006), "Electroporation as a tool to transfer the plasmid pRL489 in Oscillatoria MKU 277" *Journal of Microbiological Methods*, 66:174-176.

Rodolfi, L., et al. (2009), "Microalgae for oil: strain selection, induction of lipid synthesis and outdoor mass cultivation in a low-cost photobioreactor", *Biotechnology & Bioengineering*, 102(1): 100-112.

Sandager, L., et al. (2002), "Storage lipid synthesis is non-essential in yeast", *The Journal of Biological Chemistry*, 277(8), 6478-6482.

Saha, S., et al. (2006), "Cytosolic triacylglycerol biosynthetic pathway in oilseeds. Molecular cloning and expression of peanut cytosolic diacylglycerol acyltransferase", *Plant Physiology*, 141: 1533-1543.

Scheffzek, K., et al. (2012), "Pleckstrin homology (PH) like domains—versatile modules in protein-protein interaction platforms", *FEBS Letters*, 586: 2662-2673.

Schroda, M., et al. (2000), "The HSP70A promoter as a tool for improved expression of transgenes in Chlamydomonas", *The plant journal* 21(2):121-131.

Scott, S., et al. (2010), "Biodiesel from algae: challenges and prospects", *Current Opinion in Biotechnology* 21: 1-10.

Siloto, RM, et al, (2009), "Simple methods to detect triacylglycerol biosynthesis in a yeast-based recombinant system", *Lipids*, 44(10): 963-973.

Siloto, RM, et al., (2009), "Directed evolution of acyl-CoA: diacylglycerol acyltransferase: development and characterization of Brassica napus DGAT1 mutagenized libraries", *Plant Physiology and Chemistry*, 47(6): 456-461.

Smith, T., et al., (1981), "Comparison of biosequences", *Advances in Applied Mathematics*, 2: 482-489.

Steinbrenner, J., et al. (2006), "Transformation of the Green Alga *Haematococcus pluvialis* with a phytoene Desaturase for accelerated astaxanthin biosynthesis" *Applied and Environmental Microbiology* 72(12):7477-7484.

Stemmer, W., (1994), "DNA shuffling by random fragmentation and reassembly: in vitro recombination for molecular evolution", *Proc. Natl. Acad. Sci. USA*, 91: 10747-10751.

Stone, S., et al. (2009), "The endoplasmic reticulum enzyme DGAT2 is found in mitochondria-associated membranes and has a mitochondrial targeting signal that promotes its association with mitochondria", *Journal of Biological Chemistry*, 284(8): 5352-5361.

Stöveken, T., et al (2008), "Bacterial acyltransferases as an alternative for lipase-catalyzed acylation for the production of oleochemicals and fuels", *Angew Chem Int Ed Engl.*, 47(20): 3688-3694.

Sun, Y., et al. (2006), "Functional complementation of a nitrate reductase defective mutant of a green alga *dunaliella viridis* by introducing the nitrate reductase gene", *Gene* 377:140-149.

Tan, C., et al. (2005), "Establishment of a micro-particle bombardment transformation system for dunaliella saline", *The Journal of Microbiology* 43:361-365.

Turchetto-Zolet, A., et al., (2011), "Evolutionary view of acyl-CoA diacylglycerol acyltransferase (DGAT), a key enzyme in neutral lipid biosynthesis", *BMC Evolutionary Biology*, 11: 263.

Wagner, M., et al. (2010), "Identification and characterization of an acyl-coa:diacylglycerol acyltransferase 2 (DGAT2) gene from the microalga *O. tauri*", *Plant Physiology and Biochemistry*, 48(6): 407-416.

Walker, T., et al. (2004), "Characterization of the *Dunaliella teritiolecta RbcS* genes and their promoter activity in *Chlamydomonas reinhardtii*", *Plant Cell Reports*, 23: 727-735.

Wältermann, M., et al. (2007), "Key enzymes for biosynthesis of neutral lipid storage compounds in prokaryotes: properties, function and occurrence of wax ester synthases/acyl-CoA: diacylglycerol acyltransferases", *Biochimie*, 89: 230-242.

Wang, P., et al. (2004), "Rapid isolation and functional analysis of promoter sequences of the nitrate reductase gene from *Chlorella ellipsoidea*", *Journal of Applied Phycology*, 16(1): 11-16.

Watt, S., et al. (2008), "urg1: A uracil-regulatable promoter system for fission yeast with short induction and repression times" *PloS one*, 1: e1428.

Weber, W., et al. (2011) "Molecular diversity—the toolbox for synthetic gene switches and networks", *Curr Opin Chem Biol.*, 15(3): 414-420.

Weselake, R., et al. (2008), "Metabolic control analysis is helpful for informed genetic manipulation of oilseed rape (*Brassica napus*) to increase seed oil content", *Journal of Experimental Botany*, 59(13): 3543-3549.

Wijffels, R., et al., (2010), "An outlook on microalgal biofuels", *Science Magazine*, 329(5993): 796-799.

Wurch, L., et al., (2011), "Nutrient-regulated transcriptional responses in the brown tide forming alga *Aureococcus anophageferens*", *Environ Microbiol*, 13(2): 468-481.

Xut, J., et al., (2008), "Cloning and characterization of an acyl-CoA-dependent diacylglycerol acyltransferase 1 (DGAT1) gene from Tropaeolum majus, and a study of the functional motifs of the DGAT protein using site-directed mutagenesis to modify enzyme activity and oil content", *Plant Biotechnol J.*, 6(8): 799-818.

Yehudai-Resheff, S., et al. (2007), "Integration of chloroplast nucleic acid metabolism into the phosphate deprivation response in *Chlamydomonas reinhardtii*", *The Plant Cell*, 19: 1023-1038.

Yen, C., et al., (2005), "The Triacylglycerol synthesis enzyme DGAT1 also catalyzes the synthesis of diacylglycerols, waxes, and retinyl esters" *Journal of Lipid Research*, 46: 1501-1511.

Yen, C., et al. (2008), "DGAT enzymes and triacylglycerol biosynthesis", *Journal of Lipid Research*, 49: 2283-2301.

Yu, W., et al. (2011), "Modifications of the metabolic pathways of lipid and triacylglycerol production in microalgae", *Microbial Cell Factories*, 10(91).

Zheng, P., et al., (2008), "A phenylalanine in DGAT is a key determinant of oil content and composition in maize", *Nature Genetics*, 40: 367-372.

International Search Report and Written Opinion issued in PCT/US2012/060435 dated Feb. 27, 2013.

International Search Report and Written Opinion issued in PCT/US2012/068272 dated Mar. 25, 2013.

(56) References Cited

OTHER PUBLICATIONS

I0YRH1, UniProtKB submission I0YRH1_9CHLO, Oct. 31, 2012 [online]. [Retrieved on Feb. 17, 2013]. Retrieved from the Internet <URL:http://www.uniprot.org/uniprot/I0YRH1.txt?version=4>.
E1ZTZ7, UniProtKB submission E1ZTZ7_CHLVA, Oct. 31, 2012 [online]. [Retrieved on Feb. 17, 2013]. Retrieved from the Internet <URL:http://www.uniprot.org/uniprot/E1ZTZ7.txt?version=8>.
G9L2I1, UniProtKB submission G9L2I1_MUSPF, Nov. 28, 2012 [online]. [Retrieved on Feb. 17, 2013]. Retrieved from the Internet <URL:http://www.uniprot.org/uniprot/G9L2I1.txt?version=4>.
B4LX14, UniProtKB submission B4LX14_DROVI, Nov. 28, 2012 [online]. [Retrieved on Feb. 17, 2013]. Retrieved from the Internet <URL:http://www.uniprot.org/uniprot/B4LX14.txt?version=29>.
E3X631, UniProtKB submission E3X631_ANODA, Nov. 28, 2012 [online]. [Retrieved on Mar. 5, 2013]. Retrieved from the Internet <URL:http://www.uniprot.org/uniprot/ E3X631.txt?version=10>.
Boyle, N. R., et al. "Three acyltransferases and nitrogen-responsive regulator are inplicated in nitrogen starvation-induced triacylglycerol accumulation in *Chlamydomonas*", (2012) *The Journal of Biological Chemistry*, 287(19):15811-15825.
Guihéneuf, F., et al. "Cloning and molecular characterization of a novel acy-CoA:diacylglycerol acyltransferase 1-like gene (*PtDGAT1*) from the diatom *Phaeodactylum tricornutum*", (2011) *The FEBS Journal*, 278:3651-3666.
Jing, Y., et al. *No Title*, Submitted (Jul. 2011) to the EMBL/GenBank/DDBJ databases.
Saraste, M., et al. "Pleckstrin homology domains: a fact file", (1995) *Current Opinion in Structural Biology*, 5:403-408.
Wang, T., et al. "Fluorescence quantitative RT-PCR detection of key enzymes of *Thalassiosira pseudonana* neutral lipid synthesis in different growth periods", Submitted (Jan. 2011) to the EMBL/GenBank/DDBJ databases.
Xu, J., et al. "Cloning and characterization of an acyl-CoA-dependent *diacylglycerol acyltransferase 1* (*DGAT1*) gene from *Tropaeolum majus*, and a study of the functional motifs of the DGAT protein using site-directed mutagenesis to modify enzyme activity and oil content", (2008) *Plant Biotechnology Journal*, 6:799-818.
Xu, J., et al. "Triacylglycerol synthesis by PDAT1 in the absence of DGAT1 activity is dependent on re-acylation of LPC by LPCAT2", (2012) *BMC Plant Biology*, 12:4.

\* cited by examiner

```
                           1                                                    50
        Botryococcus   (1) ----------------------------------------MSEALGELQAE
       Flagilariopsis  (1) -------------------------------------------MDSLRDE
        Thalassiosira  (1) ----------------------------------MDSTPSETEDDLRRE
     WT297_Cyclotella  (1) ---------------------------------------METEEELRHE
         Phaeodactylum (1) -MTTPVSSEDT---------------------------ATLQQKIVALQAQ
        WT229_Navicula (1) MIGLPIDDSSNNLAEKANDKNIDHILSGGKLGKATIERELQRRIEKLQQE
              Jatropha (1) --------------------------------------------------
               Ricinus (1) --------------------------------------------------
              Medicago (1) --------------------------------------------------
       WT234_Tetraselmis(1) -----------------------MLFAPQPRRPSAAEEDSDVPSEAGENSED
         WT58_chlorella(1) -----------------------MLRSRKASQEQSPADARVVALAKE
             Consensus (1)                                                L  E 51                                                  100
        Botryococcus  (12) NVRLRNMLTLRERRE-----------------------------------
       Flagilariopsis  (8) KARLLKELERVDFEI------------EEYDEHNPGPSSSRKK-----IV
        Thalassiosira (16) IQRLRQQLHEASRAS------------GNSDAALPTLGQTDST----IST
     WT297_Cyclotella (11) ITRLKQQLASLNSAV------------TSSSTEGIKDGDNRSTGSVCIVN
         Phaeodactylum(24) LLSATHALERMK-----NERGASSADHSKSAQRNGSDPSSDPTGTAP-VA
        WT229_Navicula(51) LQTAQEDLSRFRNVVENNDNGTTKRTPSASPPVIASTYSSDSNDNAPEIF
              Jatropha (1) --------------------------------------------------
               Ricinus (1) --------------------------------------------------
              Medicago (1) --------------------------------------------------
       WT234_Tetraselmis(30) VEILRNAIRRLRATN-----------------------SKLQAALQAKG
         WT58_chlorella(25) NERLRDLLSEKAFKG-----------------------------------
             Consensus(51)     L   L 101                                                  150
        Botryococcus  (27) --PDHCGYLFKHRPYSTS-LFSPPWELRYFTLAGSVLSHFHSEKDTSANP
       Flagilariopsis (41) IPASKSGYLFKWQDRQIG-WGGTKWDLRFVKLDKGRFGYFLNHDDT---AP
        Thalassiosira (50) APPEKSGYLFKWQDRTIG-WGGTKWALRYVRLNHGQLSYYKSHEER---SP
     WT297_Cyclotella (49) APPEKSGYLFKWQDRAIG-WCGTKWGLRFVRLDHGQLSYYKTHEDR---SA
         Phaeodactylum(68) APPAKSGYLFKELDRAIG-WCGIKWSLRYVKLESGRISYYGSHHDT---SP
        WT229_Navicula(101) LPPSKRGYLFRWVDRSIG-WSGSKWALRFVTLENGNLSYYGSHTDT---AP
              Jatropha (1) --------------------------------------------------
               Ricinus (1) --------------------------------------------------
              Medicago (1) --------------------------------------------------
       WT234_Tetraselmis(56) TDFIKCGYLFKYRPFAHG-LWDNPWERRFVVLRKGILEYFLTEADTQYPP
         WT58_chlorella(40) -ATCSGYLWKYRSHAESSLWANTWELRYMVLKGSTLLYYKQEQDVQFPP Consensus(101)     K GYLFKW   A G  G  W LRFV L  GL YY S  D     P
```

Figure 2A

```
                             151                                                200
         Botryococcus   (74)  RGRLDIAGCLVDVQSGEHGKYHAFSIVDR------------------KGQ
         Flagilariopsis (88)  RYLITLKNCATRDDGSKPNKRFRCSKENG----------KEVKESTPGA
         Thalassiosira  (97)  RYIMTLKNCAVRDEGSKVNKRHGSAKN-G----------EDSDHHAVGS
   WT297_Cyclotella     (96)  RYVLTLKNCAVRDEGSKVNKRHATSKKRGSVESSRLPGAESETEGHEAGS
         Phaeodactylum (115)  RYELQLRGCAVRDDGWKRNPRFKTKRNSP-------------PPLLDTTGA
         WT229_Navicula(148)  RYVLSLRGCAVRDEGHKPNKRYKRTEDDDT------------PPRLDKVGA
         Jatropha        (1)  ------------------------MTTLET------------------TTS
         Ricinus         (1)  ------------------------MTTLET------------------PET
         Medicago        (1)  ------------------------MAISDT------------------PET
   WT234_Tetraselmis   (105)  RGIVKLESCVVEVEPLKKRKYFTFSLIDDN------------------ENM
   WT58_chlorella       (88)  RGQIDLQGAYVESEGLKRRKYLAFNVYNA-------------------AGV Consensus     (151)  R    L  L  C  V   EG  K   K       SI D                 GA 201                                                250
         Botryococcus  (106)  LMMRLASSKQE-----------DVGL--WVKALKGAGCERYDAKDAARRS
         Flagilariopsis(127)  FFHVFSLYQRP-K------GRTTLITAANLDEDDNIVPLLRFSTNSLAEKV
         Thalassiosira (135)  RFYVFSVYRR--------VKNWGDSDAQYDNEDDIIPLLRFSTQSLAEKI
   WT297_Cyclotella    (146)  HFYVFSVYRRPNKYEVEANARSGEDDAQHDSEEHIIPLLRFSTQSYAEKL
         Phaeodactylum (153)  YFFLFSVYHAP--------DAAAEKEID-----ETEITPLLRFSTPSRAEHS
         WT229_Navicula(187)  YFFLFSIYLRN--------DASPAHQDP-TAELTEITPLLRFSTDSYAEKK
         Jatropha       (10)  GGDGVAESS--------------------SDLNVSLRRRRK--------
         Ricinus        (10)  LGVISSSAT--------------------SDLNLSLRRRRT--------
         Medicago       (10)  TATATATVTT-------------IE---TDTDLKRSSLRRRPSATSTAGG
   WT234_Tetraselmis   (138)  LALRVSTENVP-------------EGERWVSALKMAGVRRRK--------
   WT58_chlorella      (120)  SLIRLSSESQV-----------DYAK--WMEALERAGCERR-GDDDARSV Consensus     (201)        V S                        DL  IA L RFST S A 251                                                300
         Botryococcus  (143)  SLPPTRPPDARSSMESTMRAGATSGDL---------SDDHSKHPRPARVVG
         Flagilariopsis(171)  Q-WMDLLIESCAYCDSDYFDQNEASSF---------VAHNGSLPTSTTHTKG
         Thalassiosira (177)  L-WVDLISESCAYCDSEEFALYQQQQQ---------EIQQKQQEQQIRTEKG
   WT297_Cyclotella    (196)  Q-WIDLISQSCAYCDSEEFALYQQQQQ---------EMLKQQQRQ---PPKG
         Phaeodactylum (191)  S-WIKLASESCAYSETDEFLADEAARATQRALQHQEALQMAQAMPGAKPG
         WT229_Navicula(229)  Q-WVQLISETCAYCESDAFVAEMERRQ--------EEKQTMTLAMPEAKVG
         Jatropha       (31)  -----GTSSDGALPELTSNIVELE-----------SESGGQ--VMMDPGM
         Ricinus        (31)  -----SNDSDGALADLASKFDDDDVR---------SEDSAENIIEDPVAA
         Medicago       (44)  -----LFDAESAAADAVRDSGSDDSLN---------GKINNEEEVKDRKTD
   WT234_Tetraselmis   (167)  --------DNSKQSLRSPRRSKDIRGSR--------GEVSAEKETQSNELQR
   WT58_chlorella      (156)  ATSLQRVSGSSAVSSPTASGMSDSGEA---------AAQLLQRHSPSKLQG Consensus     (251)        I L  S S A   DS                             G
```

Figure 2B

```
                        301                                                350
    Botryococcus  (185) LSEAALKASGFSRGPVPNYGSDSGMSEAGPMCRPGLGNAPVPP---LPVA
   Flagilariopsis (213) TLSPLYFETP---TVKIGRTPSYAHLLTKKPSHLKLN-LNKDSAKSNSRK
    Thalassiosira (219) TLPALVFEAP---RLTHKRLPSGH-KLNEMGKSFRKKSVDKDAARSN---
 WT297_Cyclotella (235) TLPALVFEAPPP-KQDIQGYPSGYNLLNSRAKHFRRKSNMKDAARSN---
     Phaeodactylum(240) TLPPLYFAPTIKRSRSFAKLQEHHGDGMPRVNMRRTKSRDFNADKLDARS
   WT229_Navicula (271) TLPPLYFAPVQQKHSRHPSFTRK-----PNAAMFRTKSQNMDPSQVES--
          Jatropha (63) VTEPETEKINGKDCGG--DKDKIDNRENRGRSDIKFTYRPSVP-------
           Ricinus (68) VTELATAKSNGKDCVANSNKDKIDSHG--GSSDFKLAYRPSVP-------
          Medicago (81) HAEGIVDDDDDNAVKKNGGNDVINDREN-VAVDFKFTYRPSVP-------
  WT234_Tetraselmis(203) RGSNAADLLRKSQWKVPFVPLPEGADKEGSVAAEVASQQPKAK-------
    WT58_chlorella(198) KGEDEVSSAARQLAQQEAHQSRGYTSDQSDVARQLRTRQPSSKGGHRGKG Consensus (301)       L                          A    P 351                                                400
    Botryococcus  (232) RKQITGSSMMHVTSRPSMLSSDRIALTQHSGILNVMMLILVAANFRLIVE
   Flagilariopsis (259) KNDYPPSKPMHRRAEGSYLSHD-SPTPNYRGLLNLGVIILVISNFRILLG
    Thalassiosira (262) KISYPPSKPMHRQSNPSYLSDG-SHVQNYRGLFNLLLLILVLSNFRLLLD
 WT297_Cyclotella (281) KISYPPSKPMHRQSNPSYLSEG-AHAQNYHGLFNLFLLILVLSNFRLLMH
     Phaeodactylum(290) TKGYPPSKPMHRAAEPSYLSAD-APIQNYRGFLNLGVIILIVSNFRLILG
   WT229_Navicula (314) -KGYPPSKPMHRCAAPSYLSVE-GPTQNYRGFFNLGVIVLVVSNIRLVLS
          Jatropha (104) ---------AHRALRESPLSSDAIFKQSHAGLFNLCIVVLVAVNSRLIIE
           Ricinus (109) ---------AHRSLKESPLSSDLIFKQSHAGLFNLCIVVLVAVNSRLIIE
          Medicago (123) ---------AHRRSKESPLSSGNIFRQSHAGLFNLCIVVLVAVNSRLIIE
  WT234_Tetraselmis(246) RGPFTGGVPVHAAPKFSMLSSEEVANQNHAGLINLVMVIMFATHSRLIIE
    WT58_chlorella(248) RDALLGSSLVHTAPRWSFLSTERIDFSNQNGLLTLGMIILVTTNARLILE Consensus (351) K  Y  S PMHR SK SYLSSD I  QNH GLFNL IIILV SN RLILE 401                                                450
    Botryococcus  (282) NLLKYGVLVNP------LNWIRALMP-RGNLPLLLCWPALALFSLTALSI
   Flagilariopsis (308) TMREYGFVLTHGYFSVPDEEYSFKWKDIVDVPFVFTMIMLNIFVIFAYLI
    Thalassiosira (311) TVAQHGFTLDK------LATLQGFSQAPLDFPFVSGLLTVQAFVVGAYAI
 WT297_Cyclotella (330) AVSQHGFFFDK------IPSFHDFSEAPLDFPFVSGLLVVQAFVLGAYAI
     Phaeodactylum(339) TIRSNGFVLTTA-VKHYKNLNHLKEDPWQFFPFVSGFLLQLVFVSIAFGI
   WT229_Navicula (362) SFKKHGFVL----LRHLSEIPRLGDHPWKNFPFVSGFLLLFVFVMVTYLL
          Jatropha (145) NLMKYGWLIKT------GFWFSSRSL--RDWPLLMCCLTLPIFSLAAYLV
           Ricinus (150) NLMKYGWLIKT------GFWFSSRSL--RDWPLFMCCLSLPVFPLAAYLV
          Medicago (164) NLMKYGWLIRS------GFWFSSKSL--RDWPLFMCCLSLAIFPLAAFVV
  WT234_Tetraselmis(296) NSLKYGVRFNP------LYWVTRLAESELPWQVLVCWPLMACFILFSYWI
    WT58_chlorella(298) NILKYGLRFNP------VTFLRAAFTPSGNVMLLLCWPFLGMCCLCALGV Consensus (401) NLLKYGFLL           W    S     DFPLVMC LLL IFVL AY I
```

Figure 2C

```
                         451                                                     500
      Botryococcus (325) QQFGVWRLKQEKKVLTTKKKKDMKPSEARRVAANMAN------TTEGIIL
      Flagilariopsis (358) ELGISRRF-----------------------------------IKEWLGI
       Thalassiosira (355) EKMLSVGL-----------------------------------TGNQFGM
    WT297_Cyclotella (374) EKMLVLGF-----------------------------------VGGRVGI
       Phaeodactylum (388) EWMLCRKY-----------------------------------FNENFGM
       WT229_Navicula (408) ELGLSRKK-----------------------------------TPQRLGI
            Jatropha (187) EKLAYRKY-----------------------------------ISAPIVI
             Ricinus (192) EKAAYRKY-----------------------------------TSPPIVI
             Medicago (206) EKLAQQKR-----------------------------------TSFPVIV
    WT234_Tetraselmis (340) EVLGARSVQAELRAKAAACKKTDCDPDDSVPAPAAHPSRSSVAWSESLII
      WT58_chlorella (342) EALGVRCLAMEQKANAANRKREVGYGEGRRRAARQAK------LTENLLL Consensus (451) E LA RK                                    ISE LII 501                                                     550
       Botryococcus (369) LANVVNVALSMAVPCAVVHYTKSEAVPGSVITAFTIVLFLKLASYSHCNA
      Flagilariopsis (373) SLHIINTNLSLLLPMVIVWKYINSPVNGAVLQMSSTVLWMKLISYAHANA
       Thalassiosira (370) LLHVINSNATLGVVVAIVWYLIDQPFVGAGLIMQATITWLKLISYAHANY
    WT297_Cyclotella (389) FLHAINCNASLGVVLSIVWYLIDQPIIGAILILQATITWLKLISYAHANY
       Phaeodactylum (403) ILHHFNAHSALLIPLGIVWNLIDRPAVGAILLLHATITWMKLISYMLANE
       WT229_Navicula (423) LLHYANAHACMGVSIWIVWYLVDAPAVGAVLLLFATSTWMKLISYVHTNE
            Jatropha (202) FFHMLITTTAVLYPVSVILSCGSAVLSGVALMLFACIVWLKLVSYAHTNY
             Ricinus (207) FLHVIITSAAVLYPASVILSCESAFLSGVTLMELACMVWLKLVSYAHTNY
            Medicago (221) LLHIVITTVAIIYPVLVILWCDSAFISGSTLMLLTCIVWKLVSYAHTTY
    WT234_Tetraselmis (390) TLQCLNIGALLLLPCWVIVKHQAPPLAGSLLITASVIYWMKLVSYAHCCC
      WT58_chlorella (386) LLNLLNITAVLLLVPSLVMHITNSEPLPGFMLSMFMIVLWLKLVSYAHVNW Consensus (501) LLHVINT AALLVPV VV    S PL GAVLIL A ILWLKLVSYAH NY 551                                                     600
       Botryococcus (419) ELRAAKRV------ADQRPSSGDLRESGDGGMEMGVRYPDNVSLGNLAYF
      Flagilariopsis (423) DYRHFPD--------RNVENIIQNTDEES------ISLNYPRNITVTNIYYF
       Thalassiosira (420) DYRTSPDT-----QKVTVALVKDLDDG------QNVSYPQNVTLKDIYYF
    WT297_Cyclotella (439) DYRTSPES-----YNLTRTLVKDLDEAG-----TRLSYPQNVTLGNIYYF
       Phaeodactylum (453) DYRLSSRRVGGNPHLATLALVENLDSDE------ANINYPQNVTLRNIFYF
       WT229_Navicula (473) DYRSN-Q---MQQQATFSSMVEDLDPQE------ARVRYPQNVTISNIFYF
            Jatropha (252) DMRAIANS------ADKGDALSDTSG---------ADSSRDVSFKSLVYF
             Ricinus (257) DMRAIADT------IHKEDASNSSS----------TEYCHDVSFKTLAYF
            Medicago (271) DMRALAVS------NEKGETMPDTFNM--------EEYPHNVSFQSLAYF
    WT234_Tetraselmis (440) DLRAARRLGEVR--PGERGNMEGFAGVTEP-----LLYPENINAYNLAYF
      WT58_chlorella (436) DYRAAR-----------R-QG-----------------LYPENITLRNLAYF Consensus (551) DYRAA               V D              L YP NVTL NL YF
```

Figure 2D

```
                         601                                              650
     Botryococcus (463) LVAPTLIYQPSYPQSPAIRFRWLFWSAVRLMGLMSLMMVIVEQYLTPTLA
     Flagilariopsis (461) WFAPTLTYQMVFPRLVRRSKCQILNLVLRLFFCFVLLVFLVAQVFRPTLN
     Thalassiosira (459) WLAPTLTYQIAFPRSPFIRWPKVFSLTLQLFISVTLAVFLCAQVVAPNLD
     WT297_Cyclotella (479) WFAPTLTYQMAFPRAPFIQWPKVLRLSVQLFVSIILVLFFFAQIVAPNLD
     Phaeodactylum (498) WCAPTLTYQIAFPKSPRVRYWKIADILMRMTVSIALFTFLLAQIVQPALE
     WT229_Navicula (514) WAAPTLTYQIAFPRSPSVRLWKVAVILIRMVPILALFTFFVSQFVTPTME
     Jatropha (287) MVAPTLCYQPSYPRIDSVRKGWVVRQFVKLIIFTGFMGFIIEQYINPIVQ
     Ricinus (291) MVAPTLCYQPSYPRIAFLRKGWVFRQFVKLIIFTGFMGFIIEQYINPIVQ
     Medicago (307) MVAPTLCYQPSYPRTPSVRKGWVCRQLLKLVIFTGVMGFIIEQYMNPIVQ
     WT234_Tetraselmis (483) CVAPTLTYQVNYPRSSRFRKRWVARRLLELVAWLSVGAFIIEQYILPSCL
     WT58_chlorella (459) LVAPTLCYQPVYPRSSRFRVKWLARRVIVLCFALSLMLFINEQYIEPIVE Consensus (601)        VAPTLTYQIAYPRSP IR  WV R LLRLVI L LM FIIEQYI P L 651                                              700
     Botryococcus (513) NSLIPLRSL--------NWAHMLERVLKLSLPTLYGWVIMFYCLFHLWLN
     Flagilariopsis (511) NLMEELNELKGEDMHILSVHIFAEYILKLGLASSYIWLLVFYGFFHVLLN
     Thalassiosira (509) SLVKNLEANKGE----VRTQQIFDYLLKLSITSTYIWLLGFYCFFHCFMN
     WT297_Cyclotella (529) SLVRDLENDKGE----VRVHVIGDYLLRMSTASTYIWLLGFFGFFHCFMN
     Phaeodactylum (548) ELVSDLDETNGS----YTAAIFAEYWLKLSIANTYLWLLMFYTYFHLYLN
     WT229_Navicula (564) GLVADLEANCGR----YTVTMLAEYWLRLSIANTYLWLLMFYFFHLFLN
     Jatropha (337) NSQHPLKG--------DLLYAIERVLKLSVPNLYVWLCMFYCFFHLWLN
     Ricinus (341) NSQHPLKG--------DLLYAIERVLKLSVPNLYVWLCLFYCFFHLWLN
     Medicago (357) NSQHPLKG--------NLLYAIERVLKLSVPNVYVWLCMFYCFFHLWLN
     WT234_Tetraselmis (533) NSLHPLNT--------MDIGHILERVLKLSLPSLYVWLIAFYCIFHLWLN
     WT58_chlorella (509) NSLGPLRNM--------DWMRMTERILKLSLPTLYFWLSMFYALFHLWLN Consensus (651)        NSV PL            L  I ERVLKLSIPSLYVWLLMFY FFHLWLN 701                                              750
     Botryococcus (555) ILAEVTYFGDREFYKDWWNATTIGDYWRLWNMPVHKWMLRHVYFPLLRLG
     Flagilariopsis (561) LLAQLLRFGDRVFYRDWWNSTNMSSYWRLWNLPVHYWLVRHLYFPCIRIG
     Thalassiosira (555) LAAELLRFGDRVFYRDWWNASEVSAYWRLWNMPVHYWLVRHVYFPCIRVG
     WT297_Cyclotella (575) ITAELLRFGDRVFYRDWWNASEVSAYWRLWNMPVHYWLVRHVYFPCIRIG
     Phaeodactylum (594) LFAELLRFGDRVFYKDWWNSSEVSAYWRLWNMPVHYWLIRHVYFPCVRLK
     WT229_Navicula (610) LFAEILRFGDRVFYKDWWNSSEVSAYWRLWNMPVHFWLVRHLYFPCVRMG
     Jatropha (378) ILAELLRFGDREFYKDWWNARTVEEYWRMWNMPVHKWMVRHIYFPCLRHK
     Ricinus (382) IVAELLRFGDREFYKDWWNAKTVEEYWRMWNMPVHKWMVRHIYFPCLRRK
     Medicago (398) ILAELLRFGDREFYKDWWNAQTVEEYWRMWNMPVHKWMVRHVYFPCIRFG
     WT234_Tetraselmis (575) ILAEFTYFGDRQFYDDWWNATTVDEYWRRWNQPVHKWLMRTVYFPCMRLG
     WT58_chlorella (551) ILAELTGFADREFYKEWWNATTLGEYWRQWNQPVHKWMLRHVYFPCIRHG Consensus (701)        ILAELLRFGDR FYKDWWNASTV EYWRLWNMPVHKWLVRHVYFPCIRLG
```

Figure 2E

```
                              751
800
    Botryococcus  (605)  VGKFLAGVGVFAVSGLLHELAVGLPLHMVRYWAFLGVMFQVPMVYLTEYL
   Flagilariopsis (611)  MSKSAAMFMVFFFSAVVHEMLISV--------------------------
     Thalassiosira (605)  MSKKGATFVVFFFSAVLHEVLISVPCHMIRAWSFLAMMGQIPLIILTKIL
    WT297_Cyclotella (625)  LSKKGATFVVFLLSAVLHEVLISVFCHMIRVWSFLAMMGQIPLIILTKKL
     Phaeodactylum (644)  MPKVAATFVVFTLSAVMHEVLVSVPFHIIRPWSTIGMMMQIPLVAFIKYL
      WT229_Navicula (660)  MSKTLTTFIVFFVSAVLHEVLVSVPFHMVRPWSFLGMMMQIPLVGMTKVL
          Jatropha (428)  IPRGVALLTAFFVSAVFHELCIAVPCHMFKLWAFIGIMFQIPLVGITNYL
            Ricinus (432)  IPRGVAIVIAFFVSAVFHELCIAVPCHMFKLWAFFGIMFQIPLVVITNYF
           Medicago (448)  IPKGAAALTAFLVSAVFHELCIAVPCRMFKLWAFIGIMFQVPLVLITNYL
    WT234_Tetraselmis (625)  LSRYVSILATFLSAVFHELLVGVPLHMLRAWAFAGMMGQIPLIAMITML
      WT58_chlorella (601)  ISKFMAGIIVFFVSAVFHELVVGVPLHMLRSWSFWGIMGQVPLIWVIELL Consensus (751)  ISK VA LIVFFVSAVLHELLISVP HMIR WAFLGMM QIPLV IT  L 801                                              850
    Botryococcus  (655)  KKRMKSDQIGNLIFWISFCIIGQPISLILYYHDWILMNRPDWLPQATAAP
   Flagilariopsis (635)  --------------------------------------------------
     Thalassiosira (655)  DKRVPGSSIGNIIFWISFCLVGQPMAMLLYTIDYWEVHFNAAITESTIEV
    WT297_Cyclotella (675)  DRRMPGSSIGNIIFWISFCLVGQPMAMLLYTIDYWETHSVLTPEAMTDYV
     Phaeodactylum (694)  YRKFPGGSFGNVLFWMTFCVIGQPMAILLYTVDYQYGKHHSTNMEIFDTD
      WT229_Navicula (710)  SRQYP--TLGNVIFWISFCIVGQPMAVLLYTVDYQYAKHNMTAQECVV--
          Jatropha (478)  QNKFRSSMVGNMIFWFIFCILGQPMCVLLYYHDLMNRKGNAELR------
            Ricinus (482)  QRKFRSSMVGNMIFWFFFCILGQPMCVLLYYHDLMNRDGN----------
           Medicago (498)  KNKYRNSMVGNMIFWFIFCILGQPMCVLLYYHDLMNRKGEID--------
    WT234_Tetraselmis (675)  KRKMKSDIIGNIFWLSFCIFGQPIAVLLYYHDYIQEHM------------
      WT58_chlorella (651)  KKKVGSEHIGNMIFWLSFCFVGQPIAILLYYHDYRKQIGLIAD-------

Consensus (801)  RK    IGNMIFWISFCIVGQPMAVLLYYHDY 851          871
    Botryococcus  (705)  FPANATLAA------------
   Flagilariopsis (635)  ---------------------
     Thalassiosira (705)  PRKSFRFDKIGRFFGAHSEL-
    WT297_Cyclotella (725)  SRRGLPFAAIGRFFGASPEL-
     Phaeodactylum (744)  DCRFLWKNSCLIR--------
      WT229_Navicula (756)  ---------------------
          Jatropha (522)  ---------------------
            Ricinus (522)  ---------------------
           Medicago (540)  ---------------------
    WT234_Tetraselmis (714)  ---------------------
      WT58_chlorella (694)  ---------------------

Consensus (851)
```

Figure 2F

DGAT GENES COMPRISING PLECKSTRIN HOMOLOGY DOMAINS AND METHODS OF USE FOR TRIGLYCERIDE PRODUCTION IN RECOMBINANT MICROORGANISMS

REFERENCE TO A SEQUENCE LISTING

This application contains references to amino acid sequences and/or nucleic acid sequences which have been submitted concurrently herewith as the sequence listing text file "61038985_1.txt", file size 150 KiloBytes (KB), created on 6 Dec. 2012. The aforementioned sequence listing is hereby incorporated by reference in its entirety pursuant to 37 C.F.R.§1.52(e)(iii)(5).

FIELD

The present invention relates to diacylglycerol acyltransferase (DGAT) genes and the production of triglyceride (TAG) in a recombinant microorganism or host cell engineered to increase and/or maximize TAG synthesis; and to methods of producing TAG using such recombinant microorganisms or host cells. The present invention also relates to Pleckstrin homology (PH) domains and to methods for increasing TAG synthesis by expressing a DGAT comprising a PH domain.

BACKGROUND

Producing renewable sources for a variety of fuels and chemicals is of great importance to a world with increasing demand for such products. While petroleum is a product of decayed plant and other matter that has been incubated beneath the earth's surface for millions of years, some efforts today focus on the direct use of plants and other organisms to generate, e.g., lipids, which can include fatty acids and derivatives thereof, for use in the fuel and chemical industries. Specifically, recent effort has been directed to designing algae to produce lipids for biofuel production because algae can proliferate over a wide range of environmental conditions and because algae do not compete with food crops for arable growth space. See, Hu et al. (2008) *Plant J.* 54:621-39.

Algal cells are a promising source of biofuels. Wijffels & Barbosa (2010) *Science* 329:796-99. Their ability to harness solar energy to convert carbon dioxide into carbon-rich lipids already exceeds the abilities of oil-producing agricultural crops, with the added advantage that algae grown for biofuel do not compete with crops for agricultural land (Wijffels & Barbosa, 2010). In order to maximize algal fuel production, new algal strains will need to be engineered for growth and carbon fixation at an industrial scale (Wijffels & Barbosa, 2010).

Triacylglycerol or triglyceride (TAG), a heterogeneous group of molecules with a glycerol backbone and three fatty acids attached by ester bonds, is an excellent molecule for high-concentration metabolic-energy storage. TAG is the major form of energy storage in many eukaryotic algae under stress conditions, such as under nutrient limitation or depletion. Nitrogen depletion (where there is essentially no available nitrogen in the culture medium) is particularly effective in increasing TAG production in many eukaryotic algal species. However, culturing algae under nitrogen deficiency simultaneously limits overall lipid productivity of the culture by limiting overall biomass accumulation (Brennan & Owende (2010) *Renewable and Sustainable Energy Reviews* 14:557-77). Improving the scalability, controllability, and cost-effectiveness of TAG production would be beneficial to the development of renewable energy and chemical sources.

One means of boosting TAG production is to grow algae in a two-step process alternating between nutrient-rich and nutrient-limited conditions. The nutrient-rich growth phase allows the algae to proliferate, while nutrient limitation (e.g., nitrogen depletion) results in the production of storage lipids. See, Rodolfi et al. (2009) *Biotechnol. Bioeng.* 102:100-12. This process makes TAG production more expensive, because it requires long periods of growth during which the algae are producing little to no TAG.

Another means of boosting TAG production is to grow the algae heterotrophically by supplying extra organic carbon. For example, in various scenarios, organic carbon may be supplied as glycerol, one or more sugars, one or more organic acids, or other reduced carbon sources added to the growth medium. See, Allnutt et al. (WO 2011/026008). This heterotrophic growth technique not only increases the expense of TAG production, it also risks the contamination of the algal cultures with exogenous bacteria or fungi whose growth can be stimulated by the added carbohydrates. See, Scott et al. (2010) *Curr. Opin. Biotechnol.* 21:277-86.

The biosynthesis pathways leading to the production of TAG have been studied. In the final reaction of the Kennedy pathway, diacylglycerol (DAG), a precursor to both membrane and storage lipids, is covalently linked to a fatty acyl to produce TAG. This reaction is catalyzed by the diacylglycerol acyltransferase (DGAT) enzyme (Kennedy (1961) *Fed. Pro. Fed. Am. Soc. Exp. Biol.* 20:934-40). There are two distinct gene families in eukaryotic organisms which encode enzymes which catalyze this reaction, DGAT1 and DGAT2, which have little sequence similarity. Evidence from higher plants as well as mammals suggests that the two gene families have different functions, although the exact role of each type of DGAT has not been elucidated, and may differ in different species (Yen et al. (2008) *J. Lipid Res.* 49:2283-301).

Although the use of recombinant DGAT enzymes to enhance TAG production in oleaginous organisms is known to the art (Xu et al. (2008) *Plant Biotechnol. J.* 6:799-818), comparatively little attention has been given to the subcellular localization of these recombinant DGAT enzymes.

It has recently been reported that a DGAT1 gene in the diatom species *Phaeodactylum tricornutum* contains a PH domain-encoding sequence. However, PH domains are not found in known plant DGATs, despite close evolutionary relationships to orthologous algal DGATs. See, FIGS. 1 & 2.

Guiheneuf et al. (WO 2012/059925) reports a PH domain at the amino-terminal end of a DGAT1 in *Phaeodactylum tricornutum*.

Further, Liu et al. (CN 102492672) report a DGAT1 sequence from the diatom *Thalassiosira pseudonana* with a PH domain at the amino-terminal end.

SUMMARY

The present invention provides novel acyltransferase genes that include Pleckstrin Homology (PH) domains. The presence of a PH domain in a DGAT gene introduced into a cell is demonstrated to improve lipid production in the recombinant cell as compared with a cell that includes a DGAT gene that lacks the PH domain. DGAT1 genes from a variety of algal species, each of which includes a sequence encoding a PH domain, are disclosed herein. As demonstrated herein, in addition to the diatoms *Thalassiosira, Phaeodactylum, Navicula, Fragilariopsis*, and *Cyclotella*, the PH domain is found in DGAT1 genes of the green algae *Botryococcus, Chlorella*, and *Tetraselmis*. This is a surprising since green algae (division Chlorophyta) are more closely related to higher plants than to the diatoms (division Heterokontophyta) (FIG. 1), and yet documented higher plant DGATs do not have PH domains. The present invention also provides novel PH domains, which may be operably linked to acyltransferases, such as DGATs, including acyltransferases that do not naturally include PH domains, to provide acyltransferases having heterologous PH domains, whose expression may enhance TAG production. The present invention also provides recombinant cells, such as fungi, heterokonts, and algae, transformed with acyltransferase genes, such as DGAT genes, that include sequences encoding homologous or heterologous PH domains, and their use in producing TAG. Novel methods of TAG production are provided herein that result in increased amounts of TAG being produced by a culture of a recombinant microorganism with respect to the amount produced by a control microorganism.

In one aspect, an isolated or recombinant DNA molecule is provided which comprises a nucleotide sequence encoding a DGAT that comprises an amino acid sequence selected from the group consisting of: an amino acid sequence having at least 80% identity to SEQ ID NO:2 or a functional fragment thereof; an amino acid sequence having at least 80% identity to SEQ ID NO:8 or a functional fragment thereof; an amino acid sequence having at least 80% identity to SEQ ID NO:14 or a functional fragment thereof; an amino acid sequence having at least 80% identity to SEQ ID NO:20 or a functional fragment thereof; an amino acid sequence having at least 80% identity to SEQ ID NO:26 or a functional fragment thereof; and an amino acid sequence having at least 80% identity to SEQ ID NO:32 or a functional fragment thereof.

Also provided is an isolated or recombinant DNA molecule which comprises a nucleotide sequence encoding a PH domain selected from the group consisting of: an amino acid sequence having at least 80% identity to SEQ ID NO:6 or a functional fragment thereof; an amino acid sequence having at least 80% identity to SEQ ID NO:12 or a functional fragment thereof; an amino acid sequence having at least 80% identity to SEQ ID NO:18 or a functional fragment thereof; an amino acid sequence having at least 80% identity to SEQ ID NO:24 or a functional fragment thereof; an amino acid sequence having at least 80% identity to SEQ ID NO:30 or a functional fragment thereof; and an amino acid sequence having at least 80% identity to SEQ ID NO:36 or a functional fragment thereof.

An isolated or recombinant DNA molecule as provided herein can comprise a nucleotide sequence encoding an amino acid sequence having at least 85%, e.g., at least 86%, at least 87%, at least 88%, at least 89%, at least 90%, at least 91%, at least 92%, at least 93%, at least 94%, at least 95%, at least 96%, at least 97%, at least 98%, or at least 99%, sequence identity to any one or more of SEQ ID NOs:2, 4, 8, 10, 14, 16, 20, 22, 26, 28, 32, 34, 38, 40, 44, and 46.

Also provided is an isolated or recombinant DNA molecule which comprises a nucleotide sequence encoding a PH domain, operably linked to a nucleotide sequence encoding a polypeptide of interest, where the PH domain is heterologous with respect to the polypeptide of interest. For example, an isolated DNA molecule encoding a PH domain described herein can be operably linked to a nucleotide sequence encoding a polypeptide of interest, such as but not limited to an acyltransferase, such as, for example, a monoacylglycerol acyltransferase (MGAT), a diacylglycerol acyltransferase type 1 (DGAT1), a diacylglycerol acyltransferase type 2 (DGAT2), a diacylglycerol acyltransferase type 3 (DGAT3), a wax synthase (WS) that has DGAT activity (WS/DGAT), a diacylglycerol acetyltransferase (DGAcT), a diacylglycerol transacylase (DGTA), a phospholipid:diacylglycerol acyltransferase (PDAT), a lysophospholipid acyltransferase (LPLAT), a lysophosphatidic acid acyltransferase (LPAAT), a glycerolphosphate acyltransferase (GPAT), or a combination thereof. In particular examples, the PH domain has at least 80% identity to SEQ ID NO:6 or a functional fragment thereof, at least 80% identity to SEQ ID NO:12 or a functional fragment thereof, at least 80% identity to SEQ ID NO:18 or a functional fragment thereof, at least 80% identity to SEQ ID NO:24 or a functional fragment thereof, at least 80% identity to SEQ ID NO:30 or a functional fragment thereof, at least 80% identity to SEQ ID NO:36 or a functional fragment thereof, at least 80% identity to SEQ ID NO:42 or a functional fragment thereof, and/or at least 80% identity to SEQ ID NO:48 or a functional fragment thereof.

Also provided herein is an expression cassette. The expression cassette comprises a gene as provided herein operably linked to a heterologous promoter. The heterologous gene can encode an acyltransferase that includes a PH domain, for example, a DGAT having of an amino acid sequence with at least 80% identity to SEQ ID NO:2 or a functional fragment thereof; an amino acid sequence with at least 80% identity to SEQ ID NO:8 or a functional fragment thereof; an amino acid sequence with at least 80% identity to SEQ ID NO:14 or a functional fragment thereof; an amino acid sequence with at least 80% identity to SEQ ID NO:20 or a functional fragment thereof; an amino acid sequence with at least 80% identity to SEQ ID NO:26 or a functional fragment thereof; an amino acid sequence with at least 80% identity to SEQ ID NO:32 or a functional fragment thereof; an amino acid sequence with at least 80% identity to SEQ ID NO:38 or a functional fragment thereof; and/or an amino acid sequence with at least 80% identity to SEQ ID NO:44 or a functional fragment thereof. Alternatively or additionally, the expression cassette can comprise an isolated DNA molecule encoding a PH domain, such as, for example, a PH domain as described herein having at least 80% identity to SEQ ID NOs:6, 12, 18, 24, 30, 36, 42, or 48, any of which can be operably linked to a nucleotide sequence encoding a protein of interest, for example an acyltransferase enzyme such as a MGAT, DGAT1, DGAT2, DGAT3, WS/DGAT, DGAcT, DGTA, PDAT, LPLAT, LPAAT, or GPAT. For example, the expression cassette can include a nucleotide sequence encoding a PH domain upstream of, and in frame with, a sequence encoding a heterologous DGAT. The expression cassette can be provided in a vector, e.g., an expression vector, which can optionally include one or more of an origin of replication, sequences mediating recombination into a host genome, and a selectable marker.

Further provided herein is a method of targeting an ectopically-expressed protein to a membrane surface using a PH domain as described herein. For example, the method can include targeting an ectopically-expressed protein to endoplasmic reticulum membrane, the chloroplast envelope, or the plasma membrane of a cell, using a PH domain, such as, for example, any as described herein. The method comprises transfecting a cell with an expression vector comprising a nucleic acid sequence encoding a PH domain as described herein, for example, a PH domain having at least 80% identity to SEQ ID NO:6 or a functional fragment thereof, at least 80% identity to SEQ ID NO:12 or a functional fragment thereof, at least 80% identity to SEQ ID NO:18 or a functional fragment thereof, at least 80% identity to SEQ ID NO:24 or a functional fragment thereof, at least 80% identity to SEQ ID NO:30 or a functional fragment thereof, at least 80% identity to SEQ ID NO:36 or a functional fragment thereof, at least 80% identity to SEQ ID NO:42 or a functional fragment thereof, and/or at least 80% identity to SEQ ID NO:48 or a functional fragment thereof, operably linked to a nucleic acid sequence encoding a protein for ectopic expression. In particular examples, the ectopically-expressed protein can be selected from the group consisting of a MGAT, DGAT1, DGAT2, DGAT3, WS/DGAT, DGAcT, DGTA, PDAT, LPLAT, LPAAT, or GPAT, and a combination thereof; and in a particular embodiment a DGAT1 comprises or is the ectopically-expressed protein.

Further provided herein is a recombinant eukaryotic microorganism that includes a non-native gene encoding an acyltransferase that includes a PH domain, in which the eukaryotic microorganism produces a greater amount of triglyceride than is produced by a eukaryotic microorganism substantially identical to the recombinant eukaryotic microorganism, but lacking a non-native gene encoding the acyltransferase that includes a PH domain. The acyltransferase can be, for example, a monoacylglycerol acyltransferase (MGAT), a diacylglycerol acyltransferase type 1 (DGAT1), a diacylglycerol acyltransferase type 2 (DGAT2), a diacylglycerol acyltransferase type 3 (DGAT3), a wax synthase (WS) that has DGAT activity (WS/DGAT), a diacylglycerol acetyltransferase (DGAcT), a diacylglycerol transacylase (DGTA), a phospholipid:diacylglycerol acyltransferase (PDAT), a lysophospholipid acyltransferase (LPLAT), a lysophosphatidic acid acyltransferase (LPAAT), or a glycerolphosphate acyltransferase (GPAT). In some examples, the acyltransferase is a DGAT, for example, a DGAT1, a DGAT2, WS/DGAT, or a DGAT3. The PH domain-encoding sequence of a non-native acyltransferase gene as provided herein can be naturally-occurring in the acyltransferase, e.g., DGAT1, gene (i.e., homologous with respect to the acyltransferase gene) or can be heterologous with respect to the acyltransferase gene, i.e., not naturally occurring in the acyltransferase gene. In some examples, the non-native gene can encode a DGAT that includes a PH domain, where the DGAT comprises the sequence of a naturally occurring DGAT that includes a PH domain or is a variant of a naturally-occurring DGAT that includes a PH domain, such as, for example, a DGAT having at least 80%, at least 85%, at least 90%, or at least 95% amino acid sequence identity to a naturally-occurring DGAT or an active fragment thereof. Additionally or alternatively, the acyltransferase can be a PH domain-containing DGAT1 of a green alga or derived from the sequence of a PH domain-containing DGAT1 of a green alga, e.g., an alga of the Chlorophyte division.

Additionally or alternatively, a recombinant eukaryotic microorganism can include a non-native gene encoding an acyltransferase that has at least 80%, at least 85%, at least 90%, or at least 95% amino acid sequence identity to a naturally-occurring acyltransferase or an active fragment thereof, where the acyltransferase-encoding sequence is operably linked to a heterologous sequence encoding a PH domain, such as, for example, a PH domain having at least 80%, at least 85%, at least 90%, or at least 95% amino acid sequence identity to any of SEQ ID NOs:6, 12, 18, 24, 30, 36, 42, or 48. For example, a recombinant eukaryotic microorganism or alga can include a non-native gene encoding a DGAT that has at least 80%, at least 85%, at least 90%, or at least 95% amino acid sequence identity to a naturally-occurring DGAT or an active fragment thereof where the DGAT encoding sequence is operably linked to a heterologous sequence encoding a PH domain, such as, for example, a PH domain having at least 80%, at least 85%, at least 90%, or at least 95% amino acid sequence identity to any of SEQ ID NOs:6, 12, 18, 24, 30, 36, 42, or 48.

The non-native gene can additionally or alternatively encode a PH-domain including DGAT that is a truncated variant of a naturally-occurring DGAT, such as an N-terminally or C-terminally truncated variant of a naturally-occurring DGAT or a DGAT having at least 80%, at least 85%, at least 90%, or at least 95% amino acid sequence identity to a naturally-occurring DGAT. In further examples, the acyltransferase can be a DGAT1 having at least 80% identity to SEQ ID NO:2 or a functional fragment thereof; an amino acid sequence having at least 80% identity to SEQ ID NO:8 or a functional fragment thereof; an amino acid sequence having at least 80% identity to SEQ ID NO:14 or a functional fragment thereof; an amino acid sequence having at least 80% identity to SEQ ID NO:20 or a functional fragment thereof; an amino acid sequence having at least 80% identity to SEQ ID NO:26 or a functional fragment thereof; or an amino acid sequence having at least 80% identity to SEQ ID NO:32 or a functional fragment thereof.

For example, a recombinant eukaryotic alga can include a non-native gene encoding a DGAT that has at least 80%, at least 85%, at least 90%, or at least 95% amino acid sequence identity to a naturally-occurring DGAT or an active fragment thereof where the DGAT encoding sequence is operably linked to a heterologous sequence encoding a PH domain, such as, for example, a PH domain having at least 80%, at least 85%, at least 90%, or at least 95% amino acid sequence identity to any of SEQ ID NOs:6, 12, 18, 24, 30, 36, 42, or 48.

For example, a recombinant microorganism as provided herein can comprise a non-native gene encoding a PH domain, wherein the PH domain comprises an amino acid sequence having at least 80% identity to SEQ ID NOs:6, 12, 18, 24, 30, or 36, and/or to an active fragment of any thereof. For example, the non-native gene can encode a PH domain having an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to any one or more of SEQ ID NOs:6, 12, 18, 24, 30, or 36. Within the recombinant microorganism, the PH domain can be linked to any protein of interest, for example, a DGAT.

A recombinant microorganism that includes a gene encoding a non-native DGAT comprising a PH domain can produce a greater amount of at least one lipid than a substantially identical microorganism lacking the recombinant DGAT gene that includes a PH domain-encoding sequence. For example, the recombinant microorganism, that includes a gene encoding a non-native DGAT comprising a native or heterologous PH domain, can produce a greater amount of TAG in a twenty-four hour, three day, and/or seven day time period than a substantially identical microorganism lacking the recombinant DGAT gene.

Further, the recombinant microorganism that includes a gene encoding a non-native DGAT comprising a PH domain, which may optionally be a heterologous PH domain with respect to the DGAT, can be a eukaryotic microalga, and preferably can, under photoautotrophic culture conditions, produce a greater amount of lipid than a substantially identical microorganism lacking the recombinant DGAT gene. Additionally or alternatively, the recombinant eukaryotic microalga can, under nutrient replete culture conditions, or when cultured under nitrogen-replete conditions, produce a greater amount of lipid than a substantially identical microorganism lacking the recombinant DGAT gene. Preferably, the recombinant eukaryotic microalga can, under photoautotrophic nutrient replete culture conditions and/or under photoautotrophic nitrogen replete culture conditions, produce a greater amount of lipid than a substantially identical microorganism lacking the recombinant DGAT gene.

Further additionally or alternatively, the recombinant eukaryotic microorganism that includes a non-native gene encoding a DGAT that includes a PH domain can produce a greater amount of triglyceride than is produced by a microorganism substantially identical to the recombinant microorganism, when the microorganisms are cultured under nitrogen replete conditions.

The recombinant eukaryotic microorganism that includes a non-native gene encoding an acyltransferase having a PH domain can be an alga, for example, a microalga such as for example, a species of a genus selected from the group consisting of *Achnanthes, Amphiprora, Amphora, Ankistrodesmus, Asteromonas, Boekelovia, Bolidomonas, Borodinella, Botrydium, Botryococcus, Bracteococcus, Chaetoceros, Carteria, Chlamydomonas, Chlorococcum, Chlorogonium, Chlorella, Chroomonas, Chrysosphaera, Cricosphaera, Crypthecodinium, Cryptomonas, Cyclotella, Dunaliella, Ellipsoidon, Emiliania, Eremosphaera, Ernodesmius, Euglena, Eustigmatos, Franceia, Fragilaria, Fragilaropsis, Gloeothamnion, Haematococcus, Halocafeteria, Heterosigma, Hymenomonas, Isochrysis, Lepocinclis, Micractinium, Monoraphidium, Nannochloris, Nannochloropsis, Navicula, Neochloris, Nephrochloris, Nephroselmis, Nitzschia, Ochromonas, Oedogonium, Oocystis, Ostreococcus, Pavlova, Parachlorella, Pascheria, Pelagomonas, Phaeodactylum, Phagus, Picochlorum, Platymonas, Pleurochrysis, Pleurococcus, Prototheca, Pseudochlorella, Pseudoneochloris, Pseudostaurastrum, Pyramimonas, Pyrobotrys, Scenedesmus, Schizochlamydella, Skeletonema, Spyrogyra, Stichococcus, Tetrachlorella, Tetraselmis, Thalassiosira, Tribonema, Vaucheria, Viridiella, Vischeria,* and *Volvox.* As nonlimiting examples, the microalga can be a *Nannochloropsis* species, a *Tetraselmis* species, a *Chlorella* species, or a diatom species (for example, a species of *Amphora, Chaetoceros, Cyclotella, Fragilaria, Fragilaropsis, Navicula, Phaeodactylum,* or *Thalassiosira*).

For example, a recombinant eukaryotic alga as provided herein can include a non-native gene encoding a type-1, type-2, or type-3 DGAT or WS/DGAT, such as, for example, a fungus, yeast, bacterium, protozoan, animal, alga, or plant, or a variant thereof having at least 80%, at least 85%, at least 90%, or at least 95% amino acid sequence identity to the naturally-occurring DGAT1, DGAT2, DGAT3, WS/DGAT, or an active fragment thereof, and which can include a deletion, for example, a truncation, with respect to the naturally-occurring DGAT amino acid sequence, and/or can include one or more additional sequences, in addition to a PH domain. For example, the DGAT encoding sequence can be operably linked to a heterologous sequence encoding a PH domain, such as, for example, a PH domain having at least 80%, at least 85%, at least 90%, or at least 95% amino acid sequence identity to any of SEQ ID NOs:6, 12, 18, 24, 30, 36, 42, or 48.

In some examples, the DGAT1, DGAT2, WS/DGAT, or DGAT3 encoded by the non-native gene comprises a sequence at least 80%, at least 85%, at least 90%, or at least 95% identical to SEQ ID NO:2, SEQ ID NO:8, SEQ ID NO:14, SEQ ID NO:20, SEQ ID NO:26, SEQ ID NO:32, SEQ ID NO:38, SEQ ID NO:44, and/or an active portion thereof. For example, the non-native gene can encode a DGAT having an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to any one or more of SEQ ID NOs:2, 8, 14, 20, 26, 32, 38, or 44. In some examples, the DGAT comprises or is a DGAT1.

Also provided is a method for producing TAG in a recombinant eukaryotic microorganism. The method comprises culturing a recombinant microorganism as described herein that comprises a gene encoding a non-native DGAT that includes a native or heterologous PH domain, such as any disclosed herein, under culture conditions such that a DGAT encoded by gene is expressed to produce TAG. The DGAT expressed can be encoded by any DGAT gene, such as any disclosed herein, and can be configured in an expression cassette optionally to comprise a PH as described herein (e.g. SEQ ID NOs:6, 12, 18, 24, 30, 36, 42, 48, and/or sequences having at least 80% identity thereto). In some examples, the culture conditions can be nitrogen replete. Additionally or alternatively, the culture conditions can be nutrient replete. Further additionally or alternatively, the culture conditions can be substantially or entirely photoautotrophic. Still further additionally or alternatively, the recombinant microorganisms described herein can produce a greater amount of TAG under nitrogen replete conditions than is produced by a control microorganism substantially identical to the recombinant microorganism in all respects and cultured under the substantially same conditions, except that the control microorganism does not include a recombinant DGAT gene. In some examples, the recombinant microorganism can be proliferating and generating TAG at levels higher than the TAG levels generated by a non-transfected control microorganism cultured under substantially the same conditions. For example, the recombinant microorganism can generate at least 50% more lipid in comparison to a non-transfected control cell or at least two fold, at least five fold, and/or at least ten fold the amount of TAG produced by a non-transfected control cell in a twenty-four hour period, a three day period, and/or a seven day period. In certain examples, the DGAT expressed can have an amino acid sequence having at least 80% identity to SEQ ID NOs:2, 8, 14, 20, 26, 32, 38, and/or 44. For example, an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to any one or more of SEQ ID NOs:2, 8, 14, 20, 26, 32, 38, and 44. In some examples, the DGAT can comprise or be a DGAT1.

Also provided is a further method for producing TAG in a recombinant eukaryotic algal cell. The method comprises culturing a recombinant microorganism as provided herein, comprising a recombinant nucleic acid molecule encoding a polypeptide having acyltransferase activity, wherein the polypeptide comprises a heterologous PH domain, under conditions in which the recombinant nucleic acid molecule is expressed, to produce TAG. For example, the heterologous PH domain can be selected from SEQ ID NOs:6, 12, 18, 24, 30, 36, 42, 48, and/or sequences having at least 80% identity thereto and the polypeptide having acyltransferase activity can be a MGAT, DGAT1, DGAT2, DGAT3, WS/DGAT, DGAcT, DGTA, PDAT, LPLAT, LPAAT, or GPAT. Additionally or alternatively, the culture conditions can be nutrient replete. Further additionally or alternatively, the culture conditions can be substantially or entirely photoautotrophic. Still further additionally or alternatively, the recombinant microorganism described herein can produce a greater amount of TAG under nitrogen replete conditions than is produced by a control microorganism substantially identical to the recombinant microorganism in all respects and cultured under the substantially same conditions, except that the control microorganism does not comprise an acyltransferase comprising a heterologous PH domain that can direct the acyltransferase to a location within the cell. In some examples, the recombinant microorganism can be proliferating and generating TAG at levels higher than the TAG levels generated by a non-transfected control microorganism cultured under substantially the same conditions. For example, the recombinant microorganism can generate at least 50% more lipid in comparison to a non-transfected control cell or at least two fold, at least five fold, and/or at least ten fold the amount of TAG produced by a non-transfected control cell in a twenty-four hour period, a three day period, and/or a seven day period. In certain examples, the PH domain expressed can have an amino acid sequence having at least 80% identity to SEQ ID NOs:6, 12, 18, 24, 30, 36, 42, and/or 48. For example, an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to any one or more of SEQ ID NOs:6, 12, 18, 24, 30, 36, 42, and 48. In some examples, the polypeptide having acyltransferase activity can comprise or be a DGAT1.

Further areas of applicability will become apparent from the description provided herein. The description and specific examples in this summary are intended for purposes of illustration only and are not intended to limit the scope of the present disclosure.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The drawings described herein are for illustrative purposes only of selected embodiments and not all possible implementations, and are not intended to limit the scope of the present disclosure.

FIG. 2A-F is an amino acid sequence alignment (constructed in Vector NTI, Life Technologies Inc.). It contains all of the novel fusion DGAT1 enzymes found by manually curating genes from public algal genomes. The PH domain is located from approximately position 53 to 205 of the *Cyclotella* sequence.

DETAILED DESCRIPTION

Definitions

Figure 1:
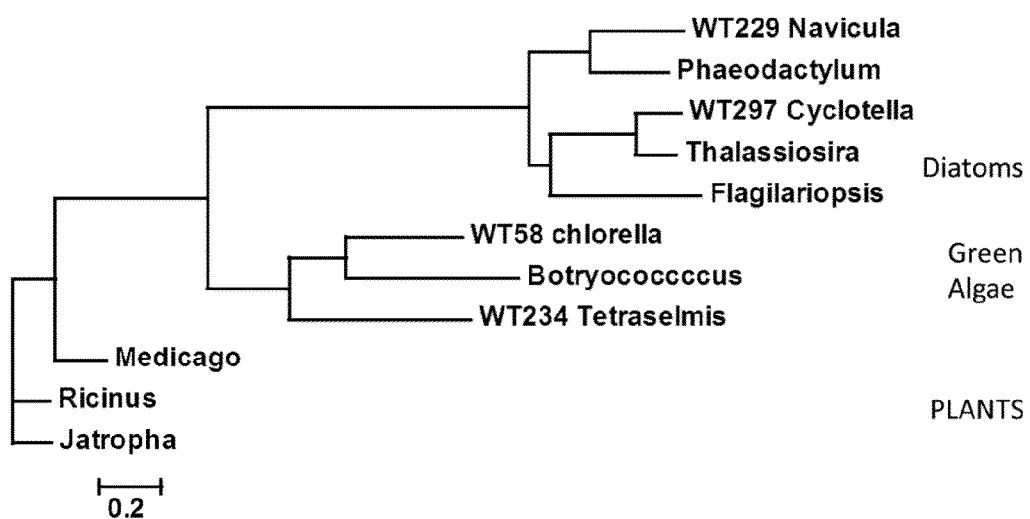
FIG. 1 is a phylogenetic tree of DGAT1 genes identified from proprietary and public algal genomes. The plant genes shown in the lower third of the figure do not include the PH domain and are included for reference purposes.

Unless defined otherwise, all technical and scientific terms used herein have the same meaning as commonly understood by one of ordinary skill in the art to which this invention belongs. In case of conflict, the present application including the definitions will control. Unless otherwise required by context, singular terms shall include pluralities and plural terms shall include the singular. All publications, patents and other references mentioned herein are incorporated by reference in their entireties for all purposes as if each individual publication or patent application were specifically and individually indicated to be incorporated by reference.

Although methods and materials similar or equivalent to those described herein can be used in practice or testing of the present invention, suitable methods and materials are described below. The materials, methods and examples are illustrative only and are not intended to be limiting. Other features and advantages of the invention will be apparent from the detailed description and from the claims.

To facilitate an understanding of the present invention, a number of terms and phrases are defined below.

As used in the present disclosure and claims, the singular forms "a," "an," and "the" include plural forms unless the context clearly dictates otherwise.

Wherever embodiments are described herein with the language "comprising," otherwise analogous embodiments described in terms of "consisting of" and/or "consisting essentially of" are also provided.

The term "and/or" as used in a phrase such as "A and/or B" herein is intended to include "A and B", "A or B", "A", and "B".

The terms "cells", "cell cultures", "cell line", "recombinant host cells", "recipient cells" and "host cells" as used herein include the primary subject cells and any progeny thereof, without regard to the number of transfers. It should be understood that not all progeny are exactly identical to the parental cell (due to deliberate or inadvertent mutations or differences in environment); however, such altered progeny are included in these terms, so long as the progeny retain substantially the same functionality as that of the originally transformed cell.

The term "gene" is used broadly to refer to any segment of a nucleic acid molecule (typically DNA, but optionally RNA) that encodes a protein or that can be transcribed into a functional RNA. Genes may include sequences that are transcribed but are not part of a final, mature, and/or functional RNA transcript, and genes that encode proteins may further comprise sequences that are transcribed but not translated, for example, 5' untranslated regions, 3' untranslated regions, introns, etc. Further, genes may optionally further comprise regulatory sequences required for their expression, and such sequences may be e.g., sequences that are not transcribed or translated. Genes can be obtained from a variety of sources, including cloning from a source of interest or synthesizing from known or predicted sequence information, and may include sequences designed to have desired parameters.

The terms "nucleic acid", "nucleic acid molecule", or "polynucleotide" are used interchangeably herein and refer to, e.g., DNA or RNA (e.g., mRNA). The nucleic acid molecules can be double-stranded or single-stranded; single stranded RNA or DNA can be the coding (sense) strand or the non-coding (antisense) strand.

The terms "coding sequence" or "coding region" as used herein, refer to a region of a DNA sequence that can be transcribed to produce an mRNA transcript that can be translated into an amino acid sequence, e.g., of a peptide or polypeptide or an RNA transcript that can be translated into an amino acid sequence, e.g., of a peptide or a polypeptide. The term "non-coding sequence" or "non-coding region" refers to (1) a region of a DNA sequence that, if transcribed, is not translated into an amino acid sequence (e.g., introns, untranslated regions, etc.); or (2) a region of an RNA sequence that is not translated into amino acids.

A "functional RNA molecule" is an RNA molecule that can interact with one or more proteins or nucleic acid molecules to perform or participate in a structural, catalytic, or regulatory function that affects the expression or activity of a gene or gene product other than the gene that produced the functional RNA. A functional RNA can be, for example, a transfer RNA (tRNA), ribosomal RNA (rRNA), anti-sense RNA (as-RNA), microRNA (miRNA), short-hairpin RNA (shRNA), small interfering RNA (siRNA), small nucleolar RNAs (snoRNAs), piwi-interacting RNA (piRNA), or a ribozyme.

A biomolecule may be "derived from" an indicated source, which includes the isolation (in whole or in part) of a nucleic acid segment from an indicated source or the purification of a polypeptide from an indicated source. A nucleic acid molecule may also be derived from an indicated source by, for example, direct cloning, PCR amplification, or artificial synthesis from the indicated polynucleotide source or based on a sequence associated with the indicated polynucleotide source. Genes or nucleic acid molecules derived from a particular source or species also include genes or nucleic acid molecules having sequence modifications with respect to the source nucleic acid molecules. For example, a gene or nucleic acid molecule derived from a source (e.g., a particular referenced gene) can incur one or more mutations with respect to the source gene or nucleic acid molecule that are unintended or that are deliberately introduced. If one or more mutations, including substitutions, deletions, or insertions, are deliberately introduced the sequence alterations can be introduced by random or targeted mutation of cells or nucleic acids, by amplification or other molecular biology techniques, or by chemical synthesis. A gene or nucleic acid molecule that is derived from a referenced gene or nucleic acid molecule that encodes a functional RNA or polypeptide can encode a functional RNA or polypeptide having at least 70%, at least 75%, at least 80%, at least 85%, at least 90%, at least 95%, at least 96%, at least 97%, at least 98%, or at least 99% sequence identity with the referenced or source functional RNA or polypeptide, or to a functional fragment thereof.

The term "isolated", such as an isolated protein or nucleic acid as used herein, refers to a biomolecule removed from the context in which the biomolecule exists in nature. An isolated biomolecule can be, in some instances, partially or substantially purified. For example, an isolated nucleic acid molecule can be a nucleic acid sequence that has been excised from the chromosome, genome, or episome into which it is integrated in nature.

A "purified" nucleic acid molecule or nucleotide sequence, or protein or polypeptide sequence, is substantially free of cellular material and cellular components. The purified nucleic acid molecule or protein may be free of chemicals beyond buffer or solvent, for example. "Substantially free" is not intended to mean that other components beyond the novel nucleic acid molecules are undetectable.

The terms "naturally-occurring" and "wild-type" (WT) refer to a form found in nature. For example, a naturally occurring or wild-type nucleic acid molecule, nucleotide sequence, or protein may be present in, and isolated from, a natural source, and is not intentionally modified by human manipulation.

As used herein "attenuated" means reduced in amount, degree, intensity, or strength. Attenuated gene expression may refer to a significantly reduced amount and/or rate of transcription of the gene in question, or of translation, folding, or assembly of the encoded protein. As nonlimiting examples, an attenuated gene may be a mutated or disrupted gene (e.g., a gene disrupted by partial or total deletion, insertional mutation, or meganuclease disruption), or a gene having decreased expression resulting from alteration of gene regulatory sequences. An attenuated gene may also be a gene that is targeted by a "gene knockdown" construct, such as, for example, a construct encoding an antisense RNA, a microRNA, a short hairpin RNA, or a ribozyme. In the case of both expression of transgenes and suppression of endogenous genes (e.g., by antisense or sense suppression) one of ordinary skill will recognize that the inserted polynucleotide sequence need not be identical, but may be only substantially identical to a sequence of the gene from which it was derived. These substantially identical variants are specifically covered by reference to a specific nucleic acid sequence.

"Exogenous nucleic acid molecule" or "exogenous gene" refers to a nucleic acid molecule or gene that has been introduced ("transformed") into a cell. A transformed cell may be referred to as a "recombinant" cell, into which additional exogenous gene(s) may be introduced. A descendent of a cell transformed with a nucleic acid molecule is also referred to as "transformed" if it has inherited the exogenous nucleic acid molecule. The exogenous gene may be from a different species (and may in this context be described as "heterologous" with respect to the host organism), or from the same species (and so may in this context be described as "homologous" with respect to the host organism), relative to the cell being transformed. An "endogenous" nucleic acid molecule, gene, or protein is a native nucleic acid molecule, gene, or protein as it occurs in, or is naturally produced by, the host.

Further, the term "exogenous" as used herein in the context of a gene or protein, refers to a gene or protein that is not derived from the host organism species.

The term "transgene" as used herein refers to an exogenous gene, that is, a gene introduced into a microorganism or its progenitor by human intervention.

The term "ortholog" of a gene or protein as used herein refers to its functional equivalent in another species.

The term "native" is used herein to refer to nucleic acid sequences or amino acid sequences as they naturally occur in the host. The term "non-native" is used herein to refer to nucleic acid sequences or amino acid sequences that do not occur naturally in the host. A nucleic acid sequence or amino acid sequence that has been removed from a host cell, subjected to laboratory manipulation, and reintroduced into a host cell is considered "non-native." Non-native genes include genes endogenous to the host microorganism operably linked to one or more heterologous regulatory sequences that have been inserted into the host genome.

The term "heterologous gene" or "heterologous nucleic acid sequence" as used herein, refers to a gene or nucleic acid sequence from a different species than the species of the host organism into which it is introduced. When used in reference to a polynucleotide, a gene, a nucleic acid, a polypeptide, or an enzyme, the term "heterologous" refers to a polynucleotide, gene, a nucleic acid, polypeptide, or an enzyme not derived from the host species. Further, when referring to a gene regulatory sequence or to an auxiliary nucleic acid sequence used for maintaining or manipulating a gene sequence (e.g. a 5' untranslated region, 3' untranslated region, Kozak sequence, poly A addition sequence, intron sequence, splice site, ribosome binding site, internal ribosome entry sequence, genome homology region, recombination site, etc.), "heterologous" means that the regulatory sequence or auxiliary sequence is from a different source than the gene with which the regulatory or auxiliary nucleic acid sequence is juxtaposed in a construct, genome, chromosome, or episome. When referring to a protein functional domain, such as a localization sequence or a receptor binding site, "heterologous" can also mean that the protein functional domain is from a different source than the rest of the protein region with which it is juxtaposed in an engineered protein. Thus, a Pleckstrin Homology domain operably linked to a polypeptide of which it is not part in its natural state (i.e. in the proteome of the non-genetically engineered organism) is referred to herein as a "heterologous Pleckstrin Homology domain," even though the Pleckstrin Homology domain may be derived from the same species (or, in some cases, the same organism) as the polypeptide to which it is linked. Similarly, when referring to a promoter sequence of an engineered gene, "heterologous" means that the promoter is derived from a different gene than that to which it is linked by genetic engineering.

The terms "recombinant" or "engineered" as used herein in reference to a nucleic acid molecule, refer to a nucleic acid molecule that has been altered through human intervention. As non-limiting examples, a cDNA is a recombinant DNA molecule, as is any nucleic acid molecule that has been generated by in vitro polymerase reaction(s), or to which linkers have been attached, or that has been integrated into a vector, such as a cloning vector or expression vector. As non-limiting examples, a recombinant nucleic acid molecule: 1) has been synthesized or modified in vitro, for example, using chemical or enzymatic techniques (for example, by use of chemical nucleic acid synthesis, or by use of enzymes for the replication, polymerization, exonucleolytic digestion, endonucleolytic digestion, ligation, reverse transcription, transcription, base modification (including, e.g., methylation), or recombination (including homologous and site-specific recombination)) of nucleic acid molecules; 2) includes conjoined nucleotide sequences that are not conjoined in nature; 3) has been engineered using molecular cloning techniques such that it lacks one or more nucleotides with respect to the naturally occurring nucleic acid molecule sequence; and/or 4) has been manipulated using molecular cloning techniques such that it has one or more sequence changes or rearrangements with respect to the naturally occurring nucleic acid sequence.

The term "recombinant protein" as used herein refers to a protein produced by genetic engineering.

When applied to organisms, the terms "transgenic" or "recombinant" or "engineered" or "genetically engineered," used interchangeably herein, refer to organisms that have been manipulated by introduction into the organism of an exogenous or recombinant nucleic acid sequence. For example, a transgenic microorganism can include an introduced exogenous regulatory sequence operably linked to an endogenous gene of the transgenic microorganism. Non-limiting examples of such manipulations include gene knockouts, targeted mutations and gene replacement, promoter replacement, deletion, or insertion, as well as introduction of transgenes into the organism. Recombinant or genetically engineered organisms can also be organisms into which constructs for gene "knock down" have been introduced. Such constructs include, but are not limited to, RNAi, microRNA, shRNA, antisense, and ribozyme constructs. Also included are organisms whose genomes have been altered by the activity of meganucleases or zinc finger nucleases. A heterologous or recombinant nucleic acid molecule can be integrated into a recombinant/genetically engineered organism's genome or, in other instances, not integrated into a recombinant/genetically engineered organism's genome. As used herein, "recombinant microorganism" or "recombinant host cell" includes progeny or derivatives of the recombinant microorganisms of the invention. Because certain modifications may occur in succeeding generations from either mutation or environmental influences, such progeny or derivatives may not, in fact, be identical to the parent cell, but are still included within the scope of the term as used herein.

The terms "regulatory sequence", "regulatory element", or "regulatory element sequence" are used interchangeable herein and refer to a nucleotide sequence located upstream (5'), within, or downstream (3') of a coding sequence. Transcription of the coding sequence and/or translation of an RNA molecule resulting from transcription of the coding sequence are typically affected by the presence or absence of the regulatory sequence. These regulatory element sequences may comprise promoters, cis-elements, enhancers, Kozak sequences, terminators, or introns. Regulatory elements may be isolated or identified from UnTranslated Regions (UTRs) from a particular polynucleotide sequence. Any of the regulatory elements described herein may be present in a chimeric or hybrid regulatory expression element. Any of the regulatory elements described herein may be present in a recombinant construct of the present invention.

The terms "promoter", "promoter region", or "promoter sequence" are used interchangeably herein and refer to a nucleic acid sequence capable of binding RNA polymerase to initiate transcription of a gene in a 5' to 3' ("downstream") direction. A gene is "under the control of" or "regulated by" a promoter when the binding of RNA polymerase to the promoter is the proximate cause of said gene's transcription. The promoter region typically provides a recognition site for RNA polymerase and other factors necessary for proper initiation of transcription. A promoter may be isolated from the 5' untranslated region (5' UTR) of a genomic copy of a gene. Alternatively, a promoter may be synthetically produced or designed by altering known DNA elements. Also considered are chimeric promoters that combine sequences of one promoter with sequences of another promoter. Promoters may be defined by their expression pattern based on, for example, metabolic, environmental, or developmental conditions. A promoter can be used as a regulatory element for modulating expression of an operably linked transcribable polynucleotide molecule, e.g., a coding sequence. Promoters may contain, in addition to sequences recognized by RNA polymerase and (preferably) other transcription factors, regulatory sequence elements such as cis-elements or enhancer domains that affect the transcription of operably linked genes. An "algal promoter" is a native or non-native promoter that is functional in algal cells.

A promoter can include a transcription initiation site as well as protein binding domains (consensus sequences) responsible for the binding of RNA polymerase. Eukaryotic promoters often, but not always, contain "TATA" boxes and "CAT" boxes. Prokaryotic promoters may contain −10 and −35 prokaryotic promoter consensus sequences. A large number of promoters, including constitutive, inducible and repressible promoters, from a variety of different sources are well known in the art. Representative sources include for example, viral, mammalian, insect, plant, yeast, and bacterial cell types, and suitable promoters from these sources are readily available, or can be made synthetically, based on sequences publicly available on line or, for example, from depositories such as the ATCC as well as other commercial or individual sources. Promoters can be unidirectional (i.e., initiate transcription in one direction) or bi-directional (i.e., initiate transcription in both directions off of opposite strands). A promoter may be a constitutive promoter, a repressible promoter, or an inducible promoter. Non-limiting examples of promoters include, for example, the T7 promoter, the cytomegalovirus (CMV) promoter, the SV40 promoter, and the RSV promoter. Examples of inducible promoters include the lac promoter, the pBAD (araA) promoter, the Tet promoter (U.S. Pat. Nos. 5,464,758 and 5,814,618), and the Ecdysone promoter (No et al. (1996) Proc. Natl. Acad. Sci. 93:3346-51). Promoters specific to Nannochloropsis are disclosed in co-pending U.S. patent application Ser. No. 13/486,930, entitled "Promoters and Terminators for Use in Eukaryotic Cells" filed on 1 Jun. 2012.

The term "constitutive" as used herein, refers to a promoter that is active under most environmental and developmental conditions. A constitutive promoter is active regardless of external environment, such as light and medium. In some examples, a constitutive promoter is active in the presence and in the absence of a nutrient. For example, a constitutive promoter may be a promoter that is active (mediates transcription of a gene to which it is operably-linked) under conditions of nitrogen depletion as well as under conditions in which nitrogen is not limiting (nitrogen replete conditions). In contrast, an "inducible" promoter is a promoter that is active in response to particular environmental conditions, such as the presence or absence of a nutrient or regulator, the presence of light, etc.

The term "terminator" or "terminator sequence" or "transcription terminator" as used herein refers to a regulatory section of genetic sequence that causes RNA polymerase to cease transcription.

The term "operably linked" as used herein denotes a configuration in which a regulatory sequence is placed at an appropriate position relative to a polynucleotide or polypeptide sequence such that the regulatory sequence affects or directs expression of the polynucleotide sequence, for example, to produce a polypeptide and/or functional RNA. Thus, a promoter is in operable linkage with a nucleic acid sequence if it can mediate transcription of the nucleic acid sequence. In the context of a polypeptide, an amino acid sequence that comprises a functional domain, such as a targeting sequence or other functional domain, is "operably linked" to the rest of the polypeptide when it is linked in such a way as to effectuate targeting to a subcellular location or otherwise becomes integrated into the polypeptide to affect protein function.

When introduced into a host cell, an expression cassette can result in transcription and/or translation of an encoded RNA or polypeptide under appropriate conditions. Antisense or sense constructs that are not or cannot be translated are not excluded by this definition.

The term "expression cassette" as used herein refers to a nucleic acid construct that contains a nucleic acid sequence, encoding for a protein or functional RNA (e.g., a tRNA, a short hairpin RNA, one or more microRNAs, a ribosomal RNA, etc.) operably linked to expression control elements, such as a promoter, and optionally, any or a combination of other nucleic acid sequences that affect transcription or translation, such as, but not limited to, a transcriptional terminator, a ribosome binding site, a splice site or splicing recognition sequence, an intron, an enhancer, a polyadenylation signal, an internal ribosome entry site, etc.

The term "vector" as used herein refers to a nucleic acid construct that is structured so as to facilitate movement of nucleic acids from one environment, intracellular or extracellular, to another environment, intracellular or extracellular. A vector optimized for use in modifying portions of the nucleic acid is a "cloning vector." A vector optimized for use in transforming a cell or expressing a gene of interest in a cell is a "transformation vector" or an "expression vector," these two terms being used interchangeably herein. A vector may optionally include one or more of: an origin of replication; a sequence mediating recombination into a host genome; or a selectable marker.

The term "microorganism" as used herein refers to any organism that is microscopic, i.e. too small to be seen by the naked eye. As used herein, the term "microorganism" may also refer to macroscopic organisms taxonomically related to microscopic organisms within the categories of yeast, heterokonts, algae, plants, bacteria, and fungi (including lichens). A microorganism may be unicellular or multicellular. A microorganism may be a bacterium, rickettsia, protozoon, or fungus. The term "microorganism" also includes microscopic plants and animals such as plankton, planaria, and amoebae, as well as arthropods such as dust mites, spider mites, etc.

The term "photosynthetic organism" as used herein is any prokaryotic or eukaryotic organism that can perform photosynthesis. Photosynthetic organisms include but are not limited to, higher plants (i.e., vascular plants), bryophytes, algae, and photosynthetic bacteria.

The terms "eukaryotic" and "eukaryote" are used in their broadest sense to include any organisms containing membrane bound nuclei and membrane bound organelles. Examples of eukaryotes include but are not limited to plants, yeast, animals, algae, diatoms, and fungi.

The terms "prokaryote" and "prokaryotic" are used in their broadest sense to include any organisms without a distinct nucleus. Examples of prokaryotes include but are not limited to bacteria, blue-green algae, archaebacteria, actinomycetes, and mycoplasma.

The term "algae" includes, but is not limited to, a species of Bacillariophyceae (diatoms), Bolidomonas, Chlorophyceae (green algae), Chrysophyceae (golden algae), Cyanophyceae (cyanobacteria), Eustigmatophyceae (pico-plankton), Glaucocystophytes, Pelagophytes, Phaeophyceae (brown algae), Prasinophyceae (pico-plankton), Raphidophytes, Rhodophyceae (red algae), Synurophyceae, and Xanthophyceae (yellow-green algae). The term "microalgae" as used herein refers to microscopic, single-celled algae species including, but not limited to, Bacillariophyceae (diatoms), Chlorophyceae, Prasinophyceae, Trebouxiophyceae, and Eustigmatophyceae. The term "algae" includes microalgae. The term "photosynthetic bacteria" includes, but is not limited to, cyanobacteria, green sulfur bacteria, purple sulfur bacteria, purple non-sulfur bacteria, and green non-sulfur bacteria.

The term "selectable marker" or "selectable marker gene" as used herein includes any gene that confers a phenotype on a cell in which it is expressed to facilitate the selection of cells that are transfected or transformed with a nucleic acid construct of the invention. The term may also be used to refer to gene products that effectuate said phenotypes. Examples of selectable markers include:

genes conferring resistance to antibiotics such as amikacin (aphA6), ampicillin (Amp®), blasticidin (bls, bsr, bsd), bleomicin or phleomycin (ZEOCIN™) (ble), chloramphenicol (cat), emetine (RBS14p or cry1-1), erythromycin (ermE), G418 or neomycin (GENETICIN™) (neo), gentamycin (aac3 or aacC4), hygromycin B (aphIV, hph, hpt), kanamycin (val), methotrexate (DHFR Mtx®), penicillin and other β-lactams (β-lactamases), streptomycin or spectinomycin (aadA, spec/strep), and tetracycline (tetA, tetM, tetQ);

genes conferring tolerance to herbicides such as aminotriazole, amitrole, andrimid, aryloxyphenoxy propionates, atrazines, bipyridyliums, bromoxynil, cyclohexandione oximes, dicamba, diclfop, dichlorophenyl dimethyl urea (DCMU), difunone, diketonitriles, diuron, fluridone, glufosinate, glyphosate, halogenated hydrobenzonitriles, haloxyfop, 4-hydroxypyridines, imidazolinones, isoxasflutole, isoxazoles, isoxazolidinones, miroamide B, p-nitrodiphenylethers, norflurazon, oxadiazoles, m-phenoxybenzamides, N-phenyl imides, pinoxadin, protoporphyrionogen oxidase inhibitors, pyridazinones, pyrazolinates, sulfonylureas, 1,2,4-triazol pyrimidine, triketones, urea;

genes that may be used in auxotrophic strains or to confer other metabolic effects, such as arg7, his3, hisD, hisG, lysA, manA, metE, nit1, trpB, ura3, xylA, a dihydrofolate reductase gene, a mannose-6-phosphate isomerase gene, a nitrate reductase gene, or an ornithine decarboxylase gene; a negative selection factor such as thymidine kinase; or toxin resistance factors such as a 2-deoxyglucose resistance gene; and acetyl CoA carboxylase (ACCase), acetohydroxy acid synthase (ahas), acetolactate synthase (als, csr1-1, csr1-2, imr1, imr2), aminoglycoside phosphotransferase (apt), anthranilate synthase, bromoxynil nitrilase (bxn), cytochrome P450-NADH-cytochrome P450 oxidoreductase, dalapon dehalogenase (dehal), dihydropteroate synthase (sul), class I 5-enolpyruvylshikimate-3-phosphate synthase (EPSPS), class II EPSPS (aroA), non-class I/II EPSPS, glutathione reductase, glyphosate acetyltransferase (gat), glyphosate oxidoreductase (gox), hydroxyphenylpyruvate dehydrogenase, hydroxy-phenylpyruvate dioxygenase (hppd), isoprenyl pyrophosphate isomerase, lycopene cyclase, phosphinothricin acetyl transferase (pat, bar), phytoene desaturase (crtI), prenyl transferase, protoporphyrin oxidase, the psbA photosystem II polypeptide (psbA), and SMM esterase (SulE), and superoxide dismutase (sod).

A "reporter gene" is a gene encoding a protein that is detectable or has an activity that produces a detectable product. A reporter gene can encode a visual marker or enzyme that produces a detectable signal, such as cat, lacZ, uidA, xylE, an alkaline phosphatase gene, an α-amylase gene, an α-galactosidase gene, a β-glucuronidase gene, a β-lactamase gene, a horseradish peroxidase gene, a luciferin/luciferase gene, an R-locus gene, a tyrosinase gene, or a gene encoding a fluorescent protein, including but not limited to a blue, cyan, green, red, or yellow fluorescent protein, a photoconvertible, photoswitchable, or optical highlighter fluorescent protein, or any of variant thereof, including codon-optimized, rapidly folding, monomeric, increased stability, and enhanced fluorescence variants.

The term "transformation" as used herein refers to the introduction of one or more exogenous nucleic acid sequences or polynucleotides into a host cell or organism by using one or more physical, chemical, or biological methods. Physical and chemical methods of transformation (i.e., "transfection") include, by way of non-limiting example, electroporation and liposome delivery. Biological methods of transformation (i.e., "transduction") include transfer of DNA using engineered viruses or microbes (e.g., *Agrobacterium*).

As used herein, "up-regulated" or "up-regulation" includes an increase in expression of a gene or nucleic acid molecule of interest or the activity of an enzyme, e.g., an increase in gene expression or enzymatic activity as compared to the expression or activity in an otherwise identical gene or enzyme that has not been up-regulated.

As used herein, "down-regulated" or "down-regulation" includes a decrease in expression of a gene or nucleic acid molecule of interest or the activity of an enzyme, e.g., a decrease in gene expression or enzymatic activity as compared to the expression or activity in an otherwise identical gene or enzyme that has not been down-regulated.

As used herein, the generic category of enzymes known as "diacylglycerol acyltransferase" (abbreviated as "DGAT") includes the specific category of enzymes known as "diacylglycerol acetyltransferase" (abbreviated as "DGAcT").

The terms, "identical" or percent "identity", in the context of two or more nucleic acids or polypeptide sequences, refer to two or more sequences or subsequences that are the same or have a specified percentage of amino acid residues or nucleotides that are the same, when compared and aligned for maximum correspondence over a comparison window. The degree of amino acid or nucleic acid sequence identity can be determined by various computer programs for aligning the sequences to be compared based on designated program parameters. For example, sequences can be aligned and compared using the local homology algorithm of Smith & Waterman (1981) *Adv. Appl. Math.* 2:482-89, the homology alignment algorithm of Needleman & Wunsch (1970) *J. Mol. Biol.* 48:443-53, or the search for similarity method of Pearson & Lipman (1988) *Proc. Nat'l. Acad. Sci. USA* 85:2444-48, and can be aligned and compared based on visual inspection or can use computer programs for the analysis (for example, GAP, BESTFIT, FASTA, and TFASTA in the Wisconsin Genetics Software Package, Genetics Computer Group, 575 Science Dr., Madison, Wis.).

The BLAST algorithm, described in Altschul et al. (1990) *J. Mol. Biol.* 215:403-10, is publicly available through software provided by the National Center for Biotechnology Information (at the web address www.ncbi.nlm.nih.gov). This algorithm identifies high scoring sequence pairs (HSPS) by identifying short words of length W in the query sequence, which either match or satisfy some positive-valued threshold score T when aligned with a word of the same length in a database sequence. T is referred to as the neighborhood word score threshold (Altschul et al., supra.). Initial neighborhood word hits act as seeds for initiating searches to find longer HSPs containing them. The word hits are then extended in both directions along each sequence for as far as the cumulative alignment score can be increased. Cumulative scores are calculated for nucleotides sequences using the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below due to the accumulation of one or more negative-scoring residue alignments; or the end of either sequence is reached. For determining the percent identity of an amino acid sequence or nucleic acid sequence, the default parameters of the BLAST programs can be used. For analysis of amino acid sequences, the BLASTP defaults are: word length (W), 3; expectation (E), 10; and the BLOSUM62 scoring matrix. For analysis of nucleic acid sequences, the BLASTN program defaults are word length (W), 11; expectation (E), 10; M=5; N=−4; and a comparison of both strands. The TBLASTN program (using a protein sequence to query nucleotide sequence databases) uses as defaults a word length (W) of 3, an expectation (E) of 10, and a BLOSUM 62 scoring matrix. See, Henikoff & Henikoff (1992) *Proc. Nat'l. Acad. Sci. USA* 89:10915-19

In addition to calculating percent sequence identity, the BLAST algorithm also performs a statistical analysis of the similarity between two sequences (see, e.g., Karlin & Altschul (1993) *Proc. Nat'l. Acad. Sci. USA* 90:5873-87). The smallest sum probability (P(N)), provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.1, preferably less than about 0.01, and more preferably less than about 0.001.

Nucleic Acid Molecules

The nucleic acid molecules and encoded polypeptides described herein can be used in any of the methods of the invention, and may be included in any of the expression cassettes, vectors, or recombinant microorganisms of the invention. Nucleic acid molecules comprising sequences that encode DGATs and PH domains are provided for use in host microorganisms and methods for producing TAG. A nucleic acid molecule as disclosed herein can be isolated, recombinant and/or purified.

Diacylglycerol acyltransferases (DGATs) are members of the O-acyltransferase superfamily, which esterify either sterols or diacylglycerols in an oleoyl-CoA-dependent manner. The DGAT enzyme performs the final step in TAG biosynthesis by transferring an acyl group from acyl-coenzyme-A to the sn-3 position of 1,2-diacylglycerol (DAG) to form TAG. Eukaryotes have two types of DGAT, abbreviated as DGAT1 and DGAT2, that belong to different gene families and share little homology. Eukaryotic DGAT1 polypeptides typically contain a FYxDWWN (SEQ ID NO:63) amino acid sequence motif, as well as a histidine (or tyrosine)-serine-phenylalanine (H/YSF) tripeptide motif, as described in Guo et al. (2001) *J. Lipid Res.* 42:1282-91. DGAT2 polypeptides typically include a HPHG, EPHSV, or PPHGV. A third type of DGAT, known as DGAT3, has been identified in peanut (Saha et al. (2006) *Plant Physiol.* 141:1533-43) and *Arabidopsis* (Hernandez et al. (2012) *Plant Physiol.* 160:215-25). Further considered as a DGAT useful for expression in microoranisms as disclosed herein is a diacylglycerol acetyltransferase (DGAcT) as has been described in *Euonymous alatus* (Durrett et al. (2010) *Proc. Nat'l. Acad. Sci. USA* 107:9464-69). In contrast, some prokaryotes that accumulate neutral lipids have genes encoding acyltransferase enzymes that form wax esters or TAG known as "WS/DGATs" (e.g., *Acinetobacter baylii, A. baumanii*, and *Mycobacterium avium*, and *M. tuberculosis* CDC1551, (see, e.g., Daniel et al. (2004) *J. Bacteriol.* 186:5017-30; see also Kalscheuer et al. (2003) *J. Biol. Chem.* 287:8075-82).

For example, an isolated or recombinant nucleic acid molecule as provided herein can encode a polypeptide having DGAT activity, in which the polypeptide comprises an amino acid sequence having:

at least 40%, at least 45%, at least 50%, at least 55%, at least 60%, at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the amino acid sequence of SEQ ID NO:2;

at least 40%, at least 45%, at least 50%, at least 55%, at least 60%, at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the amino acid sequence of SEQ ID NO:4;

at least 40%, at least 45%, at least 50%, at least 55%, at least 60%, at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the amino acid sequence of SEQ ID NO:8;

at least 40%, at least 45%, at least 50%, at least 55%, at least 60%, at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the amino acid sequence of SEQ ID NO:10;

at least 40%, at least 45%, at least 50%, at least 55%, at least 60%, at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the amino acid sequence of SEQ ID NO:14;

at least 40%, at least 45%, at least 50%, at least 55%, at least 60%, at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the amino acid sequence of SEQ ID NO:16;

at least 40%, at least 45%, at least 50%, at least 55%, at least 60%, at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the amino acid sequence of SEQ ID NO:20;

at least 40%, at least 45%, at least 50%, at least 55%, at least 60%, at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the amino acid sequence of SEQ ID NO:22;

at least 40%, at least 45%, at least 50%, at least 55%, at least 60%, at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the amino acid sequence of SEQ ID NO:26;

at least 40%, at least 45%, at least 50%, at least 55%, at least 60%, at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the amino acid sequence of SEQ ID NO:28;

at least 40%, at least 45%, at least 50%, at least 55%, at least 60%, at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the amino acid sequence of SEQ ID NO:32;

at least 40%, at least 45%, at least 50%, at least 55%, at least 60%, at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the amino acid sequence of SEQ ID NO:34;

at least 40%, at least 45%, at least 50%, at least 55%, at least 60%, at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the amino acid sequence of SEQ ID NO:38;

at least 40%, at least 45%, at least 50%, at least 55%, at least 60%, at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the amino acid sequence of SEQ ID NO:40;

at least 40%, at least 45%, at least 50%, at least 55%, at least 60%, at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the amino acid sequence of SEQ ID NO:44;

at least 40%, at least 45%, at least 50%, at least 55%, at least 60%, at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the amino acid sequence of SEQ ID NO:46;

and/or to a functional fragment of any of the provided amino acid sequences.

Assays for determining the activity of DGATs are known in the art and include, in addition to in vivo expression to evaluate increased production of TAG (see, e.g., the Examples provided in co-pending U.S. patent application Ser. No. 13/652,934, entitled "DGAT Genes and Methods of Use for Triglyceride Production in Recombinant Microorganisms" filed on 16 Oct. 2012), in vivo or in vitro assays that measure TAG production using radiolabeled substrates or detection of TAG by staining of thin layer chromatograms (see, e.g., Cases et al. (1998) *Proc. Nat'l. Acad. Sci. USA* 95:13018-23; Cases et al. (2001) *J. Biol. Chem.* 276:38870-76; Durrett et al. (2010) *Proc. Nat'l. Acad. Sci. USA* 107:9464-69; Beopoulos et al. (2012) *Appl. Microbiol. Biotechnol.* 93:1523-37).

An isolated or recombinant nucleic acid molecule encoding a DGAT can comprise a nucleic acid sequence that encodes a polypeptide having DGAT activity that has at least 40%, at least 45%, at least 50%, at least 55%, at least 60%, at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the amino acid sequence of a eukaryotic DGAT (e.g., a DGAT1), such as but not limited to: DGATs from *Cyclotella* species (SEQ ID NO:2) and orthologs in other algal species; DGATs from *Navicula* species (SEQ ID NO:8) and orthologs in other algal species; DGATs from *Fragilariopsis cylindrus* (SEQ ID NO:14) and orthologs in other algal species; DGATs from *Botryococcus* species (SEQ ID NO:20) and orthologs in other algal species; DGATs from *Tetraselmis* species (SEQ ID NO:26) and orthologs in other algal species; DGATs from *Chlorella* species (SEQ ID NO:32) and orthologs in other algal species; DGATs from *Thalassiosira pseudonana* (Genbank accession ADV58933, GI:340772255, SEQ ID NO:38) and orthologs in other algal species; and DGATs from *Phaeodactylum tricornutum* (Genebank accession XP_002177753, GI:219112003, SEQ ID NO:44) and orthologs in other algal species. For example, in some instances an isolated or recombinant nucleic acid molecule encoding a DGAT can comprise a nucleic acid sequence that encodes a polypeptide having DGAT activity that has at least 85%, at least 90%, at least 95%, or at least 99% sequence identity to the amino acid sequence of a prokaryotic DGAT, such as but not limited to: DGATs from *Cyclotella* species (SEQ ID NO:2) and orthologs in other algal species; DGATs from *Navicula* species (SEQ ID NO:8) and orthologs in other algal species; DGATs from *Fragilariopsis cylindrus* (SEQ ID NO:14) and orthologs in other algal species; DGATs from *Botryococcus* species (SEQ ID NO:20) and orthologs in other algal species; DGATs from *Tetraselmis* species (SEQ ID NO:26) and orthologs in other algal species; DGATs from *Chlorella* species (SEQ ID NO:32) and orthologs in other algal species; DGATs from *Thalassiosira pseudonana* (Genbank accession ADV58933, GI:340772255, SEQ ID NO:38) and orthologs in other algal species; and DGATs from *Phaeodactylum tricornutum* (Genebank accession XP_002177753, GI:219112003, SEQ ID NO:44) and orthologs in other algal species.

Additional DGAT genes that may find use in the microorganisms and methods of the invention (e.g., by engineering such DGAT genes to include PH domain-encoding sequences) can include those encoding DGAT enzymes of animals, higher plants, algae, bacteria, or fungii, such as, for example, those encoding DGAT enzymes of: *Mycobacterium smegmatis* (Genbank accession ABK74273, GI:118173377); *Alcanivorax borkumensis* (Genbank accession YP_694462, GI:110835603); *Marinobacter hydrocarbonoclasticus* (Genbank accession ABM17275, GI:120322960); *Rhodococcus opacus* (Genbank accession GQ923886, GI:261411835); *Homo sapiens* (NP_036211.2, GI:145864459); *Danio rerio* (NP_956024.1, GI:41054343); *Arabidopsis thaliana* (Genebank accession Q9SLD2, GI:75206653; Genbank accession Q9ASU1.1, GI:75167729); *Brassica juncea* (AAY40784.1, GI:63376226); *Brassica napus* (AAD40881.1, GI:5225382); *Ostreococcus tauri* (Wagner et al. (2010) *Plant Physiol. & Biochem.* 48:407-16); *Chlamydomonas reinhardtii* (La Russa et al. (2012) *J. Biotechnol.* 162:13-20); *Zea mays* (ABV91586.1, GI:157885767); *Yarrowia lipolytica* (Genebank accession XP504700); *Mus musculus* (Genbank accession NP_080660, GI:16975490); *Nannochloropsis gaditana* (SEQ ID NOs:18, 24, and 36 in co-pending U.S. patent application Ser. No. 13/652,934); *Arachis hypogaea* (Genbank accession AY875644, GI:62084564); *Euonymus alatus* (Genbank accession GU594061, GI:294992377); *Rhodotorula glutinis* (ABC41546.1, GI:83702260); *Ricinus communis* (XP_002519339.1, GI:255556610); and *Paracoccidiodioides brasiliensis* (EEH17170.1, GI:225678886). Also included are DGAT genes encoding DGAT enzymes having at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% identity to these enzymes, orthologs in other species, and/or functional fragments thereof.

Additionally or alternatively, the invention encompasses nucleic acid molecules encoding truncations of a DGAT where one or more amino acids have been deleted from the protein. For example, the encoded polypeptide can lack at least 1, at least 2, at least 3, at least 4, at least 5, at least 6, at least 7, at least 8, at least 9, at least 10, at least 20, at least 30, at least 40, at least 50, at least 60, at least 70, or at least 80 amino acids from the N- and/or C-terminus and can have an amino acid sequence at least 40%, at least 45%, at least 50%, at least 55%, at least 60%, at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or about 100% identical to the corresponding amino acid sequence of SEQ ID NOs:4, 10, 16, 22, 28, 34, 40, and/or 46. In some examples, the deleted sequences may include at least a portion of a functional domain, such as but not limited to a targeting or localization sequence, for example, at least a portion of a chloroplast transit peptide, at least a portion of a mitochondrial targeting sequence, at least a portion of an endoplasmic reticulum targeting sequence, at least a portion of a Pleckstrin Homology domain, etc. By way of nonlimiting example, in some instances an isolated or recombinant nucleic acid molecule encoding a DGAT can comprise a nucleic acid sequence that encodes a polypeptide having at least 40%, at least 45%, at least 50%, at least 55%, at least 60%, at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the amino acid sequence of a eukaryotic DGAT (e.g., a DGAT1), such as but not limited to: DGATs from *Cyclotella* species (SEQ ID NO:4) and orthologs in other species; DGATs from *Navicula* species (SEQ ID NO:10) and orthologs in other species; DGATs from *Fragilariopsis cylindrus* (SEQ ID NO:16) and orthologs in other species; DGATs from *Botryococcus* species (SEQ ID NO:22) and orthologs in other species; DGATs from *Tetraselmis* species (SEQ ID NO:28) and orthologs in other species; DGATs from *Chlorella* species (SEQ ID NO:34) and orthologs in other species; DGATs from *Thalassiosira pseudonana* (SEQ ID NO:40) and orthologs in other species; and DGATs from *Phaeodactylum tricornutum* (SEQ ID NO:46) and orthologs in other 1 species. For example, in some instances an isolated or recombinant nucleic acid molecule encoding a DGAT can comprise a nucleic acid sequence that encodes a polypeptide having DGAT activity that has at least 80%, at least 85%, at least 90%, at least 95%, or at least 99% sequence identity to the amino acid sequence of a DGAT1, such as but not limited to: a DGAT1 from *Cyclotella* species (SEQ ID NO:4) and orthologs in other algal species; a DGAT1 from *Navicula* species (SEQ ID NO:10) and orthologs in other algal species; a DGAT1 from *Fragilariopsis cylindrus* (SEQ ID NO:16) and orthologs in other algal species; a DGAT1 from *Botryococcus* species (SEQ ID NO:22) and orthologs in other algal species; a DGAT1 from *Tetraselmis* species (SEQ ID NO:28) and orthologs in other algal species; a DGAT1 from *Chlorella* species (SEQ ID NO:34) and orthologs in other algal species; a DGAT1 from *Thalassiosira pseudonana* (SEQ ID NO:40) and orthologs in other algal species; and a DGAT1 from *Phaeodactylum tricornutum* (SEQ ID NO:46) and orthologs in other algal species. The DGAT that includes a PH domain can be, for example, from a species of the Chlorophyta or Heterokontophyta division, and can be, for example, a species of the class Bacillariophyceae (diatoms), Prasinophyceae, or Trebouxiophyceae.

Pleckstrin Homology (PH) domains are small (100-120 amino acid) structural domains common to a wide variety and large number of proteins. Although they were first identified in the amino- and carboxy-termini of pleckstrin, they have since been identified in more than 670 proteins. Lemmon (2008) *Nat. Rev. Mol. Cell Biol.* 9:99-111. There is little primary sequence conservation within this domain, although there is significant secondary and tertiary structure conserved among the various members of this domain family (see, FIG.

2A-F). Philip et al. (2002) *FEBS Lett.* 531:28-32. Among the many roles that these domains play, one is to target and bind proteins to specific phosphatidylinositol lipids on membrane surfaces. Scheffzek & Welti (2012) *FEBS Lett.* 586:2662-73.

The present invention also provides nucleic acid molecules encoding PH domains. Without being bound by theory, PH domains may target acyltransferases of the present invention to membrane surfaces, for example to membrane surfaces, such as, for example, membrane surfaces of the endoplasmic reticulum or the chloroplast envelope. Such isolated or recombinant nucleic acid molecules as provided herein can encode a PH domain, in which the polypeptide comprises an amino acid sequence having:

- at least 40%, at least 45%, at least 50%, at least 55%, at least 60%, at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the amino acid sequence of SEQ ID NO:6;
- at least 40%, at least 45%, at least 50%, at least 55%, at least 60%, at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the amino acid sequence of SEQ ID NO:12;
- at least 40%, at least 45%, at least 50%, at least 55%, at least 60%, at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the amino acid sequence of SEQ ID NO:18;
- at least 40%, at least 45%, at least 50%, at least 55%, at least 60%, at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the amino acid sequence of SEQ ID NO:24;
- at least 40%, at least 45%, at least 50%, at least 55%, at least 60%, at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the amino acid sequence of SEQ ID NO:30;
- at least 40%, at least 45%, at least 50%, at least 55%, at least 60%, at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the amino acid sequence of SEQ ID NO:36;
- at least 40%, at least 45%, at least 50%, at least 55%, at least 60%, at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the amino acid sequence of SEQ ID NO:42;
- at least 40%, at least 45%, at least 50%, at least 55%, at least 60%, at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the amino acid sequence of SEQ ID NO:48;
- and/or to a functional fragment of any of the provided amino acid sequences.

For example, the nucleic acid molecules encoding PH domains can comprise a nucleic acid sequence that encodes a polypeptide that has at least 40%, at least 45%, at least 50%, at least 55%, at least 60%, at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the amino acid sequence of the PH domains of the present invention (e.g., SEQ ID NOs:6, 12, 18, 24, 30, 36, 42, and 48). The Pleckstrin Homology domain can optionally be derived from a gene, such as an algal DGAT1 gene, or from a eukaryotic algal species. Additionally, the nucleic acid molecules encoding PH domains can be fused in frame to a nucleic acid molecule encoding an acyltransferase, such as, for example a MGAT, DGAT1, DGAT2, DGAT3, WS/DGAT, DGAcT, DGTA, PDAT, LPLAT, LPAAT, or GPAT, where the acyltransferase may be derived from any species. For example, a nucleic acid molecule encoding a DGAT of *Saccharomyces cerevisiae* can be fused in frame to a nucleic acid molecule encoding a PH domain of the present invention. Additionally or alternatively, any nucleic acid molecule encoding a PH domain can be operably linked a nucleotide sequence encoding a MGAT, DGAT1, DGAT2, DGAT3, WS/DGAT, DGAcT, DGTA, PDAT, LPLAT, LPAAT, and/or GPAT.

The invention also provides DGAT genes that include PH domains that include sequences encoding fragments and variants of naturally-occurring DGATs. A substitution, insertion or deletion can adversely affect the protein when the altered sequence substantially inhibits a biological function associated with the protein. In certain embodiments, a variant of a DGAT may have activity that is reduced by not more than about 1%, not more than about 2%, not more than about 3%, not more than about 4%, not more than about 5%, not more than about 6%, not more than about 7%, not more than about 8%, not more than about 9%, not more than about 10%, not more than about 15%, not more than about 20%, not more than about 30%, not more than about 40%, not more than about 50%, or not more than about 90% in comparison to the activity of the DGAT from which the variant is derived (e.g., any of SEQ ID NOs:2, 8, 14, 20, 26, 32, 38, and/or 44). In some embodiments, the amount of a TAG produced by a host cell expressing the DGAT variant is not less than about 99%, not less than about 98%, not less than about 97%, not less than about 96%, not less than about 95%, not less than about 94%, not less than about 93%, not less than about 92%, not less than about 91%, not less than about 90%, not less than about 85%, not less than about 80%, not less than about 75%, or not less than about 50% of the amount or the fatty acid product produced by a host cell expressing the DGAT from which the variant is derived (e.g., any of SEQ ID NOs:2, 8, 14, 20, 26, 32, 38, and/or 44).

The invention also provides fragments and variants of a DGAT that have increased activity in comparison to the reference polypeptides. In certain embodiments, the DGAT fragment or variant may have activity that is increased by at least 5%, at least 10%, at least 20%, at least 30%, at least 40%, at least 50%, at least 60%, at least 70%, at least 80%, at least 90%, at least 100%, at least 200%, at least 300%, at least 400%, at least 500%, at least 600%, at least 700%, at least 800%, at least 900%, or at least 1000% in comparison to the activity of the DGAT from which the variant is derived. In certain embodiments, the amount of TAG produced by a host cell expressing the fragment or variant is at least 5%, at least 10%, at least 20%, at least 30%, at least 40%, at least 50%, at least 60%, at least 70%, at least 80%, at least 90%, at least 100%, at least 200%, at least 300%, at least 400%, at least 500%, at least 600%, at least 700%, at least 800%, at least 900%, or at least 1000% of the amount of TAG made by a host cell expressing the DGAT from which the fragment or variant is derived.

The invention described herein also relates to fragments of the isolated nucleic acid molecules described herein encompassing a portion of a nucleotide sequence described herein which is from at least 20 contiguous nucleotides to at least 50 contiguous nucleotides or longer in length. Such fragments may be useful as probes and primers. In particular, primers and probes may selectively hybridize to the nucleic acid molecule encoding the polypeptides described herein. For example, fragments which encode polypeptides that retain activity, as described below, are particularly useful.

The invention also provides nucleic acid molecules that hybridize under high stringency hybridization conditions, such as for selective hybridization, to the nucleotide sequences described herein (e.g. nucleic acid molecules which specifically hybridize to a nucleotide sequence encoding polypeptides described herein and encode a DGAT and/or a PH domain). Hybridization probes include synthetic oligonucleotides which bind in a base-specific manner to a complementary strand of nucleic acid. Suitable probes include polypeptide nucleic acids (PNAs), as described in Nielsen (1991) *Science,* 254:1497-500.

Such nucleic acid molecules can be detected and/or isolated by specific hybridization e.g. under high stringency conditions. "Stringency conditions" for hybridization is a term of art that refers to the incubation and wash conditions, e.g. conditions of temperature and buffer concentration, which permit hybridization of a particular nucleic acid to a second nucleic acid; the first nucleic acid may be perfectly complementary, i.e. 100%, to the second, or the first and second may share some degree of complementarity, which is less than perfect, e.g. 60%, 75%, 85%, 95% or more. For example, certain high stringency conditions can be used which distinguish perfectly complementary nucleic acids from those of less complementarity.

"High stringency conditions", "moderate stringency conditions" and "low stringency conditions" for nucleic acid hybridizations are explained in Current Protocols in Molecular Biology (2011) John Wiley & Sons). The exact conditions which determine the stringency of hybridization depend not only on ionic strength, e.g. 0.2×SSC, 0.1×SSC of the wash buffers, temperature, e.g. 23° C., 42° C., 68° C., etc. and the concentration of destabilizing agents such as formamide or denaturing agents such as SDS, but also on factors such as the length of the nucleic acid sequence, base composition, percent mismatch between hybridizing sequences and the frequency of occurrence of subsets of that sequence within other non-identical sequences. Thus, high, moderate or low stringency conditions may be determined empirically.

By varying hybridization conditions from a level of stringency at which no hybridization occurs to a level at which hybridization is first observed, conditions which will allow a given sequence to hybridize with the most similar sequences in the sample can be determined.

Exemplary conditions are described in Krause (1991) *Methods in Enzymology,* 200:546-56. Washing is the step in which conditions are usually set so as to determine a minimum level of complementarity of the hybrids. Generally, starting from the lowest temperature at which only homologous hybridization occurs, each degree (° C.) by which the final wash temperature is reduced, while holding SSC concentration constant, allows an increase by 1% in the maximum extent of mismatching among the sequences that hybridize. Generally, doubling the concentration of SSC results in an increase in melting temperature ($T_m$). Using these guidelines, the washing temperature can be determined empirically for high, moderate or low stringency, depending on the level of mismatch sought. Exemplary high stringency conditions include, but are not limited to, hybridization in 50% formamide, 1 M NaCl, 1% SDS at 37° C., and a wash in 0.1×SSC at 60° C. Example of progressively higher stringency conditions include, after hybridization, washing with 0.2×SSC and 0.1% SDS at about room temperature (low stringency conditions); washing with 0.2×SSC, and 0.1% SDS at about 42° C. (moderate stringency conditions); and washing with 0.1×SSC at about 68° C. (high stringency conditions). Washing can be carried out using only one of these conditions, e.g. high stringency conditions, washing may encompass two or more of the stringency conditions in order of increasing stringency. Optimal conditions will vary, depending on the particular hybridization reaction involved, and can be determined empirically.

Equivalent conditions can be determined by varying one or more of the parameters given as an example, as known in the art, while maintaining a similar degree of identity or similarity between the target nucleic acid molecule and the primer or probe used. Hybridizable nucleotide sequences are useful as probes and primers for identification of organisms comprising a nucleic acid of the invention and/or to isolate a nucleic acid of the invention, for example.

The nucleic acid molecules of the invention can optionally comprise additional non-coding sequences such as non-coding 3' and 5' sequences (including, e.g., regulatory sequences) that may be homologous or heterologous to a DGAT gene. Alternatively or in addition, any of the provided nucleic acid molecules can optionally further comprise an additional nucleic acid sequence of at least 50, at least 60, at least 70, at least 80, at least 90, at least 100, at least 150, at least 200, at least 250, at least 300, at least 350, at least 400, at least 450, at least 500, at least 550, at least 600, at least 700, at least 800, at least 900, at least 1000, or at least 1500 nucleotides from a photosynthetic organism. The nucleic acid molecules and polypeptides described herein can be used in any of the methods of the invention, and may be included in any of the vectors or recombinant microorganisms of the invention. Nucleic acid molecules comprising sequences that encode DGAT are provided for use in host microorganisms and methods for producing TAG.

Other Modifications

The invention also provides further variants of the nucleotide sequences of the invention. In some embodiments, the nucleotide sequence variants encode fragments or variants of the polypeptides as described herein. In some embodiments, the nucleotide sequence variants are naturally-occurring. In other embodiments, the nucleotide sequence variants are non-naturally-occurring, such as those induced by various mutagens and mutagenic processes. In certain embodiments, the nucleotide sequence variants are a combination of naturally- and non-naturally-occurring. A given nucleic acid sequence may be modified, for example, according to standard mutagenesis or artificial evolution or domain swapping methods to produce modified sequences. Accelerated evolution methods are described, e.g. by Stemmer (1994) *Nature* 370:389-91, and Stemmer (1994) *Proc. Nat'l. Acad. Sci. USA* 91:10747-51. Chemical or enzymatic alteration of expressed nucleic acids and polypeptides can be performed by standard methods. For example, a sequence can be modified by addition of phosphate groups, methyl groups, lipids, sugars, peptides or organic or inorganic compounds, by the inclusion of modified nucleotides or amino acids, or the like.

For optimal expression of a recombinant protein, in certain instances it may be beneficial to employ coding sequences that produce mRNA with codons preferentially used by the host cell to be transformed ("codon optimization"). Thus, for enhanced expression of transgenes, the codon usage of the transgene can be matched with the specific codon bias of the organism in which the transgene is desired to be expressed. Methods of recoding genes for expression in microalgae are described in, e.g., U.S. Pat. No. 7,135,290. The precise mechanisms underlying this effect are believed to be many, but can include the proper balancing of available aminoacylated tRNA pools with proteins being synthesized in the cell, coupled with more efficient translation of the transgenic messenger RNA (mRNA) when this need is met. In some examples, only a portion of the codons is changed to reflect a preferred codon usage of a host microorganism. In certain examples, one or more codons are changed to codons that are not necessarily the most preferred codon of the host microorganism encoding a particular amino acid. Additional information for codon optimization is available, e.g. at the codon usage database of GenBank. The coding sequences may be codon optimized for optimal production of a desired product in the host organism selected for expression. In certain examples, the non-native nucleic acid sequence encoding a DGAT is codon optimized for expression in a photosynthetic microorganism, e.g., a *cyanobacterium* or a eukaryotic microalga. In some aspects, the nucleic acid molecules of the invention encode fusion proteins that comprise a DGAT. For example, the nucleic acids of the invention may comprise polynucleotide sequences that encode a heterologous PH domain, the amino-terminus of a putative chloroplast inner envelope glucose-6-phosphate/phosphate antiporter or a portion thereof, glutathione-S-transferase (GST) or a portion thereof, thioredoxin or a portion thereof, maltose binding protein or a portion thereof, poly-histidine (e.g. His$_6$), poly-HN, poly-lysine, a FLAG tag sequence, a hemagglutinin tag sequence, HSV-Tag and/or at least a portion of HIV-Tat fused to the DGAT-encoding sequence.

Nucleic Acid Constructs

The invention also provides constructs, such as an isolated or recombinant nucleic acid molecule comprising a nucleotide sequence as provided herein encoding a polypeptide having acyltransferase activity, wherein the polypeptide comprises a PH domain. Additionally, the construct can further include one or more sequences that regulate or mediate transcription, translation, or integration of nucleotide sequences into a host genome. For example, the invention also provides expression constructs that comprise one or more "expression control elements" or sequences that regulate transcription of an operably linked gene, or translation of the transcribed RNA. For example, an expression control element can be a promoter that may be operably linked to the gene of interest (e.g., a DGAT gene) in an expression construct or "expression cassette." In some examples of the foregoing, the promoter is regulatable, e.g., inducible. In other examples of the foregoing, the promoter may be constitutive. The promoter in some examples can be an algal promoter or derived from an algal promoter.

In examples where the nucleic acid construct does not contain a promoter in operable linkage with the nucleic acid sequence encoding the polypeptide having acyltransferase activity (e.g., a DGAT gene) the nucleic acid sequence can be transformed into the cells such that it becomes operably linked to an endogenous promoter by, e.g., homologous recombination, site specific integration, and/or vector integration. In some examples, genomic host sequences included in a nucleic acid construct for mediating homologous recombination into the host genome can include gene regulatory sequences, for example, a promoter sequence, that can regulate expression of a DGAT gene of the nucleic acid construct. In such embodiments, the transgene(s) of the construct can become operably linked to a promoter that is endogenous to the host microorganism. In some embodiments, the endogenous promoter(s) are regulatable, e.g., inducible. Alternatively the DGAT gene can be operably linked to an endogenous promoter that is constitutive and/or active under nitrogen replete conditions.

In one aspect, the present invention provides isolated or recombinant nucleic acid molecules encoding a polypeptide having acyltransferase activity, wherein the polypeptide comprises a heterologous PH domain derived from a microorganism, for example, a microalga. In certain embodiments, the heterologous PH domain can be selected from the group consisting of: a PH domain having at least 80% identity to SEQ ID NO:6 or a functional fragment thereof; a PH domain having at least 80% identity to SEQ ID NO:12 or a functional fragment thereof; a PH domain having at least 80% identity to SEQ ID NO:18 or a functional fragment thereof; a PH domain having at least 80% identity to SEQ ID NO:24 or a functional fragment thereof; a PH domain having at least 80% identity to SEQ ID NO:30 or a functional fragment thereof; a PH domain having at least 80% identity to SEQ ID NO:36 or a functional fragment thereof; a PH domain having at least 80% identity to SEQ ID NO:42 or a functional fragment thereof; and a PH domain having at least 80% identity to SEQ ID NO:48 or a functional fragment thereof.

Alternatively or additionally, the recombinant nucleic acid molecule encoding a polypeptide having acyltransferase activity can comprise a heterologous PH domain selected from the group consisting of: a PH domain having at least 95% identity to SEQ ID NO:6 or a functional fragment thereof; a PH domain having at least 95% identity to SEQ ID NO:12 or a functional fragment thereof; a PH domain having at least 95% identity to SEQ ID NO:18 or a functional fragment thereof; a PH domain having at least 95% identity to SEQ ID NO:24 or a functional fragment thereof; a PH domain having at least 95% identity to SEQ ID NO:30 or a functional fragment thereof; a PH domain having at least 95% identity to SEQ ID NO:36 or a functional fragment thereof; a PH domain having at least 95% identity to SEQ ID NO:42 or a functional fragment thereof; and a PH domain having at least 95% identity to SEQ ID NO:48 or a functional fragment thereof.

In certain embodiments, the polypeptide having acyltransferase activity can be a MGAT, a DGAT1, a DGAT2, a WS/DGAT, a DGAT3, a DGTA, a PDAT, a LPLAT, a LPAAT, and/or a GPAT. For example, the polypeptide having acyltransferase activity can be a DGAT1 or a DGAT2. For example, the polypeptide having acyltransferase activity can be a DGAT1.

A promoter operably linked to a nucleic acid sequence encoding a acyltransferase may be a promoter that is heterologous with respect to the acyltransferase gene. Promoters considered for use in regulating acyltransferase genes in eukaryotes can include, without limitation, inducible promoters such as a GAL, MET, Lys, or Leu promoter, or a nmt1 thiamine-repressible promoter, a uracil regulatable promoter (e.g., Watt et al. (2008) *PLoS One* 3:e1428) for example from a yeast or fungus, or a Tet-On or Tet-Off promoter. Other eukaryotic promoters as they are known in the art can also be employed, such as the SV40 promoter and the Cauliflower Mosaic Virus (CaMV) promoter, active fragments thereof, or hybrid promoters that include fragments of known eukaryotic promoters such as the SV40, CaMV, and nopaline synthase promoters.

In some embodiments of the foregoing invention, the promoter may be an inducible promoter, i.e., a promoter that mediates transcription of an operably linked gene in response to a particular stimulus. Such promoters may be advantageous, e.g., to minimize any deleterious effects on the growth of the host cell and/or to maximize production of TAG. An inducible promoter can be responsive to, e.g., light or dark or high or low temperature, and/or can be responsive to specific compounds. The inducible promoter may be a hormone-responsive promoter (e.g., an ecdysone-responsive promoter, such as described in U.S. Pat. No. 6,379,945), a metallothionien promoter (e.g., U.S. Pat. No. 6,410,828), a pathogenesis-related (PR) promoter that can be responsive to a chemical such as, for example, salicylic acid, ethylene, thiamine, and/or BTH (U.S. Pat. No. 5,689,044), or the like, or some combination thereof. An inducible promoter can also be responsive to light or dark (U.S. Pat. Nos. 5,750,385, 5,639,952), metals (Quinn et al. (2003) *Eukaryot. Cell* 2:995-1002) or temperature (U.S. Pat. No. 5,447,858; Abe et al. (2008) *Plant Cell Physiol.* 49:625-32; Shroda et al. (2000) *Plant J.* 21:121-31). The foregoing list is exemplary and not limiting. The promoter sequence can be from any organism, provided that it is functional in the host organism. In certain embodiments, inducible promoters are formed by fusing one or more portions or domains from a known inducible promoter to at least a portion of a different promoter that can operate in the host cell, e.g. to confer inducibility on a promoter that operates in the host species.

Inducible promoters from eukaryotic algae include a NR promoter (ammonia regulated; Wang et al. (2004) *J. Appl. Phycol.* 16:11-16), nia promoter (U.S. Pat. No. 7,642,405), CYC6 (copper inducible, nickel and cobalt repressible) or CA1 promoter ($CO_2$-regulated; Ferrante et al. (2008) *PLos One* 3:e3200), as well as an algal Pnr (nitrogen-regulated) promoter (Poulsen and Kroger (2005) *FEBS J.* 272:3413-23), an algal inorganic phosphate transporter promoter (Wurch et al. (2011) *Environ. Microbiol.* 13:468-81), or other phosphate-status regulated promoter from algae, e.g, a PNP or PSR promoter (Yehudai-Resheff et al. (2007) *Plant Cell.* 19:1023-38). Further examples of promoters that may be induced by nitrogen limitation or depletion include but are not limited to: ammonium or ammonia transporter gene promoters (see, for example, Wurch et al., 2011); glutamine synthetase transporters (e.g., Miller et al. (2010) *Plant Physiol.* 154:737-52) or other promoters of genes upregulated at the transcriptional level during nitrogen depletion, including those disclosed in co-pending U.S. patent application Ser. No. 13/536,345, entitled "Regulation of Toxin and Antitoxin Genes for Biological Containment" filed Jun. 28, 2012, or active fragments of any thereof. The promoter can alternatively or in addition be regulated by phosphate depletion, and can be, for example, a PNPase gene promoter (Yehudai-Reseheff et al., 2007); an inorganic phosphate transporter gene promoter (Wurch et al., 2011), a phosphate permease gene promoter, or any disclosed in co-pending U.S. patent application Ser. No. 13/536,345, entitled "Regulation of Toxin and Antitoxin Genes for Biological Containment" filed Jun. 28, 2012, or an active fragment thereof. Candidate copper depletion-regulated promoters include those of CTR-type copper ion transporter genes (Castruita et al. (2011) *Plant Cell.* 23:1273-92), as well as CYC6 and CPX1 algal promoters (Quinn et al. (2000) *J. Biol. Chem.* 275:6080-89). Promoters regulated by iron deficiency may include, for example, those from the FOX1 gene or the FTR1 gene (La Fontaine et al. (2002) *Eukaryotic Cell* 1:736-57).

Specifically considered are promoters of the genes known to to be transcribed under nitrogen replete conditions. For example, promoters used to regulate acyltransferase genes, such as DGAT genes, can be active under conditions where the algae are proliferating, e.g., promoters that are active in the absence of nutrient limitation, such as, for example the *Nannochloropsis* promoters disclosed in co-pending U.S. patent application Ser. No. 13/486,930, entitled "Promoters and Terminators for Use in Eukaryotic Cells" filed 1 Jun. 2012 and co-pending U.S. patent application Ser. No. 13/693, 585, entitled "*Tetraselmis* Promoters and Terminators for Use in Eukaryotic Cells" filed 4 Dec. 2012, as well as in co-pending U.S. patent application Ser. No. 13/536,345, entitled "Regulation of Toxin and Antitoxin Genes for Biological Containment" filed 28 Jun. 2012. Additional examples of algal promoters include the *Nannochloropsis oceanica* vcp promoter sequence, which is regulated by light-exposure, (U.S. 2009/317,904); the a light-responsive fcpA promoter from *Phaeodactylum tricornutum* (U.S. Pat. No. 6,027,900); the *Chlamydomonas* psaD promoter (Fisher & Rochaix (2001) *Mol. Genet. Genomics* 265:888-94), as well as RuBisCo small subunit (ssu) promoters (Walker et al. (2004) *Plant Cell Reports* 23:727-35; Chen et al. (2008) *J. Phycol.* 44:768-76); the *Cyclotella cryptica* acc promoter, and *Chlorella* viral promoters (U.S. Pat. Nos. 6,252,140; 6,316,224). Also considered are promoters that are associated with orthologous genes in other species. For example, a gene of one algal species that is transcribed under nutrient replete or nitrogen replete conditions can be used to identify an orthologous gene in a second algal species, and the promoter of the gene in the second species can be isolated and tested for its activity under the desired culture conditions.

The examples of promoters provided are not limiting with regard to the promoters that may be used in constructs for expression of acyltransferases such as DGATs. Specifically considered are active fragments of promoters provided herein or disclosed in the art and promoters that comprise multimers of promoters or promoter fragments, as well as hybrid promoters such as but not limited to promoters that may include sequences of two or more different algal promoters (e.g., the HSP70-RBCS promoter (Schroda et al. (2000) *Plant J.* 21:121-31)), or hybrid promoters that may comprise algal and non-algal sequences, such as, for example, at least a portion of an SV40 promoter or CaMV promoter juxtaposed with at least a portion of an algal promoter. A promoter may comprise multimers of a sequence, including multimers of a hybrid promoter sequence.

A promoter used to regulate a DGAT or acyltransferase gene in a eukaryote can also be a synthetic promoter, for example, a promoter that includes a DNA binding domain that can be recognized and bound by an engineered transcription factor positioned upstream of a minimal promoter that is operable in the host microorganism. The microorganism can include an exogenous gene encoding a synthetic transcription factor that binds the synthetic promoter. The synthetic transcription factor can include, in addition to a DNA binding domain that recognizes the synthetic promoter, an activation domain (e.g., VP16, CREB, GAL10, GCN4) and a regulatory domain, where the regulatory domain may bind one or more compounds that can be added to the culture medium to induce or repress transcription (Weber & Fussenegger (2011) *Curr. Opin. Chem. Biol.* 15:414-20).

Likewise, a wide variety of transcriptional terminators can be used for expression vector construction. Nonlimiting examples of possible terminators can include, but are not limited to, those disclosed in co-pending U.S. patent application Ser. No. 13/486,930, entitled "Promoters and Terminators for Use in Eukaryotic Cells" filed Jun. 1, 2012.

Further, the present invention also provides for a nucleotide construct such as an isolated or recombinant nucleic acid molecule comprising a promoter operably linked to a nucleotide sequence encoding a polypeptide having DGAT activity, as already described herein. In a particular aspect, the nucleotide sequence encoding a polypeptide having DGAT activity is selected from the group consisting of nucleotide sequences encoding an amino acid having at least 40%, at least 45%, at least 50%, at least 55%, at least 60%, at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the amino acid sequence of any one or more of SEQ ID NOs:2, 8, 14, 20, 26, and 32.

In addition to a gene having acytransferase activity, such as a DGAT gene, one or more additional genes can optionally be included in a recombinant microorganism as provided herein, where the one or more additional genes may include, for example, one or more genes encoding enzymes or proteins of the fatty acid synthesis pathway and/or one or more genes encoding enzymes or proteins that may enhance TAG synthesis, one or more genes that may enhance photosynthesis or carbon-fixation, and/or one or more reporter genes or selectable markers. For example, the construct or expression cassette may further comprise a heterologous protein coding sequence, for example, encoding a MGAT, a DGAT1, a DGAT2, a DGAT3, a DGTA, a PDAT, a LPLAT, a LPAAT, and/or a GPAT.

Further, the present invention also provides for a nucleotide construct such as an isolated or recombinant nucleic acid molecule comprising a nucleotide sequence encoding a PH domain as already described herein. The nucleotide sequence encoding a PH domain can be fused in frame with any heterologous gene for ectopic expression in a recombinant microorganism. As nonlimiting examples the PH domain can direct a polypeptide to a chloroplast or a region thereof. In one aspect, the nucleotide sequence encoding a PH domain is fused in frame with a heterologous DGAT-encoding sequence. In a particular aspect, the nucleotide sequence encoding a PH domain is fused in frame with a nucleotide sequence encoding an amino acid having at least 40%, at least 45%, at least 50%, at least 55%, at least 60%, at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the amino acid sequence of any one or more of SEQ ID NOs:4, 10, 16, 22, 28, 34, 40, and 46.

An isolated nucleic acid construct of the present invention can include the sequences disclosed herein that encode a DGAT or other polypeptide in a vector, such as, but not limited to, an expression vector. A vector can be a nucleic acid that has been generated via human intervention, including by recombinant means and/or direct chemical synthesis, and can include, for example, one or more of: 1) an origin of replication for propagation of the nucleic acid sequences in one or more hosts (which may or may not include the production host); 2) one or more selectable markers; 3) one or more reporter genes; 4) one or more expression control sequences, such as, but not limited to, promoter sequences, enhancer sequences, terminator sequences, sequence for enhancing translation, etc.; and/or 5) one or more sequences for promoting integration of the nucleic acid sequences into a host genome, for example, one or more sequences having homology with one or more nucleotide sequences of the host microorganism. A vector can be an expression vector that includes one or more specified nucleic acid "expression control elements" that permit transcription and/or translation of a particular nucleic acid in a host cell. The vector can be a plasmid, a part of a plasmid, a viral construct, a nucleic acid fragment, or the like, or a combination thereof.

The vector can be a high copy number vector, a shuttle vector that can replicate in more than one species of cell, a cloning vector, an expression vector, an integration vector, or a combination thereof. Typically, the expression vector can include a nucleic acid comprising a gene of interest operably linked to a promoter in an "expression cassette," which can also include, but is not limited to, a PH domain encoding sequence, a transcriptional terminator, a ribosome binding site, a splice site or splicing recognition sequence, an intron, an enhancer, a polyadenylation signal, an internal ribosome entry site, and similar elements.

In one example, an expression cassette as provided herein comprises a promoter operably linked to a nucleotide sequence encoding a PH domain as described herein. The nucleotide sequence encoding a PH domain can further be operably linked to any gene of interest. In a particular aspect, the nucleotide sequence encoding a PH domain is selected from the group consisting of: a PH domain having at least 80% identity to SEQ ID NO:6 or a functional fragment thereof; a PH domain having at least 80% identity to SEQ ID NO:12 or a functional fragment thereof; a PH domain having at least 80% identity to SEQ ID NO:18 or a functional fragment thereof; a PH domain having at least 80% identity to SEQ ID NO:24 or a functional fragment thereof; a PH domain having at least 80% identity to SEQ ID NO:30 or a functional fragment thereof; a PH domain having at least 80% identity to SEQ ID NO:36 or a functional fragment thereof; a PH domain having at least 80% identity to SEQ ID NO:42 or a functional fragment thereof; and a PH domain having at least 80% identity to SEQ ID NO:48 or a functional fragment thereof.

Additionally, the present invention can involve recombinant microorganisms transformed with a vector comprising a gene of interest under control of a heterologous promoter. Alternatively, if the vector does not contain a promoter operably linked with an isolated nucleic acid comprising a gene of interest, the isolated nucleic acid can be transformed into the microorganisms or host cells such that it becomes operably linked to an endogenous promoter by homologous recombination, site specific integration, and/or vector integration.

Additionally, the present invention provides recombinant microorganisms or host cells transformed with a vector comprising a gene of interest that is operably linked to one or more expression control elements. In some instances, it can be advantageous to express the protein at a certain point during the growth of the recombinant microorganism, e.g., to minimize any deleterious effects on the growth of the recombinant microorganism and/or to maximize production of TAG. In such instances, one or more exogenous genes introduced into the recombinant microorganism or host cell can be operably linked to an inducible promoter, which mediates transcription of an operably linked gene in response to a particular stimulus.

Vectors provided herein can additionally or alternatively include a selectable marker. Transformed cells can be selected based upon the ability to grow in the presence of the antibiotic and/or other selectable marker under conditions in which cells lacking the resistance cassette or auxotrophic marker could not grow. Further, a non-selectable marker may be present on a vector, such as a gene encoding a fluorescent protein or enzyme that generates a detectable reaction product.

A vector comprising an isolated nucleic acid comprising a gene of interest can also be an integration vector that includes one or more sequences that promote integration of the gene of interest or a gene expression cassette into the genome of the host microorganism or host cell. For example, an integration vector can include at least one sequence of at least 20, at least 30, at least 40, at least 50, at least 100, at least 200, at least 300, at least 400, at least 500, or at least 600 nucleotides with homology to a sequence in the genome of the host organism to allow integration of the gene of interest or gene expression cassette into the genome of the host microorganism or host cell to occur via homologous recombination. In some examples, the gene or gene expression cassette is flanked by sequences homologous to a region of the host chromosome to promote integration of the gene of interest or gene expression cassette into the host chromosome. Alternatively or in addition, an integration vector can include one or more sequences that promote site-specific recombination or random integration such as, but not limited to, sequences recognized by recombinases, integrases, or transposases. In some embodiments, the integration vector can further include a gene encoding a recombinase, integrase, or transposase.

Microorganisms and Host Cells and Cultures

The present invention also provides recombinant microorganisms and host cells that comprise a nucleic acid molecule encoding a polypeptide having acyltransferase activity, wherein the polypeptide comprises a PH domain.

In one aspect, provided herein is a recombinant microorganism that includes a non-native gene encoding a polypeptide having acyltransferase activity and having a native or heterologous PH domain, such as a DGAT that includes a native or heterologous PH domain. The recombinant microorganism can produce a greater amount of TAG than is produced by a microorganism substantially identical to the recombinant microorganism, but lacking a non-native gene encoding a polypeptide having acyltransferase activity that includes a PH domain. The recombinant microorganism that includes a non-native gene encoding a polypeptide having acyltransferase activity, such as a DGAT, can produce a greater amount of TAG than is produced by a substantially identical microorganism when the microorganisms are cultured under conditions in which inorganic carbon is substantially the sole source of carbon in the growth medium. Additionally, the recombinant microorganism that includes a non-native gene encoding a polypeptide having acyltransferase activity, such as a DGAT, that includes a PH domain, can produce a greater amount of TAG than is produced by a microorganism substantially identical to the recombinant microorganism but lacking a non-native gene that encodes an acyltranferase that has a PH domain, when the microorganisms are cultured under nitrogen replete conditions. For example, a culture of a recombinant microorganism of the present invention can be maintained under nutrient replete conditions during the production period, and the culture can produce TAG during a culture period in which the cells of the culture are dividing.

A non-native gene encoding a polypeptide having acyltransferase activity that includes a PH domain can encode any polypeptide having acyltransferase activity, for example, a MGAT, DGAT1, DGAT2, DGAT3, WS/DGAT, DGAcT, DGTA, PDAT, LPLAT, LPAAT, or GPAT. The PH domain can be native to the acyltransferase (e.g., can be a DGAT1 gene that naturally includes a PH domain, or a variant thereof) or can be heterologous with respect to the acyltransferase, e.g., the gene encoding the acyltransferase is engineered to include a sequence encoding a PH domain. In some examples, the non-native gene can encode a DGAT that is a variant of a naturally-occurring DGAT, such as a DGAT having at least 80%, at least 85%, at least 90%, or at least 95% amino acid sequence identity to a naturally-occurring DGAT or an active fragment thereof. The non-native gene can encode a DGAT that is a truncated variant of a naturally-occurring DGAT, such as an N-terminally or C-terminally truncated variant of a naturally-occurring DGAT or a DGAT having at least 80%, at least 85%, at least 90%, or at least 95% amino acid sequence identity to a naturally-occurring DGAT. Additionally or alternatively, a recombinant microorganism or host cell can include a non-native gene encoding a DGAT that has at least 80%, at least 85%, at least 90%, or at least 95% amino acid sequence identity to a naturally-occurring DGAT or an active fragment thereof and can further include one or more additional amino acid sequences, such as, but not limited to, one or more amino acid sequences that can direct the DGAT to a location within the cell, such as, for example, a plastid or a region thereof and/or the endoplasmic reticulum or a region thereof.

Acyltransferase genes utilized according to the present invention may be isolated from any organism, including eukaryotic and prokaryotic organisms, and can be any disclosed herein. Eukaryotic organisms having an acyltransferase gene are well-known in the art, and include various animals (e.g., mammals, fruit flies, nematodes), plants, parasites, and fungi (e.g., yeast such as *Saccharomyces cerevisiae* and *Schizosaccharomyces pombe*). Examples of prokaryotic organisms include certain actinomycetes, a group of Gram-positive bacteria with high G+C ratio, such as those from the representative genera *Actinomyces, Arthrobacter, Corynebacterium, Frankia, Micrococcus, Mocrimonospora, Mycobacterium, Nocardia, Propionibacterium, Rhodococcus* and *Streptomyces*. Particular examples of actinomycetes that have one or more genes encoding polypeptides having acyltransferase activity include, for example, *Mycobacterium tuberculosis, M. avium, M. smegmatis, Micromonospora echinospora, Rhodococcus opacus, R. ruber,* and *Streptomyces lividans*. Examples of prokaryotic organisms that encode one or more enzymes having a DGAT activity include members of the genera *Acinetobacter*, such as *A. calcoaceticus, A. baumanii,* and *A. baylii*. In certain embodiments, a DGAT enzyme is isolated from *Acinetobacter baylii* sp. ADP1, a gram-negative triglyceride forming prokaryote, which contains a well-characterized DGAT (AtfA).

In further examples, a recombinant microorganism or host cell as provided herein can include a non-native gene encoding a type-1 or a type-2 DGAT from a eukaryote, such as, for example, a fungus, yeast, protozoan, animal, alga, or plant, or a variant thereof having at least 80%, at least 85%, at least 90%, or at least 95% amino acid sequence identity to the naturally-occurring DGAT1, DGAT2, or DGAT3 or an active fragment thereof, and can include a deletion, for example, a truncation, with respect to the naturally-occurring DGAT amino acid sequence, and/or can optionally include one or more additional sequences, such as, but not limited to, a PH domain. In some examples, the DGAT1, DGAT2, WS/DGAT, or DGAT3 encoded by the non-native gene comprises a sequence at least 80%, at least 85%, at least 90%, or at least 95% identical to SEQ ID NO:2, SEQ ID NO:8, SEQ ID NO:14, SEQ ID NO:20, SEQ ID NO:26, SEQ ID NO:32, SEQ ID NO:38, SEQ ID NO:44, and/or a functional fragment thereof. In some examples, the DGAT1, DGAT2, WS/DGAT, or DGAT3 encoded by the non-native gene comprises a sequence at least 80%, at least 85%, at least 90%, or at least 95% identical to SEQ ID NO:4, SEQ ID NO:10, SEQ ID NO:16, SEQ ID NO:22, SEQ ID NO:28, SEQ ID NO:34, SEQ ID NO:40, SEQ ID NO:46, and/or a functional fragment thereof. Alternatively or additionally, a recombinant eukaryotic alga as provided herein can include a non-native gene encoding a wax synthase/diacylglycerol transferase (WS/DGAT) from a prokaryote or a variant thereof having at least 80%, at least 85%, at least 90%, or at least 95% amino acid sequence identity to the naturally-occurring prokaryotic WS/DGAT or a functional fragment thereof, and may optionally comprise a PH domain sequence.

The recombinant host cell may comprise, e.g., any of the nucleic acid sequences encoding a DGAT described herein and may comprise any of the nucleic acid sequences encoding a PH domain described herein (e.g., SEQ ID NOs:6, 12, 18, 24, 30, 36, 42, and/or 48) or variants thereof. Further, the recombinant host cells may comprise, e.g., any of the vectors described herein. In some examples, the recombinant host cell includes a microalgal or heterokont DGAT1 gene that includes a PH domain or a variant thereof, and may include a DGAT gene of a green alga (Chlorophyte division) that includes a PH domain.

The recombinant microorganisms and host cells of the present invention may comprise any acyltransferase comprising any heterologous PH domain. By way of non-limiting example, a recombinant microorganism according to the present invention may comprise a polypeptide having acyltransferase activity, for example a DGAT1, comprising a PH domain selected from the group consisting of: a PH domain having at least 80% identity to SEQ ID NO:6; a PH domain having at least 80% identity to SEQ ID NO:12; a PH domain having at least 80% identity to SEQ ID NO:18; a PH domain having at least 80% identity to SEQ ID NO:24; a PH domain having at least 80% identity to SEQ ID NO:30; a PH domain having at least 80% identity to SEQ ID NO:36; a PH domain having at least 80% identity to SEQ ID NO:42; and a PH domain having at least 80% identity to SEQ ID NO:48.

Alternatively or additionally, the recombinant microorganisms and host cells of the present invention may comprise a polypeptide having acyltransferase activity, for example a DGAT1, comprising a PH domain selected from the group consisting of: a PH domain having at least 95% identity to SEQ ID NO:6; a PH domain having at least 95% identity to SEQ ID NO:12; a PH domain having at least 95% identity to SEQ ID NO:18; a PH domain having at least 95% identity to SEQ ID NO:24; a PH domain having at least 95% identity to SEQ ID NO:30; a PH domain having at least 95% identity to SEQ ID NO:36; a PH domain having at least 95% identity to SEQ ID NO:42; and a PH domain having at least 95% identity to SEQ ID NO:48.

In certain embodiments, the recombinant microorganism or host cell comprises a polypeptide having acyltransferase activity comprising a heterologous PH domain because the cell, or a progenitor, is transformed with a nucleic acid sequence encoding a heterologous PH domain, which integrates into an endogenous acyltransferase gene of the recombinant microorganism or host cell.

In some aspects, the nucleic acid sequence encoding the acyltransferase gene, for example a DGAT gene, is heterologous with respect to the recombinant host cell, and can be derived from any species, including plant, animal, or microbial species.

Additionally or alternatively, the recombinant microorganisms or host cells of the present invention may comprise an acyltransferase gene, for example a DGAT gene, that is homologous with respect to the host organism. For example, the acyltransferase gene may be native to the host microorganism and is introduced into the recombinant microorganism in an expression cassette that allows non-native patterns of regulated expression or overexpression of the endogenous acyltransferase gene. Additionally, the acyltransferase gene, for example a DGAT gene, may be endogenous to the microorganism and a heterologous promoter may be introduced into the host microorganism such that it becomes juxtaposed with and operably linked to the endogenous acyltransferase gene.

The recombinant microorganism can comprise a non-native gene encoding:

a DGAT with at least 40%, at least 45%, at least 50%, at least 55%, at least 60%, at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to SEQ ID NO:2;

a DGAT with at least 40%, at least 45%, at least 50%, at least 55%, at least 60%, at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to SEQ ID NO:4;

a DGAT with at least 40%, at least 45%, at least 50%, at least 55%, at least 60%, at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to SEQ ID NO:8;

a DGAT with at least 40%, at least 45%, at least 50%, at least 55%, at least 60%, at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to SEQ ID NO:10;

a DGAT with at least 40%, at least 45%, at least 50%, at least 55%, at least 60%, at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to SEQ ID NO:14;

a DGAT with at least 40%, at least 45%, at least 50%, at least 55%, at least 60%, at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to SEQ ID NO:16;

a DGAT with at least 40%, at least 45%, at least 50%, at least 55%, at least 60%, at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to SEQ ID NO:20;

a DGAT with at least 40%, at least 45%, at least 50%, at least 55%, at least 60%, at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to SEQ ID NO:22;

a DGAT with at least 40%, at least 45%, at least 50%, at least 55%, at least 60%, at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to SEQ ID NO:26;

a DGAT with at least 40%, at least 45%, at least 50%, at least 55%, at least 60%, at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to SEQ ID NO:28;

a DGAT with at least 40%, at least 45%, at least 50%, at least 55%, at least 60%, at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to SEQ ID NO:32;

a DGAT with at least 40%, at least 45%, at least 50%, at least 55%, at least 60%, at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to SEQ ID NO:34;

a DGAT with at least 40%, at least 45%, at least 50%, at least 55%, at least 60%, at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to SEQ ID NO:38;

a DGAT with at least 40%, at least 45%, at least 50%, at least 55%, at least 60%, at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to SEQ ID NO:40;

a DGAT with at least 40%, at least 45%, at least 50%, at least 55%, at least 60%, at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to SEQ ID NO:44;

a DGAT with at least 40%, at least 45%, at least 50%, at least 55%, at least 60%, at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to SEQ ID NO:46; and/or a functional fragment of any one of the DGAT listed sequences.

Additionally, the recombinant microorganism can comprise a non-native gene encoding the DGAT of SEQ ID NOs: 2, 4, 8, 10, 14, 16, 20, 22, 26, 28, 32, 34, 38, 40, 44, and/or 46.

Alternatively, the recombinant microorganism can comprise a non-native gene encoding a DGAT with at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to SEQ ID NOs:2, 4, 8, 10, 14, 16, 20, 22, 26, 28, 32, 34, 38, 40, 44, and/or 46; and/or can encode a DGAT with at least 90%, at least 95%, at least 96%, at least 97%, at least 98%, or at least 99% sequence identity to SEQ ID NOs:2, 4, 8, 10, 14, 16, 20, 22, 26, 28, 32, 34, 38, 40, 44, and/or 46.

Alternatively or additionally, the recombinant microorganisms or host cells of the present invention comprise a nucleic acid molecule encoding a polypeptide having DGAT1 activity comprising a sequence selected from the group consisting of: an amino acid sequence having at least 80% identity to SEQ ID NO:2 or a functional fragment thereof; an amino acid sequence having at least 80% identity to SEQ ID NO:8 or a functional fragment thereof; an amino acid sequence having at least 80% identity to SEQ ID NO:14 or a functional fragment thereof; an amino acid sequence having at least 80% identity to SEQ ID NO:20 or a functional fragment thereof; an amino acid sequence having at least 80% identity to SEQ ID NO:26 or a functional fragment thereof; and an amino acid sequence having at least 80% identity to SEQ ID NO:32 or a functional fragment thereof.

Alternatively or additionally, the recombinant microorganism or host cell of the present invention comprises a nucleic acid molecule encoding a polypeptide having DGAT1 activity comprising a sequence selected from the group consisting of: an amino acid sequence having at least 95% identity to SEQ ID NO:2 or a functional fragment thereof; an amino acid sequence having at least 95% identity to SEQ ID NO:8 or a functional fragment thereof; an amino acid sequence having at least 95% identity to SEQ ID NO:14 or a functional fragment thereof; an amino acid sequence having at least 95% identity to SEQ ID NO:20 or a functional fragment thereof; an amino acid sequence having at least 95% identity to SEQ ID NO:26 or a functional fragment thereof; and an amino acid sequence having at least 95% identity to SEQ ID NO:32 or a functional fragment thereof.

Recombinant microorganisms or host cells may be of prokaryotic or eukaryotic origin, including, without limitation, fungi, heterokonts, algae, eubacteria, archaebacteria, green nonsulfur bacteria, purple nonsulfur bacteria, or cyanobacteria.

Non-photosynthetic microorganisms and host cells such as fungi and non-algal stramenophiles are considered as hosts that can include non-native acyltransferase genes. Oleaginous yeasts, including but not limited to *Aspergillus niger, Yarrowia lipolytica, Cryptococcus curvatus, Cryptococcus terricolus, Candida* species, *Lipomyces starkeyi, Lipomyces lipofer, Endomycopsis vernalis, Rhodotorula glutinis*, and *Rhodotorula gracilis* or other fungi or yeasts, including but not limited to species of *Aspergillus, Trichoderma, Neurospora, Fusarium, Humicola, Rhizomucor, Kluyveromyces, Pichia, Mucor, Myceliophtora, Penicillium, Phanerochaete, Chrysosporium, Saccharomyces*, and *Schizosaccharomyces*, are also encompassed as microorganisms and host cells. Further considered are Labyrinthulomycete species (e.g., *Thraustichytrium*, *Ulkenia*, and *Schizochytrium* species).

In some embodiments, the microorganism or host cell can be a bacterium, such as, but not limited to, an *Acetobacter*, *Acinetobacter*, *Arthrobacter*, *Bacillus*, *Brevibacterium*, *Chromatium*, *Chlorobium*, *Clostridium*, *Corynebacterium*, *Deinococcus*, *Delftia*, *Desulfovibrio*, *Enterococcus*, *Escherichia*, *Kineococcus*, *Klebsiella*, *Lactobacillus*, *Lactococcus*, *Micrococcus*, *Mycobacterium*, *Jeotgalicoccus*, *Paenibacillus*, *Propionibacter*, *Pseudomonas*, *Rhodopseudomonas*, *Rhodobacter*, *Rhodococcus*, *Rhodospirillium*, *Rhodomicrobium*, *Salmonella*, *Serratia*, *Shewanella*, *Stenotrophomonas*, *Streptomyces*, *Streptococcus*, *Vibrio*, or *Zymomonas* species. Photosynthetic bacteria, including for example, green sulfur bacteria, purple sulfur bacteria, green nonsulfur bacteria, purple nonsulfur bacteria, or cyanobacteria can be used.

Recombinant host cells can be photosynthetic organisms. Photosynthetic organisms include, by way of example, higher plants (i.e., vascular plants), bryophytes, algae, and photosynthetic bacteria. The term "algae" includes, without limitation, cyanobacteria (Cyanophyceae), green algae (Chlorophyceae), yellow-green algae (Xanthophyceae), golden algae (Chrysophyceae), brown algae (Phceophyceae), red algae (Rhodophyceae), diatoms (Bacillariophyceae), and "picoplankton" (Prasinophyceae and Eustigmatophyceae). Also included in the term algae are members of the taxonomic classes Dinophyceae, Cryptophyceae, Euglenophyceae, Glaucophyceae, and Prymnesiophyceae. Microalgae are unicellular or colonial algae that can be seen as single organisms only with the aid of a microscope. Microalgae include both eukaryotic and prokaryotic algae (e.g., cyanobacteria).

Cyanobacterial species that can be used for production of TAG include, without limitation, *Agmenellum*, *Anabaena*, *Anabaenopsis*, *Anacystis*, *Aphanizomenon*, *Arthrospira*, *Asterocapsa*, *Borzia*, *Calothrix*, *Chamaesiphon*, *Chroococcus*, *Chlorogloeopsis*, *Chroococcidiopsis*, *Chroococcus*, *Crinalium*, *Cyanobacterium*, *Cyanobium*, *Cyanocystis*, *Cyanospira*, *Cyanothece*, *Cylindrospermopsis*, *Cylindrospermum*, *Dactylococcopsis*, *Dermocarpella*, *Fischerella*, *Fremyella*, *Geitleria*, *Geitlerinema*, *Gloeobacter*, *Gloeocapsa*, *Gloeothece*, *Halospirulina*, *Iyengariella*, *Leptolyngbya*, *Limnothrix*, *Lyngbya*, *Microcoleus*, *Microcystis*, *Myxosarcina*, *Nodularia*, *Nostoc*, *Nostochopsis*, *Oscillatoria*, *Phormidium*, *Planktothrix*, *Pleurocapsa*, *Prochlorococcus*, *Prochloron*, *Prochlorothrix*, *Pseudanabaena*, *Rivularia*, *Schizothrix*, *Scytonema*, *Spirulina*, *Stanieria*, *Starria*, *Stigonema*, *Symploca*, *Synechococcus*, *Synechocystis*, *Thermosynechococcus*, *Tolypothrix*, *Trichodesmium*, *Tychonema* and *Xenococcus*. For example, the recombinant photosynthetic microorganism can be a *Cyanobium*, *Cyanothece*, or *Cyanobacterium* species, or further alternatively, the recombinant photosynthetic microorganism can be a *Gloeobacter*, *Lyngbya* or *Leptolyngba* species. Alternatively, the recombinant photosynthetic microorganism can be a *Synechococcus*, *Synechocystis*, or *Thermosynechococcus* species. A number of cyanobacterial species are known and have been manipulated using molecular biological techniques, including the unicellular cyanobacteria *Synechocystis* sp. PCC6803 and *Synechococcus* elongates PCC7942, whose genomes have been completely sequenced.

Eukaryotic microalgae for use in the invention, include without limitation, *Achnanthes*, *Amphiprora*, *Amphora*, *Ankistrodesmus*, *Asteromonas*, *Boekelovia*, *Borodinella*, *Botryococcus*, *Bracteococcus*, *Chaetoceros*, *Carteria*, *Chlamydomonas*, *Chlorococcum*, *Chlorogonium*, *Chlorella*, *Chroomonas*, *Chrysosphaera*, *Cricosphaera*, *Crypthecodinium*, *Cryptomonas*, *Cyclotella*, *Dunaliella*, *Ellipsoidon*, *Emiliania*, *Eremosphaera*, *Ernodesmius*, *Euglena*, *Franceia*, *Fragilaria*, *Gloeothamnion*, *Haematococcus*, *Halocafeteria*, *Hymenomonas*, *Isochrysis*, *Lepocinclis*, *Micractinium*, *Monoraphidium*, *Nannochloris*, *Nannochloropsis*, *Navicula*, *Neochloris*, *Nephrochloris*, *Nephroselmis*, *Nitzschia*, *Ochromonas*, *Oedogonium*, *Oocystis*, *Ostreococcus*, *Pavlova*, *Parachlorella*, *Pascheria*, *Phaeodactylum*, *Phagus*, *Picochlorum*, *Platymonas*, *Pleurochrysis*, *Pleurococcus*, *Prototheca*, *Pseudochlorella*, *Pseudoneochloris*, *Pyramimonas*, *Pyrobotrys*, *Scenedesmus*, *Schizochytrium*, *Skeletonema*, *Spyrogyra*, *Stichococcus*, *Tetraselmis*, *Viridiella*, or *Volvox* species. In a particular aspect, *Nannochloropsis* is used as the host cell, i.e. a recombinant algal cell. Illustrative examples of recombinant microorganisms that express a non-native acyltransferase gene include recombinant microorganisms such as but not limited to *Nannochloropsis gaditana* that express a non-native gene encoding a DGAT having at least 85% identity, for example at least 90% or at least 95% identity to SEQ ID NOs:2, 4, 8, 10, 14, 16, 20, 22, 26, 28, 32, 34, 38, 40, 44, and/or 46.

Additionally or alternatively, the recombinant microorganism can comprise a non-native gene, in addition to the non-native acyltransferase, which encodes a polypeptide for the production of a lipid, such as, for example, a non-native gene encoding an enzyme for the production of fatty acids, fatty acid derivatives, and/or glycerolipids in the production of a fatty acid product not normally produced by the microorganism. For example, a recombinant microorganism as disclosed herein can include a non-native gene encoding a DGAT1 and can further include a non-native gene encoding an enzyme that participates in the production of glycerolipids, including, but not limited to, a MGAT, DGAT2, DGAT3, WS/DGAT, DGAcT, DGTA, PDAT, LPLAT, LPAAT, GPAT, and/or another DGAT1.

Additionally, the recombinant microorganism can comprise a non-native gene encoding the PH domain of SEQ ID NOs:6, 12, 18, 24, 30, 36, 42, and/or 48.

Alternatively, the recombinant microorganism can comprise a non-native gene encoding a PH domain with at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to SEQ ID NOs:6, 12, 18, 24, 30, 36, 42, and/or 48; and/or can encode a PH domain with at least 90%, at least 95%, at least 96%, at least 97%, at least 98%, or at least 99% sequence identity to SEQ ID NOs:6, 12, 18, 24, 30, 36, 42, and/or 48.

Illustrative examples of recombinant microorganisms that express a PH domain gene include recombinant microorganisms such as but not limited to *Nannochloropsis gaditana* that express a gene encoding a polypeptide having an acyltransferase activity and comprising a heterologous PH domain having at least 85% identity, for example at least 90% or at least 95% identity to SEQ ID NOs:6, 12, 18, 24, 30, 36, 42, and/or 48.

Additionally or alternatively, the recombinant microorganism can comprise a gene which encodes a polypeptide for the production of a lipid, such as, for example, an enzyme for the production of fatty acids, fatty acid derivatives, and/or glycerolipids in the production of a fatty acid product not normally produced by the microorganism, wherein said polypeptide comprises a heterologous PH domain. For example, a recombinant microorganism as disclosed herein can include a gene encoding a non-native DGAT1 and can further optionally include a gene encoding an enzyme that participates in the production of glycerolipids, including, but not limited to, a MGAT, DGAT2, DGAT3, WS/DGAT, DGAcT, DGTA, PDAT, LPLAT, LPAAT, GPAT, and/or another DGAT1, wherein said enzyme comprises a heterologous PH domain.

In further examples, the recombinant microorganism produces a greater amount of TAG than is produced by a control algal cell. In some embodiments, a recombinant microorganism or host cell as provided herein can comprise a non-native gene encoding an acyltransferase, such as DGAT, wherein the recombinant microorganism can produce a greater amount of triglyceride than is produced by a control recombinant microorganism or host cell substantially identical to the recombinant recombinant microorganism or host cell, but lacking a non-native gene encoding an acyltransferase. For example the recombinant algal cell comprising a DGAT as described herein results in a higher production level of TAG by the recombinant microorganism than the production level in a control microorganism, where the control microorganism is cultured under substantially the same conditions and is substantially identical to the microorganism expressing the non-native DGAT gene in all respects, with the exception that the control microorganism does not express a non-native DGAT gene. In particular examples, the recombinant microorganism can be a photosynthetic microorganism such as a recombinant algal cell.

Alternatively or additionally, a recombinant microorganism or host cell as provided herein can comprise a non-native gene encoding an acyltransferase, such as DGAT, comprising a heterologous PH domain and can produce a greater amount of triglyceride than is produced by a control recombinant microorganism or host cell substantially identical to the recombinant microorganism or host cell, but lacking the heterologous PH domain.

In some aspects, the amount of protein produced by a culture of the recombinant microorganism expressing a non-native acyltransferase gene comprising a PH domain is at least 10%, at least 15%, at least 20%, at least 25%, at least 30%, at least 40%, at least 50%, at least 60%, at least 65%, at least 70%, at least 75%, at least 80%, at least 90%, at least 95%, at least 100%, at least 125%, at least 150%, at least 175%, at least 200%, at least 225%, at least 250%, at least 275%, at least 300%, at least 325%, at least 350%, at least 375%, at least 400%, at least 425%, at least 450%, at least 475%, at least 500%, at least 525%, at least 550%, at least 575%, at least 600%, at least 625%, at least 650%, at least 675%, at least 700%, at least 725%, at least 750%, at least 775%, at least 800%, at least 825%, at least 850%, at least 875%, at least 900%, at least 925%, at least 950%, at least 975%, or at least 1000% greater than the amount of protein produced by a control host cell that does not express the acyltransferase gene comprising a heterologous PH domain.

In some aspects, the amount of TAG produced by a culture of the recombinant microorganism expressing a DGAT comprising a heterologous PH domain is at least 10%, at least 15%, at least 20%, at least 25%, at least 30%, at least 40%, at least 50%, at least 60%, at least 65%, at least 70%, at least 75%, at least 80%, at least 90%, at least 95%, at least 100%, at least 125%, at least 150%, at least 175%, at least 200%, at least 225%, at least 250%, at least 275%, at least 300%, at least 325%, at least 350%, at least 375%, at least 400%, at least 425%, at least 450%, at least 475%, at least 500%, at least 525%, at least 550%, at least 575%, at least 600%, at least 625%, at least 650%, at least 675%, at least 700%, at least 725%, at least 750%, at least 775%, at least 800%, at least 825%, at least 850%, at least 875%, at least 900%, at least 925%, at least 950%, at least 975%, or at least 1000% greater than the amount of TAG produced by a control host cell that does not express the DGAT comprising a heterologous PH domain.

In certain aspects, the recombinant microorganism can produce more TAG when compared to a control host cell under nitrogen replete conditions. Additionally, in certain examples, the recombinant microorganism can produce a greater amount of TAG after about one, or two or three days of culturing under nitrogen replete conditions.

Additionally, a culture of a recombinant photosynthetic microorganism as described herein is provided. The culture can produce a greater amount of TAG than is produced by a control culture substantially identical in all respects except that the recombinant photosynthetic microorganism of the control culture does not include or does not express the gene encoding a non-native DGAT or the gene encoding a DGAT comprising a heterologous PH domain. Preferably, a culture of the recombinant photosynthetic microorganism that includes a gene encoding a non-native DGAT or a DGAT comprising a heterologous PH domain (and optionally a non-native gene encoding a polypeptide that participates in the production of a lipid) produces a greater amount of fatty acid product, for example TAG, than is produced by a culture of an otherwise substantially identical recombinant photosynthetic microorganism that lacks the non-native gene encoding a DGAT. For example, a photoautotrophic culture of the recombinant photosynthetic microorganism can preferably produce a greater amount of a fatty acid product, for example TAG, than is produced by a photoautotrophic culture of an otherwise identical photosynthetic microorganism that lacks the gene encoding the non-native DGAT or the DGAT comprising a heterologous PH domain. Additionally or alternatively, a culture of the recombinant photosynthetic microorganism can achieve a higher cell density while producing TAG under photoautotrophic conditions, e.g., using inorganic (non-reduced) carbon as the carbon source for production of the fatty acid product such as TAG.

Transformation of Microorganisms and Host Cells

A vector comprising an isolated nucleic acid comprising a gene of interest can be introduced into a host cell via conventional transformation and/or transfection techniques. The terms "transformation," "transfection," "conjugation," and "transduction," as used in the present context, are intended to comprise a multiplicity of methods known to those skilled in the art for the introduction of foreign nucleic acid (for example, exogenous DNA) into a host cell, including calcium phosphate and/or calcium chloride coprecipitation, DEAE-dextran-mediated transfection, lipofection, natural competence, chemically mediated transfer, electroporation, particle bombardment, or the like, or combinations thereof. Examples of suitable methods for the transformation and/or transfection of host cells, e.g., can be found in Molecular Cloning—A Laboratory Manual (2010), Cold Spring Harbor Laboratory Press.

Host cells such as plants for use in the invention can be transformed by any feasible means, including, without limitation, the use of *Agrobacterium*, particle gun-mediated transformation, laser-mediated transformation, or electroporation. Algae and photosynthetic bacteria can be transformed by any suitable methods, including, as nonlimiting examples, natural DNA uptake (Chung et al. (1998) *FEMS Microbiol. Lett.* 164:353-61; Frigaard et al. (2004) *Methods Mol. Biol.* 274: 325-40; Zang et al. (2007) *J. Microbiol.* 45:241-45), conjugation, transduction, glass bead transformation (Kindle et al. (1989) *J. Cell Biol.* 109:2589-601; Feng et al. (2009) *Mol. Biol. Rep.* 36:1433-39; U.S. Pat. No. 5,661,017), silicon carbide whisker transformation (Dunahay et al. (1997) *Methods Mol. Biol.* 62:503-09), biolistics (Dawson et al. (1997) *Curr. Microbiol.* 3: 356-62; Hallmann et al. (1997) *Proc. Nat'l. Acad. USA* 94:7469-74; Jakobiak et al. (2004) *Protist* 155:

381-93; Tan et al. (2005) *J. Microbiol.* 43:361-65; Steinbrenner et al. (2006) *Appl. Environ. Microbiol.* 72:7477-84; Kroth (2007) *Methods Mol. Biol.* 390:257-67; U.S. Pat. No. 5,661, 017) electroporation (Kjaerulff et al. (1994) *Photosynth. Res.* 41:277-83; Iwai et al. (2004) *Plant Cell. Physiol.* 45:171-75; Ravindran et al. (2006) *J. Microbiol. Methods* 66:174-76; Sun et al. (2006) *Gene* 377:140-49; Wang et al. (2007) *Appl. Microbiol. Biotechnol.* 76:651-57; Chaurasia et al. (2008) *J. Microbiol. Methods* 73:133-41; Ludwig et al. (2008) *Appl. Microbiol. Biotechnol.* 78:729-35), laser-mediated transformation, or incubation with DNA in the presence of or after pre-treatment with any of poly(amidoamine) dendrimers (Pasupathy et al. (2008) *Biotechnol. J.* 3:1078-82), polyethylene glycol (Ohnuma et al. (2008) *Plant Cell. Physiol.* 49:117-20), cationic lipids (Muradawa et al. (2008) *J. Biosci. Bioeng.* 105:77-80), dextran, calcium phosphate, or calcium chloride (Mendez-Alvarez et al. (1994) *J. Bacteriol.* 176:7395-97), optionally after treatment of the cells with cell wall-degrading enzymes (Perrone et al. (1998) *Mol. Biol. Cell* 9:3351-65). *Agrobacterium*-mediated transformation can also be performed on algal cells, for example after removing or wounding the algal cell wall (e.g., WO 2000/62601; Kumar et al. (2004) *Plant Sci.* 166:731-38). Biolistic methods are particularly successful for transformation of the chloroplasts of plant and eukaryotic algal species (see, for example, Ramesh et al. (2004) *Methods Mol. Biol.* 274:301-07; Doestch et al. (2001) *Curr. Genet.* 39:49-60; U.S. Pat. No. 7,294,506; WO 2003/091413; WO 2005/005643; WO 2007/133558; and WO 2011/034863, all incorporated herein by reference in their entireties).

Methods of Peptide Targeting/Localization

The invention also encompasses methods of targeting or localizing a peptide to a membrane. This can be achieved by fusing a nucleic acid coding for a PH domain in frame with a nucleic acid coding for desired peptide to be expressed, and then expressing this fused nucleic acid in a cell of interest. For example, one can fuse a nucleic acid coding for a PH domain with at least 80% sequence identity to SEQ ID NOs:6, 12, 18, 24, 30, 36, 42, and/or 48 in frame with a nucleic acid coding for a desired peptide to be expressed, and then expressing this fused nucleic acid in a cell of interest. As used herein, a fused nucleic acid can be "expressed" by means described elsewhere herein and by other means well known to those skilled in the art.

Additionally, a method is provided of targeting or localizing an acyltransferase to a membrane surface comprising expressing an isolated or recombinant nucleic acid molecule encoding a polypeptide having acyltransferase activity, wherein the polypeptide comprises a heterologous PH domain. This can be achieved by fusing a nucleic acid coding for a PH domain with at least 80% sequence identity to SEQ ID NOs:6, 12, 18, 24, 30, 36, 42, and/or 48 in frame with a nucleic acid coding for a polypeptide having acyltransferase activity, such as a DGAT, to be expressed, and then expressing this fused nucleic acid in a cell of interest.

SEQ ID NOs:6, 12, 18, 24, 30, 36, 42, and 48 comprise PH domains isolated from a variety of algal species. While the invention is not bound by any one theory, it is hypothesized that a protein comprising one or more of these PH domains is directed, by virtue of the PH domain's affinity for particular lipid compositions, to a membrane or membrane region enriched in substrates for lipid biosynthesis.

In some examples, the protein to which the PH domain is fused can be a MGAT, DGAT1, DGAT2, DGAT3, WS/DGAT, DGAcT, DGTA, PDAT, LPLAT, LPAAT, and/or GPAT. While the invention is not bound by any one theory, it is believed that the chloroplastic environment is rich in substrate pools for acetyl coenzyme A, so TAG production can be enhanced by targeting a DGAT to the endoplasmic reticulum or a region thereof, the chloroplast envelope, or a region of the plasma membrane.

Methods of Producing Triglyceride (TAG)

The invention also encompasses methods of producing TAG by culturing the recombinant microorganisms and host cells described herein, under conditions in which TAG is produced. The present invention further encompasses methods of producing TAG by culturing recombinant microorganisms and host cells under conditions in which TAG is produced, wherein the recombinant microorganisms and host cells comprise DGAT enzymes comprising heterologous PH domains.

For example, by culturing a recombinant microorganism comprising a recombinant DGAT selected from the group consisting of SEQ ID NOs:2, 8, 14, 20, 26, and 32, TAG production can be enhanced relative to production achieved from a substantially identical culture of a control microorganism that lacks the recombinant DGAT. For example, the recombinant microorganism to be used in the methods of the present invention can be selected from the group consisting of a recombinant microorganism that comprises a recombinant nucleic acid molecule that encodes a polypeptide having DGAT activity comprising a sequence selected from the group consisting of: an amino acid sequence having at least 80% identity to SEQ ID NO:2 or a functional fragment thereof; an amino acid sequence having at least 80% identity to SEQ ID NO:8 or a functional fragment thereof; an amino acid sequence having at least 80% identity to SEQ ID NO:14 or a functional fragment thereof; an amino acid sequence having at least 80% identity to SEQ ID NO:20 or a functional fragment thereof; an amino acid sequence having at least 80% identity to SEQ ID NO:26 or a functional fragment thereof; and an amino acid sequence having at least 80% identity to SEQ ID NO:32 or a functional fragment thereof. This microorganism can be cultured under conditions in which the recombinant nucleic acid molecule is expressed, to produce TAG.

Alternatively or additionally, the recombinant microorganism to be used in the methods of the present invention can be selected from the group consisting of a recombinant microorganism that comprises a recombinant nucleic acid molecule that encodes a polypeptide having DGAT activity comprising a sequence selected from the group consisting of: an amino acid sequence having at least 95% identity to SEQ ID NO:2 or a functional fragment thereof; an amino acid sequence having at least 95% identity to SEQ ID NO:8 or a functional fragment thereof; an amino acid sequence having at least 95% identity to SEQ ID NO:14 or a functional fragment thereof; an amino acid sequence having at least 95% identity to SEQ ID NO:20 or a functional fragment thereof; an amino acid sequence having at least 95% identity to SEQ ID NO:26 or a functional fragment thereof; and an amino acid sequence having at least 95% identity to SEQ ID NO:32 or a functional fragment thereof. This microorganism can be cultured under conditions in which the recombinant nucleic acid molecule is expressed, to produce TAG.

Alternatively or additionally, the recombinant microorganism to be used in the methods of the present invention can comprise a nucleic acid molecule encoding a polypeptide having acyltransferase activity, where the polypeptide comprises a heterologous PH domain. For example, the recombinant microorganism can comprising a nucleic acid molecule encoding a polypeptide having acyltransferase activity, where the polypeptide comprises: a PH domain having at least 80% identity to SEQ ID NO:6; a PH domain having at least 80% identity to SEQ ID NO:12; a PH domain having at least 80% identity to SEQ ID NO:18; a PH domain having at least 80% identity to SEQ ID NO:24; a PH domain having at least 80% identity to SEQ ID NO:30; a PH domain having at least 80% identity to SEQ ID NO:36; a PH domain having at least 80% identity to SEQ ID NO:42; and a PH domain having at least 80% identity to SEQ ID NO:48.

Alternatively or additionally, the recombinant microorganism to be used in the methods of the present invention can comprise a nucleic acid molecule encoding a polypeptide having acyltransferase activity, where the polypeptide comprises: a PH domain having at least 95% identity to SEQ ID NO:6; a PH domain having at least 95% identity to SEQ ID NO:12; a PH domain having at least 95% identity to SEQ ID NO:18; a PH domain having at least 95% identity to SEQ ID NO:24; a PH domain having at least 95% identity to SEQ ID NO:30; a PH domain having at least 95% identity to SEQ ID NO:36; a PH domain having at least 95% identity to SEQ ID NO:42; and a PH domain having at least 95% identity to SEQ ID NO:48.

In certain embodiments, the polypeptide having acyltransferase activity is a DGAT. In certain embodiments the recombinant microorganism is a microalga. In certain embodiments, the microalga belongs to a species of the genus *Achnanthes, Amphiprora, Amphora, Ankistrodesmus, Asteromonas, Boekelovia, Bolidomonas, Borodinella, Botrydium, Botryococcus, Bracteococcus, Chaetoceros, Carteria, Chlamydomonas, Chlorococcum, Chlorogonium, Chlorella, Chroomonas, Chrysosphaera, Cricosphaera, Crypthecodinium, Cryptomonas, Cyclotella, Dunaliella, Ellipsoidon, Emiliania, Eremosphaera, Ernodesmius, Euglena, Eustigmatos, Franceia, Fragilaria, Gloeothamnion, Haematococcus, Halocafeteria, Heterosigma, Hymenomonas, Isochrysis, Lepocinclis, Micractinium, Monoraphidium, Nannochloris, Nannochloropsis, Navicula, Neochloris, Nephrochloris, Nephroselmis, Nitzschia, Ochromonas, Oedogonium, Oocystis, Ostreococcus, Pavlova, Parachlorella, Pascheria, Pelagomonas, Phaeodactylum, Phagus, Picochlorum, Platymonas, Pleurochrysis, Pleurococcus, Prototheca, Pseudochlorella, Pseudoneochloris, Pseudostaurastrum, Pyramimonas, Pyrobotrys, Scenedesmus, Schizochlamydella, Skeletonema, Spyrogyra, Stichococcus, Tetrachlorella, Tetraselmis, Thalassiosira, Tribonema, Vaucheria, Viridiella, Vischeria,* or *Volvox.* In some particular embodiments, the microalga belongs to a species of the genus *Nannochloropsis,* particularly the species *N. gaditana.*

The methods can further comprise isolating TAG. Additionally, the expression of a polypeptide encoded by the nucleic acid molecules described herein can be induced in the recombinant microorganism to produce the TAG. In some examples, the TAG production occurs during nitrogen-replete culture conditions. Additionally or alternatively, the TAG production occurs during photoautotrophic culture conditions. Additionally or alternatively, the TAG production occurs while the host organism is actively growing and dividing.

As discussed previously, the present invention further provides for a culture comprising the recombinant microorganisms producing TAG. Culturing refers to the intentional fostering of growth (e.g., increases in cell size, cellular contents, and/or cellular activity) and/or propagation (e.g., increases in cell numbers via mitosis) of one or more cells by use of selected and/or controlled conditions. The combination of both growth and propagation may be termed proliferation. Non-limiting examples of selected and/or controlled conditions can include the use of a defined medium (with known characteristics such as pH, ionic strength, nitrogen concentration, and/or carbon source), specified temperature, oxygen tension, carbon dioxide levels, growth in a bioreactor, or the like, or combinations thereof. In some embodiments, the microorganism or host cell can be grown heterotrophically, using a reduced carbon source, or mixotrophically, using both light and a reduced carbon source. Additionally or alternately, the microorganism or host cell can be cultured photoautotrophically. When growing photoautotrophically, the microorganism can advantageously use light as an energy source. An inorganic carbon source, such as $CO_2$ or bicarbonate, can be used for synthesis of biomolecules by the microorganism. "Inorganic carbon", as used herein, includes carbon-containing compounds or molecules that cannot be used as a sustainable energy source by an organism. Typically "inorganic carbon" can be in the form of $CO_2$ (carbon dioxide), carbonic acid, bicarbonate salts, carbonate salts, hydrogen carbonate salts, or the like, or combinations thereof, which cannot be further oxidized for sustainable energy nor used as a source of reducing power by organisms. Under conditions in which inorganic carbon is substantially the sole source of carbon, if an organic carbon molecule or compound is provided in the culture medium, it generally cannot be taken up and/or metabolized by the cell for energy and/or typically is not present in an amount sufficient to provide sustainable energy for the growth of the cell culture. However, microorganisms growing heterotrophically do utilize organic carbon provided in the culture medium. Thus, the present invention includes a process for converting a carbon source to TAG comprising contacting the carbon source with a recombinant microorganism or host cell of the invention. In some aspects the carbon source is an inorganic carbon source and in other aspects the carbon source is an organic carbon source.

Microorganisms and host cells that can be useful in accordance with the methods of the present invention can be found in various locations and environments throughout the world. Without wishing to be bound by theory, it is observed that, perhaps as a consequence of their isolation from other species and their evolutionary divergence, the particular growth medium for optimal growth and generation of lipid and/or other hydrocarbon constituents can vary. In some cases, certain strains of microorganisms may be unable to grow in a particular growth medium because of the presence of some inhibitory component or the absence of some essential nutritional requirement of the particular strain of microorganism or host cell.

Solid and liquid growth media are generally available from a wide variety of sources, as are instructions for the preparation of particular media suitable for a wide variety of strains of microorganisms. For example, various fresh water and salt water media can include those described in Barsanti (2005) Algae: Anatomy, Biochemistry & Biotechnology (CRC Press) for media and methods for culturing algae. Algal media recipes can also be found at the websites of various algal culture collections, including, as nonlimiting examples, the UTEX Culture Collection of Algae (www.sbs.utexas.edu/utex/media.aspx) (visited 15 Nov. 2012); Culture Collection of Algae and Protozoa (www.ccap.ac.uk) (visited 15 Nov. 2012); and CAUP Culture Collection (botany.natur.cuni.cz/algo/caup-media.html) (visited 15 Nov. 2012).

In some embodiments, the nitrogen content of the medium can be "replete", that is, the level of nitrogen is not limiting to culture propagation. The amount of nitrogen required in a replete nitrogen culture medium can vary depending on the algal strain and other culture conditions, but preferably is at least about 250 µM, at least 500 µM, or at least 800 µM, such as at least 1 mM, at least 2 mM, at least 3 mM, at least 4 mM, at least 5 mM, at least 6 mM, at least 7 mM, or at least 8 mM nitrogen, which is preferably supplied as ammonia and/or nitrate, but can be supplied as any utilizable nitrogen source compound. In some embodiments, the culture medium can be nitrogen replete and can lack a supplementary organic carbon source. In some embodiments, the culture medium can be nutrient replete, where no nutrients (not including a carbon source) are limiting for culture propagation, and the culture medium can lack a supplementary organic carbon source.

In some examples, a culture medium used during at least a portion of the production period may be nitrogen limited but not necessarily nitrogen depleted. For example, the amount of nitrogen provided in the culture medium might permit culture proliferation but be less than the amount required for optimal growth (e.g., optimal rates of biomass accumulation or cell division). A "nitrogen deplete" medium does not include a nitrogen source that can be utilized by the microorganism for growth or culture propagation. A microorganism cultured in a nitrogen deplete medium experiences nitrogen starvation conditions.

The culture methods can include inducing expression of a particular gene described herein for the production of TAG, and/or regulating a metabolic pathway in the microorganism. Inducing expression can include adding a nutrient or compound to the culture, removing one or more components from the culture medium, increasing or decreasing light and/or temperature, and/or other manipulations that promote expression of the gene of interest. Such manipulations can largely depend on the nature of the (heterologous) promoter operably linked to the gene of interest.

In some embodiments of the present invention, the recombinant microorganisms or host cells can be cultured in a bioreactor. "Bioreactor" refers to an enclosure or partial enclosure in which cells are cultured, optionally in suspension and, when suspended, preferably in an aqueous liquid. The bioreactor can be used to culture microalgal cells through the various phases of their physiological cycle. Bioreactors can offer many advantages for use in heterotrophic growth and propagation methods. To produce biomass for use as food, microorganisms or host cells are preferably fermented in large quantities in liquid, such as in suspension cultures as an example. Bioreactors such as steel fermentors can accommodate very large culture volumes (40 kiloliter and greater capacity bioreactors can be used in various embodiments of the invention). Bioreactors can also typically allow for the control of one or more culture conditions such as temperature, pH, oxygen tension, carbon dioxide levels, and the like, as well as combinations thereof. Bioreactors can typically be configurable, for example, using ports attached to tubing, to allow gaseous components, such as $CO_2$, $CO_2$-enriched air, oxygen, and/or nitrogen, to be contacted with (e.g., bubbled through) a liquid culture. Other culture parameters, such as the pH of the culture media, the identity and/or concentration of trace elements and/or nutrients, the identity and/or concentration of other media constituents, or the like, or combinations thereof, can typically be more readily manipulated using a bioreactor.

Microorganisms and host cells can additionally or alternately be cultured in a bioreactor equipped with an artificial light source, a "photobioreactor," and/or can have one or more walls that is transparent enough to light, including sunlight, to enable, facilitate, and/or maintain acceptable microorganism growth. For TAG production, photosynthetic microorganisms or host cells can additionally or alternately be cultured in shake flasks, test tubes, vials, microtiter dishes, petri dishes, or the like, or combinations thereof.

Additionally or alternatively, recombinant photosynthetic microorganisms or host cells may be grown in ponds, canals, sea-based growth containers, trenches, raceways, channels, or the like, or combinations thereof. As with standard bioreactors, a source of inorganic carbon (such as, but not limited to, $CO_2$, bicarbonate, carbonate salts, and the like), including, but not limited to, air, $CO_2$-enriched air, flue gas, or the like, or combinations thereof, can be supplied to the culture. When supplying flue gas and/or other sources of inorganic that may contain CO in addition to $CO_2$, it may be necessary to pretreat such sources such that the CO level introduced into the (photo)bioreactor do not constitute a dangerous and/or lethal dose with respect to the growth and/or survival of the microorganisms.

The methods include culturing a recombinant microorganism, such as a photosynthetic microorganism, such as, for example, an algae, that expresses a protein as described herein to produce TAG, in which the method results in production of at least 0.1%, at least 0.5%, at least 1%, at least 2%, at least 3%, at least 4%, at least 5%, at least 6%, at least 7%, at least 8%, at least 9%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 100%, at least 110%, at least 120%, at least 130%, at least 140%, at least 150%, at least 160%, at least 170%, at least 180%, at least 190%, at least 200%, at least 300%, at least 400%, at least 500%, at least 600%, at least 700%, at least 800%, at least 900%, or at least 1000% more than the amount of the TAG produced by an otherwise substantially identical microorganism not including the protein(s), cultured under identical conditions. Additionally or alternatively, the methods include producing at least 100 mg, at least 110 mg, at least 120 mg, at least 130 mg, at least 140 mg, at least 150 mg, at least 160 mg, at least 170 mg, at least 180 mg, at least 190 mg, at least 200 mg, at least 210 mg, at least 220 mg, at least 230 mg, at least 240 mg, at least 250 mg, at least 260 mg, at least 270 mg, at least 280 mg, at least 290 mg, at least 300 mg, at least 310 mg, at least 320 mg, at least 330 mg, at least 340 mg, at least 350 mg, at least 360 mg, at least 370 mg, at least 380 mg, at least 390 mg, at least 400 mg, at least 450 mg, at least 500 mg, at least 550 mg, at least 600 mg, at least 650 mg, at least 700 mg, at least 750 mg, at least 800 mg, at least 850 mg, at least 900 mg, or at least 950 mg, per liter of culture of TAG by culturing the recombinant microorganisms described herein.

TAG can be recovered from culture by recovery means known to those of ordinary skill in the art, such as by whole culture extraction, for example, using organic solvents. In some cases, recovery of TAG can be enhanced by homogenization of the cells. For example, lipids such as TAG can be isolated from algae by extraction of the algae with a solvent at elevated temperature and/or pressure, as described in the co-pending, commonly-assigned U.S. patent application Ser. No. 13/407,817 entitled "Solvent Extraction of Products from Algae," filed on 29 Feb. 2012, which is incorporated herein by reference in its entirety. Further, when TAG is sufficiently released or secreted from the microorganisms into the culture medium, the recovery method can be adapted to recover efficiently only the released TAG, only the TAG produced and stored within the microorganisms, or both the produced and released TAG.

It is to be understood that the disclosure of the present invention extends to methods, products and systems according to the various aspects of the invention which comprise combinations of one or more features discussed herein by reference to certain embodiments of the invention with one or more further features discussed herein by reference to certain other embodiments of the invention.

Additionally or alternatively, the present invention can include one or more of the following embodiments.

FURTHER EMBODIMENTS

Embodiment 1. An isolated or recombinant nucleic acid molecule encoding a polypeptide having acyltransferase activity comprising a sequence encoding a Pleckstrin Homology (PH) domain, optionally wherein one or more of the following are satisfied:
  a) the PH domain sequence is derived from a DGAT1 protein;
  b) the PH domain sequence is derived from a polypeptide of a eukaryotic microalga, optionally a eukaryotic microalga of the Heterokontophyta division or the Chlorophyta division, for example, a microalga of the Bacillariophyceae, Chlorophyceae, Prasinophyceae, or Trebouxiophyceae class;
  c) the PH domain is has at least 80% identity to a SEQ ID NO:6; at least 80% identity to SEQ ID NO:12; at least 80% identity to SEQ ID NO:18; at least 80% identity to SEQ ID NO:24; at least 80% identity to SEQ ID NO:30; at least 80% identity to SEQ ID NO:36; at least 80% identity to SEQ ID NO:42; or at least 80% identity to SEQ ID NO:48; and/or d) the polypeptide having acyltransferase activity is a monoacylglycerol acyltransferase (MGAT), a diacylglycerol acyltransferase type 1 (DGAT1), a diacylglycerol acyltransferase type 2 (DGAT2), a diacylglycerol acyltransferase type 3 (DGAT3), a diacylglycerol acetyltransferase (DGAcT), a diacylglycerol transacylase (DGTA), a phospholipid:diacylglycerol acyltransferase (PDAT), a lysophospholipid acyltransferase (LPLAT), a lysophosphatidic acid acyltransferase (LPAAT), or a glycerolphosphate acyltransferase (GPAT).

Embodiment 2. An isolated or recombinant nucleic acid molecule according to Embodiment 1, wherein the PH domain has:
  at least 80%, at least 85%, at least 90%, at least 95%, or at least 98% identity to a SEQ ID NO:6;
  at least 80%, at least 85%, at least 90%, at least 95%, or at least 98% identity to SEQ ID NO:12;
  at least 80%, at least 85%, at least 90%, at least 95%, or at least 98% identity to SEQ ID NO:18;
  at least 80%, at least 85%, at least 90%, at least 95%, or at least 98% identity to SEQ ID NO:24;
  at least 80%, at least 85%, at least 90%, at least 95%, or at least 98% identity to SEQ ID NO:30;
  at least 80%, at least 85%, at least 90%, at least 95%, or at least 98% identity to SEQ ID NO:36;
  at least 80%, at least 85%, at least 90%, at least 95%, or at least 98% identity to SEQ ID NO:42;
  or at least 80%, at least 85%, at least 90%, at least 95%, or at least 98% identity to SEQ ID NO:48

Embodiment 3. An isolated or recombinant nucleic acid molecule according Embodiment 1 or 2, wherein the polypeptide having acyltransferase activity has DGAT activity, and preferably is a DGAT1, a DGAT2, or a DGAT3.

Embodiment 4. An isolated or recombinant nucleic acid molecule according to any of Embodiments 1-3, wherein the PH domain is heterologous with respect to the polypeptide having acyltransferase activity.

Embodiment 5. An isolated or recombinant nucleic acid molecule according to any of Embodiments 1-3, wherein the PH domain is homologous with respect to the polypeptide having acyltransferase activity, optionally wherein the polypeptide having acyltransferase activity is a DGAT1, further optionally wherein the DGAT1 comprises an amino acid sequence having at least 80% identity to SEQ ID NO:2 or a functional fragment thereof; an amino acid sequence having at least 80% identity to SEQ ID NO:8 or a functional fragment thereof; an amino acid sequence having at least 80% identity to SEQ ID NO:14 or a functional fragment thereof; an amino acid sequence having at least 80% identity to SEQ ID NO:20 or a functional fragment thereof; an amino acid sequence having at least 80% identity to SEQ ID NO:26 or a functional fragment thereof; or an amino acid sequence having at least 80% identity to SEQ ID NO:32 or a functional fragment thereof.

Embodiment 6. An isolated or recombinant nucleic acid molecule according to Embodiment 5, wherein the DGAT1 comprises an amino acid sequence having:
  at least 80%, at least 85%, at least 90%, at least 95%, or at least 98% identity to a SEQ ID NO:2 or a functional fragment thereof;
  at least 80%, at least 85%, at least 90%, at least 95%, or at least 98% identity to SEQ ID NO:8 or a functional fragment thereof;
  at least 80%, at least 85%, at least 90%, at least 95%, or at least 98% identity to SEQ ID NO:14 or a functional fragment thereof;
  at least 80%, at least 85%, at least 90%, at least 95%, or at least 98% identity to SEQ ID NO:20 or a functional fragment thereof;
  at least 80%, at least 85%, at least 90%, at least 95%, or at least 98% identity to SEQ ID NO:26 or a functional fragment thereof; or
  at least 80%, at least 85%, at least 90%, at least 95%, or at least 98% identity to SEQ ID NO:32 or a functional fragment thereof.

Embodiment 7. A recombinant eukaryotic microorganism comprising a recombinant nucleic acid molecule according to any of Embodiments 1-6.

Embodiment 8. A recombinant microorganism according to Embodiment 7, wherein the recombinant microorganism is a fungus, heterokont, or microalga.

Embodiment 9. A recombinant microorganism according to Embodiment 8, wherein the recombinant microorganism is a species belonging to any of the following:
  the Heterokontophyta or Chlorophyta division;
  the Bacillariophyceae, Chlorophyceae, Eustigmatophyceae, Prasinophyceae, or Trebouxiophyceae class; or
  a *Achnanthes, Amphiprora, Amphora, Ankistrodesmus, Asteromonas, Boekelovia, Bolidomonas, Borodinella, Botrydium, Botryococcus, Bracteococcus, Chaetoceros, Carteria, Chlamydomonas, Chlorococcum, Chlorogonium, Chlorella, Chroomonas, Chrysosphaera, Cricosphaera, Crypthecodinium, Cryptomonas, Cyclotella, Dunaliella, Ellipsoidon, Emiliania, Eremosphaera, Ernodesmius, Euglena, Eustigmatos, Franceia, Fragilaria, Gloeothamnion, Haematococcus, Halocafeteria, Heterosigma, Hymenomonas, Isochrysis, Lepocinclis, Micractinium, Monoraphidium, Nannochloris, Nannochloropsis, Navicula, Neochloris, Nephrochloris, Nephroselmis, Nitzschia, Ochromonas, Oedogonium, Oocystis, Ostreococcus, Pavlova, Parachlorella, Pascheria, Pelagomonas, Phaeodactylum, Phagus, Picochlorum, Platymonas, Pleurochrysis, Pleurococcus, Prototheca, Pseudochlorella, Pseudoneochloris, Pseudostaurastrum, Pyramimonas, Pyrobotrys, Scenedesmus, Schizochlamydella, Skeletonema,*

*Spyrogyra, Stichococcus, Tetrachlorella, Tetraselmis, Thalassiosira, Tribonema, Vaucheria, Viridiella, Vischeria*, or *Volvox* genus.

Embodiment 10. A recombinant microorganism according to any of Embodiments 7-9, wherein the recombinant eukaryotic microorganism produces a greater amount of a lipid than a control recombinant eukaryotic identical in all respects to the recombinant eukaryotic microorganism, but lacking the recombinant nucleic acid molecule.

Embodiment 11. A recombinant microorganism according to Embodiment 10, wherein the lipid is a triglyceride.

Embodiment 12. A recombinant microorganism comprising a non-native DGAT1 gene that includes a PH domain, wherein the non-native DGAT1 gene encodes a polypeptide that has at least 80%, at least 85%, at least 90%, at least 95%, or at least 98% identity to a DGAT1 gene of a microalga of a species of the Bacillariophyceae, Prasinophyceae, or Trebouxiophyceae class, or a functional fragment thereof, wherein the recombinant microalga produces a greater amount of a lipid than a control recombinant eukaryotic identical in all respects to the recombinant eukaryotic microorganism, but lacking the non-native DGAT1 gene that includes a PH domain.

Embodiment 13. A recombinant microorganism according to Embodiment 12, wherein the recombinant DGAT1 gene encodes a polypeptide having at least 80% identity to SEQ ID NO:2 or a functional fragment thereof; at least 80% identity to SEQ ID NO:8 or a functional fragment thereof; at least 80% identity to SEQ ID NO:14 or a functional fragment thereof; at least 80% identity to SEQ ID NO:20 or a functional fragment thereof; at least 80% identity to SEQ ID NO:26 or a functional fragment thereof; or at least 80% identity to SEQ ID NO:32 or a functional fragment thereof.

Embodiment 14. recombinant microorganism according to Embodiment 12, wherein the recombinant DGAT1 gene encodes a polypeptide having:
- at least 80%, at least 85%, at least 90%, at least 95%, or at least 98% identity to a SEQ ID NO:2;
- at least 80%, at least 85%, at least 90%, at least 95%, or at least 98% identity to SEQ ID NO:8;
- at least 80%, at least 85%, at least 90%, at least 95%, or at least 98% identity to SEQ ID NO:14;
- at least 80%, at least 85%, at least 90%, at least 95%, or at least 98% identity to SEQ ID NO:20;
- at least 80%, at least 85%, at least 90%, at least 95%, or at least 98% identity to SEQ ID NO:26; or
- at least 80%, at least 85%, at least 90%, at least 95%, or at least 98% identity to SEQ ID NO:32.

Embodiment 15. A method for producing TAG, the method comprising culturing a recombinant microorganism according to any of Embodiments 7-14 under conditions in which the acyltransferase is expressed to produce TAG.

Embodiment 16. The method of Embodiment 15, wherein the recombinant microorganism is cultured under nitrogen replete conditions.

Embodiment 17. The method of Embodiment 15 or 16, wherein the microorganism is a microalga, optionally a species of *Achnanthes, Amphiprora, Amphora, Ankistrodesmus, Asteromonas, Boekelovia, Bolidomonas, Borodinella, Botrydium, Botryococcus, Bracteococcus, Chaetoceros, Carteria, Chlamydomonas, Chlorococcum, Chlorogonium, Chlorella, Chroomonas, Chrysosphaera, Cricosphaera, Crypthecodinium, Cryptomonas, Cyclotella, Dunaliella, Ellipsoidon, Emiliania, Eremosphaera, Ernodesmius, Euglena, Eustigmatos, Franceia, Fragilaria, Gloeothamnion, Haematococcus, Halocafeteria, Heterosigma, Hymenomonas, Isochrysis, Lepocinclis, Micractinium, Monoraphidium, Nannochloris, Nannochloropsis, Navicula, Neochloris, Nephrochloris, Nephroselmis, Nitzschia, Ochromonas, Oedogonium, Oocystis, Ostreococcus, Pavlova, Parachlorella, Pascheria, Pelagomonas, Phaeodactylum, Phagus, Picochlorum, Platymonas, Pleurochrysis, Pleurococcus, Prototheca, Pseudochlorella, Pseudoneochloris, Pseudostaurastrum, Pyramimonas, Pyrobotrys, Scenedesmus, Schizochlamydella, Skeletonema, Spyrogyra, Stichococcus, Tetrachlorella, Tetraselmis, Thalassiosira, Tribonema, Vaucheria, Viridiella, Vischeria,* or *Volvox*.

Embodiment 18. The method of Embodiment 17, wherein the recombinant microorganism is cultured under photoautotrophic conditions.

EXAMPLES

The invention as described above can be readily understood by reference to the following examples, which are included for purposes of illustration of certain aspects and embodiments of the present invention, and are not intended to limit the invention.

Example 1

Identification of a Pleckstrin Homology Domain in an Algal DGAT1 Gene

Figure 3:
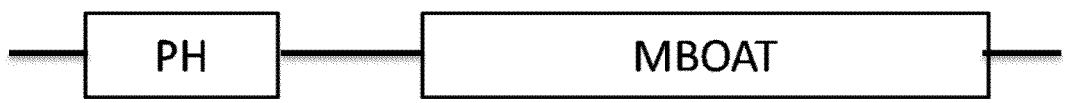
FIG. 3 is a schematic of the DGAT1 genes from algae that include the PH domain along with the MBOAT protein domain characteristic of DGATs.

Based on sequencing of the transcriptome of a proprietary *Cyclotella* strain, a DGAT1 gene (SEQ ID NO:1) was identified that included an N-terminal region not seen in previously identified DGAT1 genes. While DGAT1 genes are known to include a membrane bound O-acyltransferase (MBOAT) domain (occurring at approximately amino acid 413 to amino acid 699 of SEQ ID NO:2), DGAT1 genes were not previously known to include the Pleckstrin Homology (PH) domain, which was identified as occurring between about amino acid 52 and about amino acid 205 of SEQ ID NO:2. This protein domain is found N-terminal of the MBOAT domain in the *Cyclotella* DGAT1 (FIG. 3).

Example 2

Expression of a Full Length *Cyclotella* DGAT1 and a Truncated *Cyclotella* DGAT1 Having a Deleted PH Domain To determine the functional significance of the PH domain in an algal DGAT1 gene, constructs encoding the *Cyclotella* full-length DGAT1 and N-terminally truncated DGAT1 were expressed in a *Sacharomyces cerevisiae* strain lacking endogenous DGAT1 genes. The quadruple yeast knock out mutant—having the DGA1, LRO1, ARE1 and ARE2 genes disrupted using a kanomycin resistance gene, a his gene for auxotrophy complementation, a hygromycin resistance gene, and a leu gene for auxotrophy complementation, respectively—was used as a host. The full length DGAT1 gene from *Cyclotella* ("DGAT1-452"; SEQ ID NO:1, encoding the polypeptide of SEQ ID NO:2 that includes the PH domain) and the truncated version containing the MBOAT domain but lacking the PH domain; ("DGAT1-452T", SEQ ID NO:3, encoding the N-terminally truncated polypeptide of SEQ ID NO:4) were cloned into the p416TEF vector (Mumberg et al. (1995) *Gene* 156:119-22) for expression in yeast. DGAT1-452 was amplified from cDNA with forward primer DGAT1-452F (SEQ ID NO:49) and reverse primer DGAT1-452R (SEQ ID NO:50). DGAT1-452T was amplified from DGAT1-452 with forward primer DGAT1-452TF (SEQ ID NO:51) and the same reverse primer used for DGAT1-452. Genes were cloned into a BamHI linearized p416TEF vector via homologous recombination in *E. coli* alpha gold cells (Bioline, Boston, Mass.). The vector and PCR fragment were added to competent cells, followed by transformation and plating on LB-carbenicillin. Primers used in the cloning procedures are listed in Table 1 below, with the nucleotide residues homologous to yeast plasmid p416TEF shown in uppercase.

TABLE 1

Primers for cloning DGAT genes into p416TEF

| Name | Primer sequence | SEQ ID NO: |
|---|---|---|
| DGAT1-452F | TAGAACTAGTGGATCCatggagaccgaggaggaattac | 49 |
| DGAT1-452R | GCTTGATATCGAATTCtcaaagctcaggagaagcac | 50 |
| DGAT1-452TF | TAGAACTAGTGGATCCatgttgaaacaacaacaacgacaac | 51 |
| Phaeo-TEFF | TAGAACTAGTGGATCCatgaccacgcctgtatcttc | 52 |
| Phaeo-TEFR | GCTTGATATCGAATTCtcaacgaatcaagcaggaatt | 53 |
| Phaeo-TEFTF | TAGAACTAGTGGATCCatggcccaagccatgcctg | 54 |
| Thala-TEFF | TAGAACTAGTGGATCCatggactctaccccccagcgag | 55 |
| Thala-TEFR | GCTTGATATCGAATTCttataactcggaatgggcac | 56 |
| Thala-TEFTF | TAGAACTAGTGGATCCATGaagcaacaagaacaacaaattc | 57 |

Genes were sequence-confirmed, and transformed into the yeast DGAT1 quadruple knockout mutant BY4741: MATαhis1Δleu2Δmet15Δura3Δ0 using the Zymo frozen EZ yeast transformation II Kit™, followed by plating onto SD-URA media, where colonies appeared two days post transformation. The presence of the transformation constructs in colonies was verified with gene specific primers.

Verified colonies were picked into 10 mL aliquots of SD-URA in 50 mL filtered cap tubes. As a negative control, the wild-type (WT) strain was grown in SD media. Cultures were grown for 24 hrs at 30° C. with shaking at 230 rpm. For HPLC analysis of lipids, 2 mL samples of each culture were spun down at maximum speed for 5 minutes, the supernatants were removed, and pellets were re-suspended in 400 μL of $H_2O$.

The cell suspensions (approximately 500 μL) were transferred to 4 mL glass vials with Teflon lined caps. 500 μL of glass beads (212-300 μm diameter) were added to each of the cell suspensions, after which 50 μL of 50% $H_2SO_4$ and 100 μL of 5M NaCl were added. Bead beating was performed for 5 minutes at 1 krpm, then 2 mL of hexane was added to each sample, and bead beating was repeated for 5 minutes at 1 krpm. The samples were loaded onto a multi-tube vortexer and shaken for 30 minutes at 1 krpm, and then vortexed for 30 seconds at 2.5 krpm. 500 μL of the organic layer was transferred to an HPLC vial, and 50 μL of internal standard solution (1 mg/mL 6-ketocholestanol in toluene) was added to each vial. Standards were from NuCheck, Sigma-Aldrich, or Supelco. The vials were capped and vortexed briefly (5 seconds at 2.5 krpm) prior to HPLC analysis. The HPLC was run at a flow rate of 2 mL/minute on a Chromegasphere SI-60 150 mm×4.6 mm×10 μm column (ES Industries), with a column compartment set at 40° C. The injection volume was 25 μL with a draw and eject speed of 200 μL/minute. Eluent A was hexane and Eluent B was a 80:10:10:1 mixture of hexane, isopropanol, ethyl acetate, and 10% formic acid in isopropanaol, run as a gradient program as follows: 2% B at 0.0 min; 2% B at 1.0 min; 35% B at 8.0 min; 98% B at 8.5 min; 98% B at 11.5 min; 2% B at 11.6 min; stop time: 11.6 minutes; 5 minutes post time. The detector was ELSD at 30° C. and 3.5 bar $N_2$, with a gain of 5.

Figure 4:
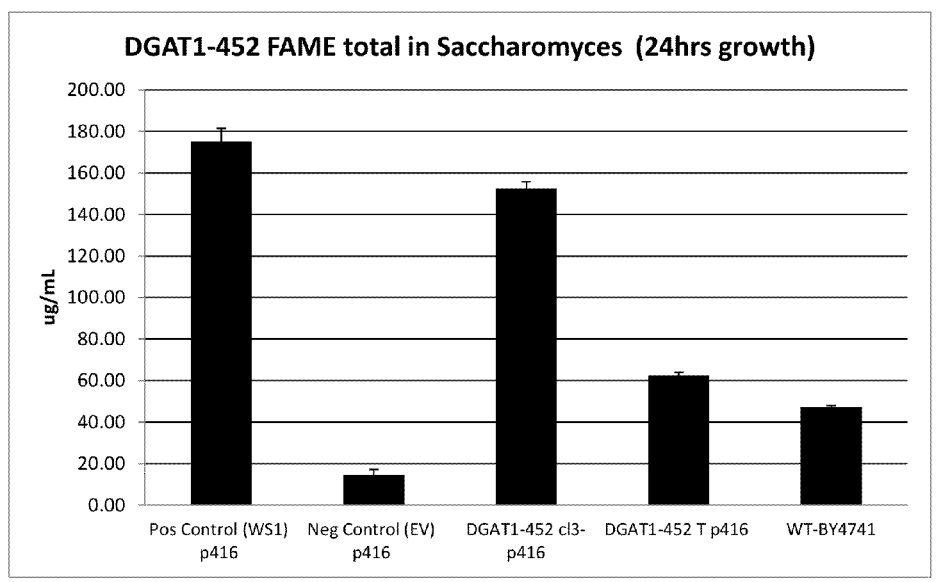
FIG. 4 summarizes total TAG production from yeast transfected to express a full length *Cyclotella* DGAT1 (DGAT1-452 c13-p416) and a truncated *Cyclotella* DGAT1 lacking the PH domain (DGAT1-452T p416). TAG production from a yeast transfected with the *Marinobacter* WS1 wax-synthase (WS1 p416) is included as a positive control. TAG from wild-type yeast (WT-BY4741) and yeast transfected with empty vector (EV p416) are included as negative controls. Production of TAG is clearly improved when the full-length DGAT1, containing the PH domain, is expressed in the host strain.

The results of TAG biosynthesis are shown in FIG. 4. The results show that the presence of the PH domain greatly increases the amount of TAG produced by the mutant yeast strain, with the strain that included the PH domain-containing DGAT1 producing at least seven-fold the amount of TAG produced by the strain expressing the DGAT1 lacking the PH domain. The results are striking as yeast DGATs do not include the PH domain. Thus, the presence of the PH domain in a DGAT improves lipid yields dramatically even in strains in which the PH domain does not occur in the strain's native DGAT1.

FAME analysis was also performed to detect both storage lipid (TAG) and membrane lipids of the transformed yeast cells. 1 mL samples, measured in triplicate for fatty acid methyl ester analysis, were dried using an HT-4X GeneVac. To the dried pellets the following was added: 500 μL of 500 mM KOH in methanol, 200 μL of tetrahydrofuran containing 0.05% butylated hydroxyl toluene, 40 μL of a C11:0 free fatty acid/C13:0 triglyceride/C23:0 fatty acid methyt1 ester internal standard mix and 500 μL of glass beads (425-600 μm diameter). The vials were capped with open top PTFE septa-lined caps and placed in an SPEX GenoGrinder at 1.75 krpm for 7.5 minutes. The samples were then heated at 80° C. for five minutes and allowed to cool. For derivatization, 500 μL of 10% boron trifluoride in methanol was added to the samples prior to heating at 80° C. for 30 minutes. The tubes were allowed to cool prior to adding 2 mL of heptane and 500 μL of 5 M NaCl. The samples were vortexed for five minutes at 2 krpm and finally centrifuged for three minutes at 1 krpm. The heptane layer was sampled using a Gerstel MPS Autosampler.

The samples were run on an Agilent 7890A gas chromatography system using a J&W Scientific 127-3212 DB-FFAP, 10 m×100 μm×100 nm column and an FID detector at 260° C. The flow rate was 500 μL/minute using $H_2$ as a carrier with constant flow control. The oven was set at 100° C. for 0.98 min, then 15.301° C./minute to 230° C. and held for 1.66 min. The inlet contained a 4 mm glass wool packed liner (Agilent P/N 5183-4647), and was set at 250° C. and used a split ratio of 40:1. The injection volume was 900 nL.

Figure 5:
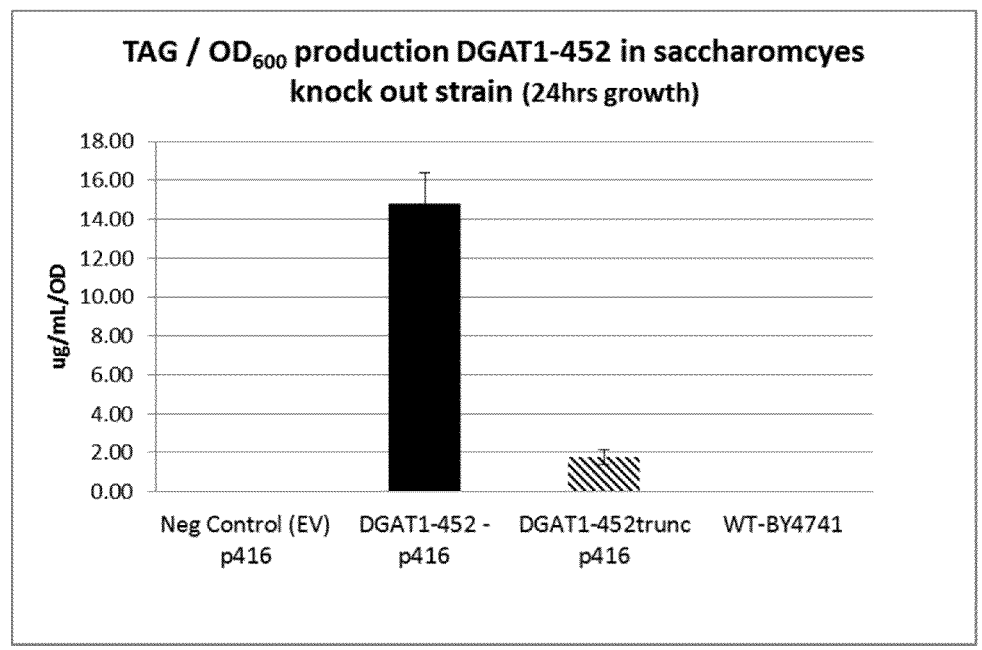
FIG. 5 summarizes TAG production, normalized for cell count, from a full length *Cyclotella* DGAT1 (black bar) and a truncated *Cyclotella* DGAT1 lacking the PH domain (striped bar) in yeast. TAG from wild-type yeast (WT-BY4741) and yeast transfected with empty vector (EV p416) are included as negative controls. Production of TAG is clearly improved when the full-length DGAT1, containing the PH domain, is expressed in the host strain.

The results of the FAME analysis show that lipid production was not simply re-directed toward TAG production, but was increased overall, both on a per unit volume basis (FIG. 4) and on a per cell basis (FIG. 5).

Example 3

Bioinformatic Analysis of Algal DGAT1s

Bioinformatic analysis of the genomes of several other algal species demonstrated that the PH domain occurs in DGAT1 genes of not only diatoms but also of some green algal species. For example, manual curation of the DGAT1 genes of other algal genomes revealed the PH domain occurs in the DGAT1 genes of species of the diatoms *Navicula, Phaeodactylum, Thalassiosira*, and *Fragilariopsis* (members of the Bacillariophyceae class and Heterokontophyta division), as well as in the green algae *Botryococcus* and *Chlorella* (members of the Trebouxiophyceae class of the Chlorophyta division) as well as *Tetraselmis*, (a member of the Chlorophyceae class of the Chlorophyta division). Alignment of the DGAT1-encoding sequences determined from bioinformatics analysis of the genomes sequences of these algal species with higher plant DGAT1 sequences (FIG. 2E-F) demonstrates the presence of a conserved region occurring approximately from amino acid 52 to amino acid 205 of the *Cyclotella* DGAT1 (SEQ ID NO:2) that is not found in the higher plant DGAT1 enzymes.

Genomic sequence analysis of a proprietary *Navicula* species resulted in the identification of the DGAT1 gene provided as SEQ ID NO:3, encoding the DGAT1 of SEQ ID NO: 8, which includes a PH domain extending from approximately amino acid 104 to amino acid 238 of SEQ ID NO:8. SEQ ID NO:43 represents a predicted protein coding region of the *Phaeodactylum tricornutum* DGAT1 as determined Bolwer analysis methods (Bowler et al. (2008) *Nature* 456:239-44; genome available at http://ncbi.nlm.nih.gov/genome/418). SEQ ID NO:43 encodes the DGAT1 of SEQ ID NO:44 having a PH domain extending from approximately amino acid 71 to amino acid 200. The protein coding region of the *Thalassiosira pseudonana* DGAT1 as determined from the public genome sequences (Armbrust et al. (2004) *Science* 306:79-86; genome available at http://ncbi.nlm.nih.gov/genome/54) is provided as SEQ ID NO:37, encoding the DGAT1 of SEQ ID NO:38 which has a PH domain extending from approximately amino acid 53 to amino acid 186. The protein coding region of the *Fragilariopsis cylindrus* DGAT1 (determined from the genome sequence available at http://genome.jgi-psf.org/Fracy1/Fracy1.home.html) is provided as SEQ ID NO:13, encoding the DGAT1 of SEQ ID NO:14 having a PH domain extending from approximately amino acid 44 to amino acid 180. The protein coding region of a DGAT1 gene of a proprietary *Botryococcus* strain (SEQ ID NO:19) encodes the DGAT1 of SEQ ID NO:20, having a PH domain extending from approximately amino acid 28 to amino acid 153. The protein coding region of DGAT1 gene of a proprietary *Tetraselmis* strain (SEQ ID NO:25) encodes the DGAT1 of SEQ ID NO:26 which includes a PH domain extending from approximately amino acid 59 to amino acid 170. The protein coding region of a DGAT1 gene determined from the genome sequence of a proprietary *Chlorella* strain is provided as SEQ ID NO:31, encoding the DGAT1 of SEQ ID NO:32 having a PH domain extending from approximately amino acid 40 to amino acid 166.

Example 4

Comparison of Effects on Lipid Production of Expressing Additional Algal DGAT1 Genes with and without a PH Domain in *Saccharomyces cerevisiae*

The full-length DGAT1 gene of *Phaeodactylum tricornutum* (SEQ ID NO:43), encoding the PH domain-containing DGAT1 (SEQ ID NO:44); a truncated gene (SEQ ID NO:45) encoding an N-terminally truncated *Phaeodactylum* DGAT1 lacking the PH domain (SEQ ID NO:46); the full-length *Thalassiosira pseudonana* DGAT1 gene (SEQ ID NO:37), encoding the PH domain-containing DGAT1 (SEQ ID NO:38); and a truncated gene (SEQ ID NO:39) encoding an N-terminally truncated *Thalassiosira pseudonana* DGAT1 lacking the PH domain (SEQ ID NO:40); were also cloned into the p416TEF vector (Mumberg et al. (1995) *Gene* 156: 119-22) for expression in yeast using gene-specific primers that include vector-homologus sequences using the strategy provided in Example 2 and Table 1, supra. The full-length *Phaaeodactylum* DGAT1 was amplified from cDNA with forward primer Phaeo-TEFF (SEQ ID NO:52) and reverse primer Phaeo-TEFR (SEQ ID NO:53). The truncated *Phaeodactylum* DGAT1 was amplified with forward primer Phaeo-TEFTF (SEQ ID NO:54) and the same reverse primer used for the full length *Phaeodactylum* DGAT1 construct. The full-length *Thalassiosira* DGAT1 was amplified from cDNA with forward primer Thala-TEFF (SEQ ID NO:55) and reverse primer Thala-TEFR (SEQ ID NO:56). The truncated *Phaeodactylum* DGAT1 was amplified with forward primer Thala-TEFTF (SEQ ID NO:57) and the same reverse primer used for the full length *Thalassiosira* DGAT1 construct. The constructs were transformed into the quadruple knock-out as provided above.

Transformants were selected and yeast cultures of clones containing each DGAT1 gene were grown and processed for lipid analysis, as provided in Example 1, supra.

Figure 6:
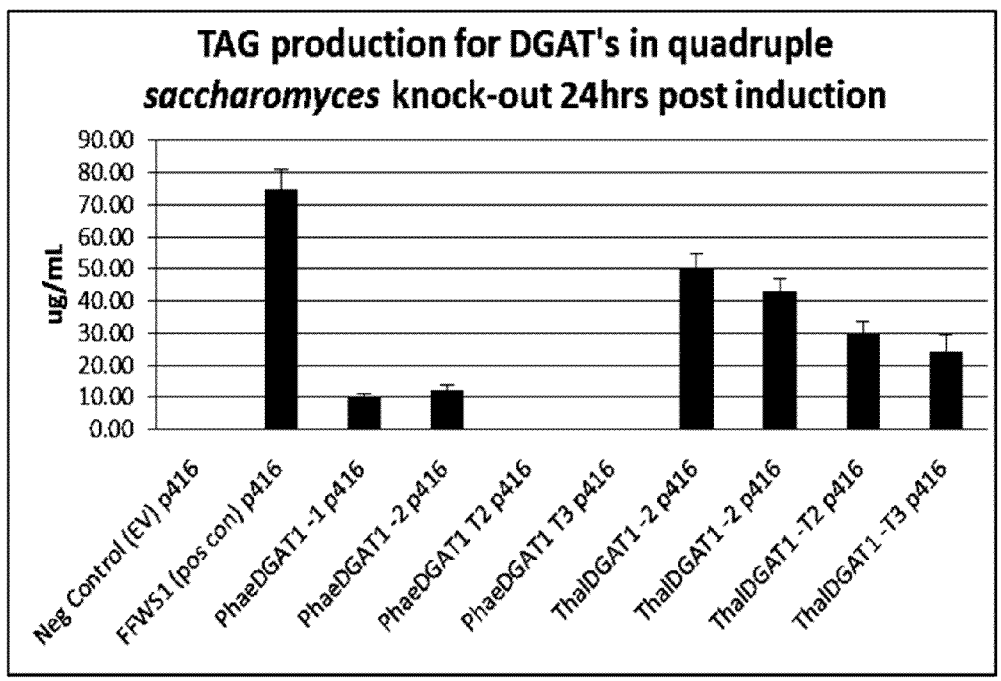
FIG. 6 summarizes TAG production from full-length *Phaeodactylum* DGAT1 clones (PhaeDGAT1-1 and -2) and truncated *Phaeodactylum* DGAT1 clones lacking a PH domain (PhaeDGAT1 T2 and T3), full length *Thalassiosira* DGAT1 clones (Tha1DGAT1-2) and truncated *Thalassiosira* DGAT1 clones lacking a PH domain (Tha1DGAT1-T2 and -T3). The negative control is the quadruple knockout yeast strains carrying the empty vector (EV), which produces no detectable TAG. The positive control (FFWS-1) is the quadruple knockout yeast strain expressing the *Marinobacter* WS1 wax-synthase.

The results for TAG analysis, provided in FIG. 6, demonstrate that expression of the full-length *Phaeodactylum* DGAT1 gene results in the production of detectable amounts of TAG in the quadruple knockout TAG-deficient yeast strain, whereas expression of the truncated *Phaeodactylum* gene that lacks the PH domain does not. Further, expression of the full-length *Thalassiosira* DGAT1 gene results in production of at least 40% more TAG than does expression of the *Thalassiosira* DGAT1 gene encoding an N-terminally truncated DGAT1 that lacks the PH domain.

Figure 7:
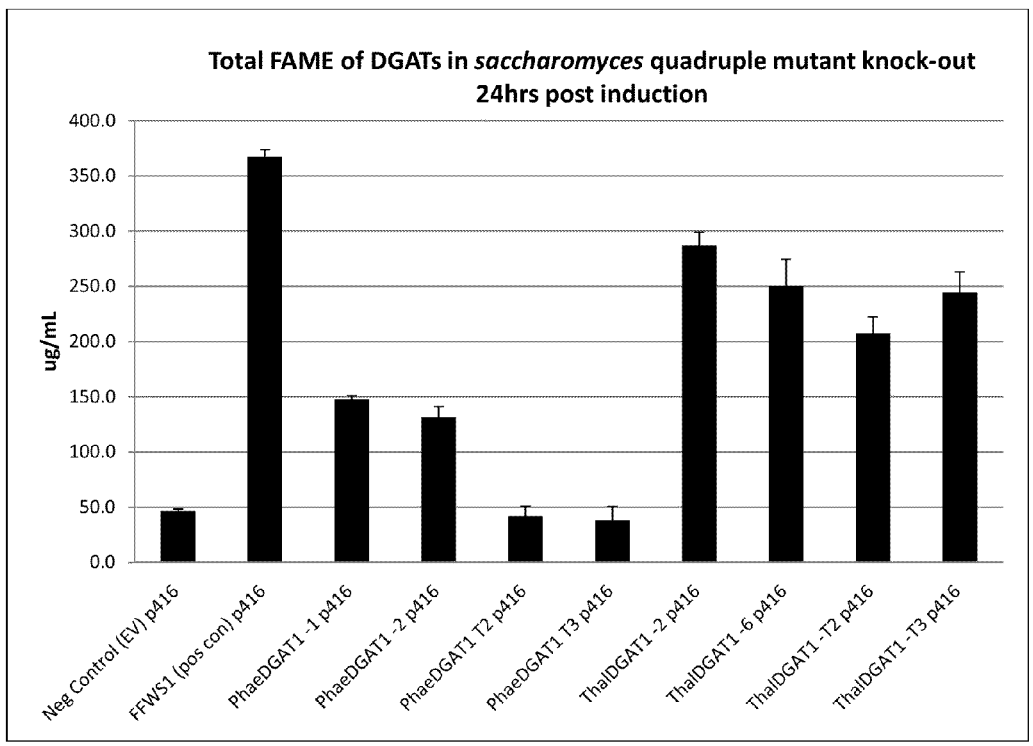
FIG. 7 summarizes total fatty acid methyl-ester (FAME)s production from full-length *Phaeodactylum* DGAT1 clones (PhaeDGAT1-1 and -2) and truncated *Phaeodactylum* DGAT1 clones lacking a PH domain (PhaeDGAT1 T2 and T3), full length *Thalassiosira* DGAT1 clones (Tha1DGAT1-2) and truncated *Thalassiosira* DGAT1 clones lacking a PH domain (Tha1DGAT1-T2 and -T3). The negative control is the quadruple knockout yeast strains carrying the empty vector (EV), which produces no detectable TAG. The positive control (FFWS-1) is the quadruple knockout yeast strain expressing the *Marinobacter* WS1 wax-synthase.

The amount of lipid produced by the full-length DGAT1 expressing yeast clones and the yeast clones expressing algal DGAT1 genes lacking the PH domain as determined by FAME analysis show a similar pattern (FIG. 7), with the strain expressing the full-length *Phaeodactylum* DGAT1 producing more FAME than the strain expressing the *Phaeodactylum* DGAT1 lacking the PH domain, and the strain expressing the full-length *Thalassiosira* DGAT1 producing more FAME than the strain expressing the *Thalassiosira* DGAT1 lacking the PH domain.

Example 5

Transformation of *Nannochloropsis* with Algal DGAT1 Genes

Media used for the growth of *Nannochloropsis* included the following:

PM024: 35 g/L Instant Ocean Salts, 10× Guillard's F/2 marine water enrichment solution (50× stock from Sigma-Aldrich, St. Louis, Mo., cat. No. G0154; final concentrations of components in media: 8.825 mM $NaNO_3$; 320 µM $NaH_2PO_4.2H_2O$; 205 nM Biotin; 420 nM $CoCl_2.6H_2O$; 400 nM $CuSO_4.5H_2O$; 117.13 µM $Na_2EDTA.2H_2O$; 9.095 µM $MnCl_2.4H_2O$; 248 nM $Na_2MoO_4.2H_2O$; 2.965 µM Thiamine.HCl; 37 nM Vitamin $B_{12}$; 765 nM $ZnSO_4.7H_2O$).

PM068: 35 g/L Instant Ocean Salts, 500 mg/L $NaHCO_3$, 17.5 mM $NaNO_3$, 770 µM $NaH_2PO_4.2H_2O$, 9.0 µM MnCl$_2$.4H$_2$O, 760 nM ZnSO$_4$.7H$_2$O, 420 nM CoCl$_2$.6H$_2$O, 390 nM CuSO$_4$.5H$_2$O, 260 nM Na$_2$MoO$_4$.2H$_2$O, 58 μM FeCl$_3$.6H$_2$O, 58 μM Na$_2$EDTA.2H$_2$O, 1.2 μM Thiamine. HCl, 8 nM biotin, 1.5 nM cyanocobalamine.

All transformants were grown in the presence of Zeocin™ (5 μg/mL) unless noted otherwise.

An *E. coli/Nannochloropsis* shuttle vector referred to as p5416 was used for cloning of algal DGAT1 genes. The vector contained 1) a chloramphenicol resistance gene for antibiotic selection of *E. coli* transformants; 2) a Bleomycin® (ble) selectable marker codon-optimized for *Nannochloropsis* under the control of the SV40 promoter for selection of algal transformants, as well as 3) the *Nannochloropsis* eIF3 promoter (SEQ ID NO:58) for operable linkage to a gene of interest. DGAT1 genes were amplified by PCR with primers having regions of homology to the shuttle vector. The *Phaeodactylum* DGAT1 gene was amplified with Phaeo-DGAT1F (SEQ ID NO:59) and Phaeo-DGAT1R (SEQ ID NO:60) primers. The *Thalassiosira* DGAT1 gene was amplified with the Thala-DGAT1F (SEQ ID NO:61) and Thala-DGAT1R (SEQ ID NO:62) primers. The amplified gene fragments and linearized p5416 were transformed together into *E. coli* as described in Example 2 for the yeast shuttle vector constructs. Clones were screened for inserts by PCR. Primers used in the cloning procedures are listed in Table 2 below, with the nucleotide residues homologous to p5416 shown in uppercase.

TABLE 2

Primers for cloning DGAT genes into p5416

| Name | Primer sequence | SEQ ID NO: |
|---|---|---|
| Phaeo-DGAT1F | CAGACAGAGACACACAGGGATCatgaccacgcctgtatcttc | 59 |
| Phaeo-DGAT1R | GAGCGGAACCGGGGTTACAGTGCCtcaacgaatcaagcaggaatt | 60 |
| Thala-DGAT1F | CAGACAGAGACACACAGGGATCatggactctaccccagcgag | 61 |
| Thala-DGAT1R | GAGCGGAACCGGGGTTACAGTGCCttataactcggaatgggcac | 62 |

Vectors having inserts that included the full length *Cyclotella* DGAT1 gene (SEQ ID NO:1); the full length *Phaeodactylum* DGAT1 gene (SEQ ID NO:43), and the full length *Thalasiossira* DGAT1 gene (SEQ ID NO:37) were linearized and introduced by electroporation into a *Nannochloropsis gaditana* wild-type strain obtained from the Center for Culture of Marine Phytoplankton (CCMP catalog number 1894). Briefly, two 2 L shake flasks each containing 500 mL of *N. gaditana* culture were grown to a cell density of 9×10$^6$ cells/mL. The cells were centrifuged for 10 minutes at 25° C. and 2500×g and resuspended in 385 mM sorbitol. This process was repeated three times to wash cells, before resuspending in 385 mM sorbitol at a concentration of 1.1×10$^{10}$ cells/mL. Approximately 1 μg of linearized DNA was mixed into 100 μL of cell suspension and transferred to a 2 mm gap cuvette (BioRad). Electroporation was performed on a BioRad GenePulser set to 50 μF capacitance, 500 ohms resistance, and 2.2 kV. Immediately after the electroporation, 1 mL of 385 mM sorbitol was gently mixed into the transformed cell suspension and the cells were allowed to sit at room temperature for a few minutes. The cell mixture was then transferred to 10 mL of PM024 liquid media and allowed to recover overnight at room temperature at 25° C. in dim light (5 μE, m$^{-2}$ s$^{-1}$). The cell mixture was then centrifuged at 2500×g at 25° C. for 10 minutes, decanted, and resuspended in PM024 to a final volume of approximately 600 μL. Resuspended cells (300 μL) were spread using sterile 4 mm glass beads onto PM024 plates containing 5 μg/mL Zeocin™ to select for transformants. Colonies were observed after 24 days of selection. Colonies were picked from each transformation to test for the presence of the respective DGAT1 gene. The colonies were patched onto fresh PM024+Zeocin™ plates and cultured in liquid media under selection. gDNA was prepared from the three transgenic clones as well as the wild-type. The presence of a DNA fragment containing the DGAT1 gene was verified using PCR with transgenic cells as the template.

Example 6

Lipid Production by *Nannochloropsis* Transformants

To determine the effect of the DGAT1 transgenes on TAG production, eight *Nannochloropsis* transformants that included the *Cyclotella* DGAT1 gene (SEQ ID NO:1) (clones designated P1A1, P1A2, P1A3, P1A6, P1B3, P1C2, P1C5, and P1D3) three *Nannochloropsis* transformants that included the *Phaeodactylum* DGAT1 gene (SEQ ID NO:43) (clones designated P2C4, P2D1, and P2D2) and one *Nannochloropsis* transformant that included the *Thalasiossira* DGAT1 gene (SEQ ID NO:37) (clone designated P4C5) were grown in 100 mL cultures in T75 tissue culture flasks under a 16 hour light: 8 hour dark diel cycle, with light provided at 90 μE, m$^{-2}$ s$^{-1}$ shaking at 115 rpm and 25° C. in the presence of ambient 1% CO$_2$. The cells were inoculated from a 25 mL starter culture with and amount of cells equivalent to 0.40 OD$_{600}$, and were grown in PM068 nitrogen-replete media, a condition that does not normally lead to TAG production during the exponential growth phase. After two days, at the end of the dark period, 2 mL aliquots of each culture were removed for determining Total Organic Carbon (TOC), TAG content, and total lipids as assessed by FAME analysis.

TAG was measured as in Example 2, supra. To determine FAME content of the cultures, FAME analysis was performed as described in Example 2, supra, except that 2 mL of culture was dried and the SPEX GenoGrinder was run at only 1.65 krpm for 7.5 minutes.

Total organic carbon (TOC) for the cultures was determined by centrifuging 2 mL cell culture aliquots to remove media and resuspending the cells in 1 mL water. Three cell samples per measurement were injected into a Shimadzy TOC-Vcsj Analyzer for determination of Total Carbon (TC) and Total Inorganic Carbon (TIC). The combustion furnace was set to 720° C., and TOC was determined by subtracting TIC from TC. The calibration range was from 2 ppm to 200 ppm. The correlation coefficient requirement was $r^2 > 0.999$.

Figure 8:
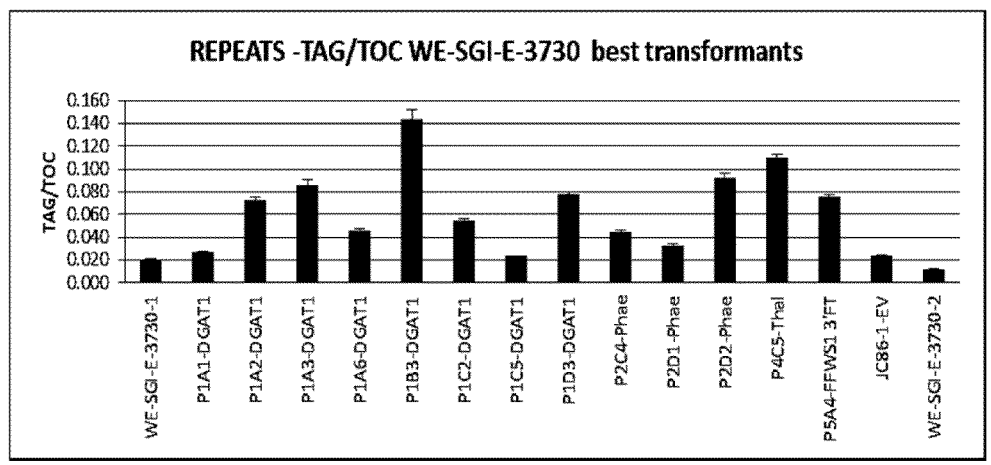
FIG. 8 summarizes TAG per total organic carbon (TOC) obtained from *Nannochloropsis* transformed with full-length algal DGAT1 genes from: *Cyclotella* (-DGAT); *Phaeodactylum* (Phae); *Thalassiosira* (Thal); *Marinobacter* WS1 (FFWS1 3'FT) (positive control); Empty vector (EV) (negative control). For comparison sake, TAG/TOC from two untransformed, clonal wild-type cultures (E-3730) are shown, one on each side of the graph. *Nannochloropsis* cultures were grown for two days under nitrogen replete conditions prior to analyzing the cultures for TAG by HPLC. Expression of algal DGAT1 genes that included the PH domain resulted in increased levels of TAG with respect to wild type.
Figure 9:
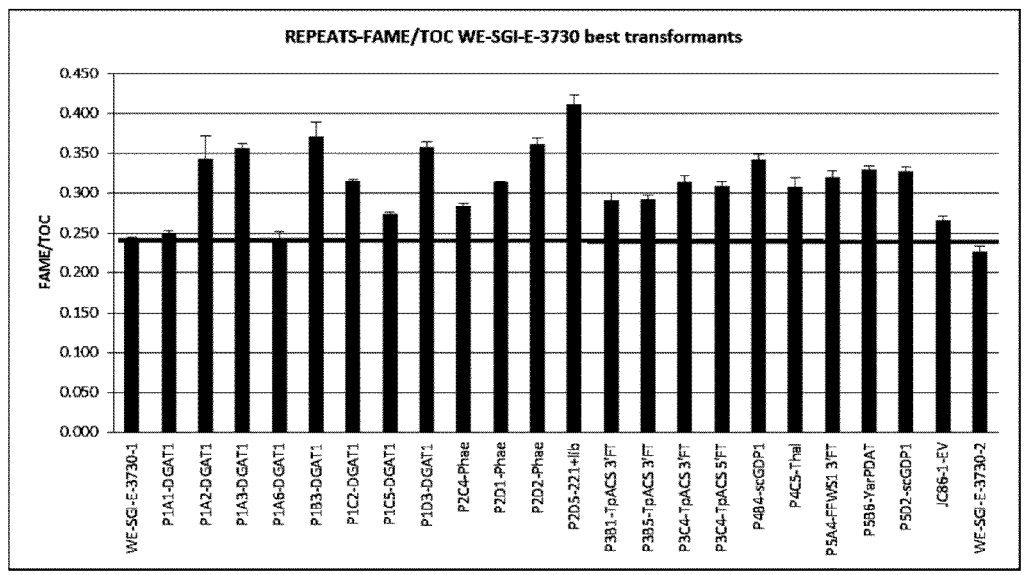
FIG. 9 summarizes FAME per TOC obtained from *Nannochloropsis* transformed with full-length algal DGAT1 genes from: *Cyclotella* (-DGAT); *Phaeodactylum* (Phae); *Thalassiosira* (Thal); *Marinobacter* WS1 (FFWS1 3'FT) (positive control); Empty vector (EV) (negative control). For comparison sake, TAG/TOC from two untransformed, clonal wild-type cultures (E-3730) are show, one on each side of the graph. *Nannochloropsis* cultures were grown for two days under nitrogen replete conditions prior to analyzing the cultures for TAG by HPLC. Expression of algal DGAT1 genes that included the PH domain resulted in increased levels of TAG with respect to wild type.

The results of the lipid analysis are presented on a per total organic carbon basis in FIGS. 8 and 9. FIG. 8 shows that nearly all *Nannochloropsis* strains expressing algal DGAT1 genes comprising the PH domain produced more TAG per TOC than the negative controls (wild type strain WT 3730 and strains that were transformed with an empty vector JC861 EV). Of the eight *Cyclotella* DGAT1 PH domain-containing isolates, seven produced more TAG/TOC than the wild type strain; the highest producing full-length clone, P1B3, produced approximately seven-fold the amount of TAG/TOC as the wild-type. All three PH domain-DGAT1-expressing *Phaeodactylum* DGAT1 transgenic algal strains (clones P2C4, P2D1, and P2D2) produced more TAG/TOC than did the wild type algal strain, as did the transgenic algal strain expressing the *Thalassiosira* PH domain containing DGAT1 (clone P4C5). FIG. 9 shows that the same pattern is also true for these same transformants with regard to FAME/TOC output.

Those skilled in the art will recognize, or be able to ascertain using no more than routine experimentation, many equivalents to the specific embodiments of the invention described herein. Such equivalents are intended to be encompassed by the following claims.

TABLE 3

Index of Sequence Listings

| SEQ ID NO: | Description |
|---|---|
| 1 | *Cyclotella* full length DGAT1 DNA |
| 2 | *Cyclotella* full length DGAT1 protein |
| 3 | *Cyclotella* truncated DGAT1 DNA |
| 4 | *Cyclotella* truncated DGAT1 protein |
| 5 | *Cyclotella* PH domain DNA |
| 6 | *Cyclotella* PH domain protein |
| 7 | *Navicula* DGAT1 DNA |
| 8 | *Navicula* DGAT1 protein |
| 9 | *Navicula* truncated DGAT1 DNA |
| 10 | *Navicula* truncated DGAT1 protein |
| 11 | *Navicula* PH domain DNA |
| 12 | *Navicula* PH domain protein |
| 13 | *Fragilariopsis* DGAT1 DNA |
| 14 | *Fragilariopsis* DGAT1 protein |
| 15 | *Fragilariopsis* truncated DGAT1 DNA |
| 16 | *Fragilariopsis* truncated DGAT1 protein |
| 17 | *Fragilariopsis* PH domain DNA |
| 18 | *Fragilariopsis* PH domain protein |
| 19 | *Botryococcus* DGAT1 DNA |
| 20 | *Botryococcus* DGAT1 protein |
| 21 | *Botryococcus* truncated DGAT1 DNA |
| 22 | *Botryococcus* truncated DGAT1 protein |
| 23 | *Botryococcus* PH domain DNA |
| 24 | *Botryococcus* PH domain protein |
| 25 | *Tetraselmis* DGAT1 DNA |
| 26 | *Tetraselmis* DGAT1 protein |
| 27 | *Tetraselmis* truncated DGAT1 DNA |
| 28 | *Tetraselmis* truncated DGAT1 protein |
| 29 | *Tetraselmis* PH domain DNA |
| 30 | *Tetraselmis* PH domain protein |
| 31 | *Chlorella* DGAT1 DNA |
| 32 | *Chlorella* DGAT1 protein |
| 33 | *Chlorella* truncated DGAT1 DNA |
| 34 | *Chlorella* truncated DGAT1 protein |
| 35 | *Chlorella* PH domain DNA |
| 36 | *Chlorella* PH domain protein |
| 37 | *Thalassiosira* DGAT1 DNA |
| 38 | *Thalassiosira* DGAT1 protein |
| 39 | *Thalassiosira* truncated DGAT1 DNA |
| 40 | *Thalassiosira* truncated DGAT1 protein |
| 41 | *Thalassiosira* PH domain DNA |
| 42 | *Thalassiosira* PH domain protein |
| 43 | *Phaeodactylum* DGAT1 DNA |
| 44 | *Phaeodactylum* DGAT1 protein |
| 45 | *Phaeodactylum* truncated DGAT1 DNA |
| 46 | *Phaeodactylum* truncated DGAT1 protein |
| 47 | *Phaeodactylum* PH domain DNA |
| 48 | *Phaeodactylum* PH domain protein |
| 49 | DGAT1-452F primer |
| 50 | DGAT1-452R primer |
| 51 | DGAT1-452TF primer |
| 52 | Phaeo-TEFF primer |
| 53 | Phaeo-TEFR primer |
| 54 | Phaeo-TEFTF primer |
| 55 | Thala-TEFF primer |
| 56 | Thala-TEFR primer |
| 57 | Thala-TEFTF primer |
| 58 | *Nannochloropsis* eIF3 promoter |
| 59 | Phaeo-DGAT1F primer |
| 60 | Phaeo-DGAT1R primer |
| 61 | Thala-DGAT1F primer |
| 62 | Thala-DGAT1R primer |
| 63 | Eukaryotic DGAT1 consensus motif |

What is claimed is:

1. An expression cassette comprising a heterologous promoter operably linked to an isolated or recombinant nucleic acid molecule encoding a DGAT1 polypeptide having DGAT activity comprising a sequence selected from the group consisting of: an amino acid sequence having at least 85% identity to SEQ ID NO:2; an amino acid sequence having at least 85% identity to SEQ ID NO:8; an amino acid sequence having at least 85% identity to SEQ ID NO:14; an amino acid sequence having at least 85% identity to SEQ ID NO:20; an amino acid sequence having at least 85% identity to SEQ ID NO:26; and an amino acid sequence having at least 85% identity to SEQ ID NO:32.

2. An expression cassette according to claim 1, wherein the isolated or recombinant nucleic acid molecule encodes a DGAT1 polypeptide having DGAT activity comprising a sequence selected from the group consisting of: an amino acid sequence having at least 95% identity to SEQ ID NO:2; an amino acid sequence having at least 95% identity to SEQ ID NO:8; an amino acid sequence having at least 95% identity to SEQ ID NO:14; an amino acid sequence having at least 95% identity to SEQ ID NO:20; an amino acid sequence having at least 95% identity to SEQ ID NO:26; and an amino acid sequence having at least 95% identity to SEQ ID NO:32.

3. An expression cassette comprising a heterologous promoter operably linked to an isolated or recombinant nucleic acid molecule encoding a Pleckstrin Homology (PH) domain, wherein the PH domain comprises a sequence selected from the group consisting of: an amino acid sequence having at least 85% identity to SEQ ID NO:6; an amino acid sequence having at least 85% identity to SEQ ID NO:12; an amino acid sequence having at least 85% identity to SEQ ID NO:18; an amino acid sequence having at least 85% identity to SEQ ID NO:24; an amino acid sequence having at least 85% identity to SEQ ID NO:30; and an amino acid sequence having at least 85% identity to SEQ ID NO:36.

4. An expression cassette according to claim 3, wherein the PH domain comprises a sequence selected from the group consisting of: an amino acid sequence having at least 95% identity to SEQ ID NO:6; an amino acid sequence having at least 95% identity to SEQ ID NO:12; an amino acid sequence having at least 95% identity to SEQ ID NO:18; an amino acid sequence having at least 95% identity to SEQ ID NO:24; an amino acid sequence having at least 95% identity to SEQ ID NO:30; and an amino acid sequence having at least 95% identity to SEQ ID NO:36.

5. A recombinant eukaryotic cell comprising an expression cassette according to claim 1.

6. A method for producing triacylglycerol (TAG), the method comprising culturing a recombinant microorganism that comprises a recombinant nucleic acid molecule under conditions in which the recombinant nucleic acid molecule is expressed, to produce TAG, wherein the recombinant nucleic acid molecule encodes a DGAT1 polypeptide having DGAT activity comprising a sequence selected from the group consisting of: an amino acid sequence having at least 85% identity to SEQ ID NO:2; an amino acid sequence having at least 85% identity to SEQ ID NO:8; an amino acid sequence having at least 85% identity to SEQ ID NO:14; an amino acid sequence having at least 85% identity to SEQ ID NO:20; an amino acid sequence having at least 85% identity to SEQ ID NO:26; and an amino acid sequence having at least 85% identity to SEQ ID NO:32.

7. The method of claim 6, wherein the recombinant nucleic acid molecule encodes a DGAT1 polypeptide having DGAT activity comprising a sequence selected from the group consisting of: an amino acid sequence having at least 95% identity to SEQ ID NO:2; an amino acid sequence having at least 95% identity to SEQ ID NO:8; an amino acid sequence having at least 95% identity to SEQ ID NO:14; an amino acid sequence having at least 95% identity to SEQ ID NO:20; an amino acid sequence having at least 95% identity to SEQ ID NO:26; and an amino acid sequence having at least 95% identity to SEQ ID NO:32.

8. The method of claim 6, wherein the recombinant microorganism is cultured under nitrogen replete conditions.

9. The method of claim 6, wherein the microorganism is a microalga.

10. The method of claim 9, wherein the microalga is a species of *Achnanthes, Amphiprora, Amphora, Ankistrodesmus, Asteromonas, Boekelovia, Bolidomonas, Borodinella, Botrydium, Botryococcus, Bracteococcus, Chaetoceros, Carteria, Chlamydomonas, Chlorococcum, Chlorogonium, Chlorella, Chroomonas, Chrysosphaera, Cricosphaera, Crypthecodinium, Cryptomonas, Cyclotella, Dunaliella, Ellipsoidon, Emiliania, Eremosphaera, Ernodesmius, Euglena, Eustigmatos, Franceia, Fragilaria, Gloeothamnion, Haematococcus, Halocafeteria, Heterosigma, Hymenomonas, Isochrysis, Lepocinclis, Micractinium, Monoraphidium, Nannochloris, Nannochloropsis, Navicula, Neochloris, Nephrochloris, Nephroselmis, Nitzschia, Ochromonas, Oedogonium, Oocystis, Ostreococcus, Pavlova, Parachlorella, Pascheria, Pelagomonas, Phaeodactylum, Phagus, Picochlorum, Platymonas, Pleurochrysis, Pleurococcus, Prototheca, Pseudochlorella, Pseudoneochloris, Pseudostaurastrum, Pyramimonas, Pyrobotrys, Scenedesmus, Schizochlamydella, Skeletonema, Spyrogyra, Stichococcus, Tetrachlorella, Tetraselmis, Thalassiosira, Tribonema, Vaucheria, Viridiella, Vischeria,* or *Volvox.*

11. The method of claim 9, wherein the microalga is a *Nannochloropsis* cell.

12. The method of claim 9, wherein the recombinant microorganism is cultured under photoautotrophic conditions.

13. The method of claim 8, wherein the recombinant microorganism generates TAG under nitrogen replete conditions at levels at least two fold the amount produced by a control microorganism substantially identical to the recombinant microorganism except that the control microorganism lacks the recombinant nucleic acid molecule having DGAT activity.

14. The method of claim 8, wherein the recombinant microorganism generates TAG under nitrogen replete conditions at levels at least five fold the amount produced by a control microorganism substantially identical to the recombinant microorganism except that the control microorganism lacks the recombinant nucleic acid molecule having DGAT activity.

15. The method of claim 8, wherein the recombinant microorganism generates TAG under nitrogen replete conditions at levels at least ten fold the amount produced by a control microorganism substantially identical to the recombinant microorganism except that the control microorganism lacks the recombinant nucleic acid molecule having DGAT activity.

16. The recombinant eukaryotic cell of claim 5, wherein the expression cassette comprises a nucleic acid molecule encoding a PH domain comprising a sequence selected from the group consisting of: an amino acid sequence having at least 95% identity to SEQ ID NO:2; an amino acid sequence having at least 95% identity to SEQ ID NO:8; an amino acid sequence having at least 95% identity to SEQ ID NO:14; an amino acid sequence having at least 95% identity to SEQ ID NO:20; an amino acid sequence having at least 95% identity to SEQ ID NO:26; and an amino acid sequence having at least 95% identity to SEQ ID NO:32.

17. The recombinant eukaryotic cell of claim 5, wherein the expression cassette comprises a nucleic acid molecule encoding a PH domain comprising a sequence selected from the group consisting of: an amino acid sequence having at least 85% identity to SEQ ID NO:2; an amino acid sequence having at least 85% identity to SEQ ID NO:8; an amino acid sequence having at least 85% identity to SEQ ID NO:14; an amino acid sequence having at least 85% identity to SEQ ID NO:20; an amino acid sequence having at least 85% identity to SEQ ID NO:26; and an amino acid sequence having at least 85% identity to SEQ ID NO:32.

18. The recombinant eukaryotic cell of claim 5, wherein the recombinant eukaryotic cell is a recombinant microorganism.

19. The recombinant microorganism of claim 18, wherein the recombinant microorganism produces a greater amount of triglyceride than is produced by a control microorganism substantially identical to the recombinant microorganism, but wherein the control microorganism lacks the isolated or recombinant nucleic acid molecule encoding the DGAT1 polypeptide having DGAT activity.

20. The recombinant microorganism of claim 18, wherein the recombinant microorganism is a photosynthetic microorganism.

* * * * *

SEQUENCE LISTING

```
<160> NUMBER OF SEQ ID NOS: 63

<210> SEQ ID NO 1
<211> LENGTH: 2235
<212> TYPE: DNA
<213> ORGANISM: Cyclotella sp.

<400> SEQUENCE: 1
atggagaccg aggaggaatt acgacacgaa atcacaagac tgaaacaaca gctagcttct      60
ttgaactccg cagtcacatc aagcagcacc gaaggcatca aggacggtga caatcgcagc     120
accggcagtg tttgtattgt gaatgctccg ccagaaaaat cgggttatct tttaaatgg     180 caggacagag cgatcgggtg gggtggtacc aaatggggat tgcgtttcgt ccgtttagat     240
cacggccaat tgagctacta taaacacac gaagaccgca gcgcgagata tgtcttgact     300
ttgaagaatt gcgcagtgag agacgaggga tccaaagtca ataagcggca cgcgacctct     360
aagaaacgcg ggagtgtcga atcgtcgcgg ttaccaggcg ccgagtcgga acggaaggt     420 cacgaggcgg gatcacattt ttacgtcttc tcagtctatc gaaggccgaa caagtacgag     480
```

```
gtcgaagcaa acgcaagaag tggcgaggat gatgcgcagc atgacagcga ggaacatatc      540
attcccttgt tgcgattctc tacgcagagt tacgcggaaa aattgcaatg gattgacctc      600
atttctcaat cttgtgccta ctgtgactct gaagaattcg ctctctatca acagcagcaa      660
caagaaatgt tgaaacaaca acaacgacaa ccgccaaaag ggactcttcc agctttggtg      720
ttcgaggccc ctcctccgaa gcaagatatt caaggatatc cttccggata caatcttttg      780
aattcaagag caaacatttt cgtagaaagt caaacatgaa ggatgcggc tcggtcaaac      840 aaaatttcat acccaccatc caagcctatg catcgccaaa gcaatccatc ttacctctcg      900
gaaggtgccc atgcccagaa ctaccacggt ctctttaatc tgttcctact catattagtc      960
ctatccaact ttcgactgtt gatgcatgca gtgagccaac atggcttttt ctttgacaag     1020
attccatcgt tccacgattt ttccgaagca ccacttgact tcccgtttgt ttcgggttta     1080
ttagttgttc aagcttttgt gctgggcgcg tatgccattg aaaaaatgct ggtgcttggt     1140
ttcgtcgggg ggcgagttgg aatattttta cacgctatca attgtaatgc atcgcttgga     1200
gttgtcattt ccattgtttg gtacttgatt gatcaaccaa tcattggagc aatcttgatt     1260
ttgcaagcga caatcacgtg gttgaagcta atatcatacg cccatgccaa ctatgactat     1320
agaacttcgc cagagtccta caacctgact cgaacattgg taaaagattt agacgaagct     1380
ggcaccagat tgtcttatcc tcaaaatgtt acattgggaa acatatacta cttttggttt     1440
gcaccaacac taacatatca gatggcgttt cccagagctc cttttattca gtggccaaag     1500
gttttgaggc tgtcagtcca gctgtttgtt tctatcattc ttgttctatt tttcttcgcc     1560
caaattgtgg caccaaatct tgacagtctc gtcagagatt tggagaacga caaaggagaa     1620
gtgagagtac atgtgatagg tgactacttg cttcgtatgt caatcgcgag cacctatata     1680
tggctgttgg gtttctttgg tttctttcac tgctttatga atattactgc tgaattactt     1740
cgatttggag atcgtgtatt ctacagagat tggtggaatg catcagaagt atctgcatat     1800
tggagattat ggaacatgcc cgttcattac tggttagttc gtcacgttta cttcccgtgc     1860
attcgcatag gcctttcaaa gaagggagcc accttcgtcg tttttctttt atcggcagtg     1920
ttgcatgaag tattgataag tgtaccgtgt cacatgattc gagtctggtc gtttcttgca     1980
atgatgggcc agatcccact gattattctc acgaaaaaga ttgacaggag aatgccaggc     2040
agctccatcg gaaacataat attctggatt tcgttttgtc ttgtggggca accaatggcc     2100
atgttgcttt atacgattga ttactgggag acgcactctg ttcttactcc agaggcaatg     2160
accgactacg tttcgagacg tgggctaccc tttgctgcca tagggcgatt ttttggtgct     2220
tctcctgagc tttga                                                      2235
```

<210> SEQ ID NO 2
<211> LENGTH: 744
<212> TYPE: PRT
<213> ORGANISM: Cyclotella sp.

<400> SEQUENCE: 2

Met Glu Thr Glu Glu Glu Leu Arg His Glu Ile Thr Arg Leu Lys Gln
1               5                   10                  15

Gln Leu Ala Ser Leu Asn Ser Ala Val Thr Ser Ser Thr Glu Gly
            20                  25                  30

Ile Lys Asp Gly Asp Asn Arg Ser Thr Gly Ser Val Cys Ile Val Asn
        35                  40                  45

Ala Pro Pro Glu Lys Ser Gly Tyr Leu Phe Lys Trp Gln Asp Arg Ala

```
             50                  55                  60
Ile Gly Trp Gly Gly Thr Lys Trp Gly Leu Arg Phe Val Arg Leu Asp
 65                  70                  75                  80

His Gly Gln Leu Ser Tyr Tyr Lys Thr His Glu Asp Arg Ser Ala Arg
                 85                  90                  95

Tyr Val Leu Thr Leu Lys Asn Cys Ala Val Arg Asp Glu Gly Ser Lys
            100                 105                 110

Val Asn Lys Arg His Ala Thr Ser Lys Lys Arg Gly Ser Val Glu Ser
        115                 120                 125

Ser Arg Leu Pro Gly Ala Glu Ser Glu Thr Glu Gly His Glu Ala Gly
    130                 135                 140

Ser His Phe Tyr Val Phe Ser Val Tyr Arg Arg Pro Asn Lys Tyr Glu
145                 150                 155                 160

Val Glu Ala Asn Ala Arg Ser Gly Glu Asp Asp Ala Gln His Asp Ser
                165                 170                 175

Glu Glu His Ile Ile Pro Leu Leu Arg Phe Ser Thr Gln Ser Tyr Ala
            180                 185                 190

Glu Lys Leu Gln Trp Ile Asp Leu Ile Ser Gln Ser Cys Ala Tyr Cys
        195                 200                 205

Asp Ser Glu Glu Phe Ala Leu Tyr Gln Gln Gln Gln Gln Glu Met Leu
210                 215                 220

Lys Gln Gln Gln Arg Gln Pro Lys Gly Thr Leu Pro Ala Leu Val
225                 230                 235                 240

Phe Glu Ala Pro Pro Lys Gln Asp Ile Gln Gly Tyr Pro Ser Gly
                245                 250                 255

Tyr Asn Leu Leu Asn Ser Arg Ala Lys His Phe Arg Arg Lys Ser Asn
            260                 265                 270

Met Lys Asp Ala Ala Arg Ser Asn Lys Ile Ser Tyr Pro Pro Ser Lys
        275                 280                 285

Pro Met His Arg Gln Ser Asn Pro Ser Tyr Leu Ser Glu Gly Ala His
    290                 295                 300

Ala Gln Asn Tyr His Gly Leu Phe Asn Leu Phe Leu Ile Leu Val
305                 310                 315                 320

Leu Ser Asn Phe Arg Leu Leu Met His Ala Val Ser Gln His Gly Phe
                325                 330                 335

Phe Phe Asp Lys Ile Pro Ser Phe His Asp Phe Ser Glu Ala Pro Leu
            340                 345                 350

Asp Phe Pro Phe Val Ser Gly Leu Leu Val Gln Ala Phe Val Leu
        355                 360                 365

Gly Ala Tyr Ala Ile Glu Lys Met Leu Val Leu Gly Phe Val Gly Gly
    370                 375                 380

Arg Val Gly Ile Phe Leu His Ala Ile Asn Cys Asn Ala Ser Leu Gly
385                 390                 395                 400

Val Val Ile Ser Ile Val Trp Tyr Leu Ile Asp Gln Pro Ile Ile Gly
                405                 410                 415

Ala Ile Leu Ile Leu Gln Ala Thr Ile Thr Trp Leu Lys Leu Ile Ser
            420                 425                 430

Tyr Ala His Ala Asn Tyr Asp Tyr Arg Thr Ser Pro Glu Ser Tyr Asn
        435                 440                 445

Leu Thr Arg Thr Leu Val Lys Asp Leu Asp Glu Ala Gly Thr Arg Leu
    450                 455                 460

Ser Tyr Pro Gln Asn Val Thr Leu Gly Asn Ile Tyr Tyr Phe Trp Phe
465                 470                 475                 480
```

Ala Pro Thr Leu Thr Tyr Gln Met Ala Phe Pro Arg Ala Pro Phe Ile
            485                 490                 495

Gln Trp Pro Lys Val Leu Arg Leu Ser Val Gln Leu Phe Val Ser Ile
        500                 505                 510

Ile Leu Val Leu Phe Phe Phe Ala Gln Ile Val Ala Pro Asn Leu Asp
        515                 520                 525

Ser Leu Val Arg Asp Leu Glu Asn Asp Lys Gly Glu Val Arg Val His
    530                 535                 540

Val Ile Gly Asp Tyr Leu Leu Arg Met Ser Ile Ala Ser Thr Tyr Ile
545                 550                 555                 560

Trp Leu Leu Gly Phe Gly Phe Phe His Cys Phe Met Asn Ile Thr
                565                 570                 575

Ala Glu Leu Leu Arg Phe Gly Asp Arg Val Phe Tyr Arg Asp Trp Trp
            580                 585                 590

Asn Ala Ser Glu Val Ser Ala Tyr Trp Arg Leu Trp Asn Met Pro Val
        595                 600                 605

His Tyr Trp Leu Val Arg His Val Tyr Phe Pro Cys Ile Arg Ile Gly
        610                 615                 620

Leu Ser Lys Lys Gly Ala Thr Phe Val Val Phe Leu Leu Ser Ala Val
625                 630                 635                 640

Leu His Glu Val Leu Ile Ser Val Pro Cys His Met Ile Arg Val Trp
                645                 650                 655

Ser Phe Leu Ala Met Met Gly Gln Ile Pro Leu Ile Ile Leu Thr Lys
            660                 665                 670

Lys Ile Asp Arg Arg Met Pro Gly Ser Ser Ile Gly Asn Ile Ile Phe
        675                 680                 685

Trp Ile Ser Phe Cys Leu Val Gly Gln Pro Met Ala Met Leu Leu Tyr
    690                 695                 700

Thr Ile Asp Tyr Trp Glu Thr His Ser Val Leu Thr Pro Glu Ala Met
705                 710                 715                 720

Thr Asp Tyr Val Ser Arg Arg Gly Leu Pro Phe Ala Ala Ile Gly Arg
                725                 730                 735

Phe Phe Gly Ala Ser Pro Glu Leu
            740

<210> SEQ ID NO 3
<211> LENGTH: 1569
<212> TYPE: DNA
<213> ORGANISM: Cyclotella sp.

<400> SEQUENCE: 3
atgttgaaac aacaacaacg acaaccgcca aaagggactc ttccagcttt ggtgttcgag    60
gcccctcctc cgaagcaaga tattcaagga tatccttccg gatacaatct tttgaattca   120
agagcaaaac attttcgtag aaagtcaaac atgaaggatg cggctcggtc aaacaaaatt   180
tcatacccac catccaagcc tatgcatcgc caaagcaatc catcttacct ctcggaaggt   240
gcccatgccc agaactacca cggtctcttt aatctgttcc tactcatatt agtcctatcc   300
aactttcgac tgttgatgca tgcagtgagc aacatggctt ttttctttga caagattcca   360
tcgttccacg attttccga agcaccactt gacttcccgt tgtttcggg tttattagtt   420 gttcaagctt ttgtgctggg cgcgtatgcc attgaaaaaa tgctggtgct tggtttcgtc   480 gggggggcgag ttgaatatt tttacacgct atcaattgta atgcatcgct tggagttgtc   540
atttccattg tttggtactt gattgatcaa ccaatcattg gagcaatctt gattttgcaa   600

-continued

```
gcgacaatca cgtggttgaa gctaatatca tacgcccatg ccaactatga ctatagaact    660
tcgccagagt cctacaacct gactcgaaca ttggtaaaag atttagacga agctggcacc    720
agattgtctt atcctcaaaa tgttacattg ggaaacatat actactttttg gtttgcacca   780
acactaacat atcagatggc gtttcccaga gctcctttta ttcagtggcc aaaggttttg    840
aggctgtcag tccagctgtt tgtttctatc attcttgttc tattttttctt cgcccaaatt   900
gtggcaccaa atcttgacag tctcgtcaga gatttggaga acgacaaagg agaagtgaga    960
gtacatgtga taggtgacta cttgcttcgt atgtcaatcg cgagcaccta tatatggctg   1020
ttgggtttct ttggtttctt tcactgcttt atgaatatta ctgctgaatt acttcgattt   1080
ggagatcgtg tattctacag agattggtgg aatgcatcag aagtatctgc atattggaga   1140
ttatggaaca tgcccgttca ttactggtta gttcgtcacg tttacttccc gtgcattcgc   1200
ataggccttt caaagaaggg agccaccttc gtcgtttttc ttttatcggc agtgttgcat   1260
gaagtattga taagtgtacc gtgtcacatg attcgagtct ggtcgtttct tgcaatgatg   1320
ggccagatcc cactgattat tctcacgaaa aagattgaca ggagaatgcc aggcagctcc   1380
atcggaaaca taatattctg gatttcgttt tgtcttgtgg ggcaaccaat ggccatgttg   1440
ctttatacga ttgattactg ggagacgcac tctgttctta ctccagaggc aatgaccgac   1500
tacgtttcga cgtgggct accctttgct gccataggc gattttttgg tgcttctcct     1560
gagctttga                                                           1569
```

```
<210> SEQ ID NO 4
<211> LENGTH: 544
<212> TYPE: PRT
<213> ORGANISM: Cyclotella sp.

<400> SEQUENCE: 4
```

| | | | | | | | | | | | | | | |
|---|---|---|---|---|---|---|---|---|---|---|---|---|---|---|
Ile Ser Gln Ser Cys Ala Tyr Cys Asp Ser Glu Glu Phe Ala Leu Tyr
1               5                   10                  15

Gln Gln Gln Gln Gln Glu Met Leu Lys Gln Gln Gln Arg Gln Pro Pro
            20                  25                  30

Lys Gly Thr Leu Pro Ala Leu Val Phe Glu Ala Pro Pro Lys Gln
        35                  40                  45

Asp Ile Gln Gly Tyr Pro Ser Gly Tyr Asn Leu Leu Asn Ser Arg Ala
    50                  55                  60

Lys His Phe Arg Arg Lys Ser Asn Met Lys Asp Ala Ala Arg Ser Asn
65                  70                  75                  80

Lys Ile Ser Tyr Pro Pro Ser Lys Pro Met His Arg Gln Ser Asn Pro
                85                  90                  95

Ser Tyr Leu Ser Glu Gly Ala His Ala Gln Asn Tyr His Gly Leu Phe
            100                 105                 110

Asn Leu Phe Leu Leu Ile Leu Val Leu Ser Asn Phe Arg Leu Leu Met
        115                 120                 125

His Ala Val Ser Gln His Gly Phe Phe Asp Lys Ile Pro Ser Phe
    130                 135                 140

His Asp Phe Ser Glu Ala Pro Leu Asp Phe Pro Phe Val Ser Gly Leu
145                 150                 155                 160

Leu Val Val Gln Ala Phe Val Leu Gly Ala Tyr Ala Ile Glu Lys Met
                165                 170                 175

Leu Val Leu Gly Phe Val Gly Gly Arg Val Gly Ile Phe Leu His Ala
            180                 185                 190

| | | | | | | | | | | | |
|---|---|---|---|---|---|---|---|---|---|---|---|
| Ile | Asn | Cys | Asn | Ala | Ser | Leu | Gly | Val | Val | Ile | Ser | Ile | Val | Trp | Tyr |
| | | | 195 | | | | 200 | | | | 205 | | | | |
| Leu | Ile | Asp | Gln | Pro | Ile | Ile | Gly | Ala | Ile | Leu | Ile | Leu | Gln | Ala | Thr |
| 210 | | | | | 215 | | | | | 220 | | | | | |
| Ile | Thr | Trp | Leu | Lys | Leu | Ile | Ser | Tyr | Ala | His | Ala | Asn | Tyr | Asp | Tyr |
| 225 | | | | 230 | | | | | 235 | | | | | 240 | |
| Arg | Thr | Ser | Pro | Glu | Ser | Tyr | Asn | Leu | Thr | Arg | Thr | Leu | Val | Lys | Asp |
| | | | | 245 | | | | | 250 | | | | | 255 | |
| Leu | Asp | Glu | Ala | Gly | Thr | Arg | Leu | Ser | Tyr | Pro | Gln | Asn | Val | Thr | Leu |
| | | | | 260 | | | | | 265 | | | | | 270 | |
| Gly | Asn | Ile | Tyr | Tyr | Phe | Trp | Phe | Ala | Pro | Thr | Leu | Thr | Tyr | Gln | Met |
| | | 275 | | | | | 280 | | | | | 285 | | | |
| Ala | Phe | Pro | Arg | Ala | Pro | Phe | Ile | Gln | Trp | Pro | Lys | Val | Leu | Arg | Leu |
| | 290 | | | | | 295 | | | | | 300 | | | | |
| Ser | Val | Gln | Leu | Phe | Val | Ser | Ile | Ile | Leu | Val | Leu | Phe | Phe | Phe | Ala |
| 305 | | | | | 310 | | | | | 315 | | | | | 320 |
| Gln | Ile | Val | Ala | Pro | Asn | Leu | Asp | Ser | Leu | Val | Arg | Asp | Leu | Glu | Asn |
| | | | | 325 | | | | | 330 | | | | | 335 | |
| Asp | Lys | Gly | Glu | Val | Arg | Val | His | Val | Ile | Gly | Asp | Tyr | Leu | Leu | Arg |
| | | | 340 | | | | | 345 | | | | | 350 | | |
| Met | Ser | Ile | Ala | Ser | Thr | Tyr | Ile | Trp | Leu | Leu | Gly | Phe | Gly | Phe |
| | | 355 | | | | | 360 | | | | | 365 | | |
| Phe | His | Cys | Phe | Met | Asn | Ile | Thr | Ala | Glu | Leu | Leu | Arg | Phe | Gly | Asp |
| | 370 | | | | | 375 | | | | | 380 | | | | |
| Arg | Val | Phe | Tyr | Arg | Asp | Trp | Trp | Asn | Ala | Ser | Glu | Val | Ser | Ala | Tyr |
| 385 | | | | | 390 | | | | | 395 | | | | | 400 |
| Trp | Arg | Leu | Trp | Asn | Met | Pro | Val | His | Tyr | Trp | Leu | Val | Arg | His | Val |
| | | | | 405 | | | | | 410 | | | | | 415 | |
| Tyr | Phe | Pro | Cys | Ile | Arg | Ile | Gly | Leu | Ser | Lys | Lys | Gly | Ala | Thr | Phe |
| | | | 420 | | | | | 425 | | | | | 430 | | |
| Val | Val | Phe | Leu | Leu | Ser | Ala | Val | Leu | His | Glu | Val | Leu | Ile | Ser | Val |
| | | | 435 | | | | | 440 | | | | | 445 | | |
| Pro | Cys | His | Met | Ile | Arg | Val | Trp | Ser | Phe | Leu | Ala | Met | Met | Gly | Gln |
| | 450 | | | | | 455 | | | | | 460 | | | | |
| Ile | Pro | Leu | Ile | Ile | Leu | Thr | Lys | Lys | Ile | Asp | Arg | Arg | Met | Pro | Gly |
| 465 | | | | | 470 | | | | | 475 | | | | | 480 |
| Ser | Ser | Ile | Gly | Asn | Ile | Ile | Phe | Trp | Ile | Ser | Phe | Cys | Leu | Val | Gly |
| | | | | 485 | | | | | 490 | | | | | 495 | |
| Gln | Pro | Met | Ala | Met | Leu | Leu | Tyr | Thr | Ile | Asp | Tyr | Trp | Glu | Thr | His |
| | | | 500 | | | | | 505 | | | | | 510 | | |
| Ser | Val | Leu | Thr | Pro | Glu | Ala | Met | Thr | Asp | Tyr | Val | Ser | Arg | Arg | Gly |
| | | | 515 | | | | | 520 | | | | | 525 | | |
| Leu | Pro | Phe | Ala | Ala | Ile | Gly | Arg | Phe | Phe | Gly | Ala | Ser | Pro | Glu | Leu |
| | | | 530 | | | | | 535 | | | | | 540 | | |

<210> SEQ ID NO 5
<211> LENGTH: 666
<212> TYPE: DNA
<213> ORGANISM: Cyclotella sp.

<400> SEQUENCE: 5

```
atggagaccg aggaggaatt acgacacgaa atcacaagac tgaaacaaca gctagcttct      60
ttgaactccg cagtcacatc aagcagcacc gaaggcatca aggacggtga caatcgcagc     120
accggcagtg tttgtattgt gaatgctccg ccagaaaaat cgggttatct ttttaaatgg     180
```

-continued

```
caggacagag cgatcgggtg gggtggtacc aaatggggat tgcgtttcgt ccgtttagat      240
cacggccaat tgagctacta taaaacacac gaagaccgca gcgcgagata tgtcttgact      300
ttgaagaatt gcgcagtgag agacgaggga tccaaagtca ataagcggca cgcgacctct      360
aagaaacgcg ggagtgtcga atcgtcgcgg ttaccaggcg ccgagtcgga gacggaaggt      420
cacgaggcgg gatcacattt ttacgtcttc tcagtctatc gaaggccgaa caagtacgag      480
gtcgaagcaa acgcaagaag tggcgaggat gatgcgcagc atgacagcga ggaacatatc      540
attcccttgt tgcgattctc tacgcagagt tacgcggaaa aattgcaatg gattgaccctc     600 atttctcaat cttgtgccta ctgtgactct gaagaattcg ctctctatca acagcagcaa      660
caagaa                                                                 666
```

<210> SEQ ID NO 6
<211> LENGTH: 200
<212> TYPE: PRT
<213> ORGANISM: Cyclotella sp.

<400> SEQUENCE: 6

```
Met Glu Thr Glu Glu Glu Leu Arg His Glu Ile Thr Arg Leu Lys Gln
1               5                   10                  15

Gln Leu Ala Ser Leu Asn Ser Ala Val Thr Ser Ser Thr Glu Gly
            20                  25                  30

Ile Lys Asp Gly Asp Asn Arg Ser Thr Gly Ser Val Cys Ile Val Asn
        35                  40                  45

Ala Pro Pro Glu Lys Ser Gly Tyr Leu Phe Lys Trp Gln Asp Arg Ala
    50                  55                  60

Ile Gly Trp Gly Gly Thr Lys Trp Gly Leu Arg Phe Val Arg Leu Asp
65                  70                  75                  80

His Gly Gln Leu Ser Tyr Tyr Lys Thr His Glu Asp Arg Ser Ala Arg
                85                  90                  95

Tyr Val Leu Thr Leu Lys Asn Cys Ala Val Arg Asp Glu Gly Ser Lys
            100                 105                 110

Val Asn Lys Arg His Ala Thr Ser Lys Lys Arg Gly Ser Val Glu Ser
        115                 120                 125

Ser Arg Leu Pro Gly Ala Glu Ser Glu Thr Glu Gly His Glu Ala Gly
    130                 135                 140

Ser His Phe Tyr Val Phe Ser Val Tyr Arg Arg Pro Asn Lys Tyr Glu
145                 150                 155                 160

Val Glu Ala Asn Ala Arg Ser Gly Glu Asp Asp Ala Gln His Asp Ser
                165                 170                 175

Glu Glu His Ile Ile Pro Leu Leu Arg Phe Ser Thr Gln Ser Tyr Ala
            180                 185                 190

Glu Lys Leu Gln Trp Ile Asp Leu
        195                 200
```

<210> SEQ ID NO 7
<211> LENGTH: 2268
<212> TYPE: DNA
<213> ORGANISM: Navicula sp.

<400> SEQUENCE: 7

```
atgatcggct tacccattga cgactcgtcg aacaatcttg ctgagaaagc caatgacaag       60
aatatagatc acatactctc cggtgggaaa ctgggcaagg cgactatcga agagagctg       120 cagcgacgca ttgaaaaact gcagcaagag ctacaaacag ctcaggagga cttgtcgcgt      180
```

```
tttcgcaatg tcgtagagaa caatgataat ggtactacca aaagaacacc atcagcatcc      240
cctcccgtga ttgcatcgac ctattcttcc gattcgaatg acaatgcgcc cgaaatattt      300
ttaccaccct cgaaacgagg atatctattc cgatggttg accgaagtat aggctggtcg       360
gggagcaagt gggcactgcg atttgttacg ctggagaatg gaaacctttc ttattatggt      420
agtcatactg acacagctcc gcgttatgtt cttagtttac gtggctgtgc ggtaagggat      480
gaaggacaca agcccaacaa acgttacaaa cgcactgaag acgatgatac tcctcctcgc      540
ttggataagg tgggagccta tttctttctt ttctctatct accttcgaaa cgatgcctct      600
cctgctcatc aagatccaac ggccgagttg accgaaatca ctccgttgct acgtttctcc      660
accgactcgt atgccgaaaa gaagcagtgg gtgcagctca tatcggaaac atgcgcctac      720
tgtgaatcag atgcattcgt tgcggaaatg gagcgaaggc aagaagagaa gcaaactatg      780
actctagcaa tgccggaagc aaaagtgggg acattgccgc cgttgtactt tgcacctgtt      840
cagcaaaagc attcgcgtca tccttctttt acaagaaagc caaatgcggc catgtttcga      900
acaaagtctc agaacatgga cccgtcgcaa gttgagtcaa aggggtatcc tccgtcgaaa      960
ccaatgcatc gttgtgcagc gccttcgtac ctctccgtag aaggaccgac tcaaaattat     1020
cgtggattct tcaacctggg agttatcgtt ctggtggttt cgaatattcg gctggtcctg     1080
tcgagtttca agaaacacgg attcgtgctc ctacgacatt tatcggagat acctcgtttg     1140
ggagatcatc cttggaaaaa cttttccattc gtctctggct tcttgctctt attcgtgttt     1200
gttatggtga catatctgct agagcttggc ttgagccgaa agaaactccc tcagcggctt     1260
ggtatattac tacactatgc gaatgctcat gcttgtatgg gggtctctat atggattgta     1320
tggtacttag tagacgcgcc tgctgtcggg gcggtactac ttcttttcgc gacaagtacg     1380
tggatgaagc tactttcgta cgtacatacg aatgaagatt atcgatccaa tcagatgcaa     1440
cagcaagcta cgttctcgtc gatggtagag gatctggacc cgcaagaagc tcgcgtccgc     1500
tatccacaaa atgtgactat ctccaacata ttctactttt gggcagctcc gactctaact     1560
taccaaattg catttccgcg gtcccctagt gtgagactat ggaaggtggc ggtgattttg     1620
atccgaatgg ttcctattct tgctctgttt acattctttg tctcgcagtt cgtcaccct      1680
acgatggagg gcttggtggc agatcttgag gcgaactgtg gacgttacac tgtgaccatg     1740
ctcgctgaat actggttacg tctgagcatt gccaacacgt atctgtggct gctgatgttt     1800
tattttatt ccatttgtt tttgaacctc tttgcggaaa tactgagatt cggggatcga      1860
gtcttttaca aagattggtg gaattcgtcc gaagtttctg cgtattggcg attatggaac     1920
atgccagtac acttttggtt agtccgacat ctctactttc cttgcgttcg catgggcatg     1980
tcaaagactt taacgacatt cattgtgttc ttcgtttcgg ctgttcttca tgaggtcttg     2040
gtcagtgtcc catttcacat ggtccgacct tggtcttttt tgggaatgat gatgcaaatc     2100
ccgttagttg gaatgacaaa agtgctcagt cgtcagtatc caacgttagg aaatgtgata     2160
ttctggatat cgttttgtat tgtggggcaa ccgatggccg tccttctgta tacggtcgac     2220
tatcaatacg cgaagcacaa catgacagca caagaatgtg tcgtctag                  2268
```

<210> SEQ ID NO 8
<211> LENGTH: 755
<212> TYPE: PRT
<213> ORGANISM: Navicula sp.

<400> SEQUENCE: 8

```
Met Ile Gly Leu Pro Ile Asp Asp Ser Ser Asn Asn Leu Ala Glu Lys
 1               5                  10                  15
Ala Asn Asp Lys Asn Ile Asp His Ile Leu Ser Gly Gly Lys Leu Gly
             20                  25                  30
Lys Ala Thr Ile Glu Arg Glu Leu Gln Arg Arg Ile Glu Lys Leu Gln
             35                  40                  45
Gln Glu Leu Gln Thr Ala Gln Glu Asp Leu Ser Arg Phe Arg Asn Val
     50                  55                  60
Val Glu Asn Asn Asp Asn Gly Thr Thr Lys Arg Thr Pro Ser Ala Ser
 65                  70                  75                  80
Pro Pro Val Ile Ala Ser Thr Tyr Ser Ser Asp Ser Asn Asp Asn Ala
                 85                  90                  95
Pro Glu Ile Phe Leu Pro Pro Ser Lys Arg Gly Tyr Leu Phe Arg Trp
                100                 105                 110
Val Asp Arg Ser Ile Gly Trp Ser Gly Ser Lys Trp Ala Leu Arg Phe
            115                 120                 125
Val Thr Leu Glu Asn Gly Asn Leu Ser Tyr Tyr Gly Ser His Thr Asp
        130                 135                 140
Thr Ala Pro Arg Tyr Val Leu Ser Leu Arg Gly Cys Ala Val Arg Asp
145                 150                 155                 160
Glu Gly His Lys Pro Asn Lys Arg Tyr Lys Arg Thr Glu Asp Asp Asp
                165                 170                 175
Thr Pro Pro Arg Leu Asp Lys Val Gly Ala Tyr Phe Phe Leu Phe Ser
                180                 185                 190
Ile Tyr Leu Arg Asn Asp Ala Ser Pro Ala His Gln Asp Pro Thr Ala
            195                 200                 205
Glu Leu Thr Glu Ile Thr Pro Leu Leu Arg Phe Ser Thr Asp Ser Tyr
        210                 215                 220
Ala Glu Lys Lys Gln Trp Val Gln Leu Ile Ser Glu Thr Cys Ala Tyr
225                 230                 235                 240
Cys Glu Ser Asp Ala Phe Val Ala Glu Met Glu Arg Arg Gln Glu Glu
                245                 250                 255
Lys Gln Thr Met Thr Leu Ala Met Pro Glu Ala Lys Val Gly Thr Leu
                260                 265                 270
Pro Pro Leu Tyr Phe Ala Pro Val Gln Gln Lys His Ser Arg His Pro
            275                 280                 285
Ser Phe Thr Arg Lys Pro Asn Ala Ala Met Phe Arg Thr Lys Ser Gln
        290                 295                 300
Asn Met Asp Pro Ser Gln Val Glu Ser Lys Gly Tyr Pro Pro Ser Lys
305                 310                 315                 320
Pro Met His Arg Cys Ala Ala Pro Ser Tyr Leu Ser Val Glu Gly Pro
                325                 330                 335
Thr Gln Asn Tyr Arg Gly Phe Phe Asn Leu Gly Val Ile Val Leu Val
                340                 345                 350
Val Ser Asn Ile Arg Leu Val Leu Ser Ser Phe Lys Lys His Gly Phe
            355                 360                 365
Val Leu Leu Arg His Leu Ser Glu Ile Pro Arg Leu Gly Asp His Pro
        370                 375                 380
Trp Lys Asn Phe Pro Phe Val Ser Gly Phe Leu Leu Phe Val Phe
385                 390                 395                 400
Val Met Val Thr Tyr Leu Leu Glu Leu Gly Leu Ser Arg Lys Lys Leu
                405                 410                 415
Pro Gln Arg Leu Gly Ile Leu Leu His Tyr Ala Asn Ala His Ala Cys
```

```
                420             425             430
Met Gly Val Ser Ile Trp Ile Val Trp Tyr Leu Val Asp Ala Pro Ala
            435                 440                 445

Val Gly Ala Val Leu Leu Leu Phe Ala Thr Ser Thr Trp Met Lys Leu
        450                 455                 460

Leu Ser Tyr Val His Thr Asn Glu Asp Tyr Arg Ser Asn Gln Met Gln
465                 470                 475                 480

Gln Gln Ala Thr Phe Ser Ser Met Val Glu Asp Leu Asp Pro Gln Glu
                485                 490                 495

Ala Arg Val Arg Tyr Pro Gln Asn Val Thr Ile Ser Asn Ile Phe Tyr
            500                 505                 510

Phe Trp Ala Ala Pro Thr Leu Thr Tyr Gln Ile Ala Phe Pro Arg Ser
        515                 520                 525

Pro Ser Val Arg Leu Trp Lys Val Ala Val Ile Leu Ile Arg Met Val
    530                 535                 540

Pro Ile Leu Ala Leu Phe Thr Phe Phe Val Ser Gln Phe Val Thr Pro
545                 550                 555                 560

Thr Met Glu Gly Leu Val Ala Asp Leu Glu Ala Asn Cys Gly Arg Tyr
                565                 570                 575

Thr Val Thr Met Leu Ala Glu Tyr Trp Leu Arg Leu Ser Ile Ala Asn
            580                 585                 590

Thr Tyr Leu Trp Leu Leu Met Phe Tyr Phe Tyr Phe His Leu Phe Leu
        595                 600                 605

Asn Leu Phe Ala Glu Ile Leu Arg Phe Gly Asp Arg Val Phe Tyr Lys
    610                 615                 620

Asp Trp Trp Asn Ser Ser Glu Val Ser Ala Tyr Trp Arg Leu Trp Asn
625                 630                 635                 640

Met Pro Val His Phe Trp Leu Val Arg His Leu Tyr Phe Pro Cys Val
                645                 650                 655

Arg Met Gly Met Ser Lys Thr Leu Thr Thr Phe Ile Val Phe Phe Val
            660                 665                 670

Ser Ala Val Leu His Glu Val Leu Val Ser Val Pro Phe His Met Val
        675                 680                 685

Arg Pro Trp Ser Phe Leu Gly Met Met Met Gln Ile Pro Leu Val Gly
    690                 695                 700

Met Thr Lys Val Leu Ser Arg Gln Tyr Pro Thr Leu Gly Asn Val Ile
705                 710                 715                 720

Phe Trp Ile Ser Phe Cys Ile Val Gly Gln Pro Met Ala Val Leu Leu
                725                 730                 735

Tyr Thr Val Asp Tyr Gln Tyr Ala Lys His Asn Met Thr Ala Gln Glu
            740                 745                 750

Cys Val Val
        755

<210> SEQ ID NO 9
<211> LENGTH: 1507
<212> TYPE: DNA
<213> ORGANISM: Navicula sp.

<400> SEQUENCE: 9
cgcctactgt gaatcagatg cattcgttgc ggaaatggag cgaaggcaag aagagaagca      60
aactatgact ctagcaatgc cggaagcaaa agtggggaca ttgccgccgt tgtactttgc     120
acctgttcag caaaagcatt cgcgtcatcc ttcttttaca agaaagccaa atgcggccat     180
```

```
gtttcgaaca aagtctcaga acatggaccc gtcgcaagtt gagtcaaagg ggtatcctcc      240
gtcgaaacca atgcatcgtt gtgcagcgcc ttcgtacctc tccgtagaag gaccgactca      300
aaattatcgt ggattcttca acctgggagt tatcgttctg gtggtttcga atattcggct      360
ggtcctgtcg agtttcaaga aacacggatt cgtgctccta cgacatttat cggagatacc      420
tcgtttggga gatcatcctt ggaaaaactt tccattcgtc tctggcttct tgctcttatt      480
cgtgtttgtt atggtgacat atctgctaga gcttggcttg agccgaaaga aactccctca      540
gcggcttggt atattactac actatgcgaa tgctcatgct tgtatggggg tctctatatg      600
gattgtatgg tacttagtag acgcgcctgc tgtcggggcg gtactacttc ttttcgcgac      660
aagtacgtgg atgaagctac tttcgtacgt acatacgaat gaagattatc gatccaatca      720
gatgcaacag caagctacgt tctcgtcgat ggtagaggat ctggacccgc aagaagctcg      780
cgtccgctat ccacaaaatg tgactatctc aacatattc tacttttggg cagctccgac      840
tctaacttac caaattgcat ttccgcggtc ccctagtgtg agactatgga aggtggcggt      900
gattttgatc cgaatggttc ctattcttgc tctgtttaca ttctttgtct cgcagttcgt      960
caccctacg atggagggct tggtggcaga tcttgaggcg aactgtggac gttacactgt     1020
gaccatgctc gctgaatact ggttacgtct gagcattgcc aacacgtatc tgtggctgct     1080
gatgttttat ttttatttcc atttgttttt gaacctcttt gcggaaatac tgagattcgg     1140
ggatcgagtc ttttacaaag attggtggaa ttcgtccgaa gtttctgcgt attggcgatt     1200
atggaacatg ccagtacact tttggttagt ccgacatctc tactttcctt gcgttcgcat     1260
gggcatgtca aagactttaa cgacattcat tgtgttcttc gtttcggctg ttcttcatga     1320
ggtcttggtc agtgtcccat ttcacatggt ccgaccttgg tctttttgg gaatgatgat     1380
gcaaatcccg ttagttggaa tgacaaaagt gctcagtcgt cagtatccaa cgttaggaaa     1440
tgtgatattc tggatatcgt tttgtattgt ggggcaaccg atggccgtcc ttctgtatac     1500
ggtcgac                                                                1507
```

<210> SEQ ID NO 10
<211> LENGTH: 482
<212> TYPE: PRT
<213> ORGANISM: Navicula sp.

<400> SEQUENCE: 10

```
Ala Tyr Cys Glu Ser Asp Ala Phe Val Ala Glu Met Glu Arg Arg Gln
 1               5                  10                  15

Glu Glu Lys Gln Thr Met Thr Leu Ala Met Pro Glu Ala Lys Val Gly
            20                  25                  30

Thr Leu Pro Pro Leu Tyr Phe Ala Pro Val Gln Gln Lys His Ser Arg
        35                  40                  45

His Pro Ser Phe Thr Arg Lys Pro Asn Ala Ala Met Phe Arg Thr Lys
    50                  55                  60

Ser Gln Asn Met Asp Pro Ser Gln Val Glu Ser Lys Gly Tyr Pro Pro
65                  70                  75                  80

Ser Lys Pro Met His Arg Cys Ala Ala Pro Ser Tyr Leu Ser Val Glu
                85                  90                  95

Gly Pro Thr Gln Asn Tyr Arg Gly Phe Phe Asn Leu Gly Val Ile Val
            100                 105                 110

Leu Val Val Ser Asn Ile Arg Leu Val Leu Ser Phe Lys Lys His
        115                 120                 125

Gly Phe Val Leu Leu Arg His Leu Ser Glu Ile Pro Arg Leu Gly Asp
```

```
                130              135              140
His Pro Trp Lys Asn Phe Pro Phe Val Ser Gly Phe Leu Leu Leu Phe
145                 150              155                 160

Val Phe Val Met Val Thr Tyr Leu Leu Glu Leu Gly Leu Ser Arg Lys
                165              170              175

Lys Leu Pro Gln Arg Leu Gly Ile Leu Leu His Tyr Ala Asn Ala His
                180              185              190

Ala Cys Met Gly Val Ser Ile Trp Ile Val Trp Tyr Leu Val Asp Ala
            195              200              205

Pro Ala Val Gly Ala Val Leu Leu Leu Phe Ala Thr Ser Thr Trp Met
210              215              220

Lys Leu Leu Ser Tyr Val His Thr Asn Glu Asp Tyr Arg Ser Asn Gln
225              230              235              240

Met Gln Gln Gln Ala Thr Phe Ser Ser Met Val Glu Asp Leu Asp Pro
                245              250              255

Gln Glu Ala Arg Val Arg Tyr Pro Gln Asn Val Thr Ile Ser Asn Ile
                260              265              270

Phe Tyr Phe Trp Ala Ala Pro Thr Leu Thr Tyr Gln Ile Ala Phe Pro
                275              280              285

Arg Ser Pro Ser Val Arg Leu Trp Lys Val Ala Val Ile Leu Ile Arg
                290              295              300

Met Val Pro Ile Leu Ala Leu Phe Thr Phe Val Ser Gln Phe Val
305              310              315              320

Thr Pro Thr Met Glu Gly Leu Val Ala Asp Leu Glu Ala Asn Cys Gly
                325              330              335

Arg Tyr Thr Val Thr Met Leu Ala Glu Tyr Trp Leu Arg Leu Ser Ile
                340              345              350

Ala Asn Thr Tyr Leu Trp Leu Leu Met Phe Tyr Phe Tyr Phe His Leu
            355              360              365

Phe Leu Asn Leu Phe Ala Glu Ile Leu Arg Phe Gly Asp Arg Val Phe
370              375              380

Tyr Lys Asp Trp Trp Asn Ser Ser Glu Val Ser Ala Tyr Trp Arg Leu
385              390              395              400

Trp Asn Met Pro Val His Phe Trp Leu Val Arg His Leu Tyr Phe Pro
                405              410              415

Cys Val Arg Met Gly Met Ser Lys Thr Leu Thr Thr Phe Ile Val Phe
                420              425              430

Phe Val Ser Ala Val Leu His Glu Val Leu Val Ser Val Pro Phe His
            435              440              445

Met Val Arg Pro Trp Ser Phe Leu Gly Met Met Gln Ile Pro Leu
450              455              460

Val Gly Met Thr Lys Val Leu Ser Arg Gln Tyr Pro Thr Leu Gly Asn
465              470              475              480

Val Ile

<210> SEQ ID NO 11
<211> LENGTH: 713
<212> TYPE: DNA
<213> ORGANISM: Navicula sp.

<400> SEQUENCE: 11
atgatcggct tacccattga cgactcgtcg aacaatcttg ctgagaaagc caatgacaag      60
aatatagatc acatactctc cggtgggaaa ctgggcaagg cgactatcga agagagctg     120
```

```
cagcgacgca ttgaaaaact gcagcaagag ctacaaacag ctcaggagga cttgtcgcgt    180
tttcgcaatg tcgtagagaa caatgataat ggtactacca aaagaacacc atcagcatcc    240
cctcccgtga ttgcatcgac ctattcttcc gattcgaatg acaatgcgcc cgaaatattt    300
ttaccaccct cgaaacgagg atatctattc cgatgggttg accgaagtat aggctggtcg    360
gggagcaagt gggcactgcg atttgttacg ctggagaatg gaaaccttc ttattatggt    420 agtcatactg acacagctcc gcgttatgtt cttagtttac gtggctgtgc ggtaagggat    480
gaaggacaca agcccaacaa acgttacaaa cgcactgaag acgatgatac tcctcctcgc    540
ttggataagg tgggagccta tttctttctt ttctctatct accttcgaaa cgatgcctct    600
cctgctcatc aagatccaac ggccgagttg accgaaatca ctccgttgct acgtttctcc    660
accgactcgt atgccgaaaa gaagcagtgg gtgcagctca tatcggaaac atg    713
```

<210> SEQ ID NO 12
<211> LENGTH: 238
<212> TYPE: PRT
<213> ORGANISM: Navicula sp.

<400> SEQUENCE: 12

```
Met Ile Gly Leu Pro Ile Asp Asp Ser Ser Asn Asn Leu Ala Glu Lys
1               5                   10                  15

Ala Asn Asp Lys Asn Ile Asp His Ile Leu Ser Gly Gly Lys Leu Gly
            20                  25                  30

Lys Ala Thr Ile Glu Arg Glu Leu Gln Arg Arg Ile Glu Lys Leu Gln
        35                  40                  45

Gln Glu Leu Gln Thr Ala Gln Glu Asp Leu Ser Arg Phe Arg Asn Val
    50                  55                  60

Val Glu Asn Asn Asp Asn Gly Thr Thr Lys Arg Thr Pro Ser Ala Ser
65                  70                  75                  80

Pro Pro Val Ile Ala Ser Thr Tyr Ser Ser Asp Ser Asn Asp Asn Ala
                85                  90                  95

Pro Glu Ile Phe Leu Pro Pro Ser Lys Arg Gly Tyr Leu Phe Arg Trp
            100                 105                 110

Val Asp Arg Ser Ile Gly Trp Ser Gly Ser Lys Trp Ala Leu Arg Phe
        115                 120                 125

Val Thr Leu Glu Asn Gly Asn Leu Ser Tyr Tyr Gly Ser His Thr Asp
    130                 135                 140

Thr Ala Pro Arg Tyr Val Leu Ser Leu Arg Gly Cys Ala Val Arg Asp
145                 150                 155                 160

Glu Gly His Lys Pro Asn Lys Arg Tyr Lys Arg Thr Glu Asp Asp Asp
                165                 170                 175

Thr Pro Pro Arg Leu Asp Lys Val Gly Ala Tyr Phe Phe Leu Phe Ser
            180                 185                 190

Ile Tyr Leu Arg Asn Asp Ala Ser Pro Ala His Gln Asp Pro Thr Ala
        195                 200                 205

Glu Leu Thr Glu Ile Thr Pro Leu Leu Arg Phe Ser Thr Asp Ser Tyr
    210                 215                 220

Ala Glu Lys Lys Gln Trp Val Gln Leu Ile Ser Glu Thr Cys
225                 230                 235
```

<210> SEQ ID NO 13
<211> LENGTH: 1902
<212> TYPE: DNA
<213> ORGANISM: Fragilariopsis cylindrus

<400> SEQUENCE: 13

```
atggatagcc tacgagatga aaggcaagg ctcttgaaag aaatagaaag ggtcgatttt      60
gaaatcgagg agtacgacga acacaatccc ggaccttctt catcccgtaa aaaaattgta    120
atccctgcaa gcaaatcagg ttatctattc aaatggcaag ataggcaaat tgggtgggga    180
ggcacgaaat gggacctaag atttgtaaaa cttgataagg gacgatttgg ttattttta    240
aatcatgacg acactgcacc aagataccta ttaacactaa agaattgtgc tatacgcgac    300
gacggttcta aaccaaataa gagattccgc tgctccaaag aaaatggaaa ggaagtgaag    360
gagagtacac cgggagcatt ctttcatgta ttttctttgt atcagcgtcc aaaggggagg    420
acaaccctaa taactgctgc caatctcgac gaagatgaca cattgttcc tttacttcga     480
ttttctacga atagcctagc cgagaaagta caatggatgg atctactcat cgaatcttgt    540
gcctactgcg attcggatta tttcgatcag aatgaagcat cttcttttgt tgcacataac    600
ggaagcctac ccacatcaac aacccacacc aaaggaactc tctccccatt atattttgaa    660
acgcccactg taaaaattgg tcggactcca tcttatgccc atttattaac aaagaagcct    720
tctcatctca aattgaatct aaataaagat tcggcaaaaa gtaattcaag aaagaagaac    780
gattatccac ctagtaaacc catgcatcgc agagcagaag gatcatatct tagtcacgac    840
tcaccaacac caaattacag aggtctgctt aacttgggtg ttataatact cgtcatttct    900
aattttagaa ttttactggg aacaatgagg gaatatgggt tgtgttaac acatggttac     960
ttttctgttc cggacgaaga gtattcattt aaatggaaag atattgtcga cgtccctttc   1020
gttttcacca tgataatgtt aaacatcttc gtcatttttg cttacctaat tgaattgggc   1080
attagtagga gatttctgaa ggagtggctt ggtatttcat tacatattat taatacaaac   1140
ctttctcttc tcctacctat ggtgattgtt tggaaatata ttaattctcc ggtaaatgga   1200
gcagtactac aaatgtcatc gactgtcctc tggatgaagt tgatttctta tgcacacgcg   1260
aatgctgatt atagacattt tcccgataga aatgtgaaaa atatcattca aaacacagat   1320
gaagaatcca tatctttgaa ctatccacgc aatatcacag taacgaacat atattacttt   1380
tggttcgcac ccacattgac ttatcaaatg gtgtttcctc gactagttag aagaagtaaa   1440
ggtcagattc ttaatcttgt tttacgctta ttttttttgct tcgttctgct ggtgtttctt   1500
gtagctcaag tcttccgccc gacacttaac aacttgatgg aagaattgaa tgagttgaaa   1560
ggagaggata tgcatatact gtctgttcat attttttgcag aatatatact gaaacttggt   1620
atcgcatcga gttatatttg gttgctggtt ttttatggat tctttcatgt tcttttgaat   1680
ctgttagccc aattgttaag gtttggagat cgagtatttt atagagactg gtggaatagt   1740
acgaatatgt catcctattg gcgactctgg aatcttccag ttcattattg gctggttcgt   1800
cacttatatt ttccatgcat tagaattgga atgagcaaat cggccgcaat gtttatggtg   1860
ttctttttct cagctgttgt ccacgagatg ctgatatctg ta                      1902
```

<210> SEQ ID NO 14
<211> LENGTH: 634
<212> TYPE: PRT
<213> ORGANISM: Fragilariopsis cylindrus

<400> SEQUENCE: 14

```
Met Asp Ser Leu Arg Asp Glu Lys Ala Arg Leu Leu Lys Glu Ile Glu
1               5                   10                  15

Arg Val Asp Phe Glu Ile Glu Glu Tyr Asp Glu His Asn Pro Gly Pro
            20                  25                  30
```

```
Ser Ser Ser Arg Lys Lys Ile Val Ile Pro Ala Ser Lys Ser Gly Tyr
            35                  40                  45

Leu Phe Lys Trp Gln Asp Arg Gln Ile Gly Trp Gly Gly Thr Lys Trp
 50                      55                  60

Asp Leu Arg Phe Val Lys Leu Asp Lys Gly Arg Phe Gly Tyr Phe Leu
 65                  70                  75                  80

Asn His Asp Asp Thr Ala Pro Arg Tyr Leu Leu Thr Leu Lys Asn Cys
                85                  90                  95

Ala Ile Arg Asp Asp Gly Ser Lys Pro Asn Lys Arg Phe Arg Cys Ser
                100                 105                 110

Lys Glu Asn Gly Lys Glu Val Lys Glu Ser Thr Pro Gly Ala Phe Phe
            115                 120                 125

His Val Phe Ser Leu Tyr Gln Arg Pro Lys Gly Arg Thr Thr Leu Ile
            130                 135                 140

Thr Ala Ala Asn Leu Asp Glu Asp Asn Ile Val Pro Leu Leu Arg
145                 150                 155                 160

Phe Ser Thr Asn Ser Leu Ala Glu Lys Val Gln Trp Met Asp Leu Leu
                165                 170                 175

Ile Glu Ser Cys Ala Tyr Cys Asp Ser Asp Tyr Phe Asp Gln Asn Glu
            180                 185                 190

Ala Ser Ser Phe Val Ala His Asn Gly Ser Leu Pro Thr Ser Thr Thr
            195                 200                 205

His Thr Lys Gly Thr Leu Ser Pro Leu Tyr Phe Glu Thr Pro Thr Val
210                 215                 220

Lys Ile Gly Arg Thr Pro Ser Tyr Ala His Leu Leu Thr Lys Lys Pro
225                 230                 235                 240

Ser His Leu Lys Leu Asn Leu Asn Lys Asp Ser Ala Lys Ser Asn Ser
                245                 250                 255

Arg Lys Lys Asn Asp Tyr Pro Pro Ser Lys Pro Met His Arg Arg Ala
                260                 265                 270

Glu Gly Ser Tyr Leu Ser His Asp Ser Pro Thr Pro Asn Tyr Arg Gly
            275                 280                 285

Leu Leu Asn Leu Gly Val Ile Ile Leu Val Ile Ser Asn Phe Arg Ile
            290                 295                 300

Leu Leu Gly Thr Met Arg Glu Tyr Gly Phe Val Leu Thr His Gly Tyr
305                 310                 315                 320

Phe Ser Val Pro Asp Glu Glu Tyr Ser Phe Lys Trp Lys Asp Ile Val
                325                 330                 335

Asp Val Pro Phe Val Phe Thr Met Ile Met Leu Asn Ile Phe Val Ile
                340                 345                 350

Phe Ala Tyr Leu Ile Glu Leu Gly Ile Ser Arg Arg Phe Leu Lys Glu
            355                 360                 365

Trp Leu Gly Ile Ser Leu His Ile Ile Asn Thr Asn Leu Ser Leu Leu
            370                 375                 380

Leu Pro Met Val Ile Val Trp Lys Tyr Ile Asn Ser Pro Val Asn Gly
385                 390                 395                 400

Ala Val Leu Gln Met Ser Ser Thr Val Leu Trp Met Lys Leu Ile Ser
                405                 410                 415

Tyr Ala His Ala Asn Ala Asp Tyr Arg His Phe Pro Asp Arg Asn Val
            420                 425                 430

Glu Asn Ile Ile Gln Asn Thr Asp Glu Glu Ser Ile Ser Leu Asn Tyr
            435                 440                 445
```

Pro Arg Asn Ile Thr Val Thr Asn Ile Tyr Tyr Phe Trp Phe Ala Pro
450                 455                 460

Thr Leu Thr Tyr Gln Met Val Phe Pro Arg Leu Val Arg Arg Ser Lys
465                 470                 475                 480

Gly Gln Ile Leu Asn Leu Val Leu Arg Leu Phe Phe Cys Phe Val Leu
            485                 490                 495

Leu Val Phe Leu Val Ala Gln Val Phe Arg Pro Thr Leu Asn Asn Leu
        500                 505                 510

Met Glu Glu Leu Asn Glu Leu Lys Gly Glu Asp Met His Ile Leu Ser
            515                 520                 525

Val His Ile Phe Ala Glu Tyr Ile Leu Lys Leu Gly Ile Ala Ser Ser
530                 535                 540

Tyr Ile Trp Leu Leu Val Phe Tyr Gly Phe Phe His Val Leu Leu Asn
545                 550                 555                 560

Leu Leu Ala Gln Leu Leu Arg Phe Gly Asp Arg Val Phe Tyr Arg Asp
                565                 570                 575

Trp Trp Asn Ser Thr Asn Met Ser Ser Tyr Trp Arg Leu Trp Asn Leu
            580                 585                 590

Pro Val His Tyr Trp Leu Val Arg His Leu Tyr Phe Pro Cys Ile Arg
            595                 600                 605

Ile Gly Met Ser Lys Ser Ala Ala Met Phe Met Val Phe Phe Phe Ser
610                 615                 620

Ala Val Val His Glu Met Leu Ile Ser Val
625                 630

<210> SEQ ID NO 15
<211> LENGTH: 1320
<212> TYPE: DNA
<213> ORGANISM: Fragilariopsis cylindrus

<400> SEQUENCE: 15
gcctactgcg attcggatta tttcgatcag aatgaagcat cttcttttgt tgcacataac      60
ggaagcctac ccacatcaac aacccacacc aaaggaactc tctccccatt atattttgaa     120
acgcccactg taaaaattgg tcggactcca tcttatgccc atttattaac aaagaagcct     180
tctcatctca aattgaatct aaataaagat tcggcaaaaa gtaattcaag aaagaagaac     240
gattatccac ctagtaaacc catgcatcgc agagcagaag gatcatatct tagtcacgac     300
tcaccaacac caaattacag aggtctgctt aacttgggtg ttataatact cgtcatttct     360
aattttagaa ttttactggg aacaatgagg gaatatgggt ttgtgttaac acatggttac     420
ttttctgttc cggacgaaga gtattcattt aaatggaaag atattgtcga cgtccctttc     480
gttttcacca tgataatgtt aaacatcttc gtcattttg cttacctaat tgaattgggc     540
attagtagga gatttctgaa ggagtggctt ggtatttcat acatattat taatacaaac     600
ctttctcttc tcctacctat ggtgattgtt tggaaatata ttaattctcc ggtaaatgga     660
gcagtactac aaatgtcatc gactgtcctc tggatgaagt tgatttctta tgcacacgcg     720
aatgctgatt atagacattt tcccgataga aatgtggaaa atatcattca aaacacagat     780
gaagaatcca tatctttgaa ctatccacgc aatatcacag taacgaacat atattacttt     840
tggttcgcac ccacattgac ttatcaaatg gtgtttcctc gactagttag aagaagtaaa     900
ggtcagattc ttaatcttgt tttacgctta tttttttgct tcgttctgct ggtgtttctt     960
gtagctcaag tcttccgccc gacacttaac aacttgatgg aagaattgaa tgagttgaaa    1020
ggagaggata tgcatatact gtctgttcat attttttgcag aatatatact gaaacttggt    1080

```
atcgcatcga gttatatttg gttgctggtt ttttatggat tctttcatgt tcttttgaat  1140
ctgttagccc aattgttaag gtttggagat cgagtatttt atagagactg gtggaatagt  1200
acgaatatgt catcctattg gcgactctgg aatcttccag ttcattattg gctggttcgt  1260
cacttatatt ttccatgcat tagaattgga atgagcaaat cggccgcaat gtttatggtg  1320

<210> SEQ ID NO 16
<211> LENGTH: 454
<212> TYPE: PRT
<213> ORGANISM: Fragilariopsis cylindrus

<400> SEQUENCE: 16
```

Ala Tyr Cys Asp Ser Asp Tyr Phe Asp Gln Asn Glu Ala Ser Ser Phe
1               5                   10                  15

Val Ala His Asn Gly Ser Leu Pro Thr Ser Thr Thr His Thr Lys Gly
            20                  25                  30

Thr Leu Ser Pro Leu Tyr Phe Glu Thr Pro Thr Val Lys Ile Gly Arg
        35                  40                  45

Thr Pro Ser Tyr Ala His Leu Leu Thr Lys Lys Pro Ser His Leu Lys
    50                  55                  60

Leu Asn Leu Asn Lys Asp Ser Ala Lys Ser Asn Ser Arg Lys Lys Asn
65                  70                  75                  80

Asp Tyr Pro Pro Ser Lys Pro Met His Arg Arg Ala Glu Gly Ser Tyr
                85                  90                  95

Leu Ser His Asp Ser Pro Thr Pro Asn Tyr Arg Gly Leu Leu Asn Leu
            100                 105                 110

Gly Val Ile Ile Leu Val Ile Ser Asn Phe Arg Ile Leu Leu Gly Thr
        115                 120                 125

Met Arg Glu Tyr Gly Phe Val Leu Thr His Gly Tyr Phe Ser Val Pro
    130                 135                 140

Asp Glu Glu Tyr Ser Phe Lys Trp Lys Asp Ile Val Asp Val Pro Phe
145                 150                 155                 160

Val Phe Thr Met Ile Met Leu Asn Ile Phe Val Ile Phe Ala Tyr Leu
                165                 170                 175

Ile Glu Leu Gly Ile Ser Arg Arg Phe Leu Lys Glu Trp Leu Gly Ile
            180                 185                 190

Ser Leu His Ile Ile Asn Thr Asn Leu Ser Leu Leu Pro Met Val
        195                 200                 205

Ile Val Trp Lys Tyr Ile Asn Ser Pro Val Asn Gly Ala Val Leu Gln
    210                 215                 220

Met Ser Ser Thr Val Leu Trp Met Lys Leu Ile Ser Tyr Ala His Ala
225                 230                 235                 240

Asn Ala Asp Tyr Arg His Phe Pro Asp Arg Asn Val Glu Asn Ile Ile
                245                 250                 255

Gln Asn Thr Asp Glu Glu Ser Ile Ser Leu Asn Tyr Pro Arg Asn Ile
            260                 265                 270

Thr Val Thr Asn Ile Tyr Tyr Phe Trp Phe Ala Pro Thr Leu Thr Tyr
        275                 280                 285

Gln Met Val Phe Pro Arg Leu Val Arg Arg Ser Lys Gly Gln Ile Leu
    290                 295                 300

Asn Leu Val Leu Arg Leu Phe Phe Cys Phe Val Leu Leu Val Phe Leu
305                 310                 315                 320

Val Ala Gln Val Phe Arg Pro Thr Leu Asn Asn Leu Met Glu Glu Leu
                325                 330                 335

```
Asn Glu Leu Lys Gly Glu Asp Met His Ile Leu Ser Val His Ile Phe
            340                 345                 350

Ala Glu Tyr Ile Leu Lys Leu Gly Ile Ala Ser Ser Tyr Ile Trp Leu
        355                 360                 365

Leu Val Phe Tyr Gly Phe Phe His Val Leu Leu Asn Leu Leu Ala Gln
370                 375                 380

Leu Leu Arg Phe Gly Asp Arg Val Phe Tyr Arg Asp Trp Trp Asn Ser
385                 390                 395                 400

Thr Asn Met Ser Ser Tyr Trp Arg Leu Trp Asn Leu Pro Val His Tyr
            405                 410                 415

Trp Leu Val Arg His Leu Tyr Phe Pro Cys Ile Arg Ile Gly Met Ser
        420                 425                 430

Lys Ser Ala Ala Met Phe Met Val Phe Phe Phe Ser Ala Val Val His
            435                 440                 445

Glu Met Leu Ile Ser Val
    450

<210> SEQ ID NO 17
<211> LENGTH: 540
<212> TYPE: DNA
<213> ORGANISM: Fragilariopsis cylindrus

<400> SEQUENCE: 17
atggatagcc tacgagatga aaggcaagg ctcttgaaag aaatagaaag ggtcgatttt    60
gaaatcgagg agtacgacga acacaatccc ggaccttctt catcccgtaa aaaaattgta   120
atccctgcaa gcaaatcagg ttatctattc aaatggcaag ataggcaaat tgggtgggga   180
ggcacgaaat gggacctaag atttgtaaaa cttgataagg gacgatttgg ttattttta   240 aatcatgacg acactgcacc aagataccta ttaacactaa agaattgtgc atacgcgac   300 gacggttcta aaccaaataa agattccgc tgctccaaag aaaatggaaa ggaagtgaag   360
gagagtacac cgggagcatt ctttcatgta ttttctttgt atcagcgtcc aaaggggagg   420
acaaccctaa taactgctgc caatctcgac gaagatgaca acattgttcc tttacttcga   480
ttttctacga atagcctagc cgagaaagta caatggatgg atctactcat cgaatcttgt   540

<210> SEQ ID NO 18
<211> LENGTH: 180
<212> TYPE: PRT
<213> ORGANISM: Fragilariopsis cylindrus

<400> SEQUENCE: 18

Met Asp Ser Leu Arg Asp Glu Lys Ala Arg Leu Leu Lys Glu Ile Glu
1               5                   10                  15

Arg Val Asp Phe Glu Ile Glu Glu Tyr Asp Glu His Asn Pro Gly Pro
            20                  25                  30

Ser Ser Ser Arg Lys Lys Ile Val Ile Pro Ala Ser Lys Ser Gly Tyr
        35                  40                  45

Leu Phe Lys Trp Gln Asp Arg Gln Ile Gly Trp Gly Gly Thr Lys Trp
    50                  55                  60

Asp Leu Arg Phe Val Lys Leu Asp Lys Gly Arg Phe Gly Tyr Phe Leu
65                  70                  75                  80

Asn His Asp Asp Thr Ala Pro Arg Tyr Leu Leu Thr Leu Lys Asn Cys
                85                  90                  95

Ala Ile Arg Asp Asp Gly Ser Lys Pro Asn Lys Arg Phe Arg Cys Ser
            100                 105                 110
```

```
Lys Glu Asn Gly Lys Glu Val Lys Glu Ser Thr Pro Gly Ala Phe Phe
            115                 120                 125

His Val Phe Ser Leu Tyr Gln Arg Pro Lys Gly Arg Thr Thr Leu Ile
        130                 135                 140

Thr Ala Ala Asn Leu Asp Glu Asp Asp Asn Ile Val Pro Leu Leu Arg
145                 150                 155                 160

Phe Ser Thr Asn Ser Leu Ala Glu Lys Val Gln Trp Met Asp Leu Leu
                165                 170                 175

Ile Glu Ser Cys
            180

<210> SEQ ID NO 19
<211> LENGTH: 2142
<212> TYPE: DNA
<213> ORGANISM: Botryococcus sp.

<400> SEQUENCE: 19
atgtcggaag ccctggggga gctacaagcg gagaatgtcc gcctgcgaaa catgttgacg      60
ctgcgggaaa gacgggagcc ggaccactgc gggtacctat ttaagcaccg cccctactcc     120
acatcactct tctccccgcc ctgggagctg cgctatttca cccttgcggg cagcgtgctc     180
agccacttcc actctgagaa agacacgtct gccaaccctc gcgggcgcct ggacattgcg     240
ggctgcctgg tggacgtgca gagcggcgag cacgggaagt accatgcctt cagcatcgtg     300
gaccgcaagg gccagctcat gatgcgccta gccagcagca gcaggagga cgtcggcctc      360 tgggttaagg cactgaaggg cgcgggctgc gagcgttacg atgccaagga cgccgcacga     420
cgttcatcac tgcccccccac cagaccccct gacgcccgct catcaatgga gtcaacgatg    480
agggcaggcg cgacgagcgg ggaccttca gatgatcaca gcaagcaccc tcgccctgca      540
cgtgtggtgg gcgctgagcga ggcagcgttg aaggcatcag gcttttcgcg gggtcccgtc    600
cccaattatg ggtcggacag tggaatgagc gaagcgggc cgatgtgccg gccggggctg     660
gggaatgcgc ccgtgccgcc cctccccgtc gcgcggaaac aaataacggg gtccagcatg    720
atgcatgtga ccagccgccc ctcaatgctg tcctcggatc gcatcgctct tacccagcat    780
tcaggcatcc tgaatgtgat gatgttgatc ctggtggctg caaatttccg gctgattgtg    840
gagaacctgc taaagtatgg agttctggtc aaccctctga actggattcg agccctgatg    900
cctcgaggca atctgccgct gctgctgtgt tggcctgcgc tggcgctgtt cagcctgact    960
gccctgtcca tccagcaatt tggcgtctgg cgcctcaagc aggagaagaa ggtgctgacg   1020
acgaagaaga agaaggacat gaagccgagc gaagcgcggc gtgtggctgc aaacatggca   1080
aacacaaccg agggcatcat cctgttggca aatgttgtga atgttgcgct gtcgatggca   1140
gtgccatgcg ccgtcgtcca ctacaccaaa tccgaggctg tcccgggatc ggtcatcacc   1200
gccttcacca tcgtgctctt cctgaagctc gcctcgtact cgcactgcaa cgccgagctg   1260
agagcggcaa agcgggtggc ggatcagagg cccagcagcg tgatctgcg ggagagcggt    1320 gacgggggca tggagatggg cgtgcgctac cccgacaatg tcagcctggg caacctggct   1380
tacttcctgg tggctcccac cctcatctac cagccctcct acccgcagtc cccgccatc    1440 cgcttccgct ggctcttctg gtcggccgta cggctgatgg ggctgatgag cctgatgatg   1500
gtgatcgtgg agcagtacct gactcccacc atcgccaaca gcctcattcc cctgcgcagc   1560
ctcaactggg cgcacatgct ggagcgggtt ctcaagctca gcctgcccac gctgtatggc   1620
tgggtcatca tgttctactg cctgttccac ctgtggctca acatcctggc cgaggtcacc   1680
```

```
tactttggcg accgtgagtt ttacaaggac tggtggaatg cgacgaccat tggagactac    1740
tggcggctgt ggaatatgcc ggtgcacaag tggatgttgc ggcacgtgta cttcccgctg    1800
ctacgcctag gggtcggcaa gttcttggcg ggagtcgggg tatttgcagt gtcaggactc    1860
ctgcatgagc tggctgtggg cctgccgctt catatggtcc gttactgggc gttcctgggc    1920
gtcatgttcc aggtgcctat ggtctatctc acagagtacc tgaagaagcg catgaagagc    1980
gatcagatcg ggaacctgat tttctggatc tccttctgca tcattgggca gcccatctcg    2040
ctcatcctgt actaccacga ttggatcctc atgaatcggc cagactggct gccccaagca    2100
acggcagcgc ccttcccagc gaatgccacg ctggcagcct ga                       2142
```

<210> SEQ ID NO 20
<211> LENGTH: 713
<212> TYPE: PRT
<213> ORGANISM: Botryococcus sp.

<400> SEQUENCE: 20

```
Met Ser Glu Ala Leu Gly Glu Leu Gln Ala Glu Asn Val Arg Leu Arg
1               5                   10                  15

Asn Met Leu Thr Leu Arg Glu Arg Arg Glu Pro Asp His Cys Gly Tyr
                20                  25                  30

Leu Phe Lys His Arg Pro Tyr Ser Thr Ser Leu Phe Ser Pro Pro Trp
            35                  40                  45

Glu Leu Arg Tyr Phe Thr Leu Ala Gly Ser Val Leu Ser His Phe His
        50                  55                  60

Ser Glu Lys Asp Thr Ser Ala Asn Pro Arg Gly Arg Leu Asp Ile Ala
65                  70                  75                  80

Gly Cys Leu Val Asp Val Gln Ser Gly Glu His Gly Lys Tyr His Ala
                85                  90                  95

Phe Ser Ile Val Asp Arg Lys Gly Gln Leu Met Met Arg Leu Ala Ser
            100                 105                 110

Ser Lys Gln Glu Asp Val Gly Leu Trp Val Lys Ala Leu Lys Gly Ala
        115                 120                 125

Gly Cys Glu Arg Tyr Asp Ala Lys Asp Ala Ala Arg Arg Ser Ser Leu
    130                 135                 140

Pro Pro Thr Arg Pro Pro Asp Ala Arg Ser Ser Met Glu Ser Thr Met
145                 150                 155                 160

Arg Ala Gly Ala Thr Ser Gly Asp Leu Ser Asp Asp His Ser Lys His
                165                 170                 175

Pro Arg Pro Ala Arg Val Val Gly Leu Ser Glu Ala Ala Leu Lys Ala
            180                 185                 190

Ser Gly Phe Ser Arg Gly Pro Val Pro Asn Tyr Gly Ser Asp Ser Gly
        195                 200                 205

Met Ser Glu Ala Gly Pro Met Cys Arg Pro Gly Leu Gly Asn Ala Pro
    210                 215                 220

Val Pro Pro Leu Pro Val Ala Arg Lys Gln Ile Thr Gly Ser Ser Met
225                 230                 235                 240

Met His Val Thr Ser Arg Pro Ser Met Leu Ser Ser Asp Arg Ile Ala
                245                 250                 255

Leu Thr Gln His Ser Gly Ile Leu Asn Val Met Met Leu Ile Leu Val
            260                 265                 270

Ala Ala Asn Phe Arg Leu Ile Val Glu Asn Leu Leu Lys Tyr Gly Val
        275                 280                 285
```

```
Leu Val Asn Pro Leu Asn Trp Ile Arg Ala Leu Met Pro Arg Gly Asn
290                 295                 300

Leu Pro Leu Leu Cys Trp Pro Ala Leu Ala Leu Phe Ser Leu Thr
305                 310                 315                 320

Ala Leu Ser Ile Gln Gln Phe Gly Val Trp Arg Leu Lys Gln Glu Lys
                325                 330                 335

Lys Val Leu Thr Thr Lys Lys Lys Asp Met Lys Pro Ser Glu Ala
                340                 345                 350

Arg Arg Val Ala Ala Asn Met Ala Asn Thr Thr Glu Gly Ile Ile Leu
                355                 360                 365

Leu Ala Asn Val Val Asn Val Ala Leu Ser Met Ala Val Pro Cys Ala
370                 375                 380

Val Val His Tyr Thr Lys Ser Glu Ala Val Pro Gly Ser Val Ile Thr
385                 390                 395                 400

Ala Phe Thr Ile Val Leu Phe Leu Lys Leu Ala Ser Tyr Ser His Cys
                405                 410                 415

Asn Ala Glu Leu Arg Ala Ala Lys Arg Val Ala Asp Gln Arg Pro Ser
                420                 425                 430

Ser Gly Asp Leu Arg Glu Ser Gly Asp Gly Met Glu Met Gly Val
                435                 440                 445

Arg Tyr Pro Asp Asn Val Ser Leu Gly Asn Leu Ala Tyr Phe Leu Val
450                 455                 460

Ala Pro Thr Leu Ile Tyr Gln Pro Ser Tyr Pro Gln Ser Pro Ala Ile
465                 470                 475                 480

Arg Phe Arg Trp Leu Phe Trp Ser Ala Val Arg Leu Met Gly Leu Met
                485                 490                 495

Ser Leu Met Met Val Ile Val Glu Gln Tyr Leu Thr Pro Thr Ile Ala
                500                 505                 510

Asn Ser Leu Ile Pro Leu Arg Ser Leu Asn Trp Ala His Met Leu Glu
                515                 520                 525

Arg Val Leu Lys Leu Ser Leu Pro Thr Leu Tyr Gly Trp Val Ile Met
                530                 535                 540

Phe Tyr Cys Leu Phe His Leu Trp Leu Asn Ile Leu Ala Glu Val Thr
545                 550                 555                 560

Tyr Phe Gly Asp Arg Glu Phe Tyr Lys Asp Trp Trp Asn Ala Thr Thr
                565                 570                 575

Ile Gly Asp Tyr Trp Arg Leu Trp Asn Met Pro Val His Lys Trp Met
                580                 585                 590

Leu Arg His Val Tyr Phe Pro Leu Leu Arg Leu Gly Val Gly Lys Phe
                595                 600                 605

Leu Ala Gly Val Gly Val Phe Ala Val Ser Gly Leu Leu His Glu Leu
610                 615                 620

Ala Val Gly Leu Pro Leu His Met Val Arg Tyr Trp Ala Phe Leu Gly
625                 630                 635                 640

Val Met Phe Gln Val Pro Met Val Tyr Leu Thr Glu Tyr Leu Lys Lys
                645                 650                 655

Arg Met Lys Ser Asp Gln Ile Gly Asn Leu Ile Phe Trp Ile Ser Phe
                660                 665                 670

Cys Ile Ile Gly Gln Pro Ile Ser Leu Ile Leu Tyr Tyr His Asp Trp
                675                 680                 685

Ile Leu Met Asn Arg Pro Asp Trp Leu Pro Gln Ala Thr Ala Ala Pro
690                 695                 700

Phe Pro Ala Asn Ala Thr Leu Ala Ala
```

<210> SEQ ID NO 21
<211> LENGTH: 1640
<212> TYPE: DNA
<213> ORGANISM: Botryococcus sp.

<400> SEQUENCE: 21

```
catcaatgga gtcaacgatg agggcaggcg cgacgagcgg ggacctttca gatgatcaca      60
gcaagcaccc tcgccctgca cgtgtggtgg ggctgagcga ggcagcgttg aaggcatcag     120
gcttttcgcg gggtcccgtc cccaattatg ggtcggacag tggaatgagc gaagcggggc     180
cgatgtgccg gccggggctg gggaatgcgc ccgtgccgcc cctccccgtc gcgcggaaac     240
aaataacggg gtccagcatg atgcatgtga ccagccgccc ctcaatgctg tcctcggatc     300
gcatcgctct tacccagcat tcaggcatcc tgaatgtgat gatgttgatc ctggtggctg     360
caaatttccg gctgattgtg gagaacctgc taaagtatgg agttctggtc aaccctctga     420
actggattcg agccctgatg cctcgaggca atctgccgct gctgctgtgt ggcctgcgc      480
tggcgctgtt cagcctgact gccctgtcca tccagcaatt tggcgtctgg cgcctcaagc     540
aggagaagaa ggtgctgacg acgaagaaga agaaggacat gaagccgagc gaagcgcggc     600
gtgtggctgc aaacatggca acacaaccg agggcatcat cctgttggca aatgttgtga      660
atgttgcgct gtcgatggca gtgccatgcg ccgtcgtcca ctacaccaaa tccgaggctg     720
tcccgggatc ggtcatcacc gccttcacca tcgtgctctt cctgaagctc gcctcgtact     780
cgcactgcaa cgccgagctg agagcggcaa agcgggtggc ggatcagagg cccagcagcg     840
gtgatctgcg ggagagcggt gacggggggca tggagatggg cgtgcgctac cccgacaatg    900
tcagcctggg caacctggct tacttcctgg tggctcccac cctcatctac cagccctcct     960
acccgcagtc cccgccatc cgcttccgct ggctcttctg gtcggccgta cggctgatgg     1020
ggctgatgag cctgatgatg gtgatcgtgg agcagtacct gactcccacc atcgccaaca    1080
gcctcattcc cctgcgcagc ctcaactggg cgcacatgct ggagcgggtt ctcaagctca    1140
gcctgcccac gctgtatggc tgggtcatca tgttctactg cctgttccac ctgtggctca    1200
acatcctggc cgaggtcacc tactttggcg accgtgagtt ttacaaggac tggtggaatg    1260
cgacgaccat tggagactac tggcggctgt ggaatatgcc ggtgcacaag tggatgttgc    1320
ggcacgtgta cttcccgctg ctacgcctag gggtcggcaa gttcttggcg ggagtcgggg    1380
tatttgcagt gtcaggactc ctgcatgagc tggctgtggg cctgccgctt catatggtcc    1440
gttactgggc gttcctgggc gtcatgttcc aggtgcctat ggtctatctc acagagtacc    1500
tgaagaagcg catgaagagc gatcagatcg ggaacctgat tttctggatc tccttctgca    1560
tcattgggca gcccatctcg ctcatcctgt actaccacga ttggatcctc atgaatcggc    1620
cagactggct gccccaagca                                                1640
```

<210> SEQ ID NO 22
<211> LENGTH: 560
<212> TYPE: PRT
<213> ORGANISM: Botryococcus sp.

<400> SEQUENCE: 22

```
Ser Ser Met Glu Ser Thr Met Arg Ala Gly Ala Thr Ser Gly Asp Leu
1               5                   10                  15

Ser Asp Asp His Ser Lys His Pro Arg Pro Ala Arg Val Val Gly Leu
            20                  25                  30
```

-continued

```
Ser Glu Ala Ala Leu Lys Ala Ser Gly Phe Ser Arg Gly Pro Val Pro
         35                  40                  45

Asn Tyr Gly Ser Asp Ser Gly Met Ser Glu Ala Gly Pro Met Cys Arg
 50                  55                  60

Pro Gly Leu Gly Asn Ala Pro Val Pro Pro Leu Pro Val Ala Arg Lys
 65              70                  75                  80

Gln Ile Thr Gly Ser Ser Met Met His Val Thr Ser Arg Pro Ser Met
                 85                  90                  95

Leu Ser Ser Asp Arg Ile Ala Leu Thr Gln His Ser Gly Ile Leu Asn
             100                 105                 110

Val Met Met Leu Ile Leu Val Ala Ala Asn Phe Arg Leu Ile Val Glu
         115                 120                 125

Asn Leu Leu Lys Tyr Gly Val Leu Val Asn Pro Leu Asn Trp Ile Arg
130                 135                 140

Ala Leu Met Pro Arg Gly Asn Leu Pro Leu Leu Cys Trp Pro Ala
145                 150                 155                 160

Leu Ala Leu Phe Ser Leu Thr Ala Leu Ser Ile Gln Gln Phe Gly Val
                 165                 170                 175

Trp Arg Leu Lys Gln Glu Lys Lys Val Leu Thr Thr Lys Lys Lys Lys
             180                 185                 190

Asp Met Lys Pro Ser Glu Ala Arg Arg Val Ala Ala Asn Met Ala Asn
         195                 200                 205

Thr Thr Glu Gly Ile Ile Leu Leu Ala Asn Val Val Asn Val Ala Leu
         210                 215                 220

Ser Met Ala Val Pro Cys Ala Val Val His Tyr Thr Lys Ser Glu Ala
225                 230                 235                 240

Val Pro Gly Ser Val Ile Thr Ala Phe Thr Ile Val Leu Phe Leu Lys
                 245                 250                 255

Leu Ala Ser Tyr Ser His Cys Asn Ala Glu Leu Arg Ala Ala Lys Arg
                 260                 265                 270

Val Ala Asp Gln Arg Pro Ser Ser Gly Asp Leu Arg Glu Ser Gly Asp
             275                 280                 285

Gly Gly Met Glu Met Gly Val Arg Tyr Pro Asp Asn Val Ser Leu Gly
         290                 295                 300

Asn Leu Ala Tyr Phe Leu Val Ala Pro Thr Leu Ile Tyr Gln Pro Ser
305                 310                 315                 320

Tyr Pro Gln Ser Pro Ala Ile Arg Phe Arg Trp Leu Phe Trp Ser Ala
                 325                 330                 335

Val Arg Leu Met Gly Leu Met Ser Leu Met Met Val Ile Val Glu Gln
             340                 345                 350

Tyr Leu Thr Pro Thr Ile Ala Asn Ser Leu Ile Pro Leu Arg Ser Leu
             355                 360                 365

Asn Trp Ala His Met Leu Glu Arg Val Leu Lys Leu Ser Leu Pro Thr
         370                 375                 380

Leu Tyr Gly Trp Val Ile Met Phe Tyr Cys Leu Phe His Leu Trp Leu
385                 390                 395                 400

Asn Ile Leu Ala Glu Val Thr Tyr Phe Gly Asp Arg Glu Phe Tyr Lys
                 405                 410                 415

Asp Trp Trp Asn Ala Thr Thr Ile Gly Asp Tyr Trp Arg Leu Trp Asn
             420                 425                 430

Met Pro Val His Lys Trp Met Leu Arg His Val Tyr Phe Pro Leu Leu
         435                 440                 445
```

```
Arg Leu Gly Val Gly Lys Phe Leu Ala Gly Val Gly Val Phe Ala Val
            450                 455                 460

Ser Gly Leu Leu His Glu Leu Ala Val Gly Leu Pro Leu His Met Val
465                 470                 475                 480

Arg Tyr Trp Ala Phe Leu Gly Val Met Phe Gln Val Pro Met Val Tyr
                485                 490                 495

Leu Thr Glu Tyr Leu Lys Lys Arg Met Lys Ser Asp Gln Ile Gly Asn
                500                 505                 510

Leu Ile Phe Trp Ile Ser Phe Cys Ile Ile Gly Gln Pro Ile Ser Leu
                515                 520                 525

Ile Leu Tyr Tyr His Asp Trp Ile Leu Met Asn Arg Pro Asp Trp Leu
            530                 535                 540

Pro Gln Ala Thr Ala Ala Pro Phe Pro Ala Asn Ala Thr Leu Ala Ala
545                 550                 555                 560

<210> SEQ ID NO 23
<211> LENGTH: 460
<212> TYPE: DNA
<213> ORGANISM: Botryococcus sp.

<400> SEQUENCE: 23
atgtcggaag ccctggggga gctacaagcg gagaatgtcc gcctgcgaaa catgttgacg      60
ctgcgggaaa gacgggagcc ggaccactgc gggtacctat ttaagcaccg ccccctactcc    120 acatcactct tctccccgcc ctgggagctg cgctatttca cccttgcggg cagcgtgctc    180
agccacttcc actctgagaa agacacgtct gccaaccctc gcgggcgcct ggacattgcg    240
ggctgcctgg tggacgtgca gagcggcgag acgggaagt accatgcctt cagcatcgtg     300
gaccgcaagg gccagctcat gatgcgccta gccagcagca agcaggagga cgtcggcctc    360
tgggttaagg cactgaaggg cgcgggctgc gagcgttacg atgccaagga cgccgcacga    420
cgttcatcac tgccccccac cagacccccct gacgcccgct                         460

<210> SEQ ID NO 24
<211> LENGTH: 153
<212> TYPE: PRT
<213> ORGANISM: Botryococcus sp.

<400> SEQUENCE: 24

Met Ser Glu Ala Leu Gly Glu Leu Gln Ala Glu Asn Val Arg Leu Arg
1               5                   10                  15

Asn Met Leu Thr Leu Arg Glu Arg Arg Glu Pro Asp His Cys Gly Tyr
                20                  25                  30

Leu Phe Lys His Arg Pro Tyr Ser Thr Ser Leu Phe Ser Pro Pro Trp
            35                  40                  45

Glu Leu Arg Tyr Phe Thr Leu Ala Gly Ser Val Leu Ser His Phe His
    50                  55                  60

Ser Glu Lys Asp Thr Ser Ala Asn Pro Arg Gly Arg Leu Asp Ile Ala
65                  70                  75                  80

Gly Cys Leu Val Asp Val Gln Ser Gly Glu His Gly Lys Tyr His Ala
                85                  90                  95

Phe Ser Ile Val Asp Arg Lys Gly Gln Leu Met Met Arg Leu Ala Ser
            100                 105                 110

Ser Lys Gln Glu Asp Val Gly Leu Trp Val Lys Ala Leu Lys Gly Ala
        115                 120                 125

Gly Cys Glu Arg Tyr Asp Ala Lys Asp Ala Ala Arg Arg Ser Ser Leu
    130                 135                 140
```

<210> SEQ ID NO 25
<211> LENGTH: 2142
<212> TYPE: DNA
<213> ORGANISM: Unknown
<220> FEATURE:
<223> OTHER INFORMATION: Environmental isolate from South Laguna Madre,
Texas, USA identified as a member of the genus Tetraselmis.

<400> SEQUENCE: 25

| | | | | | | |
|---|---|---|---|---|---|---|
| atgctcttcg | cgcctcagcc | acgtcgcccc | tcggccgcgg | aggaggacag | cgatgtcccc | 60 |
| tcggaggcag | gggagaactc | ggaggatgtg | gagatcctga | ggaacgccat | tcggaggctg | 120 |
| cgagccacca | acagtaagct | ccaggcggcg | cttcaggcca | aggggacgga | cttcatcaag | 180 |
| tgtggatacc | tgtttaagta | ccgccccttt | gcccatgggc | tctgggacaa | cccatgggag | 240 |
| cgccgcttcg | tggtcctgag | gaagggcatc | atcgagtact | tcctcaccga | agctgacacg | 300 |
| cagtatcccc | cgcgtggcat | cgtcaagctc | gagtcctgtg | ttgttgaggt | ggagcccctg | 360 |
| aagaagcgga | agtacttcac | cttcagcatc | atagatgaca | acgaaaacat | gcttgccctt | 420 |
| cgagttttca | ccgagaacgt | tcctgagggc | gagaggtggg | tgtccgcgtt | gaagatggct | 480 |
| ggcgtcaggc | gccgcaagga | caactccaag | caatccctca | ggtctccgcg | gagatccaag | 540 |
| gacatcaggg | gatccagagg | ggaagtctct | gctgagaagg | aaacccagtc | gaatgagttg | 600 |
| cagcggcgag | ggagcaatgc | agctgacctc | ctgaggaagt | ctcagtggaa | ggttcccttt | 660 |
| gtgccacttc | cagagggcgc | agataaagag | ggatctgtag | ccgctgaggt | ggcctcacag | 720 |
| caaccaaagg | caaagagagg | cccattcact | ggcggagtgc | cggtgcacgc | agccccaaag | 780 |
| ttcagcatgc | tatccagcga | ggaggtggca | aatcagaacc | acgctggcct | gatcaatctg | 840 |
| gtgatggtca | tcatgtttgc | aacgcacagc | aggctcatta | tcgagaattc | cctcaagtac | 900 |
| ggggtccgct | tcaacccgct | gtactgggtg | acacggctgg | ccgagagtga | gctgccatgg | 960 |
| caggtgctcg | tttgttggcc | tctgatggcg | tgcttcattc | tgttctcata | ctggatagag | 1020 |
| gtgctgggtg | caagatcggt | gcaggccgag | ttgagggcaa | aggcggcagc | ctgcaagaaa | 1080 |
| acggattgcg | acccggatga | ctcggttccg | gcgcccgcag | cacatcccag | caggagcagc | 1140 |
| gtggcgtggt | cagagagctt | gatcatcacc | cttcagtgcc | tgaacatcgg | cgccctgctg | 1200 |
| ttgctcccct | gctgggtcat | agtaaaacac | caggctcccc | ctctggcagg | atctctcttg | 1260 |
| attacggcct | cggtcatcta | ctggatgaaa | ctcgtcagct | acgcccactg | ctgctgtgat | 1320 |
| ttgcgggctg | cacgccggct | tggggaggtg | cggccaggag | agcgaggaaa | catggaggga | 1380 |
| tttgcagggg | tcaccgagcc | gctgctctac | ccggagaaca | tcaatgctta | caaccttgcg | 1440 |
| tacttttgtg | tggcaccaac | tctgacatac | caggttaact | atccgcggtc | cagccgcttc | 1500 |
| cgcaagcgct | gggtggcgag | gcggctcctg | gagctggtgg | cttggctgtc | cgtggggggca | 1560 |
| ttcatcatcg | agcagtacat | tctgccctcg | tgcctcaaca | gcctacaccc | gctcaacaca | 1620 |
| atggacatcg | gcacatcct | ggagagggtt | ctgaagctca | gcctgccctc | cctgtacgtg | 1680 |
| tggctgattg | ccttctactg | catcttccac | ctgtggctca | catcctggc | cgaattcact | 1740 |
| tacttcggag | accggcagtt | ctatgatgat | tggtggaacg | ccaccacagt | cgatgagtac | 1800 |
| tggcgccgct | ggaatcaacc | tgtgcacaag | tggctcatgc | gcaccgtgta | ctttccatgc | 1860 |
| atgcgcctgg | gactgtcgcg | ttacgtgtca | atcctggcca | cgttcctcat | atcggccgtg | 1920 |

-continued

```
tttcatgagc tacttgtggg cgttcctctc cacatgctgc gggcctgggc atttgcaggc    1980
atgatgggac agatcccgct gattgccatg acgaccatgc tgaagcgcaa gatgaagagt    2040
gacatcattg gcaatgtgat cttctggctg tccttctgca tattcggcca gcccattgcg    2100
gtgctgctgt actatcatga ctacatccag gagcatatgt ga                       2142
```

<210> SEQ ID NO 26
<211> LENGTH: 713
<212> TYPE: PRT
<213> ORGANISM: Unknown
<220> FEATURE:
<223> OTHER INFORMATION: Environmental isolate from South Laguna Madre, Texas, USA identified as a member of the genus Tetraselmis.

<400> SEQUENCE: 26

| | | | | | | | | | | | | | | |
|---|---|---|---|---|---|---|---|---|---|---|---|---|---|---|
| Met | Leu | Phe | Ala | Pro | Gln | Pro | Arg | Arg | Pro | Ser | Ala | Ala | Glu | Glu | Asp |
| 1 | | | | 5 | | | | | 10 | | | | | 15 | |
| Ser | Asp | Val | Pro | Ser | Glu | Ala | Gly | Glu | Asn | Ser | Glu | Asp | Val | Glu | Ile |
| | | | 20 | | | | | 25 | | | | | 30 | | |
| Leu | Arg | Asn | Ala | Ile | Arg | Arg | Leu | Arg | Ala | Thr | Asn | Ser | Lys | Leu | Gln |
| | | 35 | | | | | 40 | | | | | 45 | | | |
| Ala | Ala | Leu | Gln | Ala | Lys | Gly | Thr | Asp | Phe | Ile | Lys | Cys | Gly | Tyr | Leu |
| 50 | | | | | 55 | | | | | 60 | | | | | |
| Phe | Lys | Tyr | Arg | Pro | Phe | Ala | His | Gly | Leu | Trp | Asp | Asn | Pro | Trp | Glu |
| 65 | | | | 70 | | | | | 75 | | | | | 80 | |
| Arg | Arg | Phe | Val | Val | Leu | Arg | Lys | Gly | Ile | Ile | Glu | Tyr | Phe | Leu | Thr |
| | | | | 85 | | | | | 90 | | | | | 95 | |
| Glu | Ala | Asp | Thr | Gln | Tyr | Pro | Pro | Arg | Gly | Ile | Val | Lys | Leu | Glu | Ser |
| | | | 100 | | | | | 105 | | | | | 110 | | |
| Cys | Val | Val | Glu | Val | Glu | Pro | Leu | Lys | Lys | Arg | Lys | Tyr | Phe | Thr | Phe |
| | | 115 | | | | | 120 | | | | | 125 | | | |
| Ser | Ile | Ile | Asp | Asp | Asn | Glu | Asn | Met | Leu | Ala | Leu | Arg | Val | Ser | Thr |
| | 130 | | | | | 135 | | | | | 140 | | | | |
| Glu | Asn | Val | Pro | Glu | Gly | Glu | Arg | Trp | Val | Ser | Ala | Leu | Lys | Met | Ala |
| 145 | | | | | 150 | | | | | 155 | | | | | 160 |
| Gly | Val | Arg | Arg | Lys | Asp | Asn | Ser | Lys | Gln | Ser | Leu | Arg | Ser | Pro | |
| | | | | 165 | | | | | 170 | | | | | 175 | |
| Arg | Arg | Ser | Lys | Asp | Ile | Arg | Gly | Ser | Arg | Gly | Glu | Val | Ser | Ala | Glu |
| | | | 180 | | | | | 185 | | | | | 190 | | |
| Lys | Glu | Thr | Gln | Ser | Asn | Glu | Leu | Gln | Arg | Arg | Gly | Ser | Asn | Ala | Ala |
| | | | 195 | | | | | 200 | | | | | 205 | | |
| Asp | Leu | Leu | Arg | Lys | Ser | Gln | Trp | Lys | Val | Pro | Phe | Val | Pro | Leu | Pro |
| | 210 | | | | | 215 | | | | | 220 | | | | |
| Glu | Gly | Ala | Asp | Lys | Glu | Gly | Ser | Val | Ala | Ala | Glu | Val | Ala | Ser | Gln |
| 225 | | | | | 230 | | | | | 235 | | | | | 240 |
| Gln | Pro | Lys | Ala | Lys | Arg | Gly | Pro | Phe | Thr | Gly | Gly | Val | Pro | Val | His |
| | | | | 245 | | | | | 250 | | | | | 255 | |
| Ala | Ala | Pro | Lys | Phe | Ser | Met | Leu | Ser | Ser | Glu | Glu | Val | Ala | Asn | Gln |
| | | | 260 | | | | | 265 | | | | | 270 | | |
| Asn | His | Ala | Gly | Leu | Ile | Asn | Leu | Val | Met | Val | Ile | Met | Phe | Ala | Thr |
| | | 275 | | | | | 280 | | | | | 285 | | | |
| His | Ser | Arg | Leu | Ile | Ile | Glu | Asn | Ser | Leu | Lys | Tyr | Gly | Val | Arg | Phe |
| | 290 | | | | | 295 | | | | | 300 | | | | |
| Asn | Pro | Leu | Tyr | Trp | Val | Thr | Arg | Leu | Ala | Glu | Ser | Glu | Leu | Pro | Trp |
| 305 | | | | | 310 | | | | | 315 | | | | | 320 |

Gln Val Leu Val Cys Trp Pro Leu Met Ala Cys Phe Ile Leu Phe Ser
            325                 330                 335

Tyr Trp Ile Glu Val Leu Gly Ala Arg Ser Val Gln Ala Glu Leu Arg
            340                 345                 350

Ala Lys Ala Ala Ala Cys Lys Lys Thr Asp Cys Asp Pro Asp Asp Ser
            355                 360                 365

Val Pro Ala Pro Ala Ala His Pro Ser Arg Ser Ser Val Ala Trp Ser
370                 375                 380

Glu Ser Leu Ile Ile Thr Leu Gln Cys Leu Asn Ile Gly Ala Leu Leu
385                 390                 395                 400

Leu Leu Pro Cys Trp Val Ile Val Lys His Gln Ala Pro Pro Leu Ala
            405                 410                 415

Gly Ser Leu Leu Ile Thr Ala Ser Val Ile Tyr Trp Met Lys Leu Val
            420                 425                 430

Ser Tyr Ala His Cys Cys Cys Asp Leu Arg Ala Ala Arg Arg Leu Gly
            435                 440                 445

Glu Val Arg Pro Gly Glu Arg Gly Asn Met Glu Gly Phe Ala Gly Val
            450                 455                 460

Thr Glu Pro Leu Leu Tyr Pro Glu Asn Ile Asn Ala Tyr Asn Leu Ala
465                 470                 475                 480

Tyr Phe Cys Val Ala Pro Thr Leu Thr Tyr Gln Val Asn Tyr Pro Arg
            485                 490                 495

Ser Ser Arg Phe Arg Lys Arg Trp Val Ala Arg Leu Leu Glu Leu
            500                 505                 510

Val Ala Trp Leu Ser Val Gly Ala Phe Ile Ile Glu Gln Tyr Ile Leu
            515                 520                 525

Pro Ser Cys Leu Asn Ser Leu His Pro Leu Asn Thr Met Asp Ile Gly
            530                 535                 540

His Ile Leu Glu Arg Val Leu Lys Leu Ser Leu Pro Ser Leu Tyr Val
545                 550                 555                 560

Trp Leu Ile Ala Phe Tyr Cys Ile Phe His Leu Trp Leu Asn Ile Leu
            565                 570                 575

Ala Glu Phe Thr Tyr Phe Gly Asp Arg Gln Phe Tyr Asp Asp Trp Trp
            580                 585                 590

Asn Ala Thr Thr Val Asp Glu Tyr Trp Arg Arg Trp Asn Gln Pro Val
            595                 600                 605

His Lys Trp Leu Met Arg Thr Val Tyr Phe Pro Cys Met Arg Leu Gly
            610                 615                 620

Leu Ser Arg Tyr Val Ser Ile Leu Ala Thr Phe Leu Ile Ser Ala Val
625                 630                 635                 640

Phe His Glu Leu Leu Val Gly Val Pro Leu His Met Leu Arg Ala Trp
            645                 650                 655

Ala Phe Ala Gly Met Met Gly Gln Ile Pro Leu Ile Ala Met Thr Thr
            660                 665                 670

Met Leu Lys Arg Lys Met Lys Ser Asp Ile Ile Gly Asn Val Ile Phe
            675                 680                 685

Trp Leu Ser Phe Cys Ile Phe Gly Gln Pro Ile Ala Val Leu Leu Tyr
            690                 695                 700

Tyr His Asp Tyr Ile Gln Glu His Met
705                 710

<210> SEQ ID NO 27
<211> LENGTH: 1590
<212> TYPE: DNA

<213> ORGANISM: Unknown
<220> FEATURE:
<223> OTHER INFORMATION: Environmental isolate from South Laguna Madre, Texas, USA identified as a member of the genus Tetraselmis.

<400> SEQUENCE: 27

```
caatccctca ggtctccgcg gagatccaag gacatcaggg gatccagagg ggaagtctct     60
gctgagaagg aaacccagtc gaatgagttg cagcggcgag ggagcaatgc agctgacctc    120
ctgaggaagt ctcagtggaa ggttcccttt gtgccacttc cagagggcgc agataaagag    180
ggatctgtag ccgctgaggt ggcctcacag caaccaaagg caaagagagg cccattcact    240
ggcggagtgc cggtgcacgc agccccaaag ttcagcatgc tatccagcga ggaggtggca    300
aatcagaacc acgctggcct gatcaatctg gtgatggtca tcatgtttgc aacgcacagc    360
aggctcatta tcgagaattc cctcaagtac ggggtccgct tcaacccgct gtactgggtg    420
acacggctgg ccgagagtga gctgccatgg caggtgctcg tttgttggcc tctgatggcg    480
tgcttcattc tgttctcata ctggatagag gtgctgggtg caagatcggt gcaggccgag    540
ttgagggcaa aggcggcagc ctgcaagaaa acggattgcg acccggatga ctcggttccg    600
gcgcccgcag cacatcccag caggagcagc gtggcgtggt cagagagctt gatcatcacc    660
cttcagtgcc tgaacatcgg cgccctgctg ttgctcccct gctgggtcat agtaaaacac    720
caggctcccc ctctggcagg atctctcttg attacggcct cggtcatcta ctggatgaaa    780
ctcgtcagct acgcccactg ctgctgtgat ttgcgggctg cacgccggct ggggaggtg     840
cggccaggag agcgaggaaa catggaggga tttgcagggg tcaccgagcc gctgctctac    900
ccggagaaca tcaatgctta caaccttgcg tactttgtg tggcaccaac tctgacatac     960
caggttaact atccgcggtc cagccgcttc cgcaagcgct gggtggcgag gcggctcctg   1020
gagctggtgg cttggctgtc cgtgggggca ttcatcatcg agcagtacat tctgccctcg   1080
tgcctcaaca gcctacaccc gctcaacaca atggacatcg gcacatcct ggagagggtt    1140
ctgaagctca gcctgccctc cctgtacgtg tggctgattg ccttctactg catcttccac   1200
ctgtggctca acatcctggc cgaattcact tacttcggag accggcagtt ctatgatgat   1260
tggtggaacg ccaccacagt cgatgagtac tggcgccgct ggaatcaacc tgtgcacaag   1320
tggctcatgc gcaccgtgta cttttccatgc atgcgcctgg gactgtcgcg ttacgtgtca   1380
atcctggcca cgttcctcat atcggccgtg tttcatgagc tacttgtggg cgttcctctc   1440
cacatgctgc gggcctgggc atttgcaggc atgatgggac agatcccgct gattgccatg   1500
acgaccatgc tgaagcgcaa gatgaagagt gacatcattg gcaatgtgat cttctggctg   1560
tccttctgca tattcggcca gcccattgcg                                    1590
```

<210> SEQ ID NO 28
<211> LENGTH: 543
<212> TYPE: PRT
<213> ORGANISM: Unknown
<220> FEATURE:
<223> OTHER INFORMATION: Environmental isolate from South Laguna Madre, Texas, USA identified as a member of the genus Tetraselmis.

<400> SEQUENCE: 28

```
Gln Ser Leu Arg Ser Pro Arg Arg Ser Lys Asp Ile Arg Gly Ser Arg
 1               5                  10                  15

Gly Glu Val Ser Ala Glu Lys Glu Thr Gln Ser Asn Glu Leu Gln Arg
                20                  25                  30

Arg Gly Ser Asn Ala Ala Asp Leu Leu Arg Lys Ser Gln Trp Lys Val
```

```
                35                  40                  45
Pro Phe Val Pro Leu Pro Glu Gly Ala Asp Lys Glu Gly Ser Val Ala
 50                  55                  60

Ala Glu Val Ala Ser Gln Gln Pro Lys Ala Lys Arg Gly Pro Phe Thr
 65                  70                  75                  80

Gly Gly Val Pro Val His Ala Ala Pro Lys Phe Ser Met Leu Ser Ser
                 85                  90                  95

Glu Glu Val Ala Asn Gln Asn His Ala Gly Leu Ile Asn Leu Val Met
                100                 105                 110

Val Ile Met Phe Ala Thr His Ser Arg Leu Ile Ile Glu Asn Ser Leu
                115                 120                 125

Lys Tyr Gly Val Arg Phe Asn Pro Leu Tyr Trp Val Thr Arg Leu Ala
130                 135                 140

Glu Ser Glu Leu Pro Trp Gln Val Leu Val Cys Trp Pro Leu Met Ala
145                 150                 155                 160

Cys Phe Ile Leu Phe Ser Tyr Trp Ile Glu Val Leu Gly Ala Arg Ser
                165                 170                 175

Val Gln Ala Glu Leu Arg Ala Lys Ala Ala Cys Lys Lys Thr Asp
                180                 185                 190

Cys Asp Pro Asp Ser Val Pro Ala Pro Ala His Pro Ser Arg
                195                 200                 205

Ser Ser Val Ala Trp Ser Glu Ser Leu Ile Ile Thr Leu Gln Cys Leu
210                 215                 220

Asn Ile Gly Ala Leu Leu Leu Pro Cys Trp Val Ile Val Lys His
225                 230                 235                 240

Gln Ala Pro Pro Leu Ala Gly Ser Leu Leu Ile Thr Ala Ser Val Ile
                245                 250                 255

Tyr Trp Met Lys Leu Val Ser Tyr Ala His Cys Cys Cys Asp Leu Arg
                260                 265                 270

Ala Ala Arg Arg Leu Gly Glu Val Arg Pro Gly Glu Arg Gly Asn Met
                275                 280                 285

Glu Gly Phe Ala Gly Val Thr Glu Pro Leu Leu Tyr Pro Glu Asn Ile
290                 295                 300

Asn Ala Tyr Asn Leu Ala Tyr Phe Cys Val Ala Pro Thr Leu Thr Tyr
305                 310                 315                 320

Gln Val Asn Tyr Pro Arg Ser Ser Arg Phe Arg Lys Arg Trp Val Ala
                325                 330                 335

Arg Arg Leu Leu Glu Leu Val Ala Trp Leu Ser Val Gly Ala Phe Ile
                340                 345                 350

Ile Glu Gln Tyr Ile Leu Pro Ser Cys Leu Asn Ser Leu His Pro Leu
                355                 360                 365

Asn Thr Met Asp Ile Gly His Ile Leu Glu Arg Val Leu Lys Leu Ser
                370                 375                 380

Leu Pro Ser Leu Tyr Val Trp Leu Ile Ala Phe Tyr Cys Ile Phe His
385                 390                 395                 400

Leu Trp Leu Asn Ile Leu Ala Glu Phe Thr Tyr Phe Gly Asp Arg Gln
                405                 410                 415

Phe Tyr Asp Asp Trp Trp Asn Ala Thr Thr Val Asp Glu Tyr Trp Arg
                420                 425                 430

Arg Trp Asn Gln Pro Val His Lys Trp Leu Met Arg Thr Val Tyr Phe
                435                 440                 445

Pro Cys Met Arg Leu Gly Leu Ser Arg Tyr Val Ser Ile Leu Ala Thr
450                 455                 460
```

```
Phe Leu Ile Ser Ala Val Phe His Glu Leu Leu Val Gly Val Pro Leu
465                 470                 475                 480

His Met Leu Arg Ala Trp Ala Phe Ala Gly Met Met Gly Gln Ile Pro
                485                 490                 495

Leu Ile Ala Met Thr Thr Met Leu Lys Arg Lys Met Lys Ser Asp Ile
            500                 505                 510

Ile Gly Asn Val Ile Phe Trp Leu Ser Phe Cys Ile Phe Gly Gln Pro
        515                 520                 525

Ile Ala Val Leu Leu Tyr Tyr His Asp Tyr Ile Gln Glu His Met
    530                 535                 540
```

<210> SEQ ID NO 29
<211> LENGTH: 510
<212> TYPE: DNA
<213> ORGANISM: Unknown
<220> FEATURE:
<223> OTHER INFORMATION: Environmental isolate from South Laguna Madre,
      Texas, USA identified as a member of the genus Tetraselmis.

<400> SEQUENCE: 29

```
atgctcttcg cgcctcagcc acgtcgcccc tcggccgcgg aggaggacag cgatgtcccc    60
tcggaggcag gggagaactc ggaggatgtg gagatcctga ggaacgccat tcggaggctg   120
cgagccacca acagtaagct ccaggcggcg cttcaggcca aggggacgga cttcatcaag   180
tgtggatacc tgtttaagta ccgccccttt gcccatgggc tctgggacaa cccatgggag   240
cgccgcttcg tggtcctgag gaagggcatc atcgagtact ccctcaccga agctgacacg   300
cagtatcccc cgcgtggcat cgtcaagctc gagtcctgtg ttgttgaggt ggagcccctg   360
aagaagcgga agtacttcac cttcagcatc atagatgaca cgaaaacat gcttgccctt    420 cgagtttcca ccgagaacgt tcctgagggc gagaggtggg tgtccgcgtt gaagatggct   480
ggcgtcaggc gccgcaagga caactccaag                                    510
```

<210> SEQ ID NO 30
<211> LENGTH: 170
<212> TYPE: PRT
<213> ORGANISM: Unknown
<220> FEATURE:
<223> OTHER INFORMATION: Environmental isolate from South Laguna Madre,
      Texas, USA identified as a member of the genus Tetraselmis.

<400> SEQUENCE: 30

```
Met Leu Phe Ala Pro Gln Pro Arg Arg Pro Ser Ala Ala Glu Glu Asp
1               5                   10                  15

Ser Asp Val Pro Ser Glu Ala Gly Glu Asn Ser Glu Asp Val Glu Ile
            20                  25                  30

Leu Arg Asn Ala Ile Arg Arg Leu Arg Ala Thr Asn Ser Lys Leu Gln
        35                  40                  45

Ala Ala Leu Gln Ala Lys Gly Thr Asp Phe Ile Lys Cys Gly Tyr Leu
    50                  55                  60

Phe Lys Tyr Arg Pro Phe Ala His Gly Leu Trp Asp Asn Pro Trp Glu
65                  70                  75                  80

Arg Arg Phe Val Val Leu Arg Lys Gly Ile Ile Glu Tyr Phe Leu Thr
                85                  90                  95

Glu Ala Asp Thr Gln Tyr Pro Pro Arg Gly Ile Val Lys Leu Glu Ser
            100                 105                 110

Cys Val Val Glu Val Glu Pro Leu Lys Lys Arg Lys Tyr Phe Thr Phe
        115                 120                 125
```

```
Ser Ile Ile Asp Asp Asn Glu Asn Met Leu Ala Leu Arg Val Ser Thr
    130                 135                 140

Glu Asn Val Pro Glu Gly Glu Arg Trp Val Ser Ala Leu Lys Met Ala
145                 150                 155                 160

Gly Val Arg Arg Arg Lys Asp Asn Ser Lys
            165                 170

<210> SEQ ID NO 31
<211> LENGTH: 2082
<212> TYPE: DNA
<213> ORGANISM: Chlorella sp.

<400> SEQUENCE: 31
atgctgcgat caaggaaagc cagccaggag cagagcccag cggatgcaag ggtggtggcc      60
ctcgcaaagg aaaacgagag actcagggat ctgctgtctg agaaggcgtt caagggcgcc     120
acgtgcagcg ggtacttatg gaagtaccgc tcccacgcgg agagctccct gtgggccaac     180
acttgggagc tgcggtatat ggtcctgaag gcagtacgc tgctgtatta caagcaggag      240
caggacgtgc agtttccccc acgcggccag atcgacttgc agggcgcgta cgtggagagt     300
gaggggctga gcgccgcaa gtacctggcc ttcaacgtgt acaatgcggc ggggtgagc       360
ctcatccggc tgtcctcgga gtcgcaggtg gactacgcca gtggatgga ggcgctggag      420
agggcggggt gtgaaaggcg cggggacgac gatgcgcgct ccgtcgccac cagcctccag     480
cgcgtgagtg gcagcagcgc agtgtccagc ccaccgcca gcggcatgtc ggacagcggg      540
gaagctgcgg cgcagctgct ccagaggcac agccccagca agctgcaggg gaagggggag     600
gacgaggtca gcagtgctgc ccgccagctg gcgcagcagg aggcgcacca gagcaggggg     660
tacacctcgg accagtctga cgtggcgcgc agctcagga cgcgtcagcc ctcctccaag      720
ggcggccacc gcggcaaggg gcgggacgca ctgctggggt cgtcgctggt gcacaccgcg     780
cccaggtgga gcttcctgtc cacggagagg atcgactttt cgaatcagaa cggtctgctg     840
acccgggca tgatcatcct ggtcacaacc aacgcccgcc ttattctgga acatcctg       900
aagtatggcc tccgcttcaa ccctgtcacc ttcctccgcg ccgccttcac ccctccggc     960
aacgtcatgc tgctgctgtg ctggcccttc ctggggatgt gctgcctgtg cgccctgggg    1020
gtggaggcgc tggggtgag gtgcctggcc atggagcaaa aggccaacgc cgccaaccgc    1080
aaacgggagg tggggtacgg ggagggcagg cgcagggcgg cccggcaggc caagctgacg    1140
gagaacctgc cctcctgct gaatttgctg aacaccaccg ccgtcctgct ggtgccctcc     1200
ctggtcatgc acatcacgaa ctctgagccg ctgccgggtt tcatgctgtc catgttcatg    1260
atcgtgctgt ggctcaagct ggtcagctac gcccacgtca actgggacta ccgcgcggcg    1320
cggaggcagg ggttgtaccc cgagaacatc acgctgcgca acctggccta cttcctggtg    1380
gcccccacgc tgtgctacca gccggtgtac ccccggtcgt cgcggttcag ggtcaagtgg    1440
ctggccagc gcgtcatcgt gctgtgcttt gcgctgagcc tcatgctgtt catcaacgag    1500
cagtacatcg agccgattgt ggagaacagc cttgggcccc tcagaaacat ggactggatg    1560
cgcatgactg agcgcatcct gaagctcagc ctccccacgc tgtacttctg gctcagcatg    1620
ttctacgccc tgttccacct ctggctcaac atcctggcgg agctcaccgg attcgcggac    1680
agggagttct acaaggagtg gtggaacgcc accacgctgg gcgagtactg cgccagtgg    1740
aaccagccgg tgcacaagtg gatgctgcgc cacgtgtact cccatgcat ccgccacggc     1800
atcagcaagt tcatggcagg catcatcgtg ttctttgtga gcgccgtgtt ccacgagctg    1860
```

```
gtggtggggg tgccgctgca catgctgcgc agctggtcct tctgggggat catggggcag    1920
gtgcccctca tctgggtgac ggagctcctg aagaagaagg tgggcagcga gcacatcggc    1980
aacatgatct tctggctgtc cttctgcttt gtggggcagc ccatcgccat catcctgtac    2040
taccacgact accgcaagca gattgggctg attgcagact ga                       2082
```

<210> SEQ ID NO 32
<211> LENGTH: 693
<212> TYPE: PRT
<213> ORGANISM: Chlorella sp.

<400> SEQUENCE: 32

```
Met Leu Arg Ser Arg Lys Ala Ser Gln Glu Gln Ser Pro Ala Asp Ala
1               5                   10                  15

Arg Val Val Ala Leu Ala Lys Glu Asn Glu Arg Leu Arg Asp Leu Leu
                20                  25                  30

Ser Glu Lys Ala Phe Lys Gly Ala Thr Cys Ser Gly Tyr Leu Trp Lys
            35                  40                  45

Tyr Arg Ser His Ala Glu Ser Ser Leu Trp Ala Asn Thr Trp Glu Leu
        50                  55                  60

Arg Tyr Met Val Leu Lys Gly Ser Thr Leu Leu Tyr Tyr Lys Gln Glu
65                  70                  75                  80

Gln Asp Val Gln Phe Pro Pro Arg Gly Gln Ile Asp Leu Gln Gly Ala
                85                  90                  95

Tyr Val Glu Ser Glu Gly Leu Lys Arg Arg Lys Tyr Leu Ala Phe Asn
            100                 105                 110

Val Tyr Asn Ala Ala Gly Val Ser Leu Ile Arg Leu Ser Ser Glu Ser
        115                 120                 125

Gln Val Asp Tyr Ala Lys Trp Met Glu Ala Leu Glu Arg Ala Gly Cys
    130                 135                 140

Glu Arg Arg Gly Asp Asp Asp Ala Arg Ser Val Ala Thr Ser Leu Gln
145                 150                 155                 160

Arg Val Ser Gly Ser Ser Ala Val Ser Ser Pro Thr Ala Ser Gly Met
                165                 170                 175

Ser Asp Ser Gly Glu Ala Ala Ala Gln Leu Leu Gln Arg His Ser Pro
            180                 185                 190

Ser Lys Leu Gln Gly Lys Gly Glu Asp Glu Val Ser Ser Ala Ala Arg
        195                 200                 205

Gln Leu Ala Gln Gln Glu Ala His Gln Ser Arg Gly Tyr Thr Ser Asp
    210                 215                 220

Gln Ser Asp Val Ala Arg Gln Leu Arg Thr Arg Gln Pro Ser Ser Lys
225                 230                 235                 240

Gly Gly His Arg Gly Lys Gly Arg Asp Ala Leu Leu Gly Ser Ser Leu
                245                 250                 255

Val His Thr Ala Pro Arg Trp Ser Phe Leu Ser Thr Glu Arg Ile Asp
            260                 265                 270

Phe Ser Asn Gln Asn Gly Leu Leu Thr Leu Gly Met Ile Ile Leu Val
        275                 280                 285

Thr Thr Asn Ala Arg Leu Ile Leu Glu Asn Ile Leu Lys Tyr Gly Leu
    290                 295                 300

Arg Phe Asn Pro Val Thr Phe Leu Arg Ala Ala Phe Thr Pro Ser Gly
305                 310                 315                 320

Asn Val Met Leu Leu Leu Cys Trp Pro Phe Leu Gly Met Cys Cys Leu
                325                 330                 335
```

Cys Ala Leu Gly Val Glu Ala Leu Gly Val Arg Cys Leu Ala Met Glu
            340                 345                 350

Gln Lys Ala Asn Ala Ala Asn Arg Lys Arg Glu Val Gly Tyr Gly Glu
            355                 360                 365

Gly Arg Arg Arg Ala Ala Arg Gln Ala Lys Leu Thr Glu Asn Leu Leu
        370                 375                 380

Leu Leu Leu Asn Leu Leu Asn Thr Thr Ala Val Leu Leu Val Pro Ser
385                 390                 395                 400

Leu Val Met His Ile Thr Asn Ser Glu Pro Leu Pro Gly Phe Met Leu
            405                 410                 415

Ser Met Phe Met Ile Val Leu Trp Leu Lys Leu Val Ser Tyr Ala His
            420                 425                 430

Val Asn Trp Asp Tyr Arg Ala Ala Arg Arg Gln Gly Leu Tyr Pro Glu
            435                 440                 445

Asn Ile Thr Leu Arg Asn Leu Ala Tyr Phe Leu Val Ala Pro Thr Leu
            450                 455                 460

Cys Tyr Gln Pro Val Tyr Pro Arg Ser Ser Arg Phe Arg Val Lys Trp
465                 470                 475                 480

Leu Ala Arg Arg Val Ile Val Leu Cys Phe Ala Leu Ser Leu Met Leu
            485                 490                 495

Phe Ile Asn Glu Gln Tyr Ile Glu Pro Ile Val Glu Asn Ser Leu Gly
            500                 505                 510

Pro Leu Arg Asn Met Asp Trp Met Arg Met Thr Glu Arg Ile Leu Lys
            515                 520                 525

Leu Ser Leu Pro Thr Leu Tyr Phe Trp Leu Ser Met Phe Tyr Ala Leu
            530                 535                 540

Phe His Leu Trp Leu Asn Ile Leu Ala Glu Leu Thr Gly Phe Ala Asp
545                 550                 555                 560

Arg Glu Phe Tyr Lys Glu Trp Trp Asn Ala Thr Thr Leu Gly Glu Tyr
                565                 570                 575

Trp Arg Gln Trp Asn Gln Pro Val His Lys Trp Met Leu Arg His Val
            580                 585                 590

Tyr Phe Pro Cys Ile Arg His Gly Ile Ser Lys Phe Met Ala Gly Ile
            595                 600                 605

Ile Val Phe Phe Val Ser Ala Val Phe His Glu Leu Val Val Gly Val
            610                 615                 620

Pro Leu His Met Leu Arg Ser Trp Ser Phe Trp Gly Ile Met Gly Gln
625                 630                 635                 640

Val Pro Leu Ile Trp Val Thr Glu Leu Leu Lys Lys Val Gly Ser
                645                 650                 655

Glu His Ile Gly Asn Met Ile Phe Trp Leu Ser Phe Cys Phe Val Gly
            660                 665                 670

Gln Pro Ile Ala Ile Ile Leu Tyr Tyr His Asp Tyr Arg Lys Gln Ile
            675                 680                 685

Gly Leu Ile Ala Asp
    690

<210> SEQ ID NO 33
<211> LENGTH: 1542
<212> TYPE: DNA
<213> ORGANISM: Chlorella sp.

<400> SEQUENCE: 33
gcagtgtcca gccccaccgc cagcggcatg tcggacagcg gggaagctgc ggcgcagctg     60

```
ctccagaggc acagccccag caagctgcag gggaaggggg aggacgaggt cagcagtgct      120
gcccgccagc tggcgcagca ggaggcgcac cagagcaggg ggtacacctc ggaccagtct      180
gacgtggcgc gccagctcag gacgcgtcag ccctcctcca agggcggcca ccgcggcaag      240
gggcgggacg cactgctggg gtcgtcgctg gtgcacaccg cgcccaggtg gagcttcctg      300
tccacggaga ggatcgactt ttcgaatcag aacggtctgc tgaccctggg catgatcatc      360
ctggtcacaa ccaacgcccg ccttattctg gagaacatcc tgaagtatgg cctccgcttc      420
aaccctgtca ccttcctccg cgccgccttc accccctccg gcaacgtcat gctgctgctg      480
tgctggccct tcctggggat gtgctgcctg tgcgccctgg gggtggaggc gctggggtg       540
aggtgcctgg ccatggagca aaaggccaac gccgccaacc gcaaacggga ggtggggtac      600
ggggagggca ggcgcagggc ggcccggcag gccaagctga cggagaacct gctcctcctg      660
ctgaatttgc tgaacaccac cgccgtcctg ctggtgccct ccctggtcat gcacatcacg      720
aactctgagc cgctgccggg tttcatgctg tccatgttca tgatcgtgct gtggctcaag      780
ctggtcagct acgcccacgt caactgggac taccgcgcgg cgcggaggca ggggttgtac      840
cccgagaaca tcacgctgcg caacctggcc tacttcctgg tggcccccac gctgtgctac      900
cagccggtgt accccggtc gtcgcggttc agggtcaagt ggctggccag gcgcgtcatc      960
gtgctgtgct ttgcgctgag cctcatgctg ttcatcaacg agcagtacat cgagccgatt     1020
gtggagaaca gccttgggcc cctcagaaac atggactgga tgcgcatgac tgagcgcatc     1080
ctgaagctca gcctccccac gctgtacttc tggctcagca tgttctacgc cctgttccac     1140
ctctggctca acatcctggc ggagctcacc ggattcgcgg acagggagtt ctacaaggag     1200
tggtggaacg ccaccacgct gggcgagtac tggcgccagt ggaaccagcc ggtgcacaag     1260
tggatgctgc gccacgtgta cttcccatgc atccgccacg gcatcagcaa gttcatggca     1320
ggcatcatcg tgttctttgt gagcgccgtg ttccacgagc tggtggtggg ggtgccgctg     1380
cacatgctgc gcagctggtc cttctggggg atcatggggc aggtgcccct catctgggtg     1440
acggagctcc tgaagaagaa ggtgggcagc gagcacatcg gcaacatgat cttctggctg     1500
tccttctgct tgtggggca gcccatcgcc atcatcctgt ac                         1542
```

<210> SEQ ID NO 34
<211> LENGTH: 494
<212> TYPE: PRT
<213> ORGANISM: Chlorella sp.

<400> SEQUENCE: 34

Ala Val Ser Ser Pro Thr Ala Ser Gly Met Ser Asp Ser Gly Glu Ala
1               5                   10                  15

Ala Ala Gln Leu Leu Gln Arg His Ser Pro Ser Lys Leu Gln Gly Lys
            20                  25                  30

Gly Glu Asp Glu Val Ser Ser Ala Ala Arg Gln Leu Ala Gln Gln Glu
        35                  40                  45

Ala His Gln Ser Arg Gly Tyr Thr Ser Asp Gln Ser Asp Val Ala Arg
    50                  55                  60

Gln Leu Arg Thr Arg Gln Pro Ser Ser Lys Gly His Arg Gly Lys
65                  70                  75                  80

Gly Arg Asp Ala Leu Leu Gly Ser Ser Leu Val His Thr Ala Pro Arg
                85                  90                  95

Trp Ser Phe Leu Ser Thr Glu Arg Ile Asp Phe Ser Asn Gln Asn Gly
            100                 105                 110

```
Leu Leu Thr Leu Gly Met Ile Ile Leu Val Thr Thr Asn Ala Arg Leu
            115                 120                 125

Ile Leu Glu Asn Ile Leu Lys Tyr Gly Leu Arg Phe Asn Pro Val Thr
        130                 135                 140

Phe Leu Arg Ala Ala Phe Thr Pro Ser Gly Asn Val Met Leu Leu Leu
145                 150                 155                 160

Cys Trp Pro Phe Leu Gly Met Cys Cys Leu Cys Ala Leu Gly Val Glu
                165                 170                 175

Ala Leu Gly Val Arg Cys Leu Ala Met Glu Gln Lys Ala Asn Ala Ala
                180                 185                 190

Asn Arg Lys Arg Glu Val Gly Tyr Gly Glu Gly Arg Arg Arg Ala Ala
                195                 200                 205

Arg Gln Ala Lys Leu Thr Glu Asn Leu Leu Leu Leu Asn Leu Leu
210                 215                 220

Asn Thr Thr Ala Val Leu Leu Val Pro Ser Leu Val Met His Ile Thr
225                 230                 235                 240

Asn Ser Glu Pro Leu Pro Gly Phe Met Leu Ser Met Phe Met Ile Val
                245                 250                 255

Leu Trp Leu Lys Leu Val Ser Tyr Ala His Val Asn Trp Asp Tyr Arg
                260                 265                 270

Ala Ala Arg Arg Gln Gly Leu Tyr Pro Glu Asn Ile Thr Leu Arg Asn
                275                 280                 285

Leu Ala Tyr Phe Leu Val Ala Pro Thr Leu Cys Tyr Gln Pro Val Tyr
                290                 295                 300

Pro Arg Ser Ser Arg Phe Arg Val Lys Trp Leu Ala Arg Val Ile
305                 310                 315                 320

Val Leu Cys Phe Ala Leu Ser Leu Met Leu Phe Ile Asn Glu Gln Tyr
                325                 330                 335

Ile Glu Pro Ile Val Glu Asn Ser Leu Gly Pro Leu Arg Asn Met Asp
                340                 345                 350

Trp Met Arg Met Thr Glu Arg Ile Leu Lys Leu Ser Leu Pro Thr Leu
                355                 360                 365

Tyr Phe Trp Leu Ser Met Phe Tyr Ala Leu Phe His Leu Trp Leu Asn
                370                 375                 380

Ile Leu Ala Glu Leu Thr Gly Phe Ala Asp Arg Glu Phe Tyr Lys Glu
385                 390                 395                 400

Trp Trp Asn Ala Thr Thr Leu Gly Glu Tyr Trp Arg Gln Trp Asn Gln
                405                 410                 415

Pro Val His Lys Trp Met Leu Arg His Val Tyr Phe Pro Cys Ile Arg
                420                 425                 430

His Gly Ile Ser Lys Phe Met Ala Gly Ile Ile Val Phe Phe Val Ser
                435                 440                 445

Ala Val Phe His Glu Leu Val Val Gly Val Pro Leu His Met Leu Arg
                450                 455                 460

Ser Trp Ser Phe Trp Gly Ile Met Gly Gln Val Pro Leu Ile Trp Val
465                 470                 475                 480

Thr Glu Leu Leu Lys Lys Lys Val Gly Ser Glu His Ile Gly
                485                 490

<210> SEQ ID NO 35
<211> LENGTH: 498
<212> TYPE: DNA
<213> ORGANISM: Chlorella sp.
```

<400> SEQUENCE: 35

```
atgctgcgat caaggaaagc cagccaggag cagagcccag cggatgcaag ggtggtggcc      60
ctcgcaaagg aaaacgagag actcagggat ctgctgtctg agaaggcgtt caagggcgcc     120
acgtgcagcg ggtacttatg gaagtaccgc tcccacgcgg agagctccct gtgggccaac     180
acttgggagc tgcggtatat ggtcctgaag ggcagtacgc tgctgtatta caagcaggag     240
caggacgtgc agtttccccc acgcggccag atcgacttgc agggcgcgta cgtggagagt     300
gagggggctga agcgccgcaa gtacctggcc ttcaacgtgt acaatgcggc ggggggtgagc    360
ctcatccggc tgtcctcgga gtcgcaggtg gactacgcca agtggatgga ggcgctggag     420
agggcgggt gtgaaaggcg cggggacgac gatgcgcgct ccgtcgccac cagcctccag      480
cgcgtgagtg gcagcagc                                                   498
```

<210> SEQ ID NO 36
<211> LENGTH: 166
<212> TYPE: PRT
<213> ORGANISM: Chlorella sp.

<400> SEQUENCE: 36

```
Met Leu Arg Ser Arg Lys Ala Ser Gln Glu Gln Ser Pro Ala Asp Ala
1               5                   10                  15
Arg Val Val Ala Leu Ala Lys Glu Asn Glu Arg Leu Arg Asp Leu Leu
            20                  25                  30
Ser Glu Lys Ala Phe Lys Gly Ala Thr Cys Ser Gly Tyr Leu Trp Lys
        35                  40                  45
Tyr Arg Ser His Ala Glu Ser Ser Leu Trp Ala Asn Thr Trp Glu Leu
    50                  55                  60
Arg Tyr Met Val Leu Lys Gly Ser Thr Leu Leu Tyr Tyr Lys Gln Glu
65                  70                  75                  80
Gln Asp Val Gln Phe Pro Pro Arg Gly Gln Ile Asp Leu Gln Gly Ala
                85                  90                  95
Tyr Val Glu Ser Glu Gly Leu Lys Arg Arg Lys Tyr Leu Ala Phe Asn
            100                 105                 110
Val Tyr Asn Ala Ala Gly Val Ser Leu Ile Arg Leu Ser Ser Glu Ser
        115                 120                 125
Gln Val Asp Tyr Ala Lys Trp Met Glu Ala Leu Glu Arg Ala Gly Cys
    130                 135                 140
Glu Arg Arg Gly Asp Asp Asp Ala Arg Ser Val Ala Thr Ser Leu Gln
145                 150                 155                 160
Arg Val Ser Gly Ser Ser
                165
```

<210> SEQ ID NO 37
<211> LENGTH: 2181
<212> TYPE: DNA
<213> ORGANISM: Thalassiosira pseudonana

<400> SEQUENCE: 37

```
atggactcta cccccagcga gaccgaagac gatttacgtc gcgaaattca acgtctaagg      60
cagcagctac acgaagcgtc acgtgcatcc ggcaacagcg atgcagcgtt acccactctc     120
ggccagaccg acagcaccat cacaacagga gtggcaccgc ccgagaaatc aggctatctg     180
ttcaagtggc aagatcgaac gattggatgg ggcggcacga gtgggcgtt gagatacgta      240
cgcctcaacc acggacagtt atcgtattac aagagtcatg aggagcgtag tcctcggtac     300
```

| | |
|---|---|
| atcatgacgt tgaaaaactg tgcagtgaga gacgagggat cgaaggtcaa caaacgacat | 360 |
| ggcagcgcta agaatgggga agattctgat caccatgcag tgggatcacg cttttacgtc | 420 |
| ttttccgtct atcgaagagt gaaaaattgg ggagattcag atgctcaata tgacaacgaa | 480 |
| gatgatatta tacctctttt gagattctcg acgcaaagtc ttgccgagaa gatcctttgg | 540 |
| gtcgatctga tatccgagtc ttgtgcatac tgtgattcgg aggagtttgc tttgtatcaa | 600 |
| caccagcagc aagagataca acaaaagcaa caagaacaac aaattcgtac tgagaagggg | 660 |
| acactaccag ctctagtctt tgaagcacct cgtcttactc acaagagatt gccaagtgga | 720 |
| cacaaactca atgaaatggg taaatcgttc cgaaagaagt cagttgataa ggatgcagca | 780 |
| cgatcaaaca agatatcata tcctccctcg aagccaatgc atcgtcaatc caacccatcg | 840 |
| tacttgtcgg atggatcaca tgttcagaac tacagaggac tgttcaatct acttctactc | 900 |
| atcttggtgc tatcaaactt tcgtctgttg ttggatacag tggcacagca tggattcata | 960 |
| ctcgacaaac tcgcaacgct tcaaggcttc tctcaagcgc cactagactt tccatttgtc | 1020 |
| tcgggcttgt tgatcgtgca agcctttgtg gtaggagcgt atgcaattga aaagatgttg | 1080 |
| agtgtgggat tgattggcaa tcagtttgga atgctcctac atgtcatcaa ttccaacgca | 1140 |
| actcttggcg ttgtcatggc tatagtatgg tacttgattg atcaacccct tgttggagct | 1200 |
| ggattgatca tgcaagcaac aattacatgg ctgaagctca tatcctatgc tcatgcaaat | 1260 |
| tacgactatc gtacgtctcc cgatacccaa aaggtgacgg tggctttggt caaggattta | 1320 |
| gatgatggac agaacgtatc ctatcctcag aatgtcacgt tgaaagacat ttactatttt | 1380 |
| tggcttgcac caacgttgac atatcagatt gctttcccga ggagtccatt catacgatgg | 1440 |
| ccaaaagtgt tctccctcac actgcagctg tttatatcag taacacttgc ggtgttttta | 1500 |
| tgtgctcaag ttgtcgcccc aaacttggat agcttagtga agaacttgga ggcgaacaaa | 1560 |
| ggtgaagtca ggacacaaca gatattcgac tatctgctca agctatccat tacgtcgaca | 1620 |
| tacatttggc ttctgggctt ttacggtttt ttccactgct ttatgaacct ggcggctgag | 1680 |
| ttactaaggt ttggcgatag agtctttttat cgtgactggt ggaatgcttc ggaggtgtcg | 1740 |
| gcgtactgga ggctctggaa catgcctgtg cattattggc tagtgagaca tgtctacttt | 1800 |
| ccatgcatca gagtcggtat gtcaaagaag ggagccacgt tcgttgtatt cttttttctcg | 1860 |
| gcggtattgc acgaagtgtt gatcagcgtt ccatgtcata tgataagagc ttggtcgttt | 1920 |
| ctagcaatga tgggacagat acccctcatt atattgacaa aaataataga caaacgtgtg | 1980 |
| cctggaagct ccatcggaaa catcatcttc tggatatcat tctgcttggt cggccagccg | 2040 |
| atggcaatgc ttctgtatac gatcgactac tgggaggttc atttaatgc tgcaattacg | 2100 |
| gagtctacga tagaagttcc tcgaaagagt ttccggtttg ataagatcgg gcgattcttt | 2160 |
| ggtgcccatt ccgagttata a | 2181 |

<210> SEQ ID NO 38
<211> LENGTH: 726
<212> TYPE: PRT
<213> ORGANISM: Thalassiosira pseudonana

<400> SEQUENCE: 38

Met Asp Ser Thr Pro Ser Glu Thr Glu Asp Asp Leu Arg Arg Glu Ile
1               5                   10                  15

Gln Arg Leu Arg Gln Gln Leu His Glu Ala Ser Arg Ala Ser Gly Asn
            20                  25                  30

Ser Asp Ala Ala Leu Pro Thr Leu Gly Gln Thr Asp Ser Thr Ile Thr

```
                35                  40                  45
Thr Gly Val Ala Pro Glu Lys Ser Gly Tyr Leu Phe Lys Trp Gln
 50                  55                  60

Asp Arg Thr Ile Gly Trp Gly Gly Thr Lys Trp Ala Leu Arg Tyr Val
 65                  70                  75                  80

Arg Leu Asn His Gly Gln Leu Ser Tyr Tyr Lys Ser His Glu Glu Arg
                 85                  90                  95

Ser Pro Arg Tyr Ile Met Thr Leu Lys Asn Cys Ala Val Arg Asp Glu
                100                 105                 110

Gly Ser Lys Val Asn Lys Arg His Gly Ser Ala Lys Asn Gly Glu Asp
                115                 120                 125

Ser Asp His His Ala Val Gly Ser Arg Phe Tyr Val Phe Ser Val Tyr
130                 135                 140

Arg Arg Val Lys Asn Trp Gly Asp Ser Asp Ala Gln Tyr Asp Asn Glu
145                 150                 155                 160

Asp Asp Ile Ile Pro Leu Leu Arg Phe Ser Thr Gln Ser Leu Ala Glu
                165                 170                 175

Lys Ile Leu Trp Val Asp Leu Ile Ser Glu Ser Cys Ala Tyr Cys Asp
                180                 185                 190

Ser Glu Glu Phe Ala Leu Tyr Gln His Gln Gln Glu Ile Gln Gln
                195                 200                 205

Lys Gln Gln Glu Gln Ile Arg Thr Glu Lys Gly Thr Leu Pro Ala
210                 215                 220

Leu Val Phe Glu Ala Pro Arg Leu Thr His Lys Arg Leu Pro Ser Gly
225                 230                 235                 240

His Lys Leu Asn Glu Met Gly Lys Ser Phe Arg Lys Ser Val Asp
                245                 250                 255

Lys Asp Ala Ala Arg Ser Asn Lys Ile Ser Tyr Pro Pro Ser Lys Pro
                260                 265                 270

Met His Arg Gln Ser Asn Pro Ser Tyr Leu Ser Asp Gly Ser His Val
                275                 280                 285

Gln Asn Tyr Arg Gly Leu Phe Asn Leu Leu Leu Ile Leu Val Leu
290                 295                 300

Ser Asn Phe Arg Leu Leu Leu Asp Thr Val Ala Gln His Gly Phe Ile
305                 310                 315                 320

Leu Asp Lys Leu Ala Thr Leu Gln Gly Phe Ser Gln Ala Pro Leu Asp
                325                 330                 335

Phe Pro Phe Val Ser Gly Leu Leu Ile Val Gln Ala Phe Val Val Gly
                340                 345                 350

Ala Tyr Ala Ile Glu Lys Met Leu Ser Val Gly Leu Ile Gly Asn Gln
                355                 360                 365

Phe Gly Met Leu Leu His Val Ile Asn Ser Asn Ala Thr Leu Gly Val
                370                 375                 380

Val Met Ala Ile Val Trp Tyr Leu Ile Asp Gln Pro Phe Val Gly Ala
385                 390                 395                 400

Gly Leu Ile Met Gln Ala Thr Ile Thr Trp Leu Lys Leu Ile Ser Tyr
                405                 410                 415

Ala His Ala Asn Tyr Asp Tyr Arg Thr Ser Pro Asp Thr Gln Lys Val
                420                 425                 430

Thr Val Ala Leu Val Lys Asp Leu Asp Asp Gly Gln Asn Val Ser Tyr
                435                 440                 445

Pro Gln Asn Val Thr Leu Lys Asp Ile Tyr Tyr Phe Trp Leu Ala Pro
450                 455                 460
```

Thr Leu Thr Tyr Gln Ile Ala Phe Pro Arg Ser Pro Phe Ile Arg Trp
465                 470                 475                 480

Pro Lys Val Phe Ser Leu Thr Leu Gln Leu Phe Ile Ser Val Thr Leu
            485                 490                 495

Ala Val Phe Leu Cys Ala Gln Val Val Ala Pro Asn Leu Asp Ser Leu
            500                 505                 510

Val Lys Asn Leu Glu Ala Asn Lys Gly Glu Val Arg Thr Gln Gln Ile
            515                 520                 525

Phe Asp Tyr Leu Leu Lys Leu Ser Ile Thr Ser Thr Tyr Ile Trp Leu
530                 535                 540

Leu Gly Phe Tyr Gly Phe His Cys Phe Met Asn Leu Ala Ala Glu
545                 550                 555                 560

Leu Leu Arg Phe Gly Asp Arg Val Phe Tyr Arg Asp Trp Trp Asn Ala
                565                 570                 575

Ser Glu Val Ser Ala Tyr Trp Arg Leu Trp Asn Met Pro Val His Tyr
            580                 585                 590

Trp Leu Val Arg His Val Tyr Phe Pro Cys Ile Arg Val Gly Met Ser
            595                 600                 605

Lys Lys Gly Ala Thr Phe Val Val Phe Phe Ser Ala Val Leu His
610                 615                 620

Glu Val Leu Ile Ser Val Pro Cys His Met Ile Arg Ala Trp Ser Phe
625                 630                 635                 640

Leu Ala Met Met Gly Gln Ile Pro Leu Ile Ile Leu Thr Lys Ile Ile
                645                 650                 655

Asp Lys Arg Val Pro Gly Ser Ser Ile Gly Asn Ile Ile Phe Trp Ile
            660                 665                 670

Ser Phe Cys Leu Val Gly Gln Pro Met Ala Met Leu Leu Tyr Thr Ile
            675                 680                 685

Asp Tyr Trp Glu Val His Phe Asn Ala Ala Ile Thr Glu Ser Thr Ile
            690                 695                 700

Glu Val Pro Arg Lys Ser Phe Arg Phe Asp Lys Ile Gly Arg Phe Phe
705                 710                 715                 720

Gly Ala His Ser Glu Leu
                725

<210> SEQ ID NO 39
<211> LENGTH: 624
<212> TYPE: DNA
<213> ORGANISM: Thalassiosira pseudonana

<400> SEQUENCE: 39
atggactcta cccccagcga gaccgaagac gatttacgtc gcgaaattca acgtctaagg    60
cagcagctac acgaagcgtc acgtgcatcc ggcaacagcg atgcagcgtt acccactctc   120
ggccagaccg acagcaccat acaacagga gtggcaccgc ccgagaaatc aggctatctg   180
ttcaagtggc aagatcgaac gattggatgg ggcggcacga gtgggcgtt gagatacgta   240 cgcctcaacc acggacagtt atcgtattac aagagtcatg aggagcgtag tcctcggtac   300
atcatgacgt tgaaaaactg tgcagtgaga gacgagggat cgaaggtcaa caaacgacat   360
ggcagcgcta agaatgggga agattctgat caccatgcag tgggatcacg cttttacgtc   420
ttttccgtct atcgaagagt gaaaaattgg ggagattcag atgctcaata tgacaacgaa   480
gatgatatta tacctcttt gagattctcg acgcaaagtc ttgccgagaa gatcctttgg   540
gtcgatctga tatccgagtc ttgtgcatac tgtgattcgg aggagtttgc tttgtatcaa   600
caccagcagc aagagataca acaa 624

<210> SEQ ID NO 40
<211> LENGTH: 518
<212> TYPE: PRT
<213> ORGANISM: Thalassiosira pseudonana

<400> SEQUENCE: 40

```
Lys Gln Glu Gln Gln Ile Arg Thr Glu Lys Gly Thr Leu Pro Ala
1               5                   10                  15

Leu Val Phe Glu Ala Pro Arg Leu Thr His Lys Arg Leu Pro Ser Gly
            20                  25                  30

His Lys Leu Asn Glu Met Gly Lys Ser Phe Arg Lys Lys Ser Val Asp
        35                  40                  45

Lys Asp Ala Ala Arg Ser Asn Lys Ile Ser Tyr Pro Pro Ser Lys Pro
    50                  55                  60

Met His Arg Gln Ser Asn Pro Ser Tyr Leu Ser Asp Gly Ser His Val
65                  70                  75                  80

Gln Asn Tyr Arg Gly Leu Phe Asn Leu Leu Leu Ile Leu Val Leu
                85                  90                  95

Ser Asn Phe Arg Leu Leu Leu Asp Thr Val Ala Gln His Gly Phe Ile
            100                 105                 110

Leu Asp Lys Leu Ala Thr Leu Gln Gly Phe Ser Gln Ala Pro Leu Asp
        115                 120                 125

Phe Pro Phe Val Ser Gly Leu Leu Ile Val Gln Ala Phe Val Val Gly
    130                 135                 140

Ala Tyr Ala Ile Glu Lys Met Leu Ser Val Gly Leu Ile Gly Asn Gln
145                 150                 155                 160

Phe Gly Met Leu Leu His Val Ile Asn Ser Asn Ala Thr Leu Gly Val
                165                 170                 175

Val Met Ala Ile Val Trp Tyr Leu Ile Asp Gln Pro Phe Val Gly Ala
            180                 185                 190

Gly Leu Ile Met Gln Ala Thr Ile Thr Trp Leu Lys Leu Ile Ser Tyr
        195                 200                 205

Ala His Ala Asn Tyr Asp Tyr Arg Thr Ser Pro Asp Thr Gln Lys Val
    210                 215                 220

Thr Val Ala Leu Val Lys Asp Leu Asp Asp Gly Gln Asn Val Ser Tyr
225                 230                 235                 240

Pro Gln Asn Val Thr Leu Lys Asp Ile Tyr Tyr Phe Trp Leu Ala Pro
                245                 250                 255

Thr Leu Thr Tyr Gln Ile Ala Phe Pro Arg Ser Pro Phe Ile Arg Trp
            260                 265                 270

Pro Lys Val Phe Ser Leu Thr Leu Gln Leu Phe Ile Ser Val Thr Leu
        275                 280                 285

Ala Val Phe Leu Cys Ala Gln Val Val Ala Pro Asn Leu Asp Ser Leu
    290                 295                 300

Val Lys Asn Leu Glu Ala Asn Lys Gly Glu Val Arg Thr Gln Gln Ile
305                 310                 315                 320

Phe Asp Tyr Leu Leu Lys Leu Ser Ile Thr Ser Thr Tyr Ile Trp Leu
                325                 330                 335

Leu Gly Phe Tyr Gly Phe Phe His Cys Phe Met Asn Leu Ala Ala Glu
            340                 345                 350

Leu Leu Arg Phe Gly Asp Arg Val Phe Tyr Arg Asp Trp Trp Asn Ala
        355                 360                 365
```

```
Ser Glu Val Ser Ala Tyr Trp Arg Leu Trp Asn Met Pro Val His Tyr
        370                 375                 380

Trp Leu Val Arg His Val Tyr Phe Pro Cys Ile Arg Val Gly Met Ser
385                 390                 395                 400

Lys Lys Gly Ala Thr Phe Val Val Phe Phe Ser Ala Val Leu His
                405                 410                 415

Glu Val Leu Ile Ser Val Pro Cys His Met Ile Arg Ala Trp Ser Phe
                420                 425                 430

Leu Ala Met Met Gly Gln Ile Pro Leu Ile Ile Leu Thr Lys Ile Ile
            435                 440                 445

Asp Lys Arg Val Pro Gly Ser Ser Ile Gly Asn Ile Ile Phe Trp Ile
    450                 455                 460

Ser Phe Cys Leu Val Gly Gln Pro Met Ala Met Leu Leu Tyr Thr Ile
465                 470                 475                 480

Asp Tyr Trp Glu Val His Phe Asn Ala Ala Ile Thr Glu Ser Thr Ile
                485                 490                 495

Glu Val Pro Arg Lys Ser Arg Phe Asp Lys Ile Gly Arg Phe Phe
                500                 505                 510

Gly Ala His Ser Glu Leu
            515

<210> SEQ ID NO 41
<211> LENGTH: 1557
<212> TYPE: DNA
<213> ORGANISM: Thalassiosira pseudonana

<400> SEQUENCE: 41
aagcaacaag aacaacaaat tcgtactgag aagggacac taccagctct agtctttgaa      60
gcacctcgtc ttactcacaa gagattgcca agtggacaca aactcaatga atgggtaaa    120 tcgttccgaa agaagtcagt tgataaggat gcagcacgat caaacaagat atcatatcct    180
ccctcgaagc caatgcatcg tcaatccaac ccatcgtact tgtcggatgg atcacatgtt    240
cagaactaca gaggactgtt caatctactt ctactcatct tggtgctatc aaactttcgt    300
ctgttgttgg atacagtggc acagcatgga ttcatactcg acaaactcgc aacgcttcaa    360
ggcttctctc aagcgccact agactttcca tttgtctcgg gcttgttgat cgtgcaagcc    420
tttgtggtag gagcgtatgc aattgaaaag atgttgagtg tgggattgat tggcaatcag    480
tttggaatgc tcctacatgt catcaattcc aacgcaactc ttggcgttgt catggctata    540
gtatggtact tgattgatca acccttgtt ggagctggat tgatcatgca agcaacaatt    600
acatggctga agctcatatc ctatgctcat gcaaattacg actatcgtac gtctcccgat    660
acccaaaagg tgacggtggc tttggtcaag gatttagatg atggacagaa cgtatcctat    720
cctcagaatg tcacgttgaa agacatttac tattttttggc ttgcaccaac gttgacatat    780
cagattgctt tcccgaggag tccattcata cgatggccaa agtgttctc cctcacactg    840 cagctgttta tatcagtaac acttgcggtg tttttatgtg ctcaagttgt cgccccaaac    900
ttggatagct tagtgaagaa cttggaggcg aacaaaggtg aagtcaggac acaacagata    960
ttcgactatc tgctcaagct atccattacg tcgacataca tttggcttct ggcttttac    1020 ggtttttttcc actgctttat gaacctggcg gctgagttac taaggtttgg cgatagagtc    1080 tttatcgtg actggtggaa tgcttcggag gtgtcggcgt actggaggct ctggaacatg    1140
cctgtgcatt attggctagt gagacatgtc tactttccat gcatcagagt cggtatgtca    1200
```

```
aagaagggag ccacgttcgt tgtattctt ttctcggcgg tattgcacga agtgttgatc    1260
agcgttccat gtcatatgat aagagcttgg tcgtttctag caatgatggg acagataccc    1320
ctcattatat tgacaaaaat aatagacaaa cgtgtgcctg gaagctccat cggaaacatc    1380
atcttctgga tatcattctg cttggtcggc cagccgatgg caatgcttct gtatacgatc    1440
gactactggg aggttcattt taatgctgca attacggagt ctacgataga agttcctcga    1500
aagagtttcc ggtttgataa gatcgggcga ttctttggtg cccattccga gttataa       1557
```

<210> SEQ ID NO 42  
<211> LENGTH: 518  
<212> TYPE: PRT  
<213> ORGANISM: Thalassiosira pseudonana

<400> SEQUENCE: 42

```
Lys Gln Gln Glu Gln Gln Ile Arg Thr Glu Lys Gly Thr Leu Pro Ala
1               5                   10                  15

Leu Val Phe Glu Ala Pro Arg Leu Thr His Lys Arg Leu Pro Ser Gly
            20                  25                  30

His Lys Leu Asn Glu Met Gly Lys Ser Phe Arg Lys Ser Val Asp
        35                  40                  45

Lys Asp Ala Ala Arg Ser Asn Lys Ile Ser Tyr Pro Pro Ser Lys Pro
    50                  55                  60

Met His Arg Gln Ser Asn Pro Ser Tyr Leu Ser Asp Gly Ser His Val
65                  70                  75                  80

Gln Asn Tyr Arg Gly Leu Phe Asn Leu Leu Leu Ile Leu Val Leu
                85                  90                  95

Ser Asn Phe Arg Leu Leu Leu Asp Thr Val Ala Gln His Gly Phe Ile
            100                 105                 110

Leu Asp Lys Leu Ala Thr Leu Gln Gly Phe Ser Gln Ala Pro Leu Asp
        115                 120                 125

Phe Pro Phe Val Ser Gly Leu Leu Ile Val Gln Ala Phe Val Val Gly
    130                 135                 140

Ala Tyr Ala Ile Glu Lys Met Leu Ser Val Gly Leu Ile Gly Asn Gln
145                 150                 155                 160

Phe Gly Met Leu Leu His Val Ile Asn Ser Asn Ala Thr Leu Gly Val
                165                 170                 175

Val Met Ala Ile Val Trp Tyr Leu Ile Asp Gln Pro Phe Val Gly Ala
            180                 185                 190

Gly Leu Ile Met Gln Ala Thr Ile Thr Trp Leu Lys Leu Ile Ser Tyr
        195                 200                 205

Ala His Ala Asn Tyr Asp Tyr Arg Thr Ser Pro Asp Thr Gln Lys Val
    210                 215                 220

Thr Val Ala Leu Val Lys Asp Leu Asp Asp Gly Gln Asn Val Ser Tyr
225                 230                 235                 240

Pro Gln Asn Val Thr Leu Lys Asp Ile Tyr Tyr Phe Trp Leu Ala Pro
                245                 250                 255

Thr Leu Thr Tyr Gln Ile Ala Phe Pro Arg Ser Pro Phe Ile Arg Trp
            260                 265                 270

Pro Lys Val Phe Ser Leu Thr Leu Gln Leu Phe Ile Ser Val Thr Leu
        275                 280                 285

Ala Val Phe Leu Cys Ala Gln Val Val Ala Pro Asn Leu Asp Ser Leu
    290                 295                 300

Val Lys Asn Leu Glu Ala Asn Lys Gly Glu Val Arg Thr Gln Gln Ile
305                 310                 315                 320
```

```
Phe Asp Tyr Leu Leu Lys Leu Ser Ile Thr Ser Thr Tyr Ile Trp Leu
            325                 330                 335

Leu Gly Phe Tyr Gly Phe Phe His Cys Phe Met Asn Leu Ala Ala Glu
        340                 345                 350

Leu Leu Arg Phe Gly Asp Arg Val Phe Tyr Arg Asp Trp Trp Asn Ala
            355                 360                 365

Ser Glu Val Ser Ala Tyr Trp Arg Leu Trp Asn Met Pro Val His Tyr
    370                 375                 380

Trp Leu Val Arg His Val Tyr Phe Pro Cys Ile Arg Val Gly Met Ser
385                 390                 395                 400

Lys Lys Gly Ala Thr Phe Val Val Phe Phe Ser Ala Val Leu His
                405                 410                 415

Glu Val Leu Ile Ser Val Pro Cys His Met Ile Arg Ala Trp Ser Phe
                420                 425                 430

Leu Ala Met Met Gly Gln Ile Pro Leu Ile Ile Leu Thr Lys Ile Ile
        435                 440                 445

Asp Lys Arg Val Pro Gly Ser Ser Ile Gly Asn Ile Ile Phe Trp Ile
        450                 455                 460

Ser Phe Cys Leu Val Gly Gln Pro Met Ala Met Leu Leu Tyr Thr Ile
465                 470                 475                 480

Asp Tyr Trp Glu Val His Phe Asn Ala Ala Ile Thr Glu Ser Thr Ile
                485                 490                 495

Glu Val Pro Arg Lys Ser Phe Arg Phe Asp Lys Ile Gly Arg Phe Phe
            500                 505                 510

Gly Ala His Ser Glu Leu
        515

<210> SEQ ID NO 43
<211> LENGTH: 2271
<212> TYPE: DNA
<213> ORGANISM: Phaeodactylum tricornutum

<400> SEQUENCE: 43
atgaccacgc ctgtatcttc cgaagatacg gctactttgc aacaaaagat cgtggcgtta      60
caggcacagc tattgtcagc gactcacgct cttgagcgaa tgaagaatga cgaggcgcg     120 tcttctgctg accattccaa atcagcacag aggaacggtt ccgatcctag cagcgacccc    180
acaggaactg cccctgtcgc tgctcctcca gccaagagcg gctatctgtt caaggagctc    240
gatcgcgcca ttggctgggg cggtattaag tggagcttgc gatacgtgaa actagaaagc    300
ggccgaatat catactacgg atcgcatcac gatacttctc cacgttacga gcttcagttg    360
cgtggatgcg ctgtacgaga cgatggctgg aaacgcaacc cgcgctttaa gaccaaacgg    420
aatgaacccc cgcctttgct agatacaacc ggcgcttact tttcctcttt tccgtgtac    480 catgcacccg acgcagctga gaaggaaatt gatgagaccg aaattacacc tttgttgcgt    540
ttttcgacac cttcccgagc cgaacactcg tcctggataa agcttgcctc ggaatcctgt    600
gcttacagcg aaacggacga gtttctcgct gacgaggccg ctcgcgcaac ccagcgtgct    660
ttgcaacatc aagaagcgct gcaaatggcc caagccatgc tggggcaaa gccaggaacg    720 ctgccgccac tctacttcgc gcctaccata aagcgttcgc gttcctttgc taagctacaa    780
gaacatcatg agatgggat gcctcgggta aatatgcgtc ggaccaaatc gcgagatttt    840
aacgcggata gttggatgc gcgaagtacc aaggcgtatc ccccttccaa gccgatgcat    900
cgtgcggcag agccctcata cctcagcgcg gatgctccca ttcaaaacta ccgaggattt    960
```

```
ctgaatttag gcgttattat tttgattgtt tctaactttc ggctgatctt gggcacaatc    1020
cgtagcaacg gatttgtctt gacgactgca gtgaagcact acaagaacct aaatcacctc    1080
aaggaagatc cctggcagga atttcctttt gtatcaggat tcttctcca gctcgtcttt     1140 gtttcgattg cgtttgggat cgaatggatg ttgtgccgga atacttcaa cgaaaacttc     1200 ggcatgatcc ttcatcactt caatgcccac tcagccttgc tgatacctt aggtattgtt    1260 tggaatctca tcgatagacc tgcggttggt gcaattttgc ttttacacgc tacgataaca    1320
tggatgaaac tcatttctta catgttggcg aacgaagatt accggctatc atcgcgtcgc    1380
gttgggggca acccacacct agctacgctc gcattagtcg aaaatctaga ttcagatgag    1440
gcgaacatta actacccca aaatgttact ctccgcaaca ttttttattt tggtgtgct     1500 ccgacgttga cttaccagat tgccttcccg aagtccccgc gagttcgcta ttggaaaatc    1560
gcggatatcc tgatgcgcat gacggtgtcc atcgcactat tcaccttttt gctggcacaa    1620
attgttcagc ctgcattgga agagctagtg agcgacctgg acgagaccaa tggatcctac    1680
accgcagcaa tatttgccga gtactggctg aaactttcga ttgctaacac atatttatgg    1740
cttcttatgt tctatacata tttccatttg tatctgaacc tctttgctga gcttctgcga    1800
tttggagatc gtgtgttcta caaagattgg tggaattcgt cggaagtatc tgcatattgg    1860
aggctttgga atatgcctgt tcactattgg ttgatccgac atgtgtattt ccctgcgtg    1920 cgactgaaga tgccgaaggt cgctgcaacc tttgtcgttt ttttcctctc cgccgttatg    1980
cacgaggtgc ttgtcagcgt acccttcat attattcgtc cgtggtcttt tatcgggatg    2040
atgatgcaga ttcctttggt tgcgttcaca agtatctct atcgcaaatt cccgggcggc    2100
tcgtttggta atgtcctgtt ctggatgaca ttttgcgtca ttggccagcc aatggcgatt    2160
ctcttgtaca cagttgatta ccagtatggg aaacaccaca gcacgaacat ggagatattc    2220
gatacggacg actgccgctt tttatggaaa aattcctgct tgattcgttg a            2271
```

<210> SEQ ID NO 44
<211> LENGTH: 756
<212> TYPE: PRT
<213> ORGANISM: Phaeodactylum tricornutum

<400> SEQUENCE: 44

Met Thr Thr Pro Val Ser Ser Glu Asp Thr Ala Thr Leu Gln Gln Lys
1               5                   10                  15

Ile Val Ala Leu Gln Ala Gln Leu Leu Ser Ala Thr His Ala Leu Glu
            20                  25                  30

Arg Met Lys Asn Glu Arg Gly Ala Ser Ser Ala Asp His Ser Lys Ser
        35                  40                  45

Ala Gln Arg Asn Gly Ser Asp Pro Ser Ser Asp Pro Thr Gly Thr Ala
    50                  55                  60

Pro Val Ala Ala Pro Ala Lys Ser Gly Tyr Leu Phe Lys Glu Leu
65                  70                  75                  80

Asp Arg Ala Ile Gly Trp Gly Ile Lys Trp Ser Leu Arg Tyr Val
                85                  90                  95

Lys Leu Glu Ser Gly Arg Ile Ser Tyr Tyr Gly Ser His His Asp Thr
            100                 105                 110

Ser Pro Arg Tyr Glu Leu Gln Leu Arg Gly Cys Ala Val Arg Asp Asp
        115                 120                 125

Gly Trp Lys Arg Asn Pro Arg Phe Lys Thr Lys Arg Asn Glu Pro Pro
    130                 135                 140

```
Pro Leu Leu Asp Thr Thr Gly Ala Tyr Phe Phe Leu Phe Ser Val Tyr
145                 150                 155                 160

His Ala Pro Asp Ala Ala Glu Lys Glu Ile Asp Glu Thr Glu Ile Thr
            165                 170                 175

Pro Leu Leu Arg Phe Ser Thr Pro Ser Arg Ala Glu His Ser Ser Trp
            180                 185                 190

Ile Lys Leu Ala Ser Glu Ser Cys Ala Tyr Ser Glu Thr Asp Glu Phe
            195                 200                 205

Leu Ala Asp Glu Ala Ala Arg Ala Thr Gln Arg Ala Leu Gln His Gln
210                 215                 220

Glu Ala Leu Gln Met Ala Gln Ala Met Pro Gly Ala Lys Pro Gly Thr
225                 230                 235                 240

Leu Pro Pro Leu Tyr Phe Ala Pro Thr Ile Lys Arg Ser Arg Ser Phe
            245                 250                 255

Ala Lys Leu Gln Glu His His Gly Asp Gly Met Pro Arg Val Asn Met
            260                 265                 270

Arg Arg Thr Lys Ser Arg Asp Phe Asn Ala Asp Lys Leu Asp Ala Arg
            275                 280                 285

Ser Thr Lys Gly Tyr Pro Pro Ser Lys Pro Met His Arg Ala Ala Glu
290                 295                 300

Pro Ser Tyr Leu Ser Ala Asp Ala Pro Ile Gln Asn Tyr Arg Gly Phe
305                 310                 315                 320

Leu Asn Leu Gly Val Ile Ile Leu Ile Val Ser Asn Phe Arg Leu Ile
            325                 330                 335

Leu Gly Thr Ile Arg Ser Asn Gly Phe Val Leu Thr Thr Ala Val Lys
            340                 345                 350

His Tyr Lys Asn Leu Asn His Leu Lys Glu Asp Pro Trp Gln Glu Phe
            355                 360                 365

Pro Phe Val Ser Gly Phe Leu Leu Gln Leu Val Phe Val Ser Ile Ala
370                 375                 380

Phe Gly Ile Glu Trp Met Leu Cys Arg Lys Tyr Phe Asn Glu Asn Phe
385                 390                 395                 400

Gly Met Ile Leu His His Phe Asn Ala His Ser Ala Leu Leu Ile Pro
            405                 410                 415

Leu Gly Ile Val Trp Asn Leu Ile Asp Arg Pro Ala Val Gly Ala Ile
            420                 425                 430

Leu Leu Leu His Ala Thr Ile Thr Trp Met Lys Leu Ile Ser Tyr Met
            435                 440                 445

Leu Ala Asn Glu Asp Tyr Arg Leu Ser Ser Arg Arg Val Gly Gly Asn
450                 455                 460

Pro His Leu Ala Thr Leu Ala Leu Val Glu Asn Leu Asp Ser Asp Glu
465                 470                 475                 480

Ala Asn Ile Asn Tyr Pro Gln Asn Val Thr Leu Arg Asn Ile Phe Tyr
            485                 490                 495

Phe Trp Cys Ala Pro Thr Leu Thr Tyr Gln Ile Ala Phe Pro Lys Ser
            500                 505                 510

Pro Arg Val Arg Tyr Trp Lys Ile Ala Asp Ile Leu Met Arg Met Thr
            515                 520                 525

Val Ser Ile Ala Leu Phe Thr Phe Leu Leu Ala Gln Ile Val Gln Pro
530                 535                 540

Ala Leu Glu Glu Leu Val Ser Asp Leu Asp Glu Thr Asn Gly Ser Tyr
545                 550                 555                 560
```

```
Thr Ala Ala Ile Phe Ala Glu Tyr Trp Leu Lys Leu Ser Ile Ala Asn
                565                 570                 575

Thr Tyr Leu Trp Leu Leu Met Phe Tyr Thr Tyr Phe His Leu Tyr Leu
            580                 585                 590

Asn Leu Phe Ala Glu Leu Leu Arg Phe Gly Asp Arg Val Phe Tyr Lys
        595                 600                 605

Asp Trp Trp Asn Ser Ser Glu Val Ser Ala Tyr Trp Arg Leu Trp Asn
    610                 615                 620

Met Pro Val His Tyr Trp Leu Ile Arg His Val Tyr Phe Pro Cys Val
625                 630                 635                 640

Arg Leu Lys Met Pro Lys Val Ala Ala Thr Phe Val Val Phe Phe Leu
                645                 650                 655

Ser Ala Val Met His Glu Val Leu Val Ser Val Pro Phe His Ile Ile
            660                 665                 670

Arg Pro Trp Ser Phe Ile Gly Met Met Met Gln Ile Pro Leu Val Ala
        675                 680                 685

Phe Thr Lys Tyr Leu Tyr Arg Lys Phe Pro Gly Gly Ser Phe Gly Asn
    690                 695                 700

Val Leu Phe Trp Met Thr Phe Cys Val Ile Gly Gln Pro Met Ala Ile
705                 710                 715                 720

Leu Leu Tyr Thr Val Asp Tyr Gln Tyr Gly Lys His His Ser Thr Asn
                725                 730                 735

Met Glu Ile Phe Asp Thr Asp Asp Cys Arg Phe Leu Trp Lys Asn Ser
            740                 745                 750

Cys Leu Ile Arg
        755

<210> SEQ ID NO 45
<211> LENGTH: 684
<212> TYPE: DNA
<213> ORGANISM: Phaeodactylum tricornutum

<400> SEQUENCE: 45
atgaccacgc ctgtatcttc cgaagatacg gctactttgc aacaaaagat cgtggcgtta      60
caggcacagc tattgtcagc gactcacgct cttgagcgaa tgaagaatga acgaggcgcg     120
tcttctgctg accattccaa atcagcacag aggaacggtt ccgatcctag cagcgacccc     180
acaggaactg cccctgtcgc tgctcctcca gccaagagcg gctatctgtt caaggagctc     240
gatcgcgcca ttggctgggg cggtattaag tggagcttgc gatacgtgaa actagaaagc     300
ggccgaatat catactacgg atcgcatcac gatacttctc cacgttacga gcttcagttg     360
cgtggatgcg ctgtacgaga cgatggctgg aaacgcaacc cgcgctttaa gaccaaacgg     420
aatgaacccc cgcctttgct agatacaacc ggcgcttact tttcctctt ttccgtgtac     480 catgcacccg acgcagctga aaggaaatt gatgagaccg aaattacacc tttgttgcgt     540
ttttcgacac cttcccgagc cgaacactcg tcctggataa agcttgcctc ggaatcctgt     600
gcttacagcg aaacggacga gtttctcgct gacgaggccg ctcgcgcaac ccagcgtgct     660
ttgcaacatc aagaagcgct gcaa                                           684

<210> SEQ ID NO 46
<211> LENGTH: 228
<212> TYPE: PRT
<213> ORGANISM: Phaeodactylum tricornutum

<400> SEQUENCE: 46
```

```
Met Thr Thr Pro Val Ser Ser Glu Asp Thr Ala Thr Leu Gln Gln Lys
1               5                   10                  15

Ile Val Ala Leu Gln Ala Gln Leu Leu Ser Ala Thr His Ala Leu Glu
            20                  25                  30

Arg Met Lys Asn Glu Arg Gly Ala Ser Ser Ala Asp His Ser Lys Ser
        35                  40                  45

Ala Gln Arg Asn Gly Ser Asp Pro Ser Ser Asp Pro Thr Gly Thr Ala
    50                  55                  60

Pro Val Ala Ala Pro Ala Lys Ser Gly Tyr Leu Phe Lys Glu Leu
65                  70                  75                  80

Asp Arg Ala Ile Gly Trp Gly Gly Ile Lys Trp Ser Leu Arg Tyr Val
                85                  90                  95

Lys Leu Glu Ser Gly Arg Ile Ser Tyr Tyr Gly Ser His His Asp Thr
            100                 105                 110

Ser Pro Arg Tyr Glu Leu Gln Leu Arg Gly Cys Ala Val Arg Asp Asp
        115                 120                 125

Gly Trp Lys Arg Asn Pro Arg Phe Lys Thr Lys Arg Asn Glu Pro Pro
    130                 135                 140

Pro Leu Leu Asp Thr Thr Gly Ala Tyr Phe Phe Leu Phe Ser Val Tyr
145                 150                 155                 160

His Ala Pro Asp Ala Ala Glu Lys Glu Ile Asp Glu Thr Glu Ile Thr
                165                 170                 175

Pro Leu Leu Arg Phe Ser Thr Pro Ser Arg Ala Glu His Ser Ser Trp
        180                 185                 190

Ile Lys Leu Ala Ser Glu Ser Cys Ala Tyr Ser Glu Thr Asp Glu Phe
    195                 200                 205

Leu Ala Asp Glu Ala Ala Arg Ala Thr Gln Arg Ala Leu Gln His Gln
210                 215                 220

Glu Ala Leu Gln
225

<210> SEQ ID NO 47
<211> LENGTH: 1587
<212> TYPE: DNA
<213> ORGANISM: Phaeodactylum tricornutum

<400> SEQUENCE: 47
atggcccaag ccatgcctgg ggcaaagcca ggaacgctgc cgccactcta cttcgcgcct      60
accataaagc gttcgcgttc ctttgctaag ctacaagaac atcatggaga tgggatgcct     120
cgggtaaata tgcgtcggac caaatcgcga gattttaacg cggataagtt ggatgcgcga     180
agtaccaagg gctatccccc ttccaagccg atgcatcgtg cggcagagcc ctcataccto     240 agcgcggatg ctcccattca aaactaccga ggatttctga atttaggcgt tattattttg     300
attgtttcta actttcggct gatcttgggc acaatccgta gcaacggatt tgtcttgacg     360
actgcagtga agcactacaa gaacctaaat cacctcaagg aagatccctg caggaatttt    420 cctttttgtat caggatttct tctccagctc gtctttgttt cgattgcgtt tgggatcgaa    480
tggatgttgt gccggaaata cttcaacgaa aacttcggca tgatccttca tcacttcaat    540
gcccactcag ccttgctgat acctttaggt attgtttgga atctcatcga tagacctgcg    600
gttggtgcaa ttttgctttt acacgctacg ataacatgga tgaaactcat ttcttacatg    660
ttggcgaacg aagattaccg gctatcatcg cgtcgcgttg ggggcaaccc acacctagct    720
acgctcgcat tagtcgaaaa tctagattca gatgaggcga acattaacta cccccaaaat    780
```

-continued

```
gttactctcc gcaacatttt ttattttttgg tgtgctccga cgttgactta ccagattgcc      840
ttcccgaagt ccccgcgagt tcgctattgg aaaatcgcgg atatcctgat gcgcatgacg      900
gtgtccatcg cactattcac cttttttgctg gcacaaattg ttcagcctgc attggaagag      960
ctagtgagcg acctggacga gaccaatgga tcctacaccg cagcaatatt tgccgagtac     1020
tggctgaaac tttcgattgc taacacatat ttatggcttc ttatgttcta tacatatttc     1080
catttgtatc tgaacctctt tgctgagctt ctgcgatttg agatcgtgt gttctacaaa      1140
gattggtgga attcgtcgga agtatctgca tattggaggc tttggaatat gcctgttcac     1200
tattggttga tccgacatgt gtatttcccc tgcgtgcgac tgaagatgcc gaaggtcgct     1260
gcaacctttg tcgtttttttt cctctccgcc gttatgcacg aggtgcttgt cagcgtaccc     1320
tttcatatta ttcgtccgtg gtcttttatc gggatgatga tgcagattcc tttggttgcg     1380
ttcacaaagt atctctatcg caaattcccg ggcggctcgt ttggtaatgt cctgttctgg     1440
atgacatttt gcgtcattgg ccagccaatg gcgattctct tgtacacagt tgattaccag     1500
tatgggaaac accacagcac gaacatggag atattcgata cggacgactg ccgctttta      1560
tggaaaaatt cctgcttgat tcgttga                                          1587
```

<210> SEQ ID NO 48
<211> LENGTH: 528
<212> TYPE: PRT
<213> ORGANISM: Phaeodactylum tricornutum
<400> SEQUENCE: 48

```
Met Ala Gln Ala Met Pro Gly Ala Lys Pro Gly Thr Leu Pro Pro Leu
1               5                   10                  15

Tyr Phe Ala Pro Thr Ile Lys Arg Ser Arg Ser Phe Ala Lys Leu Gln
            20                  25                  30

Glu His His Gly Asp Gly Met Pro Arg Val Asn Met Arg Arg Thr Lys
        35                  40                  45

Ser Arg Asp Phe Asn Ala Asp Lys Leu Asp Ala Arg Ser Thr Lys Gly
    50                  55                  60

Tyr Pro Pro Ser Lys Pro Met His Arg Ala Ala Glu Pro Ser Tyr Leu
65                  70                  75                  80

Ser Ala Asp Ala Pro Ile Gln Asn Tyr Arg Gly Phe Leu Asn Leu Gly
                85                  90                  95

Val Ile Ile Leu Ile Val Ser Asn Phe Arg Leu Ile Leu Gly Thr Ile
            100                 105                 110

Arg Ser Asn Gly Phe Val Leu Thr Thr Ala Val Lys His Tyr Lys Asn
        115                 120                 125

Leu Asn His Leu Lys Glu Asp Pro Trp Gln Glu Phe Pro Phe Val Ser
    130                 135                 140

Gly Phe Leu Leu Gln Leu Val Phe Val Ser Ile Ala Phe Gly Ile Glu
145                 150                 155                 160

Trp Met Leu Cys Arg Lys Tyr Phe Asn Glu Asn Phe Gly Met Ile Leu
                165                 170                 175

His His Phe Asn Ala His Ser Ala Leu Leu Ile Pro Leu Gly Ile Val
            180                 185                 190

Trp Asn Leu Ile Asp Arg Pro Ala Val Gly Ala Ile Leu Leu His
        195                 200                 205

Ala Thr Ile Thr Trp Met Lys Leu Ile Ser Tyr Met Leu Ala Asn Glu
    210                 215                 220

Asp Tyr Arg Leu Ser Ser Arg Arg Val Gly Gly Asn Pro His Leu Ala
```

```
            225                 230                 235                 240
        Thr Leu Ala Leu Val Glu Asn Leu Asp Ser Asp Glu Ala Asn Ile Asn
                        245                 250                 255
        Tyr Pro Gln Asn Val Thr Leu Arg Asn Ile Phe Tyr Phe Trp Cys Ala
                        260                 265                 270
        Pro Thr Leu Thr Tyr Gln Ile Ala Phe Pro Lys Ser Pro Arg Val Arg
                        275                 280                 285
        Tyr Trp Lys Ile Ala Asp Ile Leu Met Arg Met Thr Val Ser Ile Ala
                        290                 295                 300
        Leu Phe Thr Phe Leu Leu Ala Gln Ile Val Gln Pro Ala Leu Glu Glu
        305                 310                 315                 320
        Leu Val Ser Asp Leu Asp Glu Thr Asn Gly Ser Tyr Thr Ala Ala Ile
                        325                 330                 335
        Phe Ala Glu Tyr Trp Leu Lys Leu Ser Ile Ala Asn Thr Tyr Leu Trp
                        340                 345                 350
        Leu Leu Met Phe Tyr Thr Tyr Phe His Leu Tyr Leu Asn Leu Phe Ala
                        355                 360                 365
        Glu Leu Leu Arg Phe Gly Asp Arg Val Phe Tyr Lys Asp Trp Trp Asn
        370                 375                 380
        Ser Ser Glu Val Ser Ala Tyr Trp Arg Leu Trp Asn Met Pro Val His
        385                 390                 395                 400
        Tyr Trp Leu Ile Arg His Val Tyr Phe Pro Cys Val Arg Leu Lys Met
                        405                 410                 415
        Pro Lys Val Ala Ala Thr Phe Val Val Phe Leu Ser Ala Val Met
                        420                 425                 430
        His Glu Val Leu Val Ser Val Pro Phe His Ile Ile Arg Pro Trp Ser
                        435                 440                 445
        Phe Ile Gly Met Met Met Gln Ile Pro Leu Val Ala Phe Thr Lys Tyr
                        450                 455                 460
        Leu Tyr Arg Lys Phe Pro Gly Gly Ser Phe Gly Asn Val Leu Phe Trp
        465                 470                 475                 480
        Met Thr Phe Cys Val Ile Gly Gln Pro Met Ala Ile Leu Leu Tyr Thr
                        485                 490                 495
        Val Asp Tyr Gln Tyr Gly Lys His His Ser Thr Asn Met Glu Ile Phe
                        500                 505                 510
        Asp Thr Asp Asp Cys Arg Phe Leu Trp Lys Asn Ser Cys Leu Ile Arg
                        515                 520                 525

<210> SEQ ID NO 49
<211> LENGTH: 38
<212> TYPE: DNA
<213> ORGANISM: Artificial Sequence
<220> FEATURE:
<223> OTHER INFORMATION: DGAT1-452F primer

<400> SEQUENCE: 49
tagaactagt ggatccatgg agaccgagga ggaattac                              38

<210> SEQ ID NO 50
<211> LENGTH: 36
<212> TYPE: DNA
<213> ORGANISM: Artificial Sequence
<220> FEATURE:
<223> OTHER INFORMATION: DGAT1-452R primer

<400> SEQUENCE: 50
gcttgatatc gaattctcaa agctcaggag aagcac                                36
```

<210> SEQ ID NO 51
<211> LENGTH: 41
<212> TYPE: DNA
<213> ORGANISM: Artificial Sequence
<220> FEATURE:
<223> OTHER INFORMATION: DGAT1-452TF primer

<400> SEQUENCE: 51
tagaactagt ggatccatgt tgaaacaaca acaacgacaa c         41

<210> SEQ ID NO 52
<211> LENGTH: 36
<212> TYPE: DNA
<213> ORGANISM: Artificial Sequence
<220> FEATURE:
<223> OTHER INFORMATION: Phaeo-TEFF primer

<400> SEQUENCE: 52
tagaactagt ggatccatga ccacgcctgt atcttc                36

<210> SEQ ID NO 53
<211> LENGTH: 37
<212> TYPE: DNA
<213> ORGANISM: Artificial Sequence
<220> FEATURE:
<223> OTHER INFORMATION: Phaeo-TEFR primer

<400> SEQUENCE: 53
gcttgatatc gaattctcaa cgaatcaagc aggaatt               37

<210> SEQ ID NO 54
<211> LENGTH: 35
<212> TYPE: DNA
<213> ORGANISM: Artificial Sequence
<220> FEATURE:
<223> OTHER INFORMATION: Phaeo-TEFTF primer

<400> SEQUENCE: 54
tagaactagt ggatccatgg cccaagccat gcctg                 35

<210> SEQ ID NO 55
<211> LENGTH: 37
<212> TYPE: DNA
<213> ORGANISM: Artificial Sequence
<220> FEATURE:
<223> OTHER INFORMATION: Thala-TEFF primer

<400> SEQUENCE: 55
tagaactagt ggatccatgg actctacccc cagcgag               37

<210> SEQ ID NO 56
<211> LENGTH: 36
<212> TYPE: DNA
<213> ORGANISM: Artificial Sequence
<220> FEATURE:
<223> OTHER INFORMATION: Thala-TEFR primer

<400> SEQUENCE: 56
gcttgatatc gaattcttat aactcggaat gggcac                36

<210> SEQ ID NO 57
<211> LENGTH: 41
<212> TYPE: DNA
<213> ORGANISM: Artificial Sequence
<220> FEATURE:

<223> OTHER INFORMATION: Thala-TEFTF primer

<400> SEQUENCE: 57
tagaactagt ggatccatga agcaacaaga acaacaaatt c        41

<210> SEQ ID NO 58
<211> LENGTH: 1000
<212> TYPE: DNA
<213> ORGANISM: Nannochloropsis gaditana

<400> SEQUENCE: 58

```
tcataatcaa agatgagcca gccacgaagc taccggagaa ttctgtaaga aaaatgttta      60
aagttgaaaa tgctaacagt gaagtgatat cctttttaa tggagtgttg aggtgaagtc     120
tagcatcgta ggggaaaaca ggattctgtg tcttccattc tactccttga taaagcgaag   180
aaatccgaca aaccaaaga gattgttcaa gtttaagatt tgtaagcgta caactatgaa    240
cttcttctct ttgtaggcct gagtggtcgt atgcatacga ttcatgaagt gaatcagtat   300
cgctggattt tgcttaggag taaagcacaa ctaagaaaat atgctgcctg gcaggcatcc   360
tgagacatga ggcaagcgac gtagcaattg aatcctaatt taagccaggg catctgtatg   420
actctgttag ttaattgatg aaccaatgag ctttaaaaaa aaatcgttgc gcgtaatgta   480
gttttaattc tccgccttga ggtgcggggc catttcggac aaggttcttt ggacggagat   540
ggcagcatgt gtcccttctc caaattggtc cgtgtggtag ttgagatgct gccttaaaat   600
tctgctcggt catcctgcct tcgcattcac tcctttcgag ctgtcgggtt cctcacgagg   660
cctccgggag cggattgcgc agaaaggcga cccggagaca cagagaccat acaccgacta   720
aattgcactg gacgatacgg catggcgacg acgatggcca agcattgcta cgtgattatt   780
cgccttgtca ttcagggaga aatgatgaca tgtgtggac ggtctttaca tgggaagagg    840
gcatgaaaat aacatggcct ggcgggatgg agcgtcacac ctgtgtatgc gttcgatcca   900
caagcaactc accatttgcg tcggggcctg tctccaatct gctttaggct acttttctct   960
aatttagcct attctataca gacagagaca cacagggatc                         1000
```

<210> SEQ ID NO 59
<211> LENGTH: 42
<212> TYPE: DNA
<213> ORGANISM: Artificial Sequence
<220> FEATURE:
<223> OTHER INFORMATION: Phaeo-DGAT1F primer

<400> SEQUENCE: 59
cagacagaga cacacaggga tcatgaccac gcctgtatct tc        42

<210> SEQ ID NO 60
<211> LENGTH: 45
<212> TYPE: DNA
<213> ORGANISM: Artificial Sequence
<220> FEATURE:
<223> OTHER INFORMATION: Phaeo-DGAT1R primer

<400> SEQUENCE: 60
gagcggaacc ggggttacag tgcctcaacg aatcaagcag gaatt     45

<210> SEQ ID NO 61
<211> LENGTH: 43
<212> TYPE: DNA
<213> ORGANISM: Artificial Sequence
<220> FEATURE:
<223> OTHER INFORMATION: Thala-DGAT1F primer

```
<400> SEQUENCE: 61
cagacagaga cacacaggga tcatggactc taccccagc gag                    43

<210> SEQ ID NO 62
<211> LENGTH: 44
<212> TYPE: DNA
<213> ORGANISM: Artificial Sequence
<220> FEATURE:
<223> OTHER INFORMATION: Thala-DGAT1R primer

<400> SEQUENCE: 62
gagcggaacc ggggttacag tgccttataa ctcggaatgg gcac                  44

<210> SEQ ID NO 63
<211> LENGTH: 7
<212> TYPE: PRT
<213> ORGANISM: Artificial Sequence
<220> FEATURE:
<223> OTHER INFORMATION: Eukaryotic DGAT1 consensus motif
<220> FEATURE:
<221> NAME/KEY: misc_feature
<222> LOCATION: (3)..(3)
<223> OTHER INFORMATION: Xaa can be any naturally occurring amino acid

<400> SEQUENCE: 63

Phe Tyr Xaa Asp Trp Trp Asn
1               5
```